(12) United States Patent
Bruno

(10) Patent No.: US 8,658,613 B2
(45) Date of Patent: Feb. 25, 2014

(54) METHODS AND COMPOSITIONS OF NUCLEIC ACID LIGANDS FOR DETECTION OF CLINICAL ANALYTES RELATED TO HUMAN HEALTH

(75) Inventor: John G. Bruno, San Antonio, TX (US)

(73) Assignee: OTC Biotechnologies, LLC, San Antonio, TX (US)

( * ) Notice: Subject to any disclaimer, the term of this patent is extended or adjusted under 35 U.S.C. 154(b) by 0 days.

(21) Appl. No.: 13/199,484

(22) Filed: Aug. 31, 2011

(65) Prior Publication Data

US 2012/0135540 A1    May 31, 2012

Related U.S. Application Data

(60) Provisional application No. 61/402,491, filed on Nov. 30, 2010, provisional application No. 61/463,020, filed on Feb. 10, 2011.

(51) Int. Cl.
*C12N 15/11* (2006.01)
*C07H 21/02* (2006.01)

(52) U.S. Cl.
USPC ........................................ 514/44 A; 536/23.1

(58) Field of Classification Search
None
See application file for complete search history.

*Primary Examiner* — Tracy Vivlemore
*Assistant Examiner* — Kate Poliakova
(74) *Attorney, Agent, or Firm* — Rosenthal Pauerstein Sandoloski Agather LLP; William H. Quirk; Daniel A. Rogers

(57) ABSTRACT

Specific DNA sequences for binding various clinically relevant analytes from the human body are described. Each of these sequences or their linear, two- and three-dimensional linked sequences can function in varying assay and sensor formats with varying degrees of success. Linkage of the whole or partial DNA sequences (putative binding sites) can be used to enhance specificity and affinity towards complex targets, thereby improving assay selectivity and sensitivity in many instances. In addition, a FRET-based quantitative method is described for normalizing analyte data by assessing urine creatinine and urea levels. Finally, a method is described for removing creatinine or urea by size-exclusion chromatography prior to a FRET-based aptamer assay to avoid the denaturing effects of these compounds.

2 Claims, 34 Drawing Sheets

A. Antibody Hypervariable Regions Linked Together

B. Multi-Aptamer or Linked Aptamer Binding Pockets

CTx 2F

5' (1)
3' (72)
10 O'clock (10h)
2 O'clock (2h)
6 O'clock (6h)

CTx 2R 15b
5' 3'
10 O'clock (10h)
2 O'clock (2h)
13b
6 O'clock (6h)

Figure 2

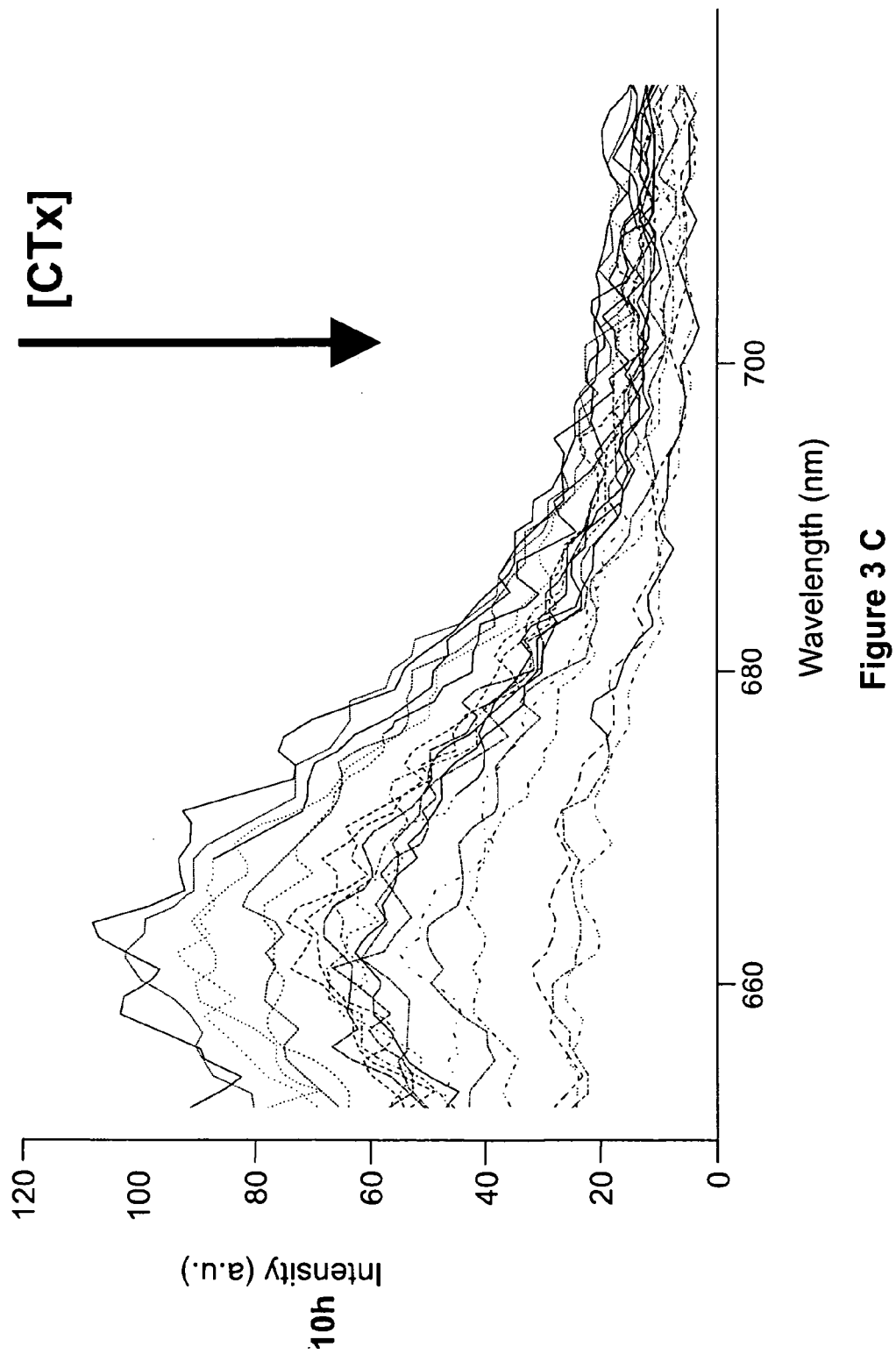

SEQUENCE LISTING

```
<160> NUMBER OF SEQ ID NOS: 906

<210> SEQ ID NO 1
<211> LENGTH: 59
<212> TYPE: DNA
<213> ORGANISM: Artificial Sequence
<220> FEATURE:
<223> OTHER INFORMATION: chemically synthesized

<400> SEQUENCE: 1
atacgggagc caacaccact aacttgttgc tgatcttatc cagagcaggt gtgacggat        59

<210> SEQ ID NO 2
<211> LENGTH: 59
<212> TYPE: DNA
<213> ORGANISM: Artificial Sequence
<220> FEATURE:
<223> OTHER INFORMATION: chemically synthesized

<400> SEQUENCE: 2
atccgtcaca cctgctctgg ataagatcag caacaagtta gtggtgttgg ctcccgtat        59

<210> SEQ ID NO 3
<211> LENGTH: 72
<212> TYPE: DNA
<213> ORGANISM: Artificial Sequence
<220> FEATURE:
<223> OTHER INFORMATION: chemically synthesized

<400> SEQUENCE: 3
atacgggagc caacaccacc cgtttttgat ctaatgagga tacaatattc gtctagagca        60
ggtgtgacgg at                                                          72

<210> SEQ ID NO 4
<211> LENGTH: 72
<212> TYPE: DNA
<213> ORGANISM: Artificial Sequence
<220> FEATURE:
<223> OTHER INFORMATION: chemically synthesized

<400> SEQUENCE: 4
atccgtcaca cctgctctag acgaatattg tatcctcatt agatcaaaaa cgggtggtgt        60
tggctcccgt at                                                          72

<210> SEQ ID NO 5
<211> LENGTH: 72
<212> TYPE: DNA
<213> ORGANISM: Artificial Sequence
<220> FEATURE:
<223> OTHER INFORMATION: chemically synthesized

<400> SEQUENCE: 5
atacgggagc caacaccaat cgatggttag actattacac tagatggaat tcatagagca        60
ggtgtgacgg at                                                          72

<210> SEQ ID NO 6
```

-continued

```
<211> LENGTH: 72
<212> TYPE: DNA
<213> ORGANISM: Artificial Sequence
<220> FEATURE:
<223> OTHER INFORMATION: chemically synthesized

<400> SEQUENCE: 6
atccgtcaca cctgctctat gaattccatc tagtgtaata gtctaaccat cgattggtgt    60
tggctcccgt at                                                        72

<210> SEQ ID NO 7
<211> LENGTH: 72
<212> TYPE: DNA
<213> ORGANISM: Artificial Sequence
<220> FEATURE:
<223> OTHER INFORMATION: chemically synthesized

<400> SEQUENCE: 7
atacgggagc caacaccaat ctgccgacta ggccaagtaa ttatattcag ctggagagca    60
ggtgtgacgg at                                                        72

<210> SEQ ID NO 8
<211> LENGTH: 72
<212> TYPE: DNA
<213> ORGANISM: Artificial Sequence
<220> FEATURE:
<223> OTHER INFORMATION: chemically synthesized

<400> SEQUENCE: 8
atccgtcaca cctgctctcc agctgaatat aattacttgg cctagtcggc agattggtgt    60
tggctcccgt at                                                        72

<210> SEQ ID NO 9
<211> LENGTH: 59
<212> TYPE: DNA
<213> ORGANISM: Artificial Sequence
<220> FEATURE:
<223> OTHER INFORMATION: chemically synthesized

<400> SEQUENCE: 9
atacgggagc caacaccaca gctgatattg gatggtccgg cagagcaggt gtgacggat     59

<210> SEQ ID NO 10
<211> LENGTH: 59
<212> TYPE: DNA
<213> ORGANISM: Artificial Sequence
<220> FEATURE:
<223> OTHER INFORMATION: chemically synthesized

<400> SEQUENCE: 10
atccgtcaca cctgctctgc cggaccatcc aatatcagct gtggtgttgg ctcccgtat     59

<210> SEQ ID NO 11
<211> LENGTH: 72
<212> TYPE: DNA
<213> ORGANISM: Artificial Sequence
<220> FEATURE:
<223> OTHER INFORMATION: chemically synthesized

<400> SEQUENCE: 11
atacgggagc caacaccaca ttacaataga tgtattgaca tatccggaca gtcgagagca    60
ggtgtgacgg at                                                        72

<210> SEQ ID NO 12
```

-continued

```
<211> LENGTH: 72
<212> TYPE: DNA
<213> ORGANISM: Artificial Sequence
<220> FEATURE:
<223> OTHER INFORMATION: chemically synthesized

<400> SEQUENCE: 12
atccgtcaca cctgctctcg actgtccgga tatgtcaata catctattgt aatgtggtgt    60
tggctcccgt at                                                        72

<210> SEQ ID NO 13
<211> LENGTH: 72
<212> TYPE: DNA
<213> ORGANISM: Artificial Sequence
<220> FEATURE:
<223> OTHER INFORMATION: chemically synthesized

<400> SEQUENCE: 13
atacgggagc caacaccact cgtgtagtgc tgtctttgtg gaatccttgc atcgagagca    60
ggtgtgacgg at                                                        72

<210> SEQ ID NO 14
<211> LENGTH: 72
<212> TYPE: DNA
<213> ORGANISM: Artificial Sequence
<220> FEATURE:
<223> OTHER INFORMATION: chemically synthesized

<400> SEQUENCE: 14
atccgtcaca cctgctctcg atgcaaggat tccacaaaga cagcactaca cgagtggtgt    60
tggctcccgt at                                                        72

<210> SEQ ID NO 15
<211> LENGTH: 72
<212> TYPE: DNA
<213> ORGANISM: Artificial Sequence
<220> FEATURE:
<223> OTHER INFORMATION: chemically synthesized

<400> SEQUENCE: 15
atacgggagc caacaccacc acgtgaccca tacgatacaa caaataattg ctcaagagca    60
ggtgtgacgg at                                                        72

<210> SEQ ID NO 16
<211> LENGTH: 72
<212> TYPE: DNA
<213> ORGANISM: Artificial Sequence
<220> FEATURE:
<223> OTHER INFORMATION: chemically synthesized

<400> SEQUENCE: 16
atccgtcaca cctgctcttg agcaattatt tgttgtatcg tatgggtcac gtggtggtgt    60
tggctcccgt at                                                        72

<210> SEQ ID NO 17
<211> LENGTH: 72
<212> TYPE: DNA
<213> ORGANISM: Artificial Sequence
<220> FEATURE:
<223> OTHER INFORMATION: chemically synthesized

<400> SEQUENCE: 17
atacgggagc caacaccatc catagctcat ctataccctc ttccgagtcc caccagagca    60
```
ggtgtgacgg at                                                         72

<210> SEQ ID NO 18
<211> LENGTH: 72
<212> TYPE: DNA
<213> ORGANISM: Artificial Sequence
<220> FEATURE:
<223> OTHER INFORMATION: chemically synthesized

<400> SEQUENCE: 18
atccgtcaca cctgctctgg tgggactcgg aagagggtat agatgagcta tggatggtgt    60
tggctcccgt at                                                         72

<210> SEQ ID NO 19
<211> LENGTH: 72
<212> TYPE: DNA
<213> ORGANISM: Artificial Sequence
<220> FEATURE:
<223> OTHER INFORMATION: chemically synthesized

<400> SEQUENCE: 19
atacgggagc caacaccaga cgcggaacga ctcatcgcaa aatgtcgtga tgcaagagca    60
ggtgtgacgg at                                                         72

<210> SEQ ID NO 20
<211> LENGTH: 72
<212> TYPE: DNA
<213> ORGANISM: Artificial Sequence
<220> FEATURE:
<223> OTHER INFORMATION: chemically synthesized

<400> SEQUENCE: 20
atccgtcaca cctgctcttg catcacgaca ttttgcgatg agtcgttccg cgtctggtgt    60
tggctcccgt at                                                         72

<210> SEQ ID NO 21
<211> LENGTH: 72
<212> TYPE: DNA
<213> ORGANISM: Artificial Sequence
<220> FEATURE:
<223> OTHER INFORMATION: chemically synthesized

<400> SEQUENCE: 21
atacgggagc caacaccatg gttaggctgc tccatatatt cccgccccgc acgtagagca    60
ggtgtgacgg at                                                         72

<210> SEQ ID NO 22
<211> LENGTH: 72
<212> TYPE: DNA
<213> ORGANISM: Artificial Sequence
<220> FEATURE:
<223> OTHER INFORMATION: chemically synthesized

<400> SEQUENCE: 22
atccgtcaca cctgctctac gtgcggggcg ggaatatatg gagcagccta accatggtgt    60
tggctcccgt at                                                         72

<210> SEQ ID NO 23
<211> LENGTH: 69
<212> TYPE: DNA
<213> ORGANISM: Artificial Sequence
<220> FEATURE:
<223> OTHER INFORMATION: chemically synthesized

```
<400> SEQUENCE: 23
atacgggagc caacaccata gtgttgggcc aatacggtaa cgtgtccttg gagagcaggt    60
gtgacggat                                                             69

<210> SEQ ID NO 24
<211> LENGTH: 69
<212> TYPE: DNA
<213> ORGANISM: Artificial Sequence
<220> FEATURE:
<223> OTHER INFORMATION: chemically synthesized

<400> SEQUENCE: 24
atccgtcaca cctgctctcc aaggacacgt taccgtattg gcccaacact atggtgttgg    60
ctcccgtat                                                             69

<210> SEQ ID NO 25
<211> LENGTH: 72
<212> TYPE: DNA
<213> ORGANISM: Artificial Sequence
<220> FEATURE:
<223> OTHER INFORMATION: chemically synthesized

<400> SEQUENCE: 25
atacgggagc caacaccatg ctgaactaac agatacaaga tacagatccg agttagagca    60
ggtgtgacgg at                                                         72

<210> SEQ ID NO 26
<211> LENGTH: 75
<212> TYPE: DNA
<213> ORGANISM: Artificial Sequence
<220> FEATURE:
<223> OTHER INFORMATION: chemically synthesized

<400> SEQUENCE: 26
atccgtcaca cctgctctaa ctcggatctg tatcttgtat ctgttagttc agcatggtgt    60
tggctcccgt atata                                                      75

<210> SEQ ID NO 27
<211> LENGTH: 72
<212> TYPE: DNA
<213> ORGANISM: Artificial Sequence
<220> FEATURE:
<223> OTHER INFORMATION: chemically synthesized

<400> SEQUENCE: 27
atacgggagc caacaccatg tcgctggtca catccctagt taacaaactt ggatagagca    60
ggtgtgacgg at                                                         72

<210> SEQ ID NO 28
<211> LENGTH: 72
<212> TYPE: DNA
<213> ORGANISM: Artificial Sequence
<220> FEATURE:
<223> OTHER INFORMATION: chemically synthesized

<400> SEQUENCE: 28
atccgtcaca cctgctctat ccaagtttgt taactaggga tgtgaccagc gacatggtgt    60
tggctcccgt at                                                         72

<210> SEQ ID NO 29
<211> LENGTH: 72
<212> TYPE: DNA
```

<213> ORGANISM: Artificial Sequence
<220> FEATURE:
<223> OTHER INFORMATION: chemically synthesized

<400> SEQUENCE: 29
atacgggagc caacaccatt ggcgttacta gaggattact gaaagccata aactagagca    60
ggtgtgacgg at    72

<210> SEQ ID NO 30
<211> LENGTH: 72
<212> TYPE: DNA
<213> ORGANISM: Artificial Sequence
<220> FEATURE:
<223> OTHER INFORMATION: chemically synthesized

<400> SEQUENCE: 30
atccgtcaca cctgctctag tttatggctt tcagtaatcc tctagtaacg ccaatggtgt    60
tggctcccgt at    72

<210> SEQ ID NO 31
<211> LENGTH: 72
<212> TYPE: DNA
<213> ORGANISM: Artificial Sequence
<220> FEATURE:
<223> OTHER INFORMATION: chemically synthesized

<400> SEQUENCE: 31
atacgggagc caacaccatc actataattc cttcgaacct tacttgtgtt agctagagca    60
ggtgtgacgg at    72

<210> SEQ ID NO 32
<211> LENGTH: 72
<212> TYPE: DNA
<213> ORGANISM: Artificial Sequence
<220> FEATURE:
<223> OTHER INFORMATION: chemically synthesized

<400> SEQUENCE: 32
atccgtcaca cctgctctag ctaacacaag taaggttcga aggaattata gtgatggtgt    60
tggctcccgt at    72

<210> SEQ ID NO 33
<211> LENGTH: 72
<212> TYPE: DNA
<213> ORGANISM: Artificial Sequence
<220> FEATURE:
<223> OTHER INFORMATION: chemically synthesized

<400> SEQUENCE: 33
atacgggagc caacaccact atcgactttt acattcgtgt acgattcccg cttcagagca    60
ggtgtgacgg at    72

<210> SEQ ID NO 34
<211> LENGTH: 72
<212> TYPE: DNA
<213> ORGANISM: Artificial Sequence
<220> FEATURE:
<223> OTHER INFORMATION: chemically synthesized

<400> SEQUENCE: 34
atccgtcaca cctgctctga agcgggaatc gtacacgaat gtaaaagtcg atagtggtgt    60
tggctcccgt at    72

<210> SEQ ID NO 35
<211> LENGTH: 72
<212> TYPE: DNA
<213> ORGANISM: Artificial Sequence
<220> FEATURE:
<223> OTHER INFORMATION: chemically synthesized

<400> SEQUENCE: 35
atacgggagc caacaccatc ccctcgggcg agctatacta aaccagatcc taagagagca    60
ggtgtgacgg at    72

<210> SEQ ID NO 36
<211> LENGTH: 72
<212> TYPE: DNA
<213> ORGANISM: Artificial Sequence
<220> FEATURE:
<223> OTHER INFORMATION: chemically synthesized

<400> SEQUENCE: 36
atccgtcaca cctgctctct taggatctgg tttagtatag ctcgcccgag gggatggtgt    60
tggctcccgt at    72

<210> SEQ ID NO 37
<211> LENGTH: 72
<212> TYPE: DNA
<213> ORGANISM: Artificial Sequence
<220> FEATURE:
<223> OTHER INFORMATION: chemically synthesized

<400> SEQUENCE: 37
atacgggagc caacaccaag ctacacaacg aggcgtataa tcagcatgtt ggatagagca    60
ggtgtgacgg at    72

<210> SEQ ID NO 38
<211> LENGTH: 72
<212> TYPE: DNA
<213> ORGANISM: Artificial Sequence
<220> FEATURE:
<223> OTHER INFORMATION: chemically synthesized

<400> SEQUENCE: 38
atccgtcaca cctgctctat ccaacatgct gattatacgc ctcgttgtgt agcttggtgt    60
tggctcccgt at    72

<210> SEQ ID NO 39
<211> LENGTH: 72
<212> TYPE: DNA
<213> ORGANISM: Artificial Sequence
<220> FEATURE:
<223> OTHER INFORMATION: chemically synthesized

<400> SEQUENCE: 39
atacgggagc caacaccagg aaactactaa acgaacatga gctgtatcaa aaacagagca    60
ggtgtgacgg at    72

<210> SEQ ID NO 40
<211> LENGTH: 72
<212> TYPE: DNA
<213> ORGANISM: Artificial Sequence
<220> FEATURE:
<223> OTHER INFORMATION: chemically synthesized

<400> SEQUENCE: 40

```
atccgtcaca cctgctctgt ttttgataca gctcatgttc gtttagtagt ttcctggtgt      60
tggctcccgt at                                                         72
```

<210> SEQ ID NO 41
<211> LENGTH: 72
<212> TYPE: DNA
<213> ORGANISM: Artificial Sequence
<220> FEATURE:
<223> OTHER INFORMATION: chemically synthesized

<400> SEQUENCE: 41

```
atacgggagc caacaccatc cagagtaaac gataaggggg aatctcaatg aaccagagca      60
ggtgtgacgg at                                                         72
```

<210> SEQ ID NO 42
<211> LENGTH: 72
<212> TYPE: DNA
<213> ORGANISM: Artificial Sequence
<220> FEATURE:
<223> OTHER INFORMATION: chemically synthesized

<400> SEQUENCE: 42

```
atccgtcaca cctgctctgg ttcattgaga ttccccctta tcgtttactc tggatggtgt      60
tggctcccgt at                                                         72
```

<210> SEQ ID NO 43
<211> LENGTH: 72
<212> TYPE: DNA
<213> ORGANISM: Artificial Sequence
<220> FEATURE:
<223> OTHER INFORMATION: chemically synthesized

<400> SEQUENCE: 43

```
atacgggagc caacaccaat actctcaaaa cctaacaaga caacccgagg gcccagagca      60
ggtgtgacgg at                                                         72
```

<210> SEQ ID NO 44
<211> LENGTH: 72
<212> TYPE: DNA
<213> ORGANISM: Artificial Sequence
<220> FEATURE:
<223> OTHER INFORMATION: chemically synthesized

<400> SEQUENCE: 44

```
atccgtcaca cctgctctgg gccctcgggt tgtcttgtta ggttttgaga gtattggtgt      60
tggctcccgt at                                                         72
```

<210> SEQ ID NO 45
<211> LENGTH: 72
<212> TYPE: DNA
<213> ORGANISM: Artificial Sequence
<220> FEATURE:
<223> OTHER INFORMATION: chemically synthesized

<400> SEQUENCE: 45

```
atacgggagc caacaccatg agactgggtc gatccaggac atacatttgt actaagagca      60
ggtgtgacgg at                                                         72
```

<210> SEQ ID NO 46
<211> LENGTH: 72
<212> TYPE: DNA
<213> ORGANISM: Artificial Sequence
<220> FEATURE:

-continued

<223> OTHER INFORMATION: chemically synthesized

<400> SEQUENCE: 46
atccgtcaca cctgctctta gtacaaatgt atgtcctgga tcgacccagt ctcatggtgt    60
tggctcccgt at                                                        72

<210> SEQ ID NO 47
<211> LENGTH: 72
<212> TYPE: DNA
<213> ORGANISM: Artificial Sequence
<220> FEATURE:
<223> OTHER INFORMATION: chemically synthesized

<400> SEQUENCE: 47
atacgggagc caacaccaga gccagaataa tggccccctt tacgagacga ctgtagagca    60
ggtgtgacgg at                                                        72

<210> SEQ ID NO 48
<211> LENGTH: 72
<212> TYPE: DNA
<213> ORGANISM: Artificial Sequence
<220> FEATURE:
<223> OTHER INFORMATION: chemically synthesized

<400> SEQUENCE: 48
atccgtcaca cctgctctac agtcgtctcg taaggggggc cattattctg gctctggtgt    60
tggctcccgt at                                                        72

<210> SEQ ID NO 49
<211> LENGTH: 72
<212> TYPE: DNA
<213> ORGANISM: Artificial Sequence
<220> FEATURE:
<223> OTHER INFORMATION: chemically synthesized

<400> SEQUENCE: 49
atacgggagc caacaccatc aggccgaaat gtatacgaag gtaagcgata aagtagagca    60
ggtgtgacgg at                                                        72

<210> SEQ ID NO 50
<211> LENGTH: 72
<212> TYPE: DNA
<213> ORGANISM: Artificial Sequence
<220> FEATURE:
<223> OTHER INFORMATION: chemically synthesized

<400> SEQUENCE: 50
atccgtcaca cctgctctac tttatcgctt accttcgtat acatttcggc ctgatggtgt    60
tggctcccgt at                                                        72

<210> SEQ ID NO 51
<211> LENGTH: 72
<212> TYPE: DNA
<213> ORGANISM: Artificial Sequence
<220> FEATURE:
<223> OTHER INFORMATION: chemically synthesized

<400> SEQUENCE: 51
atacgggagc caacaccagt cgtacgacac ccatccaaga ctttattccg cctaagagca    60
ggtgtgacgg at                                                        72

<210> SEQ ID NO 52

```
<211> LENGTH: 72
<212> TYPE: DNA
<213> ORGANISM: Artificial Sequence
<220> FEATURE:
<223> OTHER INFORMATION: chemically synthesized

<400> SEQUENCE: 52
atccgtcaca cctgctctta ggcggaataa agtcttggat gggtgtcgta cgactggtgt      60
tggctcccgt at                                                          72

<210> SEQ ID NO 53
<211> LENGTH: 72
<212> TYPE: DNA
<213> ORGANISM: Artificial Sequence
<220> FEATURE:
<223> OTHER INFORMATION: chemically synthesized

<400> SEQUENCE: 53
atacgggagc caacaccacg gtacaaactc tcaacaagct accactttag tccaagagca      60
ggtgtgacgg at                                                          72

<210> SEQ ID NO 54
<211> LENGTH: 72
<212> TYPE: DNA
<213> ORGANISM: Artificial Sequence
<220> FEATURE:
<223> OTHER INFORMATION: chemically synthesized

<400> SEQUENCE: 54
atccgtcaca cctgctcttg gactaaagtg gtagcttgtt gagagtttgt accgtggtgt      60
tggctcccgt at                                                          72

<210> SEQ ID NO 55
<211> LENGTH: 72
<212> TYPE: DNA
<213> ORGANISM: Artificial Sequence
<220> FEATURE:
<223> OTHER INFORMATION: chemically synthesized

<400> SEQUENCE: 55
atacgggagc caacaccact cgtttggccc acgagtcaat catatatcag ctaaagagca      60
ggtgtgacgg at                                                          72

<210> SEQ ID NO 56
<211> LENGTH: 72
<212> TYPE: DNA
<213> ORGANISM: Artificial Sequence
<220> FEATURE:
<223> OTHER INFORMATION: chemically synthesized

<400> SEQUENCE: 56
atccgtcaca cctgctcttt agctgatata tgattgactc gtgggccaaa cgagtggtgt      60
tggctcccgt at                                                          72

<210> SEQ ID NO 57
<211> LENGTH: 72
<212> TYPE: DNA
<213> ORGANISM: Artificial Sequence
<220> FEATURE:
<223> OTHER INFORMATION: chemically synthesized

<400> SEQUENCE: 57
atacgggagc caacaccatt attatcaaga cgctatctac agagattcac ggacagagca      60
```

```
ggtgtgacgg at                                                         72

<210> SEQ ID NO 58
<211> LENGTH: 72
<212> TYPE: DNA
<213> ORGANISM: Artificial Sequence
<220> FEATURE:
<223> OTHER INFORMATION: chemically synthesized

<400> SEQUENCE: 58
atccgtcaca cctgctctgt ccgtgaatct ctgtagatag cgtcttgata ataatggtgt    60
tggctcccgt at                                                         72

<210> SEQ ID NO 59
<211> LENGTH: 72
<212> TYPE: DNA
<213> ORGANISM: Artificial Sequence
<220> FEATURE:
<223> OTHER INFORMATION: chemically synthesized

<400> SEQUENCE: 59
atacgggagc caacaccagt gcgtgcgtgg cgacggtact actgactatg tcgtagagca    60
ggtgtgacgg at                                                         72

<210> SEQ ID NO 60
<211> LENGTH: 72
<212> TYPE: DNA
<213> ORGANISM: Artificial Sequence
<220> FEATURE:
<223> OTHER INFORMATION: chemically synthesized

<400> SEQUENCE: 60
atccgtcaca cctgctctac gacatagtca gtagtaccgt cgccacgcac gcactggtgt    60
tggctcccgt at                                                         72

<210> SEQ ID NO 61
<211> LENGTH: 72
<212> TYPE: DNA
<213> ORGANISM: Artificial Sequence
<220> FEATURE:
<223> OTHER INFORMATION: chemically synthesized

<400> SEQUENCE: 61
atacgggagc caacaccatg ccattcctgt gttagtctgt ccgttcgaca aggcagagca    60
ggtgtgacgg at                                                         72

<210> SEQ ID NO 62
<211> LENGTH: 72
<212> TYPE: DNA
<213> ORGANISM: Artificial Sequence
<220> FEATURE:
<223> OTHER INFORMATION: chemically synthesized

<400> SEQUENCE: 62
atccgtcaca cctgctctgc cttgtcgaac ggacagacta acacaggaat ggcatggtgt    60
tggctcccgt at                                                         72

<210> SEQ ID NO 63
<211> LENGTH: 72
<212> TYPE: DNA
<213> ORGANISM: Artificial Sequence
<220> FEATURE:
<223> OTHER INFORMATION: chemically synthesized
```

```
<400> SEQUENCE: 63
atacgggagc caacaccaga gtgttggcga taaacacaat gacccacagc cggaagagca    60
ggtgtgacgg at                                                        72

<210> SEQ ID NO 64
<211> LENGTH: 72
<212> TYPE: DNA
<213> ORGANISM: Artificial Sequence
<220> FEATURE:
<223> OTHER INFORMATION: chemically synthesized

<400> SEQUENCE: 64
atccgtcaca cctgctcttc cggctgtggg tcattgtgtt tatcgccaac actctggtgt    60
tggctcccgt at                                                        72

<210> SEQ ID NO 65
<211> LENGTH: 72
<212> TYPE: DNA
<213> ORGANISM: Artificial Sequence
<220> FEATURE:
<223> OTHER INFORMATION: chemically synthesized

<400> SEQUENCE: 65
atacgggagc caacaccatt ctggtgcgcg tgcaatgaga gaaatggctc gtacagagca    60
ggtgtgacgg at                                                        72

<210> SEQ ID NO 66
<211> LENGTH: 72
<212> TYPE: DNA
<213> ORGANISM: Artificial Sequence
<220> FEATURE:
<223> OTHER INFORMATION: chemically synthesized

<400> SEQUENCE: 66
atccgtcaca cctgctctgt acgagccatt tctctcattg cacgcgcacc agaatggtgt    60
tggctcccgt at                                                        72

<210> SEQ ID NO 67
<211> LENGTH: 72
<212> TYPE: DNA
<213> ORGANISM: Artificial Sequence
<220> FEATURE:
<223> OTHER INFORMATION: chemically synthesized

<400> SEQUENCE: 67
atacgggagc caacaccacc gcgttaaaga ggcgtacgat gtctcagtct cgccagagca    60
ggtgtgacgg at                                                        72

<210> SEQ ID NO 68
<211> LENGTH: 72
<212> TYPE: DNA
<213> ORGANISM: Artificial Sequence
<220> FEATURE:
<223> OTHER INFORMATION: chemically synthesized

<400> SEQUENCE: 68
atccgtcaca cctgctctgg cgagactgag acatcgtacg cctctttaac gcggtggtgt    60
tggctcccgt at                                                        72

<210> SEQ ID NO 69
<211> LENGTH: 72
<212> TYPE: DNA
```

<213> ORGANISM: Artificial Sequence
<220> FEATURE:
<223> OTHER INFORMATION: chemically synthesized

<400> SEQUENCE: 69
atacgggagc caacaccatt ctggtgcgcg tgcaatgaga gaaatggctc gtacagagca    60
ggtgtgacgg at    72

<210> SEQ ID NO 70
<211> LENGTH: 72
<212> TYPE: DNA
<213> ORGANISM: Artificial Sequence
<220> FEATURE:
<223> OTHER INFORMATION: chemically synthesized

<400> SEQUENCE: 70
atccgtcaca cctgctctgt acgagccatt tctctcattg cacgcgcacc agaatggtgt    60
tggctcccgt at    72

<210> SEQ ID NO 71
<211> LENGTH: 72
<212> TYPE: DNA
<213> ORGANISM: Artificial Sequence
<220> FEATURE:
<223> OTHER INFORMATION: chemically synthesized

<400> SEQUENCE: 71
atacgggagc caacaccacc gcgttaaaga ggcgtacgat gtctcagtct cgccagagca    60
ggtgtgacgg at    72

<210> SEQ ID NO 72
<211> LENGTH: 72
<212> TYPE: DNA
<213> ORGANISM: Artificial Sequence
<220> FEATURE:
<223> OTHER INFORMATION: chemically synthesized

<400> SEQUENCE: 72
atccgtcaca cctgctctgg cgagactgag acatcgtacg cctctttaac gcggtggtgt    60
tggctcccgt at    72

<210> SEQ ID NO 73
<211> LENGTH: 72
<212> TYPE: DNA
<213> ORGANISM: Artificial Sequence
<220> FEATURE:
<223> OTHER INFORMATION: chemically synthesized

<400> SEQUENCE: 73
atacgggagc caacaccatc taactgatgt gttgcgaagg gtctgctgtg tgatagagca    60
ggtgtgacgg at    72

<210> SEQ ID NO 74
<211> LENGTH: 72
<212> TYPE: DNA
<213> ORGANISM: Artificial Sequence
<220> FEATURE:
<223> OTHER INFORMATION: chemically synthesized

<400> SEQUENCE: 74
atccgtcaca cctgctctat cacacagcag acccttcgca acacatcagt tagatggtgt    60
tggctcccgt at    72

```
<210> SEQ ID NO 75
<211> LENGTH: 72
<212> TYPE: DNA
<213> ORGANISM: Artificial Sequence
<220> FEATURE:
<223> OTHER INFORMATION: chemically synthesized

<400> SEQUENCE: 75
atacgggagc caacaccagg cgggagaata gatagagtta gtcgtagtta gagcagagca    60
ggtgtgacgg at                                                        72

<210> SEQ ID NO 76
<211> LENGTH: 72
<212> TYPE: DNA
<213> ORGANISM: Artificial Sequence
<220> FEATURE:
<223> OTHER INFORMATION: chemically synthesized

<400> SEQUENCE: 76
atccgtcaca cctgctctgc tctaactacg actaactcta tctattctcc cgcctggtgt    60
tggctcccgt at                                                        72

<210> SEQ ID NO 77
<211> LENGTH: 72
<212> TYPE: DNA
<213> ORGANISM: Artificial Sequence
<220> FEATURE:
<223> OTHER INFORMATION: chemically synthesized

<400> SEQUENCE: 77
atacgggagc caacaccaga agaaccgcta aagcctatga ggaaaggatc atgcagagca    60
ggtgtgacgg at                                                        72

<210> SEQ ID NO 78
<211> LENGTH: 72
<212> TYPE: DNA
<213> ORGANISM: Artificial Sequence
<220> FEATURE:
<223> OTHER INFORMATION: chemically synthesized

<400> SEQUENCE: 78
atccgtcaca cctgctctgc atgatccttt cctcataggc tttagcggtt cttctggtgt    60
tggctcccgt at                                                        72

<210> SEQ ID NO 79
<211> LENGTH: 72
<212> TYPE: DNA
<213> ORGANISM: Artificial Sequence
<220> FEATURE:
<223> OTHER INFORMATION: chemically synthesized

<400> SEQUENCE: 79
atacgggagc caacaccagc cacgtcgaac cgggtgtcca tatacgtaat atgcagagca    60
ggtgtgacgg at                                                        72

<210> SEQ ID NO 80
<211> LENGTH: 72
<212> TYPE: DNA
<213> ORGANISM: Artificial Sequence
<220> FEATURE:
<223> OTHER INFORMATION: chemically synthesized

<400> SEQUENCE: 80
```

```
atccgtcaca cctgctctgc atattacgta tatggacacc cggttcgacg tggctggtgt    60
tggctcccgt at                                                       72

<210> SEQ ID NO 81
<211> LENGTH: 72
<212> TYPE: DNA
<213> ORGANISM: Artificial Sequence
<220> FEATURE:
<223> OTHER INFORMATION: chemically synthesized

<400> SEQUENCE: 81
atacgggagc caacaccatg ccatgtaccg gtacctactc tatcaggata taggagagca    60
ggtgtgacgg at                                                       72

<210> SEQ ID NO 82
<211> LENGTH: 72
<212> TYPE: DNA
<213> ORGANISM: Artificial Sequence
<220> FEATURE:
<223> OTHER INFORMATION: chemically synthesized

<400> SEQUENCE: 82
atccgtcaca cctgctctcc tatatcctga tagagtaggt accggtacat ggcatggtgt    60
tggctcccgt at                                                       72

<210> SEQ ID NO 83
<211> LENGTH: 72
<212> TYPE: DNA
<213> ORGANISM: Artificial Sequence
<220> FEATURE:
<223> OTHER INFORMATION: chemically synthesized

<400> SEQUENCE: 83
atacgggagc caacaccaga gtattccgct cacctatcgc caccatgtac accaagagca    60
ggtgtgacgg at                                                       72

<210> SEQ ID NO 84
<211> LENGTH: 72
<212> TYPE: DNA
<213> ORGANISM: Artificial Sequence
<220> FEATURE:
<223> OTHER INFORMATION: chemically synthesized

<400> SEQUENCE: 84
atccgtcaca cctgctcttg gtgtacatgg tggcgatagg tgagcggaat actctggtgt    60
tggctcccgt at                                                       72

<210> SEQ ID NO 85
<211> LENGTH: 72
<212> TYPE: DNA
<213> ORGANISM: Artificial Sequence
<220> FEATURE:
<223> OTHER INFORMATION: chemically synthesized

<400> SEQUENCE: 85
atacgggagc caacaccaac attgagagtg tggacatagt ggaacgcgaa cctgagagca    60
ggtgtgacgg at                                                       72

<210> SEQ ID NO 86
<211> LENGTH: 72
<212> TYPE: DNA
<213> ORGANISM: Artificial Sequence
<220> FEATURE:
```

<223> OTHER INFORMATION: chemically synthesized

<400> SEQUENCE: 86
atccgtcaca cctgctctca ggttcgcgtt ccactatgtc cacactctca atgttggtgt        60
tggctcccgt at                                                            72

<210> SEQ ID NO 87
<211> LENGTH: 72
<212> TYPE: DNA
<213> ORGANISM: Artificial Sequence
<220> FEATURE:
<223> OTHER INFORMATION: chemically synthesized

<400> SEQUENCE: 87
atacgggagc caacaccaag cgacaaggaa gaattatcaa ggtacgaacc ggatagagca        60
ggtgtgacgg at                                                            72

<210> SEQ ID NO 88
<211> LENGTH: 72
<212> TYPE: DNA
<213> ORGANISM: Artificial Sequence
<220> FEATURE:
<223> OTHER INFORMATION: chemically synthesized

<400> SEQUENCE: 88
atccgtcaca cctgctctat ccggttcgta ccttgataat tcttccttgt cgcttggtgt        60
tggctcccgt at                                                            72

<210> SEQ ID NO 89
<211> LENGTH: 72
<212> TYPE: DNA
<213> ORGANISM: Artificial Sequence
<220> FEATURE:
<223> OTHER INFORMATION: chemically synthesized

<400> SEQUENCE: 89
atacgggagc caacaccatg tcatcatata ccaacactgg cgcggatagt ccagagagca        60
ggtgtgacgg at                                                            72

<210> SEQ ID NO 90
<211> LENGTH: 72
<212> TYPE: DNA
<213> ORGANISM: Artificial Sequence
<220> FEATURE:
<223> OTHER INFORMATION: chemically synthesized

<400> SEQUENCE: 90
atccgtcaca cctgctctct ggactatccg cgccagtgtt ggtatatgat gacatggtgt        60
tggctcccgt at                                                            72

<210> SEQ ID NO 91
<211> LENGTH: 72
<212> TYPE: DNA
<213> ORGANISM: Artificial Sequence
<220> FEATURE:
<223> OTHER INFORMATION: chemically synthesized

<400> SEQUENCE: 91
atacgggagc caacaccagc ctcgtgattt gatgaagttt cttgatctgc acgtagagca        60
ggtgtgacgg at                                                            72

<210> SEQ ID NO 92

```
<211> LENGTH: 72
<212> TYPE: DNA
<213> ORGANISM: Artificial Sequence
<220> FEATURE:
<223> OTHER INFORMATION: chemically synthesized

<400> SEQUENCE: 92
atccgtcaca cctgctctac gtgcagatca agaaacttca tcaaatcacg aggctggtgt      60
tggctcccgt at                                                         72

<210> SEQ ID NO 93
<211> LENGTH: 72
<212> TYPE: DNA
<213> ORGANISM: Artificial Sequence
<220> FEATURE:
<223> OTHER INFORMATION: chemically synthesized

<400> SEQUENCE: 93
atacgggagc caacaccatc gatgaacggc tcaccctcgt ccctatataa cactagagca      60
ggtgtgacgg at                                                         72

<210> SEQ ID NO 94
<211> LENGTH: 72
<212> TYPE: DNA
<213> ORGANISM: Artificial Sequence
<220> FEATURE:
<223> OTHER INFORMATION: chemically synthesized

<400> SEQUENCE: 94
atccgtcaca cctgctctag tgttatatag gacgagggt gagccgttca tcgatggtgt       60
tggctcccgt at                                                         72

<210> SEQ ID NO 95
<211> LENGTH: 72
<212> TYPE: DNA
<213> ORGANISM: Artificial Sequence
<220> FEATURE:
<223> OTHER INFORMATION: chemically synthesized

<400> SEQUENCE: 95
atacgggagc caacaccaaa ggacacaaga agcttgaatc tccagttagt ggggagagca      60
ggtgtgacgg at                                                         72

<210> SEQ ID NO 96
<211> LENGTH: 72
<212> TYPE: DNA
<213> ORGANISM: Artificial Sequence
<220> FEATURE:
<223> OTHER INFORMATION: chemically synthesized

<400> SEQUENCE: 96
atccgtcaca cctgctctcc ccactaactg gagattcaag cttcttgtgt cctttggtgt      60
tggctcccgt at                                                         72

<210> SEQ ID NO 97
<211> LENGTH: 72
<212> TYPE: DNA
<213> ORGANISM: Artificial Sequence
<220> FEATURE:
<223> OTHER INFORMATION: chemically synthesized

<400> SEQUENCE: 97
atacgggagc caacaccacg ctccccgaga tcacgtacgc tcgccccaga ctggagagca      60
```

```
ggtgtgacgg at                                                         72

<210> SEQ ID NO 98
<211> LENGTH: 72
<212> TYPE: DNA
<213> ORGANISM: Artificial Sequence
<220> FEATURE:
<223> OTHER INFORMATION: chemically synthesized

<400> SEQUENCE: 98
atccgtcaca cctgctctcc agtctggggc gagcgtacgt gatctcgggg agcgtggtgt     60
tggctcccgt at                                                         72

<210> SEQ ID NO 99
<211> LENGTH: 72
<212> TYPE: DNA
<213> ORGANISM: Artificial Sequence
<220> FEATURE:
<223> OTHER INFORMATION: chemically synthesized

<400> SEQUENCE: 99
atacgggagc caacaccatg gctcaccagg accattattt tcagctcccc cgccagagca     60
ggtgtgacgg at                                                         72

<210> SEQ ID NO 100
<211> LENGTH: 72
<212> TYPE: DNA
<213> ORGANISM: Artificial Sequence
<220> FEATURE:
<223> OTHER INFORMATION: chemically synthesized

<400> SEQUENCE: 100
atccgtcaca cctgctctgg cggggggagct gaaaataatg gtcctggtga gccatggtgt    60
tggctcccgt at                                                         72

<210> SEQ ID NO 101
<211> LENGTH: 72
<212> TYPE: DNA
<213> ORGANISM: Artificial Sequence
<220> FEATURE:
<223> OTHER INFORMATION: chemically synthesized

<400> SEQUENCE: 101
atacgggagc caacaccagt gcaccaaata aaagctgtc ccagactcga gcgaagagca      60
ggtgtgacgg at                                                         72

<210> SEQ ID NO 102
<211> LENGTH: 72
<212> TYPE: DNA
<213> ORGANISM: Artificial Sequence
<220> FEATURE:
<223> OTHER INFORMATION: chemically synthesized

<400> SEQUENCE: 102
atccgtcaca cctgctcttc gctcgagtct gggacagctt tttatttggt gcactggtgt     60
tggctcccgt at                                                         72

<210> SEQ ID NO 103
<211> LENGTH: 72
<212> TYPE: DNA
<213> ORGANISM: Artificial Sequence
<220> FEATURE:
<223> OTHER INFORMATION: chemically synthesized
```

<400> SEQUENCE: 103
atacgggagc caacaccaat cgtgtcacaa tggcatatcc tacgtcataa gccaagagca    60
ggtgtgacgg at    72

<210> SEQ ID NO 104
<211> LENGTH: 72
<212> TYPE: DNA
<213> ORGANISM: Artificial Sequence
<220> FEATURE:
<223> OTHER INFORMATION: chemically synthesized

<400> SEQUENCE: 104
atccgtcaca cctgctcttg gcttatgacg taggatatgc cattgtgaca cgattggtgt    60
tggctcccgt at    72

<210> SEQ ID NO 105
<211> LENGTH: 72
<212> TYPE: DNA
<213> ORGANISM: Artificial Sequence
<220> FEATURE:
<223> OTHER INFORMATION: chemically synthesized

<400> SEQUENCE: 105
atacgggagc caacaccata ataccagccg acagccttgg tgctatgatt tgacagagca    60
ggtgtgacgg at    72

<210> SEQ ID NO 106
<211> LENGTH: 72
<212> TYPE: DNA
<213> ORGANISM: Artificial Sequence
<220> FEATURE:
<223> OTHER INFORMATION: chemically synthesized

<400> SEQUENCE: 106
atccgtcaca cctgctctgt caaatcatag caccaaggct gtcggctggt attatggtgt    60
tggctcccgt at    72

<210> SEQ ID NO 107
<211> LENGTH: 72
<212> TYPE: DNA
<213> ORGANISM: Artificial Sequence
<220> FEATURE:
<223> OTHER INFORMATION: chemically synthesized

<400> SEQUENCE: 107
atacgggagc caacaccatc gagtgcgtgg aactcaaggg cacaatagct acacagagca    60
ggtgtgacgg at    72

<210> SEQ ID NO 108
<211> LENGTH: 72
<212> TYPE: DNA
<213> ORGANISM: Artificial Sequence
<220> FEATURE:
<223> OTHER INFORMATION: chemically synthesized

<400> SEQUENCE: 108
atccgtcaca cctgctctgt gtagctattg tgcccttgag ttccacgcac tcgatggtgt    60
tggctcccgt at    72

<210> SEQ ID NO 109
<211> LENGTH: 72
<212> TYPE: DNA

```
<213> ORGANISM: Artificial Sequence
<220> FEATURE:
<223> OTHER INFORMATION: chemically synthesized

<400> SEQUENCE: 109
atacgggagc caacaccaca tagtccctgt cgcacccctc ccgtgaccgt tatcagagca      60
ggtgtgacgg at                                                          72

<210> SEQ ID NO 110
<211> LENGTH: 72
<212> TYPE: DNA
<213> ORGANISM: Artificial Sequence
<220> FEATURE:
<223> OTHER INFORMATION: chemically synthesized

<400> SEQUENCE: 110
atccgtcaca cctgctctga taacggtcac gggaggggtg cgacagggac tatgtggtgt      60
tggctcccgt at                                                          72

<210> SEQ ID NO 111
<211> LENGTH: 72
<212> TYPE: DNA
<213> ORGANISM: Artificial Sequence
<220> FEATURE:
<223> OTHER INFORMATION: chemically synthesized

<400> SEQUENCE: 111
atacgggagc caacaccagg cgttctagag accactctta ataaccttga tgtgagagca      60
ggtgtgacgg at                                                          72

<210> SEQ ID NO 112
<211> LENGTH: 72
<212> TYPE: DNA
<213> ORGANISM: Artificial Sequence
<220> FEATURE:
<223> OTHER INFORMATION: chemically synthesized

<400> SEQUENCE: 112
atccgtcaca cctgctctca catcaaggtt attaagagtg gtctctagaa cgcctggtgt      60
tggctcccgt at                                                          72

<210> SEQ ID NO 113
<211> LENGTH: 72
<212> TYPE: DNA
<213> ORGANISM: Artificial Sequence
<220> FEATURE:
<223> OTHER INFORMATION: chemically synthesized

<400> SEQUENCE: 113
atacgggagc caacaccagt ttctcagtat ataagatatt tcatcgcagg tagaagagca      60
ggtgtgacgg at                                                          72

<210> SEQ ID NO 114
<211> LENGTH: 72
<212> TYPE: DNA
<213> ORGANISM: Artificial Sequence
<220> FEATURE:
<223> OTHER INFORMATION: chemically synthesized

<400> SEQUENCE: 114
atccgtcaca cctgctcttc tacctgcgat gaaatatctt atatactgag aaactggtgt      60
tggctcccgt at                                                          72
```

<210> SEQ ID NO 115
<211> LENGTH: 72
<212> TYPE: DNA
<213> ORGANISM: Artificial Sequence
<220> FEATURE:
<223> OTHER INFORMATION: chemically synthesized

<400> SEQUENCE: 115
atacgggagc caacaccaat gtgacagtcg cgactcctgt cgtttgcata gggtagagca    60
ggtgtgacgg at    72

<210> SEQ ID NO 116
<211> LENGTH: 72
<212> TYPE: DNA
<213> ORGANISM: Artificial Sequence
<220> FEATURE:
<223> OTHER INFORMATION: chemically synthesized

<400> SEQUENCE: 116
atccgtcaca cctgctctac cctatgcaaa cgacaggagt cgcgactgtc acattggtgt    60
tggctcccgt at    72

<210> SEQ ID NO 117
<211> LENGTH: 72
<212> TYPE: DNA
<213> ORGANISM: Artificial Sequence
<220> FEATURE:
<223> OTHER INFORMATION: chemically synthesized

<400> SEQUENCE: 117
atacgggagc caacaccaaa aaatcaacat ggtgaaacat tcgaatgcag ttgaagagca    60
ggtgtgacgg at    72

<210> SEQ ID NO 118
<211> LENGTH: 72
<212> TYPE: DNA
<213> ORGANISM: Artificial Sequence
<220> FEATURE:
<223> OTHER INFORMATION: chemically synthesized

<400> SEQUENCE: 118
atccgtcaca cctgctcttc aactgcattc gaatgtttca ccatgttgat tttttggtgt    60
tggctcccgt at    72

<210> SEQ ID NO 119
<211> LENGTH: 72
<212> TYPE: DNA
<213> ORGANISM: Artificial Sequence
<220> FEATURE:
<223> OTHER INFORMATION: chemically synthesized

<400> SEQUENCE: 119
atacgggagc caacaccatg cgcggctcat agactgtaac ccggatggga acctagagca    60
ggtgtgacgg at    72

<210> SEQ ID NO 120
<211> LENGTH: 72
<212> TYPE: DNA
<213> ORGANISM: Artificial Sequence
<220> FEATURE:
<223> OTHER INFORMATION: chemically synthesized

<400> SEQUENCE: 120

```
atccgtcaca cctgctctag gttcccatcc gggttacagt ctatgagccg cgcatggtgt    60
tggctcccgt at                                                        72
```

<210> SEQ ID NO 121
<211> LENGTH: 72
<212> TYPE: DNA
<213> ORGANISM: Artificial Sequence
<220> FEATURE:
<223> OTHER INFORMATION: chemically synthesized

<400> SEQUENCE: 121

```
atacgggagc caacaccaag tcccgttacc aaacagaacc atggagagcg atggagagca    60
ggtgtgacgg at                                                        72
```

<210> SEQ ID NO 122
<211> LENGTH: 72
<212> TYPE: DNA
<213> ORGANISM: Artificial Sequence
<220> FEATURE:
<223> OTHER INFORMATION: chemically synthesized

<400> SEQUENCE: 122

```
atccgtcaca cctgctctcc atcgctctcc atggttctgt ttggtaacgg gacttggtgt    60
tggctcccgt at                                                        72
```

<210> SEQ ID NO 123
<211> LENGTH: 72
<212> TYPE: DNA
<213> ORGANISM: Artificial Sequence
<220> FEATURE:
<223> OTHER INFORMATION: chemically synthesized

<400> SEQUENCE: 123

```
atacgggagc caacaccatt gacccgagac tccagctgag tgacacctga tgtgagagca    60
ggtgtgacgg at                                                        72
```

<210> SEQ ID NO 124
<211> LENGTH: 72
<212> TYPE: DNA
<213> ORGANISM: Artificial Sequence
<220> FEATURE:
<223> OTHER INFORMATION: chemically synthesized

<400> SEQUENCE: 124

```
atccgtcaca cctgctctca catcaggtgt cactcagctg gagtctcggg tcaatggtgt    60
tggctcccgt at                                                        72
```

<210> SEQ ID NO 125
<211> LENGTH: 72
<212> TYPE: DNA
<213> ORGANISM: Artificial Sequence
<220> FEATURE:
<223> OTHER INFORMATION: chemically synthesized

<400> SEQUENCE: 125

```
atacgggagc caacaccagt gacaccaaac catgctcagg ccattcggtt atatagagca    60
ggtgtgacgg at                                                        72
```

<210> SEQ ID NO 126
<211> LENGTH: 72
<212> TYPE: DNA
<213> ORGANISM: Artificial Sequence
<220> FEATURE:

<223> OTHER INFORMATION: chemically synthesized

<400> SEQUENCE: 126
atccgtcaca cctgctctat ataaccgaat ggcctgagca tggtttggtg tcactggtgt    60
tggctcccgt at    72

<210> SEQ ID NO 127
<211> LENGTH: 72
<212> TYPE: DNA
<213> ORGANISM: Artificial Sequence
<220> FEATURE:
<223> OTHER INFORMATION: chemically synthesized

<400> SEQUENCE: 127
atacgggagc caacaccagc caacggacac caggttgatc aatccccagt cctgagagca    60
ggtgtgacgg at    72

<210> SEQ ID NO 128
<211> LENGTH: 72
<212> TYPE: DNA
<213> ORGANISM: Artificial Sequence
<220> FEATURE:
<223> OTHER INFORMATION: chemically synthesized

<400> SEQUENCE: 128
atccgtcaca cctgctctca ggactgggga ttgatcaacc tggtgtccgt tggctggtgt    60
tggctcccgt at    72

<210> SEQ ID NO 129
<211> LENGTH: 72
<212> TYPE: DNA
<213> ORGANISM: Artificial Sequence
<220> FEATURE:
<223> OTHER INFORMATION: chemically synthesized

<400> SEQUENCE: 129
atacgggagc caacaccagc cctaccgtac cccctcaaga cagaacctgc atcaagagca    60
ggtgtgacgg at    72

<210> SEQ ID NO 130
<211> LENGTH: 72
<212> TYPE: DNA
<213> ORGANISM: Artificial Sequence
<220> FEATURE:
<223> OTHER INFORMATION: chemically synthesized

<400> SEQUENCE: 130
atccgtcaca cctgctcttg atgcaggttc tgtcttgagg gggtacggta gggctggtgt    60
tggctcccgt at    72

<210> SEQ ID NO 131
<211> LENGTH: 72
<212> TYPE: DNA
<213> ORGANISM: Artificial Sequence
<220> FEATURE:
<223> OTHER INFORMATION: chemically synthesized

<400> SEQUENCE: 131
atacgggagc caacaccact agacaaggtc aaaccgcata tggacccgtg ctatagagca    60
ggtgtgacgg at    72

<210> SEQ ID NO 132

```
<211> LENGTH: 72
<212> TYPE: DNA
<213> ORGANISM: Artificial Sequence
<220> FEATURE:
<223> OTHER INFORMATION: chemically synthesized

<400> SEQUENCE: 132
atccgtcaca cctgctctat agcacgggtc catatgcggt ttgaccttgt ctagtggtgt      60
tggctcccgt at                                                         72

<210> SEQ ID NO 133
<211> LENGTH: 72
<212> TYPE: DNA
<213> ORGANISM: Artificial Sequence
<220> FEATURE:
<223> OTHER INFORMATION: chemically synthesized

<400> SEQUENCE: 133
atacgggagc caacaccaca acatgagctg aatctgtccc taatgcgtgt gcatagagca      60
ggtgtgacgg at                                                         72

<210> SEQ ID NO 134
<211> LENGTH: 72
<212> TYPE: DNA
<213> ORGANISM: Artificial Sequence
<220> FEATURE:
<223> OTHER INFORMATION: chemically synthesized

<400> SEQUENCE: 134
atccgtcaca cctgctctat gcacacgcat tagggacaga ttcagctcat gttgtggtgt      60
tggctcccgt at                                                         72

<210> SEQ ID NO 135
<211> LENGTH: 72
<212> TYPE: DNA
<213> ORGANISM: Artificial Sequence
<220> FEATURE:
<223> OTHER INFORMATION: chemically synthesized

<400> SEQUENCE: 135
atacgggagc caacaccacg gtgaagcatg gcaatattaa ccatgatcac cttcagagca      60
ggtgtgacgg at                                                         72

<210> SEQ ID NO 136
<211> LENGTH: 72
<212> TYPE: DNA
<213> ORGANISM: Artificial Sequence
<220> FEATURE:
<223> OTHER INFORMATION: chemically synthesized

<400> SEQUENCE: 136
atccgtcaca cctgctctga aggtgatcat ggttaatatt gccatgcttc accgtggtgt      60
tggctcccgt at                                                         72

<210> SEQ ID NO 137
<211> LENGTH: 72
<212> TYPE: DNA
<213> ORGANISM: Artificial Sequence
<220> FEATURE:
<223> OTHER INFORMATION: chemically synthesized

<400> SEQUENCE: 137
atacgggagc caacaccacc acttgtcacg accgtgtctc tgtggcgctt ggggagagca      60
```

-continued

| | |
|---|---|
| ggtgtgacgg at | 72 |

<210> SEQ ID NO 138
<211> LENGTH: 72
<212> TYPE: DNA
<213> ORGANISM: Artificial Sequence
<220> FEATURE:
<223> OTHER INFORMATION: chemically synthesized

<400> SEQUENCE: 138

| | |
|---|---|
| atccgtcaca cctgctctcc ccaagcgcca cagagacacg gtcgtgacaa gtggtggtgt | 60 |
| tggctcccgt at | 72 |

<210> SEQ ID NO 139
<211> LENGTH: 72
<212> TYPE: DNA
<213> ORGANISM: Artificial Sequence
<220> FEATURE:
<223> OTHER INFORMATION: chemically synthesized

<400> SEQUENCE: 139

| | |
|---|---|
| atacgggagc caacaccata tagccgcgcc tgtgagtttt gtgggagcaa gagtagagca | 60 |
| ggtgtgacgg at | 72 |

<210> SEQ ID NO 140
<211> LENGTH: 72
<212> TYPE: DNA
<213> ORGANISM: Artificial Sequence
<220> FEATURE:
<223> OTHER INFORMATION: chemically synthesized

<400> SEQUENCE: 140

| | |
|---|---|
| atccgtcaca cctgctctac tcttgctccc acaaaactca caggcgcggc tatatggtgt | 60 |
| tggctcccgt at | 72 |

<210> SEQ ID NO 141
<211> LENGTH: 72
<212> TYPE: DNA
<213> ORGANISM: Artificial Sequence
<220> FEATURE:
<223> OTHER INFORMATION: chemically synthesized

<400> SEQUENCE: 141

| | |
|---|---|
| atacgggagc caacaccagc tacagtgtca gacggttcca ccttaacctc gtcaagagca | 60 |
| ggtgtgacgg at | 72 |

<210> SEQ ID NO 142
<211> LENGTH: 72
<212> TYPE: DNA
<213> ORGANISM: Artificial Sequence
<220> FEATURE:
<223> OTHER INFORMATION: chemically synthesized

<400> SEQUENCE: 142

| | |
|---|---|
| atccgtcaca cctgctcttg acgaggttaa ggtggaaccg tctgacactg tagctggtgt | 60 |
| tggctcccgt at | 72 |

<210> SEQ ID NO 143
<211> LENGTH: 72
<212> TYPE: DNA
<213> ORGANISM: Artificial Sequence
<220> FEATURE:
<223> OTHER INFORMATION: chemically synthesized -continued

```
<400> SEQUENCE: 143
atacgggagc caacaccatt gactaagcga ttagtcccac aggtgaccgg ggagagagca    60
ggtgtgacgg at                                                       72

<210> SEQ ID NO 144
<211> LENGTH: 72
<212> TYPE: DNA
<213> ORGANISM: Artificial Sequence
<220> FEATURE:
<223> OTHER INFORMATION: chemically synthesized
<220> FEATURE:
<221> NAME/KEY: misc_feature
<222> LOCATION: (27)..(27)
<223> OTHER INFORMATION: n is a, c, g, or t

<400> SEQUENCE: 144
atccgtcaca cctgctctct tcccggnctc ctgtgtgatt aatctgttat tctatggtgt    60
tggctcccgt at                                                       72

<210> SEQ ID NO 145
<211> LENGTH: 72
<212> TYPE: DNA
<213> ORGANISM: Artificial Sequence
<220> FEATURE:
<223> OTHER INFORMATION: chemically synthesized

<400> SEQUENCE: 145
atacgggagc caacaccaat tctaacacag gtttctccgt ttcgttagct gctaagagca    60
ggtgtgacgg at                                                       72

<210> SEQ ID NO 146
<211> LENGTH: 72
<212> TYPE: DNA
<213> ORGANISM: Artificial Sequence
<220> FEATURE:
<223> OTHER INFORMATION: chemically synthesized

<400> SEQUENCE: 146
atccgtcaca cctgctctta gcagctaacg aaacggagaa acctgtgtta gaattggtgt    60
tggctcccgt at                                                       72

<210> SEQ ID NO 147
<211> LENGTH: 72
<212> TYPE: DNA
<213> ORGANISM: Artificial Sequence
<220> FEATURE:
<223> OTHER INFORMATION: chemically synthesized

<400> SEQUENCE: 147
atacgggagc caacaccact catcccgttg gaacacttta atatggccca ctctagagca    60
ggtgtgacgg at                                                       72

<210> SEQ ID NO 148
<211> LENGTH: 72
<212> TYPE: DNA
<213> ORGANISM: Artificial Sequence
<220> FEATURE:
<223> OTHER INFORMATION: chemically synthesized

<400> SEQUENCE: 148
atccgtcaca cctgctctag agtgggccat attaaagtgt tccaacggga tgagtggtgt    60
tggctcccgt at                                                       72
```

-continued

<210> SEQ ID NO 149
<211> LENGTH: 72
<212> TYPE: DNA
<213> ORGANISM: Artificial Sequence
<220> FEATURE:
<223> OTHER INFORMATION: chemically synthesized

<400> SEQUENCE: 149
atacgggagc caacaccact actgtgcaga tccagcatct acggtgaaat ttgcagagca    60
ggtgtgacgg at    72

<210> SEQ ID NO 150
<211> LENGTH: 72
<212> TYPE: DNA
<213> ORGANISM: Artificial Sequence
<220> FEATURE:
<223> OTHER INFORMATION: chemically synthesized

<400> SEQUENCE: 150
atccgtcaca cctgctctgc aaatttcacc gtagatgctg gatctgcaca gtagtggtgt    60
tggctcccgt at    72

<210> SEQ ID NO 151
<211> LENGTH: 72
<212> TYPE: DNA
<213> ORGANISM: Artificial Sequence
<220> FEATURE:
<223> OTHER INFORMATION: chemically synthesized

<400> SEQUENCE: 151
atacgggagc caacaccatg cggaaagccc ataccaaccc agaagccagc gctaagagca    60
ggtgtgacgg at    72

<210> SEQ ID NO 152
<211> LENGTH: 72
<212> TYPE: DNA
<213> ORGANISM: Artificial Sequence
<220> FEATURE:
<223> OTHER INFORMATION: chemically synthesized

<400> SEQUENCE: 152
atccgtcaca cctgctctta gcgctggctt ctgggttggt atgggctttc cgcatggtgt    60
tggctcccgt at    72

<210> SEQ ID NO 153
<211> LENGTH: 72
<212> TYPE: DNA
<213> ORGANISM: Artificial Sequence
<220> FEATURE:
<223> OTHER INFORMATION: chemically synthesized

<400> SEQUENCE: 153
atacgggagc caacaccagc caactagcct gaaacccata attatacagc ttagagagca    60
ggtgtgacgg at    72

<210> SEQ ID NO 154
<211> LENGTH: 72
<212> TYPE: DNA
<213> ORGANISM: Artificial Sequence
<220> FEATURE:
<223> OTHER INFORMATION: chemically synthesized

<400> SEQUENCE: 154

-continued

```
atccgtcaca cctgctctct aagctgtata attatgggtt tcaggctagt tggctggtgt    60
tggctcccgt at                                                        72

<210> SEQ ID NO 155
<211> LENGTH: 72
<212> TYPE: DNA
<213> ORGANISM: Artificial Sequence
<220> FEATURE:
<223> OTHER INFORMATION: chemically synthesized

<400> SEQUENCE: 155
atacgggagc caacaccact gtatccgttg atgacaaaca gtcgcagccc acttagagca    60
ggtgtgacgg at                                                        72

<210> SEQ ID NO 156
<211> LENGTH: 72
<212> TYPE: DNA
<213> ORGANISM: Artificial Sequence
<220> FEATURE:
<223> OTHER INFORMATION: chemically synthesized

<400> SEQUENCE: 156
atccgtcaca cctgctctcc tcgactcgat ttcacttagt ctaacactaa ttggtggtgt    60
tggctcccgt at                                                        72

<210> SEQ ID NO 157
<211> LENGTH: 72
<212> TYPE: DNA
<213> ORGANISM: Artificial Sequence
<220> FEATURE:
<223> OTHER INFORMATION: chemically synthesized

<400> SEQUENCE: 157
atacgggagc caacaccaag gtaatgaagg gggaaaatgg agttttgccc ttaaagagca    60
ggtgtgacgg at                                                        72

<210> SEQ ID NO 158
<211> LENGTH: 72
<212> TYPE: DNA
<213> ORGANISM: Artificial Sequence
<220> FEATURE:
<223> OTHER INFORMATION: chemically synthesized

<400> SEQUENCE: 158
atccgtcaca cctgctcttt aagggcaaaa ctccattttc cccttcatt accttggtgt     60 tggctcccgt at                                                        72

<210> SEQ ID NO 159
<211> LENGTH: 72
<212> TYPE: DNA
<213> ORGANISM: Artificial Sequence
<220> FEATURE:
<223> OTHER INFORMATION: chemically synthesized

<400> SEQUENCE: 159
atacgggagc caacaccaag ctcgtagaag catcttacgc ggcgcccttg caccagagca    60
ggtgtgacgg at                                                        72

<210> SEQ ID NO 160
<211> LENGTH: 72
<212> TYPE: DNA
<213> ORGANISM: Artificial Sequence
<220> FEATURE:
```

<223> OTHER INFORMATION: chemically synthesized

<400> SEQUENCE: 160
atccgtcaca cctgctctgg tgcaagggcg ccgcgtaaga tgcttctacg agcttggtgt    60
tggctcccgt at    72

<210> SEQ ID NO 161
<211> LENGTH: 72
<212> TYPE: DNA
<213> ORGANISM: Artificial Sequence
<220> FEATURE:
<223> OTHER INFORMATION: chemically synthesized

<400> SEQUENCE: 161
atacgggagc caacaccacg atcattgaca tacttctcta tcccgtctgt ctgtagagca    60
ggtgtgacgg at    72

<210> SEQ ID NO 162
<211> LENGTH: 72
<212> TYPE: DNA
<213> ORGANISM: Artificial Sequence
<220> FEATURE:
<223> OTHER INFORMATION: chemically synthesized

<400> SEQUENCE: 162
atccgtcaca cctgctctac agacagacgg gatagagaag tatgtcaatg atcgtggtgt    60
tggctcccgt at    72

<210> SEQ ID NO 163
<211> LENGTH: 72
<212> TYPE: DNA
<213> ORGANISM: Artificial Sequence
<220> FEATURE:
<223> OTHER INFORMATION: chemically synthesized

<400> SEQUENCE: 163
atacgggagc caacaccacc acagagtcta cccaaggcag gctgtcaatc aacaagagca    60
ggtgtgacgg at    72

<210> SEQ ID NO 164
<211> LENGTH: 72
<212> TYPE: DNA
<213> ORGANISM: Artificial Sequence
<220> FEATURE:
<223> OTHER INFORMATION: chemically synthesized

<400> SEQUENCE: 164
atccgtcaca cctgctcttg ttgattgaca gcctgccttg ggtagactct gtggtggtgt    60
tggctcccgt at    72

<210> SEQ ID NO 165
<211> LENGTH: 72
<212> TYPE: DNA
<213> ORGANISM: Artificial Sequence
<220> FEATURE:
<223> OTHER INFORMATION: chemically synthesized

<400> SEQUENCE: 165
atacgggagc caacaccagg ctacgacaaa ggctatgaca tgaatgggtc aactagagca    60
ggtgtgacgg at    72

<210> SEQ ID NO 166

```
<211> LENGTH: 72
<212> TYPE: DNA
<213> ORGANISM: Artificial Sequence
<220> FEATURE:
<223> OTHER INFORMATION: chemically synthesized

<400> SEQUENCE: 166
atccgtcaca cctgctctag ttgacccatt catgtcatag cctttgtcgt agcctggtgt      60
tggctcccgt at                                                         72

<210> SEQ ID NO 167
<211> LENGTH: 72
<212> TYPE: DNA
<213> ORGANISM: Artificial Sequence
<220> FEATURE:
<223> OTHER INFORMATION: chemically synthesized

<400> SEQUENCE: 167
atacgggagc caacaccagg gccggagggt tcttcttgag ccttttcgcc aggcagagca      60
ggtgtgacgg at                                                         72

<210> SEQ ID NO 168
<211> LENGTH: 72
<212> TYPE: DNA
<213> ORGANISM: Artificial Sequence
<220> FEATURE:
<223> OTHER INFORMATION: chemically synthesized

<400> SEQUENCE: 168
atccgtcaca cctgctctgc ctggcgaaaa ggctcaagaa gaaccctccg gccctggtgt      60
tggctcccgt at                                                         72

<210> SEQ ID NO 169
<211> LENGTH: 72
<212> TYPE: DNA
<213> ORGANISM: Artificial Sequence
<220> FEATURE:
<223> OTHER INFORMATION: chemically synthesized

<400> SEQUENCE: 169
atacgggagc caacaccaaa tgtcttggaa ggcagatatc ggaacgagtg gaccagagca      60
ggtgtgacgg at                                                         72

<210> SEQ ID NO 170
<211> LENGTH: 72
<212> TYPE: DNA
<213> ORGANISM: Artificial Sequence
<220> FEATURE:
<223> OTHER INFORMATION: chemically synthesized

<400> SEQUENCE: 170
atccgtcaca cctgctctgg tccactcgtt ccgatatctg ccttccaaga catttggtgt      60
tggctcccgt at                                                         72

<210> SEQ ID NO 171
<211> LENGTH: 72
<212> TYPE: DNA
<213> ORGANISM: Artificial Sequence
<220> FEATURE:
<223> OTHER INFORMATION: chemically synthesized

<400> SEQUENCE: 171
atacgggagc caacaccaga cactcaggta tggagcactc gatccacgcg tgtgagagca      60
```

```
ggtgtgacgg at                                                         72

<210> SEQ ID NO 172
<211> LENGTH: 72
<212> TYPE: DNA
<213> ORGANISM: Artificial Sequence
<220> FEATURE:
<223> OTHER INFORMATION: chemically synthesized

<400> SEQUENCE: 172
atccgtcaca cctgctctca cacgcgtgga tcgagtgctc catacctgag tgtctggtgt     60
tggctcccgt at                                                         72

<210> SEQ ID NO 173
<211> LENGTH: 72
<212> TYPE: DNA
<213> ORGANISM: Artificial Sequence
<220> FEATURE:
<223> OTHER INFORMATION: chemically synthesized

<400> SEQUENCE: 173
atacgggagc caacaccatc cgcgaccaga atctgtaaag gcgttagata tgccagagca     60
ggtgtgacgg at                                                         72

<210> SEQ ID NO 174
<211> LENGTH: 72
<212> TYPE: DNA
<213> ORGANISM: Artificial Sequence
<220> FEATURE:
<223> OTHER INFORMATION: chemically synthesized

<400> SEQUENCE: 174
atccgtcaca cctgctctgg catatctaac gcctttacag attctggtcg cggatggtgt     60
tggctcccgt at                                                         72

<210> SEQ ID NO 175
<211> LENGTH: 72
<212> TYPE: DNA
<213> ORGANISM: Artificial Sequence
<220> FEATURE:
<223> OTHER INFORMATION: chemically synthesized

<400> SEQUENCE: 175
atacgggagc caacaccact caacgtaacg ggtggagacc ctcacatcga tatgagagca     60
ggtgtgacgg at                                                         72

<210> SEQ ID NO 176
<211> LENGTH: 72
<212> TYPE: DNA
<213> ORGANISM: Artificial Sequence
<220> FEATURE:
<223> OTHER INFORMATION: chemically synthesized

<400> SEQUENCE: 176
atccgtcaca cctgctctca tatcgatgtg agggtctcca cccgttacgt tgagtggtgt     60
tggctcccgt at                                                         72

<210> SEQ ID NO 177
<211> LENGTH: 72
<212> TYPE: DNA
<213> ORGANISM: Artificial Sequence
<220> FEATURE:
<223> OTHER INFORMATION: chemically synthesized
```

```
<400> SEQUENCE: 177
atacgggagc caacaccaga tggtgaccgg attacgagaa ccagagctga tagaagagca    60
ggtgtgacgg at                                                        72

<210> SEQ ID NO 178
<211> LENGTH: 72
<212> TYPE: DNA
<213> ORGANISM: Artificial Sequence
<220> FEATURE:
<223> OTHER INFORMATION: chemically synthesized

<400> SEQUENCE: 178
atccgtcaca cctgctcttc tatcagctct ggttctcgta atccggtcac catctggtgt    60
tggctcccgt at                                                        72

<210> SEQ ID NO 179
<211> LENGTH: 72
<212> TYPE: DNA
<213> ORGANISM: Artificial Sequence
<220> FEATURE:
<223> OTHER INFORMATION: chemically synthesized

<400> SEQUENCE: 179
atacgggagc caacaccaaa ccagggaata cacagcaaaa ctacggtgtc ctgtagagca    60
ggtgtgacgg at                                                        72

<210> SEQ ID NO 180
<211> LENGTH: 72
<212> TYPE: DNA
<213> ORGANISM: Artificial Sequence
<220> FEATURE:
<223> OTHER INFORMATION: chemically synthesized

<400> SEQUENCE: 180
atccgtcaca cctgctctac aggacaccgt agttttgctg tgtattccct ggtttggtgt    60
tggctcccgt at                                                        72

<210> SEQ ID NO 181
<211> LENGTH: 72
<212> TYPE: DNA
<213> ORGANISM: Artificial Sequence
<220> FEATURE:
<223> OTHER INFORMATION: chemically synthesized

<400> SEQUENCE: 181
atacgggagc caacaccagc cgataaagaa cgcagctaat ttgctctccc gagcagagca    60
ggtgtgacgg at                                                        72

<210> SEQ ID NO 182
<211> LENGTH: 72
<212> TYPE: DNA
<213> ORGANISM: Artificial Sequence
<220> FEATURE:
<223> OTHER INFORMATION: chemically synthesized

<400> SEQUENCE: 182
atccgtcaca cctgctctgc tcgggagagc aaattagctg cgttctttat cggctggtgt    60
tggctcccgt at                                                        72

<210> SEQ ID NO 183
<211> LENGTH: 72
<212> TYPE: DNA
```

```
<213> ORGANISM: Artificial Sequence
<220> FEATURE:
<223> OTHER INFORMATION: chemically synthesized

<400> SEQUENCE: 183
atacgggagc caacaccagc atatgtagtg aagcgacata caccggggca acgtagagca      60
ggtgtgacgg at                                                         72

<210> SEQ ID NO 184
<211> LENGTH: 72
<212> TYPE: DNA
<213> ORGANISM: Artificial Sequence
<220> FEATURE:
<223> OTHER INFORMATION: chemically synthesized

<400> SEQUENCE: 184
atccgtcaca cctgctctac gttgccccgg tgtatgtcgc ttcactacat atgctggtgt      60
tggctcccgt at                                                         72

<210> SEQ ID NO 185
<211> LENGTH: 72
<212> TYPE: DNA
<213> ORGANISM: Artificial Sequence
<220> FEATURE:
<223> OTHER INFORMATION: chemically synthesized

<400> SEQUENCE: 185
atacgggagc caacaccacc gaactaagag gaaagtctcg gagtgcggct agttagagca      60
ggtgtgacgg at                                                         72

<210> SEQ ID NO 186
<211> LENGTH: 72
<212> TYPE: DNA
<213> ORGANISM: Artificial Sequence
<220> FEATURE:
<223> OTHER INFORMATION: chemically synthesized

<400> SEQUENCE: 186
atccgtcaca cctgctctaa ctagccgcac tccgagactt cctcttagt tcggtggtgt       60 tggctcccgt at                                                         72

<210> SEQ ID NO 187
<211> LENGTH: 72
<212> TYPE: DNA
<213> ORGANISM: Artificial Sequence
<220> FEATURE:
<223> OTHER INFORMATION: chemically synthesized

<400> SEQUENCE: 187
atacgggagc caacaccaag gccacccagt taatgcagtc tcgttatgtt ctgtagagca      60
ggtgtgacgg at                                                         72

<210> SEQ ID NO 188
<211> LENGTH: 72
<212> TYPE: DNA
<213> ORGANISM: Artificial Sequence
<220> FEATURE:
<223> OTHER INFORMATION: chemically synthesized

<400> SEQUENCE: 188
atccgtcaca cctgctctac agaacataac gagactgcat taactgggtg gccttggtgt      60
tggctcccgt at                                                         72
```

<210> SEQ ID NO 189
<211> LENGTH: 72
<212> TYPE: DNA
<213> ORGANISM: Artificial Sequence
<220> FEATURE:
<223> OTHER INFORMATION: chemically synthesized

<400> SEQUENCE: 189
atacgggagc caacaccaat accatacctg acttatgacc tgatcatacc agtgagagca    60
ggtgtgacgg at                                                       72

<210> SEQ ID NO 190
<211> LENGTH: 72
<212> TYPE: DNA
<213> ORGANISM: Artificial Sequence
<220> FEATURE:
<223> OTHER INFORMATION: chemically synthesized

<400> SEQUENCE: 190
atccgtcaca cctgctctca ctggtatgat caggtcataa gtcaggtatg gtattggtgt    60
tggctcccgt at                                                       72

<210> SEQ ID NO 191
<211> LENGTH: 71
<212> TYPE: DNA
<213> ORGANISM: Artificial Sequence
<220> FEATURE:
<223> OTHER INFORMATION: chemically synthesized

<400> SEQUENCE: 191
atacgggagc cagcaccaca gattcttcaa ctttgctgcc atattccaac aacagagcag    60
gcgtgacgga t                                                        71

<210> SEQ ID NO 192
<211> LENGTH: 71
<212> TYPE: DNA
<213> ORGANISM: Artificial Sequence
<220> FEATURE:
<223> OTHER INFORMATION: chemically synthesized

<400> SEQUENCE: 192
atccgtcacg cctgctctgt tgttggaata tggcagcaaa gttgaagaat ctgtggtgct    60
ggctcccgta t                                                        71

<210> SEQ ID NO 193
<211> LENGTH: 72
<212> TYPE: DNA
<213> ORGANISM: Artificial Sequence
<220> FEATURE:
<223> OTHER INFORMATION: chemically synthesized

<400> SEQUENCE: 193
atacgggagc caacaccaca tgccataatt ggaccctcat cgccccgtcg tcccagagca    60
ggtgtgacgg at                                                       72

<210> SEQ ID NO 194
<211> LENGTH: 72
<212> TYPE: DNA
<213> ORGANISM: Artificial Sequence
<220> FEATURE:
<223> OTHER INFORMATION: chemically synthesized

<400> SEQUENCE: 194

```
atccgtcaca cctgctctgg gacgacgggg cgatgagggt ccaattatgg catgtggtgt    60
tggctcccgt at                                                        72

<210> SEQ ID NO 195
<211> LENGTH: 72
<212> TYPE: DNA
<213> ORGANISM: Artificial Sequence
<220> FEATURE:
<223> OTHER INFORMATION: chemically synthesized

<400> SEQUENCE: 195
atacgggagc caacaccaaa ccgcaccagt cacacaccag ttcgcctcca tgttagagca    60
ggtgtgacgg at                                                        72

<210> SEQ ID NO 196
<211> LENGTH: 72
<212> TYPE: DNA
<213> ORGANISM: Artificial Sequence
<220> FEATURE:
<223> OTHER INFORMATION: chemically synthesized

<400> SEQUENCE: 196
atccgtcaca cctgctctaa catggaggcg aactggtgtg tgactggtgc ggtttggtgt    60
tggctcccgt at                                                        72

<210> SEQ ID NO 197
<211> LENGTH: 72
<212> TYPE: DNA
<213> ORGANISM: Artificial Sequence
<220> FEATURE:
<223> OTHER INFORMATION: chemically synthesized

<400> SEQUENCE: 197
atacgggagc caacaccatt ttacagtact aaagtatgtg atatgccgcg ccggagagca    60
ggtgtgacgg at                                                        72

<210> SEQ ID NO 198
<211> LENGTH: 72
<212> TYPE: DNA
<213> ORGANISM: Artificial Sequence
<220> FEATURE:
<223> OTHER INFORMATION: chemically synthesized

<400> SEQUENCE: 198
atccgtcaca cctgctctcc ggcgcggcat atcacatact ttagtactgt aaaatggtgt    60
tggctcccgt at                                                        72

<210> SEQ ID NO 199
<211> LENGTH: 72
<212> TYPE: DNA
<213> ORGANISM: Artificial Sequence
<220> FEATURE:
<223> OTHER INFORMATION: chemically synthesized

<400> SEQUENCE: 199
atacgggagc caacaccaaa agaacgcact actttcggaa tcgaatctat ccccagagca    60
ggtgtgacgg at                                                        72

<210> SEQ ID NO 200
<211> LENGTH: 72
<212> TYPE: DNA
<213> ORGANISM: Artificial Sequence
<220> FEATURE:
```

<223> OTHER INFORMATION: chemically synthesized

<400> SEQUENCE: 200
atccgtcaca cctgctctgg ggatagattc gattccgaaa gtagtgcgtt cttttggtgt   60
tggctcccgt at   72

<210> SEQ ID NO 201
<211> LENGTH: 72
<212> TYPE: DNA
<213> ORGANISM: Artificial Sequence
<220> FEATURE:
<223> OTHER INFORMATION: chemically synthesized

<400> SEQUENCE: 201
atccgtcaca cctgctctag acgaatattg tatcctcatt agatcaaaaa cgggtggtgt   60
tggctcccgt at   72

<210> SEQ ID NO 202
<211> LENGTH: 72
<212> TYPE: DNA
<213> ORGANISM: Artificial Sequence
<220> FEATURE:
<223> OTHER INFORMATION: chemically synthesized

<400> SEQUENCE: 202
atacgggagc caacaccagc ttttcctaga atgattttct ttagctacct gagaagagca   60
ggtgtgacgg at   72

<210> SEQ ID NO 203
<211> LENGTH: 72
<212> TYPE: DNA
<213> ORGANISM: Artificial Sequence
<220> FEATURE:
<223> OTHER INFORMATION: chemically synthesized

<400> SEQUENCE: 203
atccgtcaca cctgctcttc tcaggtagct aaagaaaatc attctaggaa aagctggtgt   60
tggctcccgt at   72

<210> SEQ ID NO 204
<211> LENGTH: 58
<212> TYPE: DNA
<213> ORGANISM: Artificial Sequence
<220> FEATURE:
<223> OTHER INFORMATION: chemically synthesized

<400> SEQUENCE: 204
atacgggagc caacaccacg cttagatatt atccttgtcc agagcaggtg tgacggat   58

<210> SEQ ID NO 205
<211> LENGTH: 58
<212> TYPE: DNA
<213> ORGANISM: Artificial Sequence
<220> FEATURE:
<223> OTHER INFORMATION: chemically synthesized

<400> SEQUENCE: 205
atccgtcaca cctgctctgg acaaggataa tatctaagcg tggtgttggc tcccgtat   58

<210> SEQ ID NO 206
<211> LENGTH: 72
<212> TYPE: DNA
<213> ORGANISM: Artificial Sequence
<220> FEATURE:

```
<223> OTHER INFORMATION: chemically synthesized

<400> SEQUENCE: 206
acacgggagc caacaccatc catagctcat ctataccctc ttccgagtcc caccagagca    60
ggtgtgacgg at                                                        72

<210> SEQ ID NO 207
<211> LENGTH: 72
<212> TYPE: DNA
<213> ORGANISM: Artificial Sequence
<220> FEATURE:
<223> OTHER INFORMATION: chemically synthesized

<400> SEQUENCE: 207
atccgtcaca cctgctctgg tgggactcgg aagagggtat agatgagcta tggatggtgt    60
tggctcccgt gt                                                        72

<210> SEQ ID NO 208
<211> LENGTH: 72
<212> TYPE: DNA
<213> ORGANISM: Artificial Sequence
<220> FEATURE:
<223> OTHER INFORMATION: chemically synthesized

<400> SEQUENCE: 208
atacgggagc caacaccacc ctacaccagc gccctacact tttgtagcac ttcgagagca    60
ggtgtgacgg at                                                        72

<210> SEQ ID NO 209
<211> LENGTH: 72
<212> TYPE: DNA
<213> ORGANISM: Artificial Sequence
<220> FEATURE:
<223> OTHER INFORMATION: chemically synthesized

<400> SEQUENCE: 209
atccgtcaca cctgctctcg aagtgctaca aaagtgtagg gcgctggtgt agggtggtgt    60
tggctcccgt at                                                        72

<210> SEQ ID NO 210
<211> LENGTH: 69
<212> TYPE: DNA
<213> ORGANISM: Artificial Sequence
<220> FEATURE:
<223> OTHER INFORMATION: chemically synthesized

<400> SEQUENCE: 210
atacgggagc caaccata gtgttgggcc aatacggtaa cgtgtccttg gagagcaggt     60
gtgacggat                                                            69

<210> SEQ ID NO 211
<211> LENGTH: 69
<212> TYPE: DNA
<213> ORGANISM: Artificial Sequence
<220> FEATURE:
<223> OTHER INFORMATION: chemically synthesized

<400> SEQUENCE: 211
atccgtcaca cctgctctcc aaggacacgt taccgtattg gcccaacact atggtgttgg    60
ctcccgtat                                                            69

<210> SEQ ID NO 212
```

<211> LENGTH: 72
<212> TYPE: DNA
<213> ORGANISM: Artificial Sequence
<220> FEATURE:
<223> OTHER INFORMATION: chemically synthesized

<400> SEQUENCE: 212
atacgggagc caacaccacc cgtttttgat ctaatgagga tacaatattc gtctagagca    60
ggtgtgacgg at    72

<210> SEQ ID NO 213
<211> LENGTH: 72
<212> TYPE: DNA
<213> ORGANISM: Artificial Sequence
<220> FEATURE:
<223> OTHER INFORMATION: chemically synthesized

<400> SEQUENCE: 213
atacgggagc caacaccact atcaatttgt tggcgacact tcaacccaca cgttagagca    60
ggtgtgacgg at    72

<210> SEQ ID NO 214
<211> LENGTH: 72
<212> TYPE: DNA
<213> ORGANISM: Artificial Sequence
<220> FEATURE:
<223> OTHER INFORMATION: chemically synthesized

<400> SEQUENCE: 214
atccgtcaca cctgctctaa cgtgtgggtt gaagtgtcgc aacaaattg atagtggtgt    60 tggctcccgt at    72

<210> SEQ ID NO 215
<211> LENGTH: 72
<212> TYPE: DNA
<213> ORGANISM: Artificial Sequence
<220> FEATURE:
<223> OTHER INFORMATION: chemically synthesized

<400> SEQUENCE: 215
atacgggagc caacaccatc agcatgggtt agagctgggg gaaatatttg gtcgagagca    60
ggtgtgacgg at    72

<210> SEQ ID NO 216
<211> LENGTH: 72
<212> TYPE: DNA
<213> ORGANISM: Artificial Sequence
<220> FEATURE:
<223> OTHER INFORMATION: chemically synthesized

<400> SEQUENCE: 216
atccgtcaca cctgctctcg accaaatatt tcccccagct ctaacccatg ctgatggtgt    60
tggctcccgt at    72

<210> SEQ ID NO 217
<211> LENGTH: 69
<212> TYPE: DNA
<213> ORGANISM: Artificial Sequence
<220> FEATURE:
<223> OTHER INFORMATION: chemically synthesized

<400> SEQUENCE: 217
atacgggagc caacaccata gtgttgggcc aatacggtaa cgtgtccttg gagagcaggt    60

```
gtgacggat                                                              69

<210> SEQ ID NO 218
<211> LENGTH: 69
<212> TYPE: DNA
<213> ORGANISM: Artificial Sequence
<220> FEATURE:
<223> OTHER INFORMATION: chemically synthesized

<400> SEQUENCE: 218
atccgtcaca cctgctctcc aaggacacgt taccgtattg gcccaacact atggtgttgg     60
ctcccgtat                                                             69

<210> SEQ ID NO 219
<211> LENGTH: 72
<212> TYPE: DNA
<213> ORGANISM: Artificial Sequence
<220> FEATURE:
<223> OTHER INFORMATION: chemically synthesized

<400> SEQUENCE: 219
atacgggagc caacaccaac aaaacaacag gaatatcgtt cccaagcgga ccccagagca    60
ggtgtgacgg at                                                         72

<210> SEQ ID NO 220
<211> LENGTH: 72
<212> TYPE: DNA
<213> ORGANISM: Artificial Sequence
<220> FEATURE:
<223> OTHER INFORMATION: chemically synthesized

<400> SEQUENCE: 220
atccgtcaca cctgctctgg ggtccgcttg ggaacgatat tcctgttgtt ttgttggtgt    60
tggctcccgt at                                                         72

<210> SEQ ID NO 221
<211> LENGTH: 72
<212> TYPE: DNA
<213> ORGANISM: Artificial Sequence
<220> FEATURE:
<223> OTHER INFORMATION: chemically synthesized

<400> SEQUENCE: 221
atacgggagc caacaccata caaagtgttg ttagatttaa cccatgttgc catcagagca    60
ggtgtgacgg at                                                         72

<210> SEQ ID NO 222
<211> LENGTH: 72
<212> TYPE: DNA
<213> ORGANISM: Artificial Sequence
<220> FEATURE:
<223> OTHER INFORMATION: chemically synthesized

<400> SEQUENCE: 222
atccgtcaca cctgctctga tggcaacatg ggttaaatct aacaacactt tgtatggtgt    60
tggctcccgt at                                                         72

<210> SEQ ID NO 223
<211> LENGTH: 72
<212> TYPE: DNA
<213> ORGANISM: Artificial Sequence
<220> FEATURE:
<223> OTHER INFORMATION: chemically synthesized
```

<400> SEQUENCE: 223
atacgggagc caacaccaag ggtgttcaca ctggcaggcg acgccctcgt gttgagagca    60
ggtgtgacgg at    72

<210> SEQ ID NO 224
<211> LENGTH: 73
<212> TYPE: DNA
<213> ORGANISM: Artificial Sequence
<220> FEATURE:
<223> OTHER INFORMATION: chemically synthesized
<220> FEATURE:
<221> NAME/KEY: misc_feature
<222> LOCATION: (73)..(73)
<223> OTHER INFORMATION: n is a, c, g, or t

<400> SEQUENCE: 224
atccgtcaca cctgctctca acacgagggc gtcgcctgcc agtgtgaaca cccttggtgt    60
tggctcccgt atn    73

<210> SEQ ID NO 225
<211> LENGTH: 72
<212> TYPE: DNA
<213> ORGANISM: Artificial Sequence
<220> FEATURE:
<223> OTHER INFORMATION: chemically synthesized

<400> SEQUENCE: 225
atacgggagc caacaccaca atagtcgatt agtaatgatc cacacattgg tcggagagca    60
ggtgtgacgg at    72

<210> SEQ ID NO 226
<211> LENGTH: 72
<212> TYPE: DNA
<213> ORGANISM: Artificial Sequence
<220> FEATURE:
<223> OTHER INFORMATION: chemically synthesized

<400> SEQUENCE: 226
atccgtcaca cctgctctcc gaccaatgtg tggatcatta ctaatcgact attgtggtgt    60
tggctcccgt at    72

<210> SEQ ID NO 227
<211> LENGTH: 69
<212> TYPE: DNA
<213> ORGANISM: Artificial Sequence
<220> FEATURE:
<223> OTHER INFORMATION: chemically synthesized

<400> SEQUENCE: 227
atacgggagc caacaccata gttttgggcc aatacggtaa cgtgtccttg gagagcaggt    60
gtgacggat    69

<210> SEQ ID NO 228
<211> LENGTH: 69
<212> TYPE: DNA
<213> ORGANISM: Artificial Sequence
<220> FEATURE:
<223> OTHER INFORMATION: chemically synthesized

<400> SEQUENCE: 228
atccgtcaca cctgctctcc aaggacacgt taccgtattg gcccaaaact atggtgttgg    60
ctcccgtat    69

<210> SEQ ID NO 229
<211> LENGTH: 69
<212> TYPE: DNA
<213> ORGANISM: Artificial Sequence
<220> FEATURE:
<223> OTHER INFORMATION: chemically synthesized

<400> SEQUENCE: 229
atacgggagc caacaccata gtgctggacc aatacggtaa cgtgtccttg gagagcaggt    60
gtgacggat                                                           69

<210> SEQ ID NO 230
<211> LENGTH: 69
<212> TYPE: DNA
<213> ORGANISM: Artificial Sequence
<220> FEATURE:
<223> OTHER INFORMATION: chemically synthesized

<400> SEQUENCE: 230
atccgtcaca cctgctctcc aaggacacgt taccgtattg gtccagcact atggtgttgg    60
ctcccgtat                                                           69

<210> SEQ ID NO 231
<211> LENGTH: 58
<212> TYPE: DNA
<213> ORGANISM: Artificial Sequence
<220> FEATURE:
<223> OTHER INFORMATION: chemically synthesized

<400> SEQUENCE: 231
atacgggagc caacaccacg attagcaatg aattatctac agagcaggtg tgacggat      58

<210> SEQ ID NO 232
<211> LENGTH: 58
<212> TYPE: DNA
<213> ORGANISM: Artificial Sequence
<220> FEATURE:
<223> OTHER INFORMATION: chemically synthesized

<400> SEQUENCE: 232
atccgtcaca cctgctctgt agataattca ttgctaatcg tggtgttggc tcccgtat      58

<210> SEQ ID NO 233
<211> LENGTH: 72
<212> TYPE: DNA
<213> ORGANISM: Artificial Sequence
<220> FEATURE:
<223> OTHER INFORMATION: chemically synthesized

<400> SEQUENCE: 233
atacgggagc caacaccaat tctaacacag gtttctccgt ttcgttagct gctaagagca    60
ggtgtgacgg at                                                       72

<210> SEQ ID NO 234
<211> LENGTH: 72
<212> TYPE: DNA
<213> ORGANISM: Artificial Sequence
<220> FEATURE:
<223> OTHER INFORMATION: chemically synthesized

<400> SEQUENCE: 234
atccgtcaca cctgctctta gcagctaacg aaacggagaa acctgtgtta gaattggtgt    60
tggctcccgt at                                                       72

<210> SEQ ID NO 235
<211> LENGTH: 72
<212> TYPE: DNA
<213> ORGANISM: Artificial Sequence
<220> FEATURE:
<223> OTHER INFORMATION: chemically synthesized

<400> SEQUENCE: 235
atacgggagc caacaccatt ctatcgttcc ggacgcttat gccttgccat ctacagagca     60
ggtgtgacgg at                                                         72

<210> SEQ ID NO 236
<211> LENGTH: 72
<212> TYPE: DNA
<213> ORGANISM: Artificial Sequence
<220> FEATURE:
<223> OTHER INFORMATION: chemically synthesized

<400> SEQUENCE: 236
atccgtcaca cctgctctgt agatggcaag gcataagcgt ccggaacgat agaatggtgt     60
tggctcccgt at                                                         72

<210> SEQ ID NO 237
<211> LENGTH: 72
<212> TYPE: DNA
<213> ORGANISM: Artificial Sequence
<220> FEATURE:
<223> OTHER INFORMATION: chemically synthesized

<400> SEQUENCE: 237
atacgggagc caacaccaac tgactcagtc tgctggtggg ctatattttt gcggagagca     60
ggtgtgacgg at                                                         72

<210> SEQ ID NO 238
<211> LENGTH: 72
<212> TYPE: DNA
<213> ORGANISM: Artificial Sequence
<220> FEATURE:
<223> OTHER INFORMATION: chemically synthesized

<400> SEQUENCE: 238
atccgtcaca cctgctctcc gcaaaaatat agcccaccag cagactgagt cagttggtgt     60
tggctcccgt at                                                         72

<210> SEQ ID NO 239
<211> LENGTH: 72
<212> TYPE: DNA
<213> ORGANISM: Artificial Sequence
<220> FEATURE:
<223> OTHER INFORMATION: chemically synthesized

<400> SEQUENCE: 239
atacgggagc caacaccaga ccgggcggta aaataacaaa ttacatcccc accgagagca     60
ggtgtgacgg at                                                         72

<210> SEQ ID NO 240
<211> LENGTH: 72
<212> TYPE: DNA
<213> ORGANISM: Artificial Sequence
<220> FEATURE:
<223> OTHER INFORMATION: chemically synthesized

<400> SEQUENCE: 240

```
atccgtcaca cctgctctcg gtggggatgt aatttgttat tttaccgccc ggtctggtgt    60
tggctcccgt at                                                       72
```

<210> SEQ ID NO 241
<211> LENGTH: 72
<212> TYPE: DNA
<213> ORGANISM: Artificial Sequence
<220> FEATURE:
<223> OTHER INFORMATION: chemically synthesized

<400> SEQUENCE: 241

```
atacgggagc caacaccaat gaccatatca aaccacaccg gcccccact gatgagagca    60 ggtgtgacgg at                                                       72
```

<210> SEQ ID NO 242
<211> LENGTH: 72
<212> TYPE: DNA
<213> ORGANISM: Artificial Sequence
<220> FEATURE:
<223> OTHER INFORMATION: chemically synthesized

<400> SEQUENCE: 242

```
atccgtcaca cctgctctca tcagtggggg gccggtgtgg tttgatatgg tcattggtgt    60
tggctcccgt at                                                       72
```

<210> SEQ ID NO 243
<211> LENGTH: 72
<212> TYPE: DNA
<213> ORGANISM: Artificial Sequence
<220> FEATURE:
<223> OTHER INFORMATION: chemically synthesized

<400> SEQUENCE: 243

```
atacgggagc caacaccaat gaccatatca aaccacaccg gcccccact gatgagagca    60 ggtgtgacgg at                                                       72
```

<210> SEQ ID NO 244
<211> LENGTH: 72
<212> TYPE: DNA
<213> ORGANISM: Artificial Sequence
<220> FEATURE:
<223> OTHER INFORMATION: chemically synthesized

<400> SEQUENCE: 244

```
atccgtcaca cctgctctca tcagtggggg gccggtgtgg tttgatatgg tcattggtgt    60
tggctcccgt at                                                       72
```

<210> SEQ ID NO 245
<211> LENGTH: 72
<212> TYPE: DNA
<213> ORGANISM: Artificial Sequence
<220> FEATURE:
<223> OTHER INFORMATION: chemically synthesized

<400> SEQUENCE: 245

```
atacgggagc caacaccact caagtccaga tcacactcgt gctgctaccg gttcagagca    60
ggtgtgacgg at                                                       72
```

<210> SEQ ID NO 246
<211> LENGTH: 72
<212> TYPE: DNA
<213> ORGANISM: Artificial Sequence
<220> FEATURE:

<223> OTHER INFORMATION: chemically synthesized

<400> SEQUENCE: 246

```
atccgtcaca cctgctctga accggtagca gcacgagtgt gatctggact tgagtggtgt      60
tggctcccgt at                                                          72
```

<210> SEQ ID NO 247
<211> LENGTH: 72
<212> TYPE: DNA
<213> ORGANISM: Artificial Sequence
<220> FEATURE:
<223> OTHER INFORMATION: chemically synthesized

<400> SEQUENCE: 247

```
atacgggagc caacaccatt tctaactaat cgagtcggta ccactgggcc cctgagagca      60
ggtgtgacgg at                                                          72
```

<210> SEQ ID NO 248
<211> LENGTH: 72
<212> TYPE: DNA
<213> ORGANISM: Artificial Sequence
<220> FEATURE:
<223> OTHER INFORMATION: chemically synthesized

<400> SEQUENCE: 248

```
atccgtcaca cctgctctca ggggcccagt ggtaccgact cgattagtta gaaatggtgt      60
tggctcccgt at                                                          72
```

<210> SEQ ID NO 249
<211> LENGTH: 72
<212> TYPE: DNA
<213> ORGANISM: Artificial Sequence
<220> FEATURE:
<223> OTHER INFORMATION: chemically synthesized

<400> SEQUENCE: 249

```
atacgggagc caacaccatg gctaggaaat aatgtccatc ggcacatcct cccgagagca      60
ggtgtgacgg at                                                          72
```

<210> SEQ ID NO 250
<211> LENGTH: 72
<212> TYPE: DNA
<213> ORGANISM: Artificial Sequence
<220> FEATURE:
<223> OTHER INFORMATION: chemically synthesized

<400> SEQUENCE: 250

```
atccgtcaca cctgctctcg ggaggatgtg ccgatggaca ttatttccta gccatggtgt      60
tggctcccgt at                                                          72
```

<210> SEQ ID NO 251
<211> LENGTH: 72
<212> TYPE: DNA
<213> ORGANISM: Artificial Sequence
<220> FEATURE:
<223> OTHER INFORMATION: chemically synthesized

<400> SEQUENCE: 251

```
atacgggagc caacaccaac cgtacaaaca agctagtgtg gttaatactg cataagagca      60
ggtgtgacgg at                                                          72
```

<210> SEQ ID NO 252

```
<211> LENGTH: 72
<212> TYPE: DNA
<213> ORGANISM: Artificial Sequence
<220> FEATURE:
<223> OTHER INFORMATION: chemically synthesized

<400> SEQUENCE: 252
atccgtcaca cctgctctta tgcagtatta accacactag cttgtttgta cggttggtgt    60
tggctcccgt at                                                        72

<210> SEQ ID NO 253
<211> LENGTH: 72
<212> TYPE: DNA
<213> ORGANISM: Artificial Sequence
<220> FEATURE:
<223> OTHER INFORMATION: chemically synthesized

<400> SEQUENCE: 253
atacgggagc caacaccaga ggctaccggt aaatgggata tcattgcgtt tgcaagagca    60
ggtgtgacgg at                                                        72

<210> SEQ ID NO 254
<211> LENGTH: 72
<212> TYPE: DNA
<213> ORGANISM: Artificial Sequence
<220> FEATURE:
<223> OTHER INFORMATION: chemically synthesized

<400> SEQUENCE: 254
atccgtcaca cctgctcttg caaacgcaat gatatcccat ttaccggtag cctctggtgt    60
tggctcccgt at                                                        72

<210> SEQ ID NO 255
<211> LENGTH: 72
<212> TYPE: DNA
<213> ORGANISM: Artificial Sequence
<220> FEATURE:
<223> OTHER INFORMATION: chemically synthesized

<400> SEQUENCE: 255
atacgggagc caacaccact caaagggtta ccaatccgtt ggacacagta ctgtagagca    60
ggtgtgacgg at                                                        72

<210> SEQ ID NO 256
<211> LENGTH: 72
<212> TYPE: DNA
<213> ORGANISM: Artificial Sequence
<220> FEATURE:
<223> OTHER INFORMATION: chemically synthesized

<400> SEQUENCE: 256
atccgtcaca cctgctctac agtactgtgt ccaacggatt ggtaaccctt tgagtggtgt    60
tggctcccgt at                                                        72

<210> SEQ ID NO 257
<211> LENGTH: 72
<212> TYPE: DNA
<213> ORGANISM: Artificial Sequence
<220> FEATURE:
<223> OTHER INFORMATION: chemically synthesized

<400> SEQUENCE: 257
atacgggagc caacaccatg aacatacaag aggtagacct ggtagtcgta ttctagagca    60
```
ggtgtgacgg at                                                         72

<210> SEQ ID NO 258
<211> LENGTH: 72
<212> TYPE: DNA
<213> ORGANISM: Artificial Sequence
<220> FEATURE:
<223> OTHER INFORMATION: chemically synthesized

<400> SEQUENCE: 258
atccgtcaca cctgctctag aatacgacta ccaggtctac ctcttgtatg ttcatggtgt     60
tggctcccgt at                                                         72

<210> SEQ ID NO 259
<211> LENGTH: 72
<212> TYPE: DNA
<213> ORGANISM: Artificial Sequence
<220> FEATURE:
<223> OTHER INFORMATION: chemically synthesized

<400> SEQUENCE: 259
atacgggagc caacaccatc tgagccgtaa ttggttattt tccagtgaag tgcgagagca     60
ggtgtgacgg at                                                         72

<210> SEQ ID NO 260
<211> LENGTH: 72
<212> TYPE: DNA
<213> ORGANISM: Artificial Sequence
<220> FEATURE:
<223> OTHER INFORMATION: chemically synthesized

<400> SEQUENCE: 260
atccgtcaca cctgctctcg cacttcactg gaaaataacc aattacggct cagatggtgt     60
tggctcccgt at                                                         72

<210> SEQ ID NO 261
<211> LENGTH: 72
<212> TYPE: DNA
<213> ORGANISM: Artificial Sequence
<220> FEATURE:
<223> OTHER INFORMATION: chemically synthesized

<400> SEQUENCE: 261
atacgggagc caacaccatg actacgtggg caagacatcc cgcgcgtcca tcccagagca     60
ggtgtgacgg at                                                         72

<210> SEQ ID NO 262
<211> LENGTH: 72
<212> TYPE: DNA
<213> ORGANISM: Artificial Sequence
<220> FEATURE:
<223> OTHER INFORMATION: chemically synthesized

<400> SEQUENCE: 262
atccgtcaca cctgctctgg gatggacgcg cgggatgtct tgcccacgta gtcatggtgt     60
tggctcccgt at                                                         72

<210> SEQ ID NO 263
<211> LENGTH: 71
<212> TYPE: DNA
<213> ORGANISM: Artificial Sequence
<220> FEATURE:
<223> OTHER INFORMATION: chemically synthesized -continued

<400> SEQUENCE: 263
atacgggagc caacaccaac atggcgtggc aggtaatcta acctccctac ccaagagcag    60
gtgtgacgga t                                                         71

<210> SEQ ID NO 264
<211> LENGTH: 71
<212> TYPE: DNA
<213> ORGANISM: Artificial Sequence
<220> FEATURE:
<223> OTHER INFORMATION: chemically synthesized

<400> SEQUENCE: 264
atccgtcaca cctgctcttg ggtagggagg ttagattacc tgccacgcca tgttggtgtt    60
ggctcccgta t                                                         71

<210> SEQ ID NO 265
<211> LENGTH: 72
<212> TYPE: DNA
<213> ORGANISM: Artificial Sequence
<220> FEATURE:
<223> OTHER INFORMATION: chemically synthesized

<400> SEQUENCE: 265
atacgggagc caacaccaca cgacccaagg aattggaaaa acaccgacat tccaagagca    60
ggtgtgacgg at                                                        72

<210> SEQ ID NO 266
<211> LENGTH: 72
<212> TYPE: DNA
<213> ORGANISM: Artificial Sequence
<220> FEATURE:
<223> OTHER INFORMATION: chemically synthesized

<400> SEQUENCE: 266
atccgtcaca cctgctcttg gaatgtcggt gttttccaa ttccttgggt cgtgtggtgt    60
tggctcccgt at                                                        72

<210> SEQ ID NO 267
<211> LENGTH: 72
<212> TYPE: DNA
<213> ORGANISM: Artificial Sequence
<220> FEATURE:
<223> OTHER INFORMATION: chemically synthesized

<400> SEQUENCE: 267
atacgggagc caacaccaag actgataacc ttacgtccag taggggcaag ctatagagca    60
ggtgtgacgg at                                                        72

<210> SEQ ID NO 268
<211> LENGTH: 72
<212> TYPE: DNA
<213> ORGANISM: Artificial Sequence
<220> FEATURE:
<223> OTHER INFORMATION: chemically synthesized

<400> SEQUENCE: 268
atccgtcaca cctgctctat agcttgcccc tactggacgt aaggttatca gtcttggtgt    60
tggctcccgt at                                                        72

<210> SEQ ID NO 269
<211> LENGTH: 72
<212> TYPE: DNA

<213> ORGANISM: Artificial Sequence
<220> FEATURE:
<223> OTHER INFORMATION: chemically synthesized

<400> SEQUENCE: 269
atacgggagc caacaccaat aaccgttttc ggccatgaga atactgtcac ttacagagca    60
ggtgtgacgg at    72

<210> SEQ ID NO 270
<211> LENGTH: 72
<212> TYPE: DNA
<213> ORGANISM: Artificial Sequence
<220> FEATURE:
<223> OTHER INFORMATION: chemically synthesized

<400> SEQUENCE: 270
atccgtcaca cctgctctgt aagtgacagt attctcatgg ccgaaaacgg ttattggtgt    60
tggctcccgt at    72

<210> SEQ ID NO 271
<211> LENGTH: 72
<212> TYPE: DNA
<213> ORGANISM: Artificial Sequence
<220> FEATURE:
<223> OTHER INFORMATION: chemically synthesized

<400> SEQUENCE: 271
atacgggagc caacaccaag acgaatagct cactacctcg tgaactatcc cctgagagca    60
ggtgtgacgg at    72

<210> SEQ ID NO 272
<211> LENGTH: 72
<212> TYPE: DNA
<213> ORGANISM: Artificial Sequence
<220> FEATURE:
<223> OTHER INFORMATION: chemically synthesized

<400> SEQUENCE: 272
atccgtcaca cctgctctca ggggatagtt cacgaggtag tgagctattc gtcttggtgt    60
tggctcccgt at    72

<210> SEQ ID NO 273
<211> LENGTH: 72
<212> TYPE: DNA
<213> ORGANISM: Artificial Sequence
<220> FEATURE:
<223> OTHER INFORMATION: chemically synthesized

<400> SEQUENCE: 273
atacgggagc caacaccata caggatctat tcccagaaga gttggcatat accaagagca    60
ggtgtgacgg at    72

<210> SEQ ID NO 274
<211> LENGTH: 72
<212> TYPE: DNA
<213> ORGANISM: Artificial Sequence
<220> FEATURE:
<223> OTHER INFORMATION: chemically synthesized

<400> SEQUENCE: 274
atccgtcaca cctgctcttg gtatatgcca actcttctgg gaatagatcc tgtatggtgt    60
tggctcccgt at    72

```
<210> SEQ ID NO 275
<211> LENGTH: 72
<212> TYPE: DNA
<213> ORGANISM: Artificial Sequence
<220> FEATURE:
<223> OTHER INFORMATION: chemically synthesized

<400> SEQUENCE: 275
atacgggagc caacaccatg gagaacattt ccatgttggc gaccatgggc ctcgagagca     60
ggtgtgacgg at                                                         72

<210> SEQ ID NO 276
<211> LENGTH: 72
<212> TYPE: DNA
<213> ORGANISM: Artificial Sequence
<220> FEATURE:
<223> OTHER INFORMATION: chemically synthesized

<400> SEQUENCE: 276
atccgtcaca cctgctctcg aggcccatgg tcgccaacat ggaaatgttc tccatggtgt     60
tggctcccgt at                                                         72

<210> SEQ ID NO 277
<211> LENGTH: 72
<212> TYPE: DNA
<213> ORGANISM: Artificial Sequence
<220> FEATURE:
<223> OTHER INFORMATION: chemically synthesized

<400> SEQUENCE: 277
atacgggagc caacaccagt acgaattata ctacagaggg cgtccgcgtt ggggagagca     60
ggtgtgacgg at                                                         72

<210> SEQ ID NO 278
<211> LENGTH: 72
<212> TYPE: DNA
<213> ORGANISM: Artificial Sequence
<220> FEATURE:
<223> OTHER INFORMATION: chemically synthesized

<400> SEQUENCE: 278
atccgtcaca cctgctctcc ccaacgcgga cgccctctgt agtataattc gtactggtgt     60
tggctcccgt at                                                         72

<210> SEQ ID NO 279
<211> LENGTH: 72
<212> TYPE: DNA
<213> ORGANISM: Artificial Sequence
<220> FEATURE:
<223> OTHER INFORMATION: chemically synthesized

<400> SEQUENCE: 279
atacgggagc caacaccacg caacctacct ctcacggctg ttcatgacgg acttagagca     60
ggtgtgacgg at                                                         72

<210> SEQ ID NO 280
<211> LENGTH: 72
<212> TYPE: DNA
<213> ORGANISM: Artificial Sequence
<220> FEATURE:
<223> OTHER INFORMATION: chemically synthesized

<400> SEQUENCE: 280
```

```
atccgtcaca cctgctctaa gtccgtcatg aacagccgtg agaggtaggt tgcgtggtgt    60
tggctcccgt at                                                        72

<210> SEQ ID NO 281
<211> LENGTH: 72
<212> TYPE: DNA
<213> ORGANISM: Artificial Sequence
<220> FEATURE:
<223> OTHER INFORMATION: chemically synthesized

<400> SEQUENCE: 281
atacgggagc caacaccatg ccaggcaagt cattgtgagt atagaatcac ctttagagca    60
ggtgtgacgg at                                                        72

<210> SEQ ID NO 282
<211> LENGTH: 72
<212> TYPE: DNA
<213> ORGANISM: Artificial Sequence
<220> FEATURE:
<223> OTHER INFORMATION: chemically synthesized

<400> SEQUENCE: 282
atccgtcaca cctgctctaa aggtgattct atactcacaa tgacttgcct ggcatggtgt    60
tggctcccgt at                                                        72

<210> SEQ ID NO 283
<211> LENGTH: 72
<212> TYPE: DNA
<213> ORGANISM: Artificial Sequence
<220> FEATURE:
<223> OTHER INFORMATION: chemically synthesized

<400> SEQUENCE: 283
atacgggagc caacaccagg accgtcgatg attgcaggtg cgtggtaaat acgcagagca    60
ggtgtgacgg at                                                        72

<210> SEQ ID NO 284
<211> LENGTH: 72
<212> TYPE: DNA
<213> ORGANISM: Artificial Sequence
<220> FEATURE:
<223> OTHER INFORMATION: chemically synthesized

<400> SEQUENCE: 284
atccgtcaca cctgctctgc gtatttacca cgcacctgca atcatcgacg gtcctggtgt    60
tggctcccgt at                                                        72

<210> SEQ ID NO 285
<211> LENGTH: 72
<212> TYPE: DNA
<213> ORGANISM: Artificial Sequence
<220> FEATURE:
<223> OTHER INFORMATION: chemically synthesized

<400> SEQUENCE: 285
atacgggagc caacaccatg ctacatcggt cagaagatcc gagcctgccc gcgtagagca    60
ggtgtgacgg at                                                        72

<210> SEQ ID NO 286
<211> LENGTH: 72
<212> TYPE: DNA
<213> ORGANISM: Artificial Sequence
<220> FEATURE:
```

<223> OTHER INFORMATION: chemically synthesized

<400> SEQUENCE: 286
atccgtcaca cctgctctac gcgggcaggc tcggatcttc tgaccgatgt agcatggtgt    60
tggctcccgt at    72

<210> SEQ ID NO 287
<211> LENGTH: 72
<212> TYPE: DNA
<213> ORGANISM: Artificial Sequence
<220> FEATURE:
<223> OTHER INFORMATION: chemically synthesized

<400> SEQUENCE: 287
atacgggagc caacaccaac tgggaaacgt tgatcgtagc tgagtgatag tgctagagca    60
ggtgtgacgg at    72

<210> SEQ ID NO 288
<211> LENGTH: 72
<212> TYPE: DNA
<213> ORGANISM: Artificial Sequence
<220> FEATURE:
<223> OTHER INFORMATION: chemically synthesized

<400> SEQUENCE: 288
atccgtcaca cctgctctag cactatcact cagctacgat caacgtttcc cagttggtgt    60
tggctcccgt at    72

<210> SEQ ID NO 289
<211> LENGTH: 72
<212> TYPE: DNA
<213> ORGANISM: Artificial Sequence
<220> FEATURE:
<223> OTHER INFORMATION: chemically synthesized

<400> SEQUENCE: 289
atacgggagc caacaccaat gtttgaagca aagccgaggc atgtagaaac gtctagagca    60
ggtgtgacgg at    72

<210> SEQ ID NO 290
<211> LENGTH: 72
<212> TYPE: DNA
<213> ORGANISM: Artificial Sequence
<220> FEATURE:
<223> OTHER INFORMATION: chemically synthesized

<400> SEQUENCE: 290
atccgtcaca cctgctctag acgtttctac atgcctcggc tttgcttcaa acattggtgt    60
tggctcccgt at    72

<210> SEQ ID NO 291
<211> LENGTH: 72
<212> TYPE: DNA
<213> ORGANISM: Artificial Sequence
<220> FEATURE:
<223> OTHER INFORMATION: chemically synthesized

<400> SEQUENCE: 291
atacgggagc caacaccaga gggggtcaaa aatgctagag aatacaccgt cagcagagca    60
ggtgtgacgg at    72

<210> SEQ ID NO 292

```
<211> LENGTH: 72
<212> TYPE: DNA
<213> ORGANISM: Artificial Sequence
<220> FEATURE:
<223> OTHER INFORMATION: chemically synthesized

<400> SEQUENCE: 292
atccgtcaca cctgctctgc tgacggtgta ttctctagca tttttgaccc cctctggtgt     60
tggctcccgt at                                                        72

<210> SEQ ID NO 293
<211> LENGTH: 72
<212> TYPE: DNA
<213> ORGANISM: Artificial Sequence
<220> FEATURE:
<223> OTHER INFORMATION: chemically synthesized

<400> SEQUENCE: 293
atacgggagc caacaccaaa gcgagctcgg catgtcgacg gtgtgcgtcc accgagagca     60
ggtgtgacgg at                                                        72

<210> SEQ ID NO 294
<211> LENGTH: 72
<212> TYPE: DNA
<213> ORGANISM: Artificial Sequence
<220> FEATURE:
<223> OTHER INFORMATION: chemically synthesized

<400> SEQUENCE: 294
atccgtcaca cctgctctcg gtggacgcac accgtcgaca tgccgagctc gctttggtgt     60
tggctcccgt at                                                        72

<210> SEQ ID NO 295
<211> LENGTH: 72
<212> TYPE: DNA
<213> ORGANISM: Artificial Sequence
<220> FEATURE:
<223> OTHER INFORMATION: chemically synthesized

<400> SEQUENCE: 295
atacgggagc caacaccatt cccccctctc gttctgttgc cccgtatcct aattagagca     60
ggtgtgacgg at                                                        72

<210> SEQ ID NO 296
<211> LENGTH: 71
<212> TYPE: DNA
<213> ORGANISM: Artificial Sequence
<220> FEATURE:
<223> OTHER INFORMATION: chemically synthesized

<400> SEQUENCE: 296
atacgggagc caacaccagc cggatatccg atgtgcttgt ctgacctggt ccgagagcag     60
gtgtgacgga t                                                         71

<210> SEQ ID NO 297
<211> LENGTH: 72
<212> TYPE: DNA
<213> ORGANISM: Artificial Sequence
<220> FEATURE:
<223> OTHER INFORMATION: chemically synthesized

<400> SEQUENCE: 297
atacgggagc caacaccact gttatgttag ctcctcccta aactctttga ctcaagagca     60
```

```
ggtgtgacgg at                                                           72

<210> SEQ ID NO 298
<211> LENGTH: 72
<212> TYPE: DNA
<213> ORGANISM: Artificial Sequence
<220> FEATURE:
<223> OTHER INFORMATION: chemically synthesized

<400> SEQUENCE: 298
atacgggagc caacaccacc gcatgcgttc ccagcccgct gatgcattgt tgttagagca        60
ggtgtgacgg at                                                           72

<210> SEQ ID NO 299
<211> LENGTH: 72
<212> TYPE: DNA
<213> ORGANISM: Artificial Sequence
<220> FEATURE:
<223> OTHER INFORMATION: chemically synthesized

<400> SEQUENCE: 299
atacgggagc caacaccaga tcctgaaact atcactcctg cttataacct gttcagagca        60
ggtgtgacgg at                                                           72

<210> SEQ ID NO 300
<211> LENGTH: 71
<212> TYPE: DNA
<213> ORGANISM: Artificial Sequence
<220> FEATURE:
<223> OTHER INFORMATION: chemically synthesized

<400> SEQUENCE: 300
atacgggagc caacaccaac ccgggtgctg accactcggt ttgcgagccg ccagagcag         60 gtgtgacgga t                                                            71

<210> SEQ ID NO 301
<211> LENGTH: 72
<212> TYPE: DNA
<213> ORGANISM: Artificial Sequence
<220> FEATURE:
<223> OTHER INFORMATION: chemically synthesized

<400> SEQUENCE: 301
atacgggagc caacaccact atgttttcac ggtcttgtgg attacgtctt gcgcagagca        60
ggtgtgacgg at                                                           72

<210> SEQ ID NO 302
<211> LENGTH: 70
<212> TYPE: DNA
<213> ORGANISM: Artificial Sequence
<220> FEATURE:
<223> OTHER INFORMATION: chemically synthesized

<400> SEQUENCE: 302
atacgggagc caacaccaga gcaggtgtga tggatatacg ggagccaaca ccagagcagg        60
tgtgacggat                                                              70

<210> SEQ ID NO 303
<211> LENGTH: 70
<212> TYPE: DNA
<213> ORGANISM: Artificial Sequence
<220> FEATURE:
<223> OTHER INFORMATION: chemically synthesized
```

-continued

<400> SEQUENCE: 303
atacgggagc caacaccaga gcaggtgtga tggatatacg ggagccaaca ccagagcagg    60
tgtgacggat                                                           70

<210> SEQ ID NO 304
<211> LENGTH: 70
<212> TYPE: DNA
<213> ORGANISM: Artificial Sequence
<220> FEATURE:
<223> OTHER INFORMATION: chemically synthesized

<400> SEQUENCE: 304
atacgggagc caacaccaga gcaggtgtga tggatatacg ggagccaaca ccagagcagg    60
tgtgacggat                                                           70

<210> SEQ ID NO 305
<211> LENGTH: 72
<212> TYPE: DNA
<213> ORGANISM: Artificial Sequence
<220> FEATURE:
<223> OTHER INFORMATION: chemically synthesized

<400> SEQUENCE: 305
atccgtcaca cctgctctgc acctgaagat caagtgtgag ttataggttg cgtttggtgt    60
tggctcccgt at                                                        72

<210> SEQ ID NO 306
<211> LENGTH: 72
<212> TYPE: DNA
<213> ORGANISM: Artificial Sequence
<220> FEATURE:
<223> OTHER INFORMATION: chemically synthesized

<400> SEQUENCE: 306
atacgggagc caacaccaat gcactcgtca cgccttttt gctcttgcgc gttaagagca     60
ggtgtgacgg at                                                        72

<210> SEQ ID NO 307
<211> LENGTH: 71
<212> TYPE: DNA
<213> ORGANISM: Artificial Sequence
<220> FEATURE:
<223> OTHER INFORMATION: chemically synthesized

<400> SEQUENCE: 307
atacgggagc caacaccaac tggtctctac ggaaaccta cgccaatcta cacagagcag     60
gtgtgacgga t                                                         71

<210> SEQ ID NO 308
<211> LENGTH: 72
<212> TYPE: DNA
<213> ORGANISM: Artificial Sequence
<220> FEATURE:
<223> OTHER INFORMATION: chemically synthesized

<400> SEQUENCE: 308
atacgggagc caacaccatt agcaacgatt ccctgttag ttccggtgca tcccagagca     60
ggtgtgacgg at                                                        72

<210> SEQ ID NO 309
<211> LENGTH: 69
<212> TYPE: DNA

```
<213> ORGANISM: Artificial Sequence
<220> FEATURE:
<223> OTHER INFORMATION: chemically synthesized

<400> SEQUENCE: 309
atacgggagc caacaccaga gcaggtgtga ggtcgaattc cagcacactg gcggccgtta      60
ctagtggat                                                             69

<210> SEQ ID NO 310
<211> LENGTH: 72
<212> TYPE: DNA
<213> ORGANISM: Artificial Sequence
<220> FEATURE:
<223> OTHER INFORMATION: chemically synthesized

<400> SEQUENCE: 310
atccgtcaca cctgctctaa ttaggatacg gggcaacaga acgagagggg ggaatggtgt      60
tggctcccgt at                                                         72

<210> SEQ ID NO 311
<211> LENGTH: 71
<212> TYPE: DNA
<213> ORGANISM: Artificial Sequence
<220> FEATURE:
<223> OTHER INFORMATION: chemically synthesized

<400> SEQUENCE: 311
atccgtcaca cctgctctcg gaccaggtca gacaagcaca tcggatatcc ggctggtgtt      60
ggctcccgta t                                                          71

<210> SEQ ID NO 312
<211> LENGTH: 72
<212> TYPE: DNA
<213> ORGANISM: Artificial Sequence
<220> FEATURE:
<223> OTHER INFORMATION: chemically synthesized

<400> SEQUENCE: 312
atccgtcaca cctgctcttg agtcaaagag tttagggagg agctaacata acagtggtgt      60
tggctcccgt at                                                         72

<210> SEQ ID NO 313
<211> LENGTH: 72
<212> TYPE: DNA
<213> ORGANISM: Artificial Sequence
<220> FEATURE:
<223> OTHER INFORMATION: chemically synthesized

<400> SEQUENCE: 313
atccgtcaca cctgctctaa caacaatgca tcagcgggct gggaacgcat gcggtggtgt      60
tggctcccgt at                                                         72

<210> SEQ ID NO 314
<211> LENGTH: 72
<212> TYPE: DNA
<213> ORGANISM: Artificial Sequence
<220> FEATURE:
<223> OTHER INFORMATION: chemically synthesized

<400> SEQUENCE: 314
atccgtcaca cctgctctga acaggttata agcaggagtg atagtttcag gatctggtgt      60
tggctcccgt at                                                         72
```

```
<210> SEQ ID NO 315
<211> LENGTH: 71
<212> TYPE: DNA
<213> ORGANISM: Artificial Sequence
<220> FEATURE:
<223> OTHER INFORMATION: chemically synthesized

<400> SEQUENCE: 315
atccgtcaca cctgctctcg gcggctcgca aaccgagtgg tcagcacccg ggttggtgtt    60
ggctcccgta t                                                         71

<210> SEQ ID NO 316
<211> LENGTH: 72
<212> TYPE: DNA
<213> ORGANISM: Artificial Sequence
<220> FEATURE:
<223> OTHER INFORMATION: chemically synthesized

<400> SEQUENCE: 316
atccgtcaca cctgctctgc gcaagacgta atccacaaga ccgtgaaaac atagtggtgt    60
tggctcccgt at                                                        72

<210> SEQ ID NO 317
<211> LENGTH: 70
<212> TYPE: DNA
<213> ORGANISM: Artificial Sequence
<220> FEATURE:
<223> OTHER INFORMATION: chemically synthesized

<400> SEQUENCE: 317
atccgtcaca cctgctctgg tgttggctcc cgtatatcca tcacacctgc tctggtgttg    60
gctcccgtat                                                           70

<210> SEQ ID NO 318
<211> LENGTH: 70
<212> TYPE: DNA
<213> ORGANISM: Artificial Sequence
<220> FEATURE:
<223> OTHER INFORMATION: chemically synthesized

<400> SEQUENCE: 318
atccgtcaca cctgctctgg tgttggctcc cgtatatcca tcacacctgc tctggtgttg    60
gctcccgtat                                                           70

<210> SEQ ID NO 319
<211> LENGTH: 70
<212> TYPE: DNA
<213> ORGANISM: Artificial Sequence
<220> FEATURE:
<223> OTHER INFORMATION: chemically synthesized

<400> SEQUENCE: 319
atccgtcaca cctgctctgg tgttggctcc cgtatatcca tcacacctgc tctggtgttg    60
gctcccgtat                                                           70

<210> SEQ ID NO 320
<211> LENGTH: 72
<212> TYPE: DNA
<213> ORGANISM: Artificial Sequence
<220> FEATURE:
<223> OTHER INFORMATION: chemically synthesized

<400> SEQUENCE: 320
```

```
atccgtcaca cctgctctgc acctgaagat caagtgtgag ttataggttg cgtttggtgt    60
tggctcccgt at                                                        72

<210> SEQ ID NO 321
<211> LENGTH: 72
<212> TYPE: DNA
<213> ORGANISM: Artificial Sequence
<220> FEATURE:
<223> OTHER INFORMATION: chemically synthesized

<400> SEQUENCE: 321
atccgtcaca cctgctctta acgcgcaaga gcaaaaaagg cgtgacgagt gcattggtgt    60
tggctcccgt at                                                        72

<210> SEQ ID NO 322
<211> LENGTH: 71
<212> TYPE: DNA
<213> ORGANISM: Artificial Sequence
<220> FEATURE:
<223> OTHER INFORMATION: chemically synthesized

<400> SEQUENCE: 322
atccgtcaca cctgctctgt gtagattggc gtaaggtttc cgtagagacc agttggtgtt    60
ggctcccgta t                                                         71

<210> SEQ ID NO 323
<211> LENGTH: 72
<212> TYPE: DNA
<213> ORGANISM: Artificial Sequence
<220> FEATURE:
<223> OTHER INFORMATION: chemically synthesized

<400> SEQUENCE: 323
atccgtcaca cctgctctgg gatgcaccgg aactaacagg ggaatcgttg ctaatggtgt    60
tggctcccgt at                                                        72

<210> SEQ ID NO 324
<211> LENGTH: 69
<212> TYPE: DNA
<213> ORGANISM: Artificial Sequence
<220> FEATURE:
<223> OTHER INFORMATION: chemically synthesized

<400> SEQUENCE: 324
atccactagt aacggccgcc agtgtgctgg aattcgacct cacacctgct ctggtgttgg    60
ctcccgtat                                                            69

<210> SEQ ID NO 325
<211> LENGTH: 72
<212> TYPE: DNA
<213> ORGANISM: Artificial Sequence
<220> FEATURE:
<223> OTHER INFORMATION: chemically synthesized

<400> SEQUENCE: 325
atacgggagc caacaccagg gggatggccg cttgacattg acacgtacct gtggagagca    60
ggtgtgacgg at                                                        72

<210> SEQ ID NO 326
<211> LENGTH: 72
<212> TYPE: DNA
<213> ORGANISM: Artificial Sequence
<220> FEATURE:
```

<223> OTHER INFORMATION: chemically synthesized

<400> SEQUENCE: 326
atccgtcaca cctgctctcc acaggtacgt gtcaatgtca agcggccatc cccctggtgt    60
tggctcccgt at    72

<210> SEQ ID NO 327
<211> LENGTH: 71
<212> TYPE: DNA
<213> ORGANISM: Artificial Sequence
<220> FEATURE:
<223> OTHER INFORMATION: chemically synthesized

<400> SEQUENCE: 327
atacgggagc caacaccaca agaggccgta cgaaaaaata actatgcaat tgtagagcag    60
gtgtgacgga t    71

<210> SEQ ID NO 328
<211> LENGTH: 71
<212> TYPE: DNA
<213> ORGANISM: Artificial Sequence
<220> FEATURE:
<223> OTHER INFORMATION: chemically synthesized

<400> SEQUENCE: 328
atccgtcaca cctgctctac aattgcatag ttattttttc gtacggcctc ttgtggtgtt    60
ggctcccgta t    71

<210> SEQ ID NO 329
<211> LENGTH: 72
<212> TYPE: DNA
<213> ORGANISM: Artificial Sequence
<220> FEATURE:
<223> OTHER INFORMATION: chemically synthesized

<400> SEQUENCE: 329
atacgggagc caacaccaaa ccaaggaaga ataaaacgat cgagtgatca caccagagca    60
ggtgtgacgg at    72

<210> SEQ ID NO 330
<211> LENGTH: 72
<212> TYPE: DNA
<213> ORGANISM: Artificial Sequence
<220> FEATURE:
<223> OTHER INFORMATION: chemically synthesized

<400> SEQUENCE: 330
atccgtcaca cctgctctgg tgtgatcact cgatcgtttt attcttcctt ggtttggtgt    60
tggctcccgt at    72

<210> SEQ ID NO 331
<211> LENGTH: 72
<212> TYPE: DNA
<213> ORGANISM: Artificial Sequence
<220> FEATURE:
<223> OTHER INFORMATION: chemically synthesized

<400> SEQUENCE: 331
atacgggagc caacaccaca agcggagcta gctgggtccg tggatccaag catgagagca    60
ggtgtgacgg at    72

<210> SEQ ID NO 332

```
<211> LENGTH: 72
<212> TYPE: DNA
<213> ORGANISM: Artificial Sequence
<220> FEATURE:
<223> OTHER INFORMATION: chemically synthesized

<400> SEQUENCE: 332
atccgtcaca cctgctctca tgcttggatc cacggaccca gctagctccg cttgtggtgt      60
tggctcccgt at                                                         72

<210> SEQ ID NO 333
<211> LENGTH: 72
<212> TYPE: DNA
<213> ORGANISM: Artificial Sequence
<220> FEATURE:
<223> OTHER INFORMATION: chemically synthesized

<400> SEQUENCE: 333
atacgggagc caacaccatg gcacgcagaa aacgttaaag cagaatttcc tcagagagca      60
ggtgtgacgg at                                                         72

<210> SEQ ID NO 334
<211> LENGTH: 72
<212> TYPE: DNA
<213> ORGANISM: Artificial Sequence
<220> FEATURE:
<223> OTHER INFORMATION: chemically synthesized

<400> SEQUENCE: 334
atccgtcaca cctgctctct gaggaaattc tgctttaacg ttttctgcgt gccatggtgt      60
tggctcccgt at                                                         72

<210> SEQ ID NO 335
<211> LENGTH: 72
<212> TYPE: DNA
<213> ORGANISM: Artificial Sequence
<220> FEATURE:
<223> OTHER INFORMATION: chemically synthesized

<400> SEQUENCE: 335
atacgggagc caacaccaga cttattctcg cagatccata aaaggataca ccccagagca      60
ggtgtgacgg at                                                         72

<210> SEQ ID NO 336
<211> LENGTH: 72
<212> TYPE: DNA
<213> ORGANISM: Artificial Sequence
<220> FEATURE:
<223> OTHER INFORMATION: chemically synthesized

<400> SEQUENCE: 336
atccgtcaca cctgctctgg ggtgtatcct tttatggatc tgcgagaata agtctggtgt      60
tggctcccgt at                                                         72

<210> SEQ ID NO 337
<211> LENGTH: 72
<212> TYPE: DNA
<213> ORGANISM: Artificial Sequence
<220> FEATURE:
<223> OTHER INFORMATION: chemically synthesized

<400> SEQUENCE: 337
atacgggagc caacaccaca gaatcacgtg gagtacgaac aattgattca cccaagagca      60
```
ggtgtgacgg at                                                          72

<210> SEQ ID NO 338
<211> LENGTH: 72
<212> TYPE: DNA
<213> ORGANISM: Artificial Sequence
<220> FEATURE:
<223> OTHER INFORMATION: chemically synthesized

<400> SEQUENCE: 338
atccgtcaca cctgctcttg ggtgaatcaa ttgttcgtac tccacgtgat tctgtggtgt    60
tggctcccgt at                                                          72

<210> SEQ ID NO 339
<211> LENGTH: 72
<212> TYPE: DNA
<213> ORGANISM: Artificial Sequence
<220> FEATURE:
<223> OTHER INFORMATION: chemically synthesized

<400> SEQUENCE: 339
atacgggagc caacaccacg ggggcatctt ccattaaccc attacctcac cccaagagca    60
ggtgtgacgg at                                                          72

<210> SEQ ID NO 340
<211> LENGTH: 72
<212> TYPE: DNA
<213> ORGANISM: Artificial Sequence
<220> FEATURE:
<223> OTHER INFORMATION: chemically synthesized

<400> SEQUENCE: 340
atccgtcaca cctgctcttg gggtgaggta atgggttaat ggaagatgcc cccgtggtgt    60
tggctcccgt at                                                          72

<210> SEQ ID NO 341
<211> LENGTH: 72
<212> TYPE: DNA
<213> ORGANISM: Artificial Sequence
<220> FEATURE:
<223> OTHER INFORMATION: chemically synthesized

<400> SEQUENCE: 341
atacgggagc caacaccaga aaaaaacaaa cccaaggaat tacaccacaa aagtagagca    60
ggtgtgacgg at                                                          72

<210> SEQ ID NO 342
<211> LENGTH: 72
<212> TYPE: DNA
<213> ORGANISM: Artificial Sequence
<220> FEATURE:
<223> OTHER INFORMATION: chemically synthesized

<400> SEQUENCE: 342
atccgtcaca cctgctctac ttttgtggtg taattccttg ggtttgtttt tttctggtgt    60
tggctcccgt at                                                          72

<210> SEQ ID NO 343
<211> LENGTH: 71
<212> TYPE: DNA
<213> ORGANISM: Artificial Sequence
<220> FEATURE:
<223> OTHER INFORMATION: chemically synthesized

<400> SEQUENCE: 343
atacgggagc caacaccata agcagagaac tacaagacga tcccatattc caaagagcag    60
gtgtgacgga t    71

<210> SEQ ID NO 344
<211> LENGTH: 71
<212> TYPE: DNA
<213> ORGANISM: Artificial Sequence
<220> FEATURE:
<223> OTHER INFORMATION: chemically synthesized

<400> SEQUENCE: 344
atccgtcaca cctgctcttt ggaatatggg atcgtcttgt agttctctgc ttatggtgtt    60
ggctcccgta t    71

<210> SEQ ID NO 345
<211> LENGTH: 71
<212> TYPE: DNA
<213> ORGANISM: Artificial Sequence
<220> FEATURE:
<223> OTHER INFORMATION: chemically synthesized

<400> SEQUENCE: 345
atacgggagc caacaccagg ttggcgtcaa aagaaataag ggatatacat tagagagcag    60
gtgtgacgga t    71

<210> SEQ ID NO 346
<211> LENGTH: 71
<212> TYPE: DNA
<213> ORGANISM: Artificial Sequence
<220> FEATURE:
<223> OTHER INFORMATION: chemically synthesized

<400> SEQUENCE: 346
atccgtcaca cctgctctct aatgtatatc ccttatttct tttgacgcca acctggtgtt    60
ggctcccgta t    71

<210> SEQ ID NO 347
<211> LENGTH: 72
<212> TYPE: DNA
<213> ORGANISM: Artificial Sequence
<220> FEATURE:
<223> OTHER INFORMATION: chemically synthesized

<400> SEQUENCE: 347
atacgggagc caacaccacg gggtccccat cgtggccgac ataacaaaaa tcctagagca    60
ggtgtgacgg at    72

<210> SEQ ID NO 348
<211> LENGTH: 72
<212> TYPE: DNA
<213> ORGANISM: Artificial Sequence
<220> FEATURE:
<223> OTHER INFORMATION: chemically synthesized

<400> SEQUENCE: 348
atccgtcaca cctgctctag gattttttgtt atgtcggcca cgatggggac cccgtggtgt    60
tggctcccgt at    72

<210> SEQ ID NO 349
<211> LENGTH: 72
<212> TYPE: DNA

```
<213> ORGANISM: Artificial Sequence
<220> FEATURE:
<223> OTHER INFORMATION: chemically synthesized

<400> SEQUENCE: 349
atacgggagc caacaccatg aggctcacag taagagaagg accttggact cgtcagagca    60
ggtgtgacgg at                                                        72

<210> SEQ ID NO 350
<211> LENGTH: 72
<212> TYPE: DNA
<213> ORGANISM: Artificial Sequence
<220> FEATURE:
<223> OTHER INFORMATION: chemically synthesized

<400> SEQUENCE: 350
atccgtcaca cctgctctga cgagtccaag gtccttctct tactgtgagc ctcatggtgt    60
tggctcccgt at                                                        72

<210> SEQ ID NO 351
<211> LENGTH: 72
<212> TYPE: DNA
<213> ORGANISM: Artificial Sequence
<220> FEATURE:
<223> OTHER INFORMATION: chemically synthesized

<400> SEQUENCE: 351
atacgggagc caacaccagc acgccctact ttaccgccga gaatatgaga atagagagca    60
ggtgtgacgg at                                                        72

<210> SEQ ID NO 352
<211> LENGTH: 72
<212> TYPE: DNA
<213> ORGANISM: Artificial Sequence
<220> FEATURE:
<223> OTHER INFORMATION: chemically synthesized

<400> SEQUENCE: 352
atccgtcaca cctgctctct attctcatat tctcggcggt aaagtagggc gtgctggtgt    60
tggctcccgt at                                                        72

<210> SEQ ID NO 353
<211> LENGTH: 72
<212> TYPE: DNA
<213> ORGANISM: Artificial Sequence
<220> FEATURE:
<223> OTHER INFORMATION: chemically synthesized

<400> SEQUENCE: 353
atacgggagc caacaccacc gatgcgggcg ccttcggcgg accgcgaggc ctcgagagca    60
ggtgtgacgg at                                                        72

<210> SEQ ID NO 354
<211> LENGTH: 72
<212> TYPE: DNA
<213> ORGANISM: Artificial Sequence
<220> FEATURE:
<223> OTHER INFORMATION: chemically synthesized

<400> SEQUENCE: 354
atccgtcaca cctgctctcg aggcctcgcg gtccgccgaa ggcgcccgca tcggtggtgt    60
tggctcccgt at                                                        72
```

<210> SEQ ID NO 355
<211> LENGTH: 72
<212> TYPE: DNA
<213> ORGANISM: Artificial Sequence
<220> FEATURE:
<223> OTHER INFORMATION: chemically synthesized

<400> SEQUENCE: 355
atacgggagc caacaccagg cgtaacgtat tgagcagaat aaataagaca cgatagagca    60
ggtgtgacgg at    72

<210> SEQ ID NO 356
<211> LENGTH: 72
<212> TYPE: DNA
<213> ORGANISM: Artificial Sequence
<220> FEATURE:
<223> OTHER INFORMATION: chemically synthesized

<400> SEQUENCE: 356
atccgtcaca cctgctctat cgtgtcttat ttattctgct caatacgtta cgcctggtgt    60
tggctcccgt at    72

<210> SEQ ID NO 357
<211> LENGTH: 72
<212> TYPE: DNA
<213> ORGANISM: Artificial Sequence
<220> FEATURE:
<223> OTHER INFORMATION: chemically synthesized

<400> SEQUENCE: 357
atacgggagc caacaccagg cggacgccga ccgggcgggc ccggtcgagg ttttagagca    60
ggtgtgacgg at    72

<210> SEQ ID NO 358
<211> LENGTH: 72
<212> TYPE: DNA
<213> ORGANISM: Artificial Sequence
<220> FEATURE:
<223> OTHER INFORMATION: chemically synthesized

<400> SEQUENCE: 358
atccgtcaca cctgctctaa aacctcgacc gggcccgccc ggtcggcgtc cgcctggtgt    60
tggctcccgt at    72

<210> SEQ ID NO 359
<211> LENGTH: 72
<212> TYPE: DNA
<213> ORGANISM: Artificial Sequence
<220> FEATURE:
<223> OTHER INFORMATION: chemically synthesized

<400> SEQUENCE: 359
atacgggagc caacaccagg cgggctcgcg cgtctcccag agccgagtca tatgagagca    60
ggtgtgacgg at    72

<210> SEQ ID NO 360
<211> LENGTH: 72
<212> TYPE: DNA
<213> ORGANISM: Artificial Sequence
<220> FEATURE:
<223> OTHER INFORMATION: chemically synthesized

<400> SEQUENCE: 360

```
atccgtcaca cctgctctca tatgactcgg ctctgggaga cgcgcgagcc cgcctggtgt    60
tggctcccgt at                                                        72
```

<210> SEQ ID NO 361
<211> LENGTH: 72
<212> TYPE: DNA
<213> ORGANISM: Artificial Sequence
<220> FEATURE:
<223> OTHER INFORMATION: chemically synthesized

<400> SEQUENCE: 361

```
atacgggagc caacaccacg taccaatccc ctcggattaa ctcgaacaac ggtaagagca    60
ggtgtgacgg at                                                        72
```

<210> SEQ ID NO 362
<211> LENGTH: 72
<212> TYPE: DNA
<213> ORGANISM: Artificial Sequence
<220> FEATURE:
<223> OTHER INFORMATION: chemically synthesized

<400> SEQUENCE: 362

```
atccgtcaca cctgctctta ccgttgttcg agttaatccg aggggattgg tacgtggtgt    60
tggctcccgt at                                                        72
```

<210> SEQ ID NO 363
<211> LENGTH: 72
<212> TYPE: DNA
<213> ORGANISM: Artificial Sequence
<220> FEATURE:
<223> OTHER INFORMATION: chemically synthesized

<400> SEQUENCE: 363

```
atacgggagc caacaccact ggtgaggcgc ctgcgccgac tggccgtccc cccgagagca    60
ggtgtgacgg at                                                        72
```

<210> SEQ ID NO 364
<211> LENGTH: 72
<212> TYPE: DNA
<213> ORGANISM: Artificial Sequence
<220> FEATURE:
<223> OTHER INFORMATION: chemically synthesized

<400> SEQUENCE: 364

```
atccgtcaca cctgctctcg gggggacggc cagtcggcgc aggcgcctca ccagtggtgt    60
tggctcccgt at                                                        72
```

<210> SEQ ID NO 365
<211> LENGTH: 71
<212> TYPE: DNA
<213> ORGANISM: Artificial Sequence
<220> FEATURE:
<223> OTHER INFORMATION: chemically synthesized

<400> SEQUENCE: 365

```
atacgggagc caacaccagc agggtggcgc gaccgaccta tttgttggct attagagcag    60
gtgtgacgga t                                                         71
```

<210> SEQ ID NO 366
<211> LENGTH: 71
<212> TYPE: DNA
<213> ORGANISM: Artificial Sequence
<220> FEATURE:

<223> OTHER INFORMATION: chemically synthesized

<400> SEQUENCE: 366

```
atccgtcaca cctgctctaa tagccaacaa ataggtcggt cgcgccaccc tgctggtgtt    60
ggctcccgta t                                                         71
```

<210> SEQ ID NO 367
<211> LENGTH: 72
<212> TYPE: DNA
<213> ORGANISM: Artificial Sequence
<220> FEATURE:
<223> OTHER INFORMATION: chemically synthesized

<400> SEQUENCE: 367

```
atacgggagc caacaccact aacaagaaga acgacacgta cagcagtact taccagagca    60
ggtgtgacgg at                                                        72
```

<210> SEQ ID NO 368
<211> LENGTH: 72
<212> TYPE: DNA
<213> ORGANISM: Artificial Sequence
<220> FEATURE:
<223> OTHER INFORMATION: chemically synthesized

<400> SEQUENCE: 368

```
atccgtcaca cctgctctgg taagtactgc tgtacgtgtc gttcttcttg ttagtggtgt    60
tggctcccgt at                                                        72
```

<210> SEQ ID NO 369
<211> LENGTH: 72
<212> TYPE: DNA
<213> ORGANISM: Artificial Sequence
<220> FEATURE:
<223> OTHER INFORMATION: chemically synthesized

<400> SEQUENCE: 369

```
atacgggagc caacaccacc acgctagcgc accaaaatct ataaaccgaa tcctagagca    60
ggtgtgacgg at                                                        72
```

<210> SEQ ID NO 370
<211> LENGTH: 72
<212> TYPE: DNA
<213> ORGANISM: Artificial Sequence
<220> FEATURE:
<223> OTHER INFORMATION: chemically synthesized

<400> SEQUENCE: 370

```
atccgtcaca cctgctctag gattcggttt atagattttg gtgcgctagc gtggtggtgt    60
tggctcccgt at                                                        72
```

<210> SEQ ID NO 371
<211> LENGTH: 62
<212> TYPE: DNA
<213> ORGANISM: Artificial Sequence
<220> FEATURE:
<223> OTHER INFORMATION: chemically synthesized

<400> SEQUENCE: 371

```
atacgggagc caacaccaga gcaggtgtga cggatagagc aggtagagca ggtgtgacgg    60
at                                                                   62
```

<210> SEQ ID NO 372

```
<211> LENGTH: 62
<212> TYPE: DNA
<213> ORGANISM: Artificial Sequence
<220> FEATURE:
<223> OTHER INFORMATION: chemically synthesized

<400> SEQUENCE: 372
atccgtcaca cctgctctac ctgctctatc cgtcacacct gctctggtgt tggctcccgt    60
at                                                                  62

<210> SEQ ID NO 373
<211> LENGTH: 72
<212> TYPE: DNA
<213> ORGANISM: Artificial Sequence
<220> FEATURE:
<223> OTHER INFORMATION: chemically synthesized

<400> SEQUENCE: 373
atacgggagc caacaccacg aaccccggt ccccggggg actatattcc tacgagagca     60
ggtgtgacgg at                                                       72

<210> SEQ ID NO 374
<211> LENGTH: 72
<212> TYPE: DNA
<213> ORGANISM: Artificial Sequence
<220> FEATURE:
<223> OTHER INFORMATION: chemically synthesized

<400> SEQUENCE: 374
atccgtcaca cctgctctcg taggaatata gtcccccggg ggaccggggg ttcgtggtgt    60
tggctcccgt at                                                       72

<210> SEQ ID NO 375
<211> LENGTH: 72
<212> TYPE: DNA
<213> ORGANISM: Artificial Sequence
<220> FEATURE:
<223> OTHER INFORMATION: chemically synthesized

<400> SEQUENCE: 375
atacgggagc caacaccaac ggagagcttc tccgcatgtg aaccgttacc ttccagagca    60
ggtgtgacgg at                                                       72

<210> SEQ ID NO 376
<211> LENGTH: 72
<212> TYPE: DNA
<213> ORGANISM: Artificial Sequence
<220> FEATURE:
<223> OTHER INFORMATION: chemically synthesized

<400> SEQUENCE: 376
atccgtcaca cctgctctgg aaggtaacgg ttcacatgcg gagaagctct ccgttggtgt    60
tggctcccgt at                                                       72

<210> SEQ ID NO 377
<211> LENGTH: 72
<212> TYPE: DNA
<213> ORGANISM: Artificial Sequence
<220> FEATURE:
<223> OTHER INFORMATION: chemically synthesized

<400> SEQUENCE: 377
atacgggagc caacaccaca tgacgggtga ctaaaagacg aaatctccca attaagagca    60
```
ggtgtgacgg at                                                           72

<210> SEQ ID NO 378
<211> LENGTH: 72
<212> TYPE: DNA
<213> ORGANISM: Artificial Sequence
<220> FEATURE:
<223> OTHER INFORMATION: chemically synthesized

<400> SEQUENCE: 378
atccgtcaca cctgctctta attgggagat ttcgtctttt agtcacccgt catgtggtgt     60
tggctcccgt at                                                           72

<210> SEQ ID NO 379
<211> LENGTH: 72
<212> TYPE: DNA
<213> ORGANISM: Artificial Sequence
<220> FEATURE:
<223> OTHER INFORMATION: chemically synthesized

<400> SEQUENCE: 379
atacgggagc caacaccacc tgagcgccgg cagcactcac tatttgtccc cgcaagagca     60
ggtgtgacgg at                                                           72

<210> SEQ ID NO 380
<211> LENGTH: 72
<212> TYPE: DNA
<213> ORGANISM: Artificial Sequence
<220> FEATURE:
<223> OTHER INFORMATION: chemically synthesized

<400> SEQUENCE: 380
atccgtcaca cctgctcttg cggggacaaa tagtgagtgc tgccggcgct caggtggtgt     60
tggctcccgt at                                                           72

<210> SEQ ID NO 381
<211> LENGTH: 72
<212> TYPE: DNA
<213> ORGANISM: Artificial Sequence
<220> FEATURE:
<223> OTHER INFORMATION: chemically synthesized

<400> SEQUENCE: 381
atacgggagc caacaccaac atcctctgct gccggccgga ttcggccgag tgccagagca     60
ggtgtgacgg at                                                           72

<210> SEQ ID NO 382
<211> LENGTH: 72
<212> TYPE: DNA
<213> ORGANISM: Artificial Sequence
<220> FEATURE:
<223> OTHER INFORMATION: chemically synthesized

<400> SEQUENCE: 382
atccgtcaca cctgctctgg cactcggccg aatccggccg gcagcagagg atgttggtgt     60
tggctcccgt at                                                           72

<210> SEQ ID NO 383
<211> LENGTH: 72
<212> TYPE: DNA
<213> ORGANISM: Artificial Sequence
<220> FEATURE:
<223> OTHER INFORMATION: chemically synthesized

```
<400> SEQUENCE: 383
atacgggagc caacaccacg ccgccccagc gtcatcggaa gtctaatcag atccagagca    60
ggtgtgacgg at                                                        72

<210> SEQ ID NO 384
<211> LENGTH: 72
<212> TYPE: DNA
<213> ORGANISM: Artificial Sequence
<220> FEATURE:
<223> OTHER INFORMATION: chemically synthesized

<400> SEQUENCE: 384
atccgtcaca cctgctctgg atctgattag acttccgatg acgctggggc ggcgtggtgt    60
tggctcccgt at                                                        72

<210> SEQ ID NO 385
<211> LENGTH: 72
<212> TYPE: DNA
<213> ORGANISM: Artificial Sequence
<220> FEATURE:
<223> OTHER INFORMATION: chemically synthesized

<400> SEQUENCE: 385
atacgggagc caacaccagg gtggcgccgg ccagcgactc ctgccttcca agctagagca    60
ggtgtgacgg at                                                        72

<210> SEQ ID NO 386
<211> LENGTH: 72
<212> TYPE: DNA
<213> ORGANISM: Artificial Sequence
<220> FEATURE:
<223> OTHER INFORMATION: chemically synthesized

<400> SEQUENCE: 386
atccgtcaca cctgctctag cttggaaggc aggagtcgct ggccggcgcc accctggtgt    60
tggctcccgt at                                                        72

<210> SEQ ID NO 387
<211> LENGTH: 72
<212> TYPE: DNA
<213> ORGANISM: Artificial Sequence
<220> FEATURE:
<223> OTHER INFORMATION: chemically synthesized

<400> SEQUENCE: 387
atacgggagc caacaccaga cgggttggat cacgcctaat tgggcccatg ttttagagca    60
ggtgtgacgg at                                                        72

<210> SEQ ID NO 388
<211> LENGTH: 72
<212> TYPE: DNA
<213> ORGANISM: Artificial Sequence
<220> FEATURE:
<223> OTHER INFORMATION: chemically synthesized

<400> SEQUENCE: 388
atccgtcaca cctgctctaa aacatgggcc caattaggcg tgatccaacc cgtctggtgt    60
tggctcccgt at                                                        72

<210> SEQ ID NO 389
<211> LENGTH: 72
<212> TYPE: DNA
```

```
<213> ORGANISM: Artificial Sequence
<220> FEATURE:
<223> OTHER INFORMATION: chemically synthesized

<400> SEQUENCE: 389
atacgggagc caacaccact ctcaagtcga agatagacga aaagatttcg ccccagagca    60
ggtgtgacgg at                                                       72

<210> SEQ ID NO 390
<211> LENGTH: 72
<212> TYPE: DNA
<213> ORGANISM: Artificial Sequence
<220> FEATURE:
<223> OTHER INFORMATION: chemically synthesized

<400> SEQUENCE: 390
atccgtcaca cctgctctgg ggcgaaatct tttcgtctat cttcgacttg agagtggtgt    60
tggctcccgt at                                                       72

<210> SEQ ID NO 391
<211> LENGTH: 72
<212> TYPE: DNA
<213> ORGANISM: Artificial Sequence
<220> FEATURE:
<223> OTHER INFORMATION: chemically synthesized

<400> SEQUENCE: 391
atacgggagc caacaccatg cgagcatcat tacttcctac catggatccg gactagagca    60
ggtgtgacgg at                                                       72

<210> SEQ ID NO 392
<211> LENGTH: 72
<212> TYPE: DNA
<213> ORGANISM: Artificial Sequence
<220> FEATURE:
<223> OTHER INFORMATION: chemically synthesized

<400> SEQUENCE: 392
atccgtcaca cctgctctag tccggatcca tggtaggaag taatgatgct cgcatggtgt    60
tggctcccgt at                                                       72

<210> SEQ ID NO 393
<211> LENGTH: 72
<212> TYPE: DNA
<213> ORGANISM: Artificial Sequence
<220> FEATURE:
<223> OTHER INFORMATION: chemically synthesized

<400> SEQUENCE: 393
atacgggagc caacaccatc ggcgaccgtt agccttccgg ctacaatcag ggccagagca    60
ggtgtgacgg at                                                       72

<210> SEQ ID NO 394
<211> LENGTH: 72
<212> TYPE: DNA
<213> ORGANISM: Artificial Sequence
<220> FEATURE:
<223> OTHER INFORMATION: chemically synthesized

<400> SEQUENCE: 394
atccgtcaca cctgctctgg ccctgattgt agccggaagg ctaacggtcg ccgatggtgt    60
tggctcccgt at                                                       72
```

```
<210> SEQ ID NO 395
<211> LENGTH: 70
<212> TYPE: DNA
<213> ORGANISM: Artificial Sequence
<220> FEATURE:
<223> OTHER INFORMATION: chemically synthesized

<400> SEQUENCE: 395
atacgggagc caacaccaga gcgggtgtga cggatatacg ggagccaaca ccagagcagg    60
tgtgacggat                                                          70

<210> SEQ ID NO 396
<211> LENGTH: 70
<212> TYPE: DNA
<213> ORGANISM: Artificial Sequence
<220> FEATURE:
<223> OTHER INFORMATION: chemically synthesized

<400> SEQUENCE: 396
atccgtcaca cctgctctgg tgttggctcc cgtatatccg tcacacccgc tctggtgttg    60
gctcccgtat                                                          70

<210> SEQ ID NO 397
<211> LENGTH: 70
<212> TYPE: DNA
<213> ORGANISM: Artificial Sequence
<220> FEATURE:
<223> OTHER INFORMATION: chemically synthesized

<400> SEQUENCE: 397
atacgggagc caacaccacc gaattgattg ataaaaaggg ttagatcgct ccagagcagg    60
tgtgacggat                                                          70

<210> SEQ ID NO 398
<211> LENGTH: 70
<212> TYPE: DNA
<213> ORGANISM: Artificial Sequence
<220> FEATURE:
<223> OTHER INFORMATION: chemically synthesized

<400> SEQUENCE: 398
atccgtcaca cctgctctgg agcgatctaa ccctttttat caatcaattc ggtggtgttg    60
gctcccgtat                                                          70

<210> SEQ ID NO 399
<211> LENGTH: 72
<212> TYPE: DNA
<213> ORGANISM: Artificial Sequence
<220> FEATURE:
<223> OTHER INFORMATION: chemically synthesized

<400> SEQUENCE: 399
atacgggagc caacaccagc agggagcaat aaaaaccatt aaaagtcagc tgacagagca    60
ggtgtgacgg at                                                       72

<210> SEQ ID NO 400
<211> LENGTH: 72
<212> TYPE: DNA
<213> ORGANISM: Artificial Sequence
<220> FEATURE:
<223> OTHER INFORMATION: chemically synthesized

<400> SEQUENCE: 400
```

```
atccgtcaca cctgctctgt cagctgactt ttaatggttt ttattgctcc ctgctggtgt    60
tggctcccgt at                                                        72
```

<210> SEQ ID NO 401
<211> LENGTH: 72
<212> TYPE: DNA
<213> ORGANISM: Artificial Sequence
<220> FEATURE:
<223> OTHER INFORMATION: chemically synthesized

<400> SEQUENCE: 401

```
atacgggagc caacaccaca ggctcacgac cccggcttgg gccgggccct ccccagagca    60
ggtgtgacgg at                                                        72
```

<210> SEQ ID NO 402
<211> LENGTH: 72
<212> TYPE: DNA
<213> ORGANISM: Artificial Sequence
<220> FEATURE:
<223> OTHER INFORMATION: chemically synthesized

<400> SEQUENCE: 402

```
atccgtcaca cctgctctgg ggagggcccg gcccaagccg gggtcgtgag cctgtggtgt    60
tggctcccgt at                                                        72
```

<210> SEQ ID NO 403
<211> LENGTH: 72
<212> TYPE: DNA
<213> ORGANISM: Artificial Sequence
<220> FEATURE:
<223> OTHER INFORMATION: chemically synthesized

<400> SEQUENCE: 403

```
atacgggagc caacaccatc ccaagtcaat acctccgaaa taagttgaat taccagagca    60
ggtgtgacgg at                                                        72
```

<210> SEQ ID NO 404
<211> LENGTH: 72
<212> TYPE: DNA
<213> ORGANISM: Artificial Sequence
<220> FEATURE:
<223> OTHER INFORMATION: chemically synthesized

<400> SEQUENCE: 404

```
atccgtcaca cctgctctgg taattcaact tatttcggag gtattgactt gggatggtgt    60
tggctcccgt at                                                        72
```

<210> SEQ ID NO 405
<211> LENGTH: 72
<212> TYPE: DNA
<213> ORGANISM: Artificial Sequence
<220> FEATURE:
<223> OTHER INFORMATION: chemically synthesized

<400> SEQUENCE: 405

```
atacgggagc caacaccagt atctggatca agagaactga aggatatttc taacagagca    60
ggtgtgacgg at                                                        72
```

<210> SEQ ID NO 406
<211> LENGTH: 72
<212> TYPE: DNA
<213> ORGANISM: Artificial Sequence
<220> FEATURE:

<223> OTHER INFORMATION: chemically synthesized

<400> SEQUENCE: 406
atccgtcaca cctgctctgt tagaaatatc cttcagttct cttgatccag atactggtgt    60
tggctcccgt at    72

<210> SEQ ID NO 407
<211> LENGTH: 72
<212> TYPE: DNA
<213> ORGANISM: Artificial Sequence
<220> FEATURE:
<223> OTHER INFORMATION: chemically synthesized

<400> SEQUENCE: 407
atacgggagc caacaccacg tgctgactat actattcaaa aacaacaccc taggagagca    60
ggtgtgacgg at    72

<210> SEQ ID NO 408
<211> LENGTH: 72
<212> TYPE: DNA
<213> ORGANISM: Artificial Sequence
<220> FEATURE:
<223> OTHER INFORMATION: chemically synthesized

<400> SEQUENCE: 408
atccgtcaca cctgctctcc tagggtgttg tttttgaata gtatagtcag cacgtggtgt    60
tggctcccgt at    72

<210> SEQ ID NO 409
<211> LENGTH: 72
<212> TYPE: DNA
<213> ORGANISM: Artificial Sequence
<220> FEATURE:
<223> OTHER INFORMATION: chemically synthesized

<400> SEQUENCE: 409
atacgggagc caacaccacg gataagaatc aataggcaat gaaagaagac cggcagagca    60
ggtgtgacgg at    72

<210> SEQ ID NO 410
<211> LENGTH: 72
<212> TYPE: DNA
<213> ORGANISM: Artificial Sequence
<220> FEATURE:
<223> OTHER INFORMATION: chemically synthesized

<400> SEQUENCE: 410
atccgtcaca cctgctctgc cggtcttctt tcattgccta ttgattctta tccgtggtgt    60
tggctcccgt at    72

<210> SEQ ID NO 411
<211> LENGTH: 72
<212> TYPE: DNA
<213> ORGANISM: Artificial Sequence
<220> FEATURE:
<223> OTHER INFORMATION: chemically synthesized

<400> SEQUENCE: 411
atacgggagc caacaccacg cgaagcgaga tccgccgtat tagcaatttg tgtgagagca    60
ggtgtgacgg at    72

<210> SEQ ID NO 412

-continued

```
<211> LENGTH: 72
<212> TYPE: DNA
<213> ORGANISM: Artificial Sequence
<220> FEATURE:
<223> OTHER INFORMATION: chemically synthesized

<400> SEQUENCE: 412
atccgtcaca cctgctctca cacaaattgc taatacggcg gatctcgctt cgcgtggtgt      60
tggctcccgt at                                                         72

<210> SEQ ID NO 413
<211> LENGTH: 72
<212> TYPE: DNA
<213> ORGANISM: Artificial Sequence
<220> FEATURE:
<223> OTHER INFORMATION: chemically synthesized

<400> SEQUENCE: 413
atacgggagc caacaccacc gaccatggag cggacccatt agatcttcaa tcctagagca      60
ggtgtgacgg at                                                         72

<210> SEQ ID NO 414
<211> LENGTH: 72
<212> TYPE: DNA
<213> ORGANISM: Artificial Sequence
<220> FEATURE:
<223> OTHER INFORMATION: chemically synthesized

<400> SEQUENCE: 414
atccgtcaca cctgctctag gattgaagat ctaatgggtc cgctccatgg tcggtggtgt      60
tggctcccgt at                                                         72

<210> SEQ ID NO 415
<211> LENGTH: 72
<212> TYPE: DNA
<213> ORGANISM: Artificial Sequence
<220> FEATURE:
<223> OTHER INFORMATION: chemically synthesized

<400> SEQUENCE: 415
atacgggagc caacaccacc ccgaccagga gccggggctc ccgcccgcct ccccagagca      60
ggtgtgacgg at                                                         72

<210> SEQ ID NO 416
<211> LENGTH: 72
<212> TYPE: DNA
<213> ORGANISM: Artificial Sequence
<220> FEATURE:
<223> OTHER INFORMATION: chemically synthesized

<400> SEQUENCE: 416
atccgtcaca cctgctctgg ggaggcgggc gggagccccg gctcctggtc ggggtggtgt      60
tggctcccgt at                                                         72

<210> SEQ ID NO 417
<211> LENGTH: 72
<212> TYPE: DNA
<213> ORGANISM: Artificial Sequence
<220> FEATURE:
<223> OTHER INFORMATION: chemically synthesized

<400> SEQUENCE: 417
atacgggagc caacaccagg cgagcggtcc acggccggcc ggaccgtcaa tggtagagca      60
```

```
ggtgtgacgg at                                                           72

<210> SEQ ID NO 418
<211> LENGTH: 72
<212> TYPE: DNA
<213> ORGANISM: Artificial Sequence
<220> FEATURE:
<223> OTHER INFORMATION: chemically synthesized

<400> SEQUENCE: 418
atccgtcaca cctgctctac cattgacggt ccggccggcc gtggaccgct cgcctggtgt       60
tggctcccgt at                                                           72

<210> SEQ ID NO 419
<211> LENGTH: 72
<212> TYPE: DNA
<213> ORGANISM: Artificial Sequence
<220> FEATURE:
<223> OTHER INFORMATION: chemically synthesized

<400> SEQUENCE: 419
atacgggagc caacaccagg aggcggacga tctccctccc ggccaaaggc gcgtagagca       60
ggtgtgacgg at                                                           72

<210> SEQ ID NO 420
<211> LENGTH: 72
<212> TYPE: DNA
<213> ORGANISM: Artificial Sequence
<220> FEATURE:
<223> OTHER INFORMATION: chemically synthesized

<400> SEQUENCE: 420
atccgtcaca cctgctctac gcgcctttgg ccgggaggga gatcgtccgc ctcctggtgt       60
tggctcccgt at                                                           72

<210> SEQ ID NO 421
<211> LENGTH: 72
<212> TYPE: DNA
<213> ORGANISM: Artificial Sequence
<220> FEATURE:
<223> OTHER INFORMATION: chemically synthesized

<400> SEQUENCE: 421
atacgggagc caacaccacg gataagaatc aataggcaat gaaagaagac cggcagagca       60
ggtgtgacgg at                                                           72

<210> SEQ ID NO 422
<211> LENGTH: 72
<212> TYPE: DNA
<213> ORGANISM: Artificial Sequence
<220> FEATURE:
<223> OTHER INFORMATION: chemically synthesized

<400> SEQUENCE: 422
atccgtcaca cctgctctgc cggtcttctt tcattgccta ttgattctta tccgtggtgt       60
tggctcccgt at                                                           72

<210> SEQ ID NO 423
<211> LENGTH: 72
<212> TYPE: DNA
<213> ORGANISM: Artificial Sequence
<220> FEATURE:
<223> OTHER INFORMATION: chemically synthesized
```

-continued

```
<400> SEQUENCE: 423
atacgggagc caacaccact gtttaataaa tgcacctgaa aaaaacgtgt gtcaagagca    60
ggtgtgacgg at                                                       72

<210> SEQ ID NO 424
<211> LENGTH: 72
<212> TYPE: DNA
<213> ORGANISM: Artificial Sequence
<220> FEATURE:
<223> OTHER INFORMATION: chemically synthesized

<400> SEQUENCE: 424
atccgtcaca cctgctcttg acacacgttt ttttcaggtg catttattaa acagtggtgt    60
tggctcccgt at                                                       72

<210> SEQ ID NO 425
<211> LENGTH: 71
<212> TYPE: DNA
<213> ORGANISM: Artificial Sequence
<220> FEATURE:
<223> OTHER INFORMATION: chemically synthesized

<400> SEQUENCE: 425
atacgggagc caacaccaag cgtctagcgg gactaagctg aaacatacca gctagagcag    60
gtgtgacgga t                                                        71

<210> SEQ ID NO 426
<211> LENGTH: 71
<212> TYPE: DNA
<213> ORGANISM: Artificial Sequence
<220> FEATURE:
<223> OTHER INFORMATION: chemically synthesized

<400> SEQUENCE: 426
atccgtcaca cctgctctag ctggtatgtt tcagcttagt cccgctagac gcttggtgtt    60
ggctcccgta t                                                        71

<210> SEQ ID NO 427
<211> LENGTH: 72
<212> TYPE: DNA
<213> ORGANISM: Artificial Sequence
<220> FEATURE:
<223> OTHER INFORMATION: chemically synthesized

<400> SEQUENCE: 427
atacgggagc caacaccagg cgaccgacac gattataacc ttgtaaaggc cgtaagagca    60
ggtgtgacgg at                                                       72

<210> SEQ ID NO 428
<211> LENGTH: 72
<212> TYPE: DNA
<213> ORGANISM: Artificial Sequence
<220> FEATURE:
<223> OTHER INFORMATION: chemically synthesized

<400> SEQUENCE: 428
atccgtcaca cctgctctta cggcctttac aaggttataa tcgtgtcggt cgcctggtgt    60
tggctcccgt at                                                       72

<210> SEQ ID NO 429
<211> LENGTH: 72
<212> TYPE: DNA
```

<213> ORGANISM: Artificial Sequence
<220> FEATURE:
<223> OTHER INFORMATION: chemically synthesized

<400> SEQUENCE: 429

| atacgggagc caacaccagt acggcggtgt ccgaactcac tatacccagt gaaagagca | 60 |
|---|---|
| ggtgtgacgg at | 72 |

<210> SEQ ID NO 430
<211> LENGTH: 72
<212> TYPE: DNA
<213> ORGANISM: Artificial Sequence
<220> FEATURE:
<223> OTHER INFORMATION: chemically synthesized

<400> SEQUENCE: 430

| atccgtcaca cctgctcttt caactgggta tagtgagttc ggacaccgcc gtactggtgt | 60 |
|---|---|
| tggctcccgt at | 72 |

<210> SEQ ID NO 431
<211> LENGTH: 72
<212> TYPE: DNA
<213> ORGANISM: Artificial Sequence
<220> FEATURE:
<223> OTHER INFORMATION: chemically synthesized

<400> SEQUENCE: 431

| atacgggagc caacaccaga cctgacaacg aaaaccccag ttgtcgccat agccagagca | 60 |
|---|---|
| ggtgtgacgg at | 72 |

<210> SEQ ID NO 432
<211> LENGTH: 72
<212> TYPE: DNA
<213> ORGANISM: Artificial Sequence
<220> FEATURE:
<223> OTHER INFORMATION: chemically synthesized

<400> SEQUENCE: 432

| atccgtcaca cctgctctgg ctatggcgac aactggggtt ttcgttgtca ggtctggtgt | 60 |
|---|---|
| tggctcccgt at | 72 |

<210> SEQ ID NO 433
<211> LENGTH: 69
<212> TYPE: DNA
<213> ORGANISM: Artificial Sequence
<220> FEATURE:
<223> OTHER INFORMATION: chemically synthesized

<400> SEQUENCE: 433

| atacgggagc caacaccata gtgttgggcc aatacggtaa cgtgtccttg gagagcaggt | 60 |
|---|---|
| gtgacggat | 69 |

<210> SEQ ID NO 434
<211> LENGTH: 69
<212> TYPE: DNA
<213> ORGANISM: Artificial Sequence
<220> FEATURE:
<223> OTHER INFORMATION: chemically synthesized

<400> SEQUENCE: 434

| atccgtcaca cctgctctcc aaggacacgt taccgtattg gcccaacact atggtgttgg | 60 |
|---|---|
| ctcccgtat | 69 |

```
<210> SEQ ID NO 435
<211> LENGTH: 72
<212> TYPE: DNA
<213> ORGANISM: Artificial Sequence
<220> FEATURE:
<223> OTHER INFORMATION: chemically synthesized

<400> SEQUENCE: 435
atacgggagc caacaccata agcgcaacac agtccatccc tgagtgagat agcgagagca      60
ggtgtgacgg at                                                         72

<210> SEQ ID NO 436
<211> LENGTH: 72
<212> TYPE: DNA
<213> ORGANISM: Artificial Sequence
<220> FEATURE:
<223> OTHER INFORMATION: chemically synthesized

<400> SEQUENCE: 436
atccgtcaca cctgctctcg ctatctcact cagggatgga ctgtgttgcg cttatggtgt      60
tggctcccgt at                                                         72

<210> SEQ ID NO 437
<211> LENGTH: 58
<212> TYPE: DNA
<213> ORGANISM: Artificial Sequence
<220> FEATURE:
<223> OTHER INFORMATION: chemically synthesized

<400> SEQUENCE: 437
atacgggagc caacaccacg cacatactag ctatctcatc agagcaggtg tgacggat        58

<210> SEQ ID NO 438
<211> LENGTH: 58
<212> TYPE: DNA
<213> ORGANISM: Artificial Sequence
<220> FEATURE:
<223> OTHER INFORMATION: chemically synthesized

<400> SEQUENCE: 438
atccgtcaca cctgctctga tgagatagct agtatgtgcg tggtgttggc tcccgtat        58

<210> SEQ ID NO 439
<211> LENGTH: 58
<212> TYPE: DNA
<213> ORGANISM: Artificial Sequence
<220> FEATURE:
<223> OTHER INFORMATION: chemically synthesized

<400> SEQUENCE: 439
atacgggagc caacaccact aacttgttgc tgatcttacc agagcaggtg tgacggat        58

<210> SEQ ID NO 440
<211> LENGTH: 58
<212> TYPE: DNA
<213> ORGANISM: Artificial Sequence
<220> FEATURE:
<223> OTHER INFORMATION: chemically synthesized

<400> SEQUENCE: 440
atccgtcaca cctgctctgg taagatcagc aacaagttag tggtgttggc tcccgtat        58

<210> SEQ ID NO 441
<211> LENGTH: 72
<212> TYPE: DNA
```

<213> ORGANISM: Artificial Sequence
<220> FEATURE:
<223> OTHER INFORMATION: chemically synthesized
<220> FEATURE:
<221> NAME/KEY: misc_feature
<222> LOCATION: (54)..(54)
<223> OTHER INFORMATION: n is a, c, g, or t

<400> SEQUENCE: 441
atacgggagc caacaccacc cgtttttgat ctaatgagga tacaatattc gtcnagagca    60
ggtgtgacgg at                                                       72

<210> SEQ ID NO 442
<211> LENGTH: 72
<212> TYPE: DNA
<213> ORGANISM: Artificial Sequence
<220> FEATURE:
<223> OTHER INFORMATION: chemically synthesized
<220> FEATURE:
<221> NAME/KEY: misc_feature
<222> LOCATION: (19)..(19)
<223> OTHER INFORMATION: n is a, c, g, or t

<400> SEQUENCE: 442
atccgtcaca cctgctctng acgaatattg tatcctcatt agatcaaaaa cgggtggtgt    60
tggctcccgt at                                                       72

<210> SEQ ID NO 443
<211> LENGTH: 72
<212> TYPE: DNA
<213> ORGANISM: Artificial Sequence
<220> FEATURE:
<223> OTHER INFORMATION: chemically synthesized

<400> SEQUENCE: 443
atacgggagc caacaccagt tgtgggaaca tcaggctaag tatgagacgg aacgagagca    60
ggtgtgacgg at                                                       72

<210> SEQ ID NO 444
<211> LENGTH: 72
<212> TYPE: DNA
<213> ORGANISM: Artificial Sequence
<220> FEATURE:
<223> OTHER INFORMATION: chemically synthesized

<400> SEQUENCE: 444
atccgtcaca cctgctctcg ttccgtctca tacttagcct gatgttccca caactggtgt    60
tggctcccgt at                                                       72

<210> SEQ ID NO 445
<211> LENGTH: 72
<212> TYPE: DNA
<213> ORGANISM: Artificial Sequence
<220> FEATURE:
<223> OTHER INFORMATION: chemically synthesized

<400> SEQUENCE: 445
atacgggagc caacaccata gacaatggcg tacttttcgt aattccacaa gaatagagca    60
ggtgtgacgg at                                                       72

<210> SEQ ID NO 446
<211> LENGTH: 72
<212> TYPE: DNA
<213> ORGANISM: Artificial Sequence
<220> FEATURE:

<223> OTHER INFORMATION: chemically synthesized

<400> SEQUENCE: 446

```
atccgtcaca cctgctctat tcttgtggaa ttacgaaaag tacgccattg tctatggtgt    60
tggctcccgt at                                                       72
```

<210> SEQ ID NO 447
<211> LENGTH: 69
<212> TYPE: DNA
<213> ORGANISM: Artificial Sequence
<220> FEATURE:
<223> OTHER INFORMATION: chemically synthesized

<400> SEQUENCE: 447

```
atacgggagc caacaccata gtgttgggcc aatacggtaa cgtgtccttg gagagcaggt    60
gtgacggat                                                           69
```

<210> SEQ ID NO 448
<211> LENGTH: 69
<212> TYPE: DNA
<213> ORGANISM: Artificial Sequence
<220> FEATURE:
<223> OTHER INFORMATION: chemically synthesized

<400> SEQUENCE: 448

```
atccgtcaca cctgctctcc aaggacacgt taccgtattg gcccaacact atggtgttgg    60
ctcccgtat                                                           69
```

<210> SEQ ID NO 449
<211> LENGTH: 58
<212> TYPE: DNA
<213> ORGANISM: Artificial Sequence
<220> FEATURE:
<223> OTHER INFORMATION: chemically synthesized

<400> SEQUENCE: 449

```
atacgggagc caacaccacc acaaaagcat tcgcccttac agagcaggtg tgacggat      58
```

<210> SEQ ID NO 450
<211> LENGTH: 58
<212> TYPE: DNA
<213> ORGANISM: Artificial Sequence
<220> FEATURE:
<223> OTHER INFORMATION: chemically synthesized

<400> SEQUENCE: 450

```
atccgtcaca cctgctctgt aagggcgaat gcttttgtgg tggtgttggc tcccgtat      58
```

<210> SEQ ID NO 451
<211> LENGTH: 72
<212> TYPE: DNA
<213> ORGANISM: Artificial Sequence
<220> FEATURE:
<223> OTHER INFORMATION: chemically synthesized

<400> SEQUENCE: 451

```
atacgggagc caacaccagc gtgtagctag tttcaggatt gtagtatgta atatagagca    60
ggtgtgacgg at                                                       72
```

<210> SEQ ID NO 452
<211> LENGTH: 72
<212> TYPE: DNA
<213> ORGANISM: Artificial Sequence
<220> FEATURE:

<223> OTHER INFORMATION: chemically synthesized

<400> SEQUENCE: 452
atccgtcaca cctgctctat attacatact acaatcctga aactagctac acgctggtgt    60
tggctcccgt at    72

<210> SEQ ID NO 453
<211> LENGTH: 58
<212> TYPE: DNA
<213> ORGANISM: Artificial Sequence
<220> FEATURE:
<223> OTHER INFORMATION: chemically synthesized

<400> SEQUENCE: 453
atacgggagc caacaccacg cacatactag ctatctcatc agagcaggtg tgacggat    58

<210> SEQ ID NO 454
<211> LENGTH: 58
<212> TYPE: DNA
<213> ORGANISM: Artificial Sequence
<220> FEATURE:
<223> OTHER INFORMATION: chemically synthesized

<400> SEQUENCE: 454
atccgtcaca cctgctctga tgagatagct agtatgtgcg tggtgttggc tcccgtat    58

<210> SEQ ID NO 455
<211> LENGTH: 72
<212> TYPE: DNA
<213> ORGANISM: Artificial Sequence
<220> FEATURE:
<223> OTHER INFORMATION: chemically synthesized

<400> SEQUENCE: 455
atacgggagc caacaccatc agagatcatc taacgaaaat catgggtctc gcccagagca    60
ggtgtgacgg at    72

<210> SEQ ID NO 456
<211> LENGTH: 72
<212> TYPE: DNA
<213> ORGANISM: Artificial Sequence
<220> FEATURE:
<223> OTHER INFORMATION: chemically synthesized

<400> SEQUENCE: 456
atccgtcaca cctgctctgg gcgagaccca tgattttcgt tagatgatct ctgatggtgt    60
tggctcccgt at    72

<210> SEQ ID NO 457
<211> LENGTH: 72
<212> TYPE: DNA
<213> ORGANISM: Artificial Sequence
<220> FEATURE:
<223> OTHER INFORMATION: chemically synthesized

<400> SEQUENCE: 457
atacgggagc caacaccagc aaagaatagt gagccctatg atcatctgtt cgtcagagca    60
ggtgtgacgg at    72

<210> SEQ ID NO 458
<211> LENGTH: 72
<212> TYPE: DNA
<213> ORGANISM: Artificial Sequence
<220> FEATURE:

<223> OTHER INFORMATION: chemically synthesized

<400> SEQUENCE: 458

```
atccgtcaca cctgctctga cgaacagatg atcatagggc tcactattct ttgctggtgt    60
tggctcccgt at                                                        72
```

<210> SEQ ID NO 459
<211> LENGTH: 72
<212> TYPE: DNA
<213> ORGANISM: Artificial Sequence
<220> FEATURE:
<223> OTHER INFORMATION: chemically synthesized

<400> SEQUENCE: 459

```
atacgggagc caacaccaga catcatgtcg catatctgga tctagaggct attcagagca    60
ggtgtgacgg at                                                        72
```

<210> SEQ ID NO 460
<211> LENGTH: 72
<212> TYPE: DNA
<213> ORGANISM: Artificial Sequence
<220> FEATURE:
<223> OTHER INFORMATION: chemically synthesized

<400> SEQUENCE: 460

```
atccgtcaca cctgctctga atagcctcta gatccagata tgcgacatga tgtctggtgt    60
tggctcccgt at                                                        72
```

<210> SEQ ID NO 461
<211> LENGTH: 69
<212> TYPE: DNA
<213> ORGANISM: Artificial Sequence
<220> FEATURE:
<223> OTHER INFORMATION: chemically synthesized

<400> SEQUENCE: 461

```
atacgggagc caacaccata gtgttgggcc aatacggtaa cgtgtacttg gagagcaggt    60
gtgacggat                                                            69
```

<210> SEQ ID NO 462
<211> LENGTH: 69
<212> TYPE: DNA
<213> ORGANISM: Artificial Sequence
<220> FEATURE:
<223> OTHER INFORMATION: chemically synthesized

<400> SEQUENCE: 462

```
atccgtcaca cctgctctcc aagtacacgt taccgtattg gcccaacact atggtgttgg    60
ctcccgtat                                                            69
```

<210> SEQ ID NO 463
<211> LENGTH: 72
<212> TYPE: DNA
<213> ORGANISM: Artificial Sequence
<220> FEATURE:
<223> OTHER INFORMATION: chemically synthesized

<400> SEQUENCE: 463

```
atacgggagc caacaccaga gagttcatgt tgcacccggg tcgtcgcgtt atgcagagca    60
ggtgtgacgg at                                                        72
```

<210> SEQ ID NO 464

```
<211> LENGTH: 72
<212> TYPE: DNA
<213> ORGANISM: Artificial Sequence
<220> FEATURE:
<223> OTHER INFORMATION: chemically synthesized

<400> SEQUENCE: 464
atccgtcaca cctgctctgc ataacgcgac gacccgggtg caacatgaac tctctggtgt      60
tggctcccgt at                                                         72

<210> SEQ ID NO 465
<211> LENGTH: 72
<212> TYPE: DNA
<213> ORGANISM: Artificial Sequence
<220> FEATURE:
<223> OTHER INFORMATION: chemically synthesized

<400> SEQUENCE: 465
atacgggagc caacaccatc tatctgaggc ctatttagca cctgttgtca ccctagagca      60
ggtgtgacgg at                                                         72

<210> SEQ ID NO 466
<211> LENGTH: 72
<212> TYPE: DNA
<213> ORGANISM: Artificial Sequence
<220> FEATURE:
<223> OTHER INFORMATION: chemically synthesized

<400> SEQUENCE: 466
atccgtcaca cctgctctag ggtgacaaca ggtgctaaat aggcctcaga tagatggtgt      60
tggctcccgt at                                                         72

<210> SEQ ID NO 467
<211> LENGTH: 72
<212> TYPE: DNA
<213> ORGANISM: Artificial Sequence
<220> FEATURE:
<223> OTHER INFORMATION: chemically synthesized

<400> SEQUENCE: 467
atacgggagc caacaccatt ctatcgttcc ggacgcttat gccttgccat ctacagagca      60
ggtgtgacgg at                                                         72

<210> SEQ ID NO 468
<211> LENGTH: 72
<212> TYPE: DNA
<213> ORGANISM: Artificial Sequence
<220> FEATURE:
<223> OTHER INFORMATION: chemically synthesized

<400> SEQUENCE: 468
atccgtcaca cctgctctgt agatggcaag gcataagcgt ccggaacgat agaatggtgt      60
tggctcccgt at                                                         72

<210> SEQ ID NO 469
<211> LENGTH: 72
<212> TYPE: DNA
<213> ORGANISM: Artificial Sequence
<220> FEATURE:
<223> OTHER INFORMATION: chemically synthesized

<400> SEQUENCE: 469
atacgggagc caacaccaca tttcgcacac ccgagcccta gagggctagg gaccagagca      60
```
ggtgtgacgg at                                                           72

<210> SEQ ID NO 470
<211> LENGTH: 72
<212> TYPE: DNA
<213> ORGANISM: Artificial Sequence
<220> FEATURE:
<223> OTHER INFORMATION: chemically synthesized

<400> SEQUENCE: 470
atccgtcaca cctgctctgg tccctagccc tctagggctc gggtgtgcga aatgtggtgt      60
tggctcccgt at                                                           72

<210> SEQ ID NO 471
<211> LENGTH: 72
<212> TYPE: DNA
<213> ORGANISM: Artificial Sequence
<220> FEATURE:
<223> OTHER INFORMATION: chemically synthesized

<400> SEQUENCE: 471
atacgggagc caacaccact ggcacgaaca atcatgaaat agggcatccg agagagagca      60
ggtgtgacgg at                                                           72

<210> SEQ ID NO 472
<211> LENGTH: 72
<212> TYPE: DNA
<213> ORGANISM: Artificial Sequence
<220> FEATURE:
<223> OTHER INFORMATION: chemically synthesized

<400> SEQUENCE: 472
atccgtcaca cctgctctct ctcggatgcc ctatttcatg attgttcgtg ccagtggtgt      60
tggctcccgt at                                                           72

<210> SEQ ID NO 473
<211> LENGTH: 72
<212> TYPE: DNA
<213> ORGANISM: Artificial Sequence
<220> FEATURE:
<223> OTHER INFORMATION: chemically synthesized

<400> SEQUENCE: 473
atacgggagc caacaccatg tgtcatggtg ggcgtggcta tccgagcaag ctctagagca      60
ggtgtgacgg at                                                           72

<210> SEQ ID NO 474
<211> LENGTH: 72
<212> TYPE: DNA
<213> ORGANISM: Artificial Sequence
<220> FEATURE:
<223> OTHER INFORMATION: chemically synthesized

<400> SEQUENCE: 474
atccgtcaca cctgctctag agcttgctcg gatagccacg cccaccatga cacatggtgt      60
tggctcccgt at                                                           72

<210> SEQ ID NO 475
<211> LENGTH: 72
<212> TYPE: DNA
<213> ORGANISM: Artificial Sequence
<220> FEATURE:
<223> OTHER INFORMATION: chemically synthesized

```
<400> SEQUENCE: 475
atacgggagc caacaccaca tgcaaataca catcatgatg acggatccta ttgtagagca      60
ggtgtgacgg at                                                          72

<210> SEQ ID NO 476
<211> LENGTH: 72
<212> TYPE: DNA
<213> ORGANISM: Artificial Sequence
<220> FEATURE:
<223> OTHER INFORMATION: chemically synthesized

<400> SEQUENCE: 476
atccgtcaca cctgctctac aataggatcc gtcatcatga tgtgtatttg catgtggtgt      60
tggctcccgt at                                                          72

<210> SEQ ID NO 477
<211> LENGTH: 72
<212> TYPE: DNA
<213> ORGANISM: Artificial Sequence
<220> FEATURE:
<223> OTHER INFORMATION: chemically synthesized

<400> SEQUENCE: 477
atacgggagc caacaccagt agagcaagct attacgcgaa gctagaatga gatcagagca      60
ggtgtgacgg at                                                          72

<210> SEQ ID NO 478
<211> LENGTH: 72
<212> TYPE: DNA
<213> ORGANISM: Artificial Sequence
<220> FEATURE:
<223> OTHER INFORMATION: chemically synthesized

<400> SEQUENCE: 478
atccgtcaca cctgctctga tctcattcta gcttcgcgta atagcttgct ctactggtgt      60
tggctcccgt at                                                          72

<210> SEQ ID NO 479
<211> LENGTH: 72
<212> TYPE: DNA
<213> ORGANISM: Artificial Sequence
<220> FEATURE:
<223> OTHER INFORMATION: chemically synthesized

<400> SEQUENCE: 479
atacgggagc caacaccacc cattggggat gcattagatg cagttgatta tgcgagagca      60
ggtgtgacgg at                                                          72

<210> SEQ ID NO 480
<211> LENGTH: 72
<212> TYPE: DNA
<213> ORGANISM: Artificial Sequence
<220> FEATURE:
<223> OTHER INFORMATION: chemically synthesized

<400> SEQUENCE: 480
atccgtcaca cctgctctcg cataatcaac tgcatctaat gcatccccaa tgggtggtgt      60
tggctcccgt at                                                          72

<210> SEQ ID NO 481
<211> LENGTH: 72
<212> TYPE: DNA
```

```
<213> ORGANISM: Artificial Sequence
<220> FEATURE:
<223> OTHER INFORMATION: chemically synthesized

<400> SEQUENCE: 481
atacgggagc caacaccata caaccgtcca agcgttactc tttacatact ctccagagca    60
ggtgtgacgg at                                                        72

<210> SEQ ID NO 482
<211> LENGTH: 72
<212> TYPE: DNA
<213> ORGANISM: Artificial Sequence
<220> FEATURE:
<223> OTHER INFORMATION: chemically synthesized

<400> SEQUENCE: 482
atccgtcaca cctgctctgg agagtatgta aagagtaacg cttggacggt tgtatggtgt    60
tggctcccgt at                                                        72

<210> SEQ ID NO 483
<211> LENGTH: 72
<212> TYPE: DNA
<213> ORGANISM: Artificial Sequence
<220> FEATURE:
<223> OTHER INFORMATION: chemically synthesized

<400> SEQUENCE: 483
atacgggagc caacaccaat tttgactgtt ccaggctcag tattggtatt caggagagca    60
ggtgtgacgg at                                                        72

<210> SEQ ID NO 484
<211> LENGTH: 72
<212> TYPE: DNA
<213> ORGANISM: Artificial Sequence
<220> FEATURE:
<223> OTHER INFORMATION: chemically synthesized

<400> SEQUENCE: 484
atccgtcaca cctgctctcc tgaataccaa tactgagcct ggaacagtca aaattggtgt    60
tggctcccgt at                                                        72

<210> SEQ ID NO 485
<211> LENGTH: 72
<212> TYPE: DNA
<213> ORGANISM: Artificial Sequence
<220> FEATURE:
<223> OTHER INFORMATION: chemically synthesized

<400> SEQUENCE: 485
atacgggagc caacaccacg aaatgatgta tctagttcct cgtgtcctga ttcgagagca    60
ggtgtgacgg at                                                        72

<210> SEQ ID NO 486
<211> LENGTH: 72
<212> TYPE: DNA
<213> ORGANISM: Artificial Sequence
<220> FEATURE:
<223> OTHER INFORMATION: chemically synthesized

<400> SEQUENCE: 486
atccgtcaca cctgctctcg aatcaggaca cgaggaacta gatacatcat ttcgtggtgt    60
tggctcccgt at                                                        72
```

```
<210> SEQ ID NO 487
<211> LENGTH: 72
<212> TYPE: DNA
<213> ORGANISM: Artificial Sequence
<220> FEATURE:
<223> OTHER INFORMATION: chemically synthesized

<400> SEQUENCE: 487
atacgggagc caacaccacc gctgcccagg tataacaccg cggtacgatc tcatagagca      60
ggtgtgacgg at                                                         72

<210> SEQ ID NO 488
<211> LENGTH: 72
<212> TYPE: DNA
<213> ORGANISM: Artificial Sequence
<220> FEATURE:
<223> OTHER INFORMATION: chemically synthesized

<400> SEQUENCE: 488
atccgtcaca cctgctctat gagatcgtac cgcggtgtta tacctgggca gcggtggtgt      60
tggctcccgt at                                                         72

<210> SEQ ID NO 489
<211> LENGTH: 72
<212> TYPE: DNA
<213> ORGANISM: Artificial Sequence
<220> FEATURE:
<223> OTHER INFORMATION: chemically synthesized

<400> SEQUENCE: 489
atacgggagc caacaccaaa gggatctgga aaaccccgta ttgatctaag gcgcagagca      60
ggtgtgacgg at                                                         72

<210> SEQ ID NO 490
<211> LENGTH: 72
<212> TYPE: DNA
<213> ORGANISM: Artificial Sequence
<220> FEATURE:
<223> OTHER INFORMATION: chemically synthesized

<400> SEQUENCE: 490
atccgtcaca cctgctctgc gccttagatc aatacggggt tttccagatc cctttggtgt      60
tggctcccgt at                                                         72

<210> SEQ ID NO 491
<211> LENGTH: 72
<212> TYPE: DNA
<213> ORGANISM: Artificial Sequence
<220> FEATURE:
<223> OTHER INFORMATION: chemically synthesized

<400> SEQUENCE: 491
atacgggagc caacaccata cccccctctt taggccatca cgttctgtcg atttagagca      60
ggtgtgacgg at                                                         72

<210> SEQ ID NO 492
<211> LENGTH: 72
<212> TYPE: DNA
<213> ORGANISM: Artificial Sequence
<220> FEATURE:
<223> OTHER INFORMATION: chemically synthesized

<400> SEQUENCE: 492
```

```
atccgtcaca cctgctctaa atcgacagaa cgtgatggcc taaagagggg ggtatggtgt    60
tggctcccgt at                                                       72

<210> SEQ ID NO 493
<211> LENGTH: 72
<212> TYPE: DNA
<213> ORGANISM: Artificial Sequence
<220> FEATURE:
<223> OTHER INFORMATION: chemically synthesized

<400> SEQUENCE: 493
atacgggagc caacaccata cccccctctt taggccatca cgttctctcg atttagagca    60
ggtgtgacgg at                                                       72

<210> SEQ ID NO 494
<211> LENGTH: 72
<212> TYPE: DNA
<213> ORGANISM: Artificial Sequence
<220> FEATURE:
<223> OTHER INFORMATION: chemically synthesized

<400> SEQUENCE: 494
atccgtcaca cctgctctaa atcgagagaa cgtgatggcc taaagagggg ggtatggtgt    60
tggctcccgt at                                                       72

<210> SEQ ID NO 495
<211> LENGTH: 72
<212> TYPE: DNA
<213> ORGANISM: Artificial Sequence
<220> FEATURE:
<223> OTHER INFORMATION: chemically synthesized

<400> SEQUENCE: 495
atacgggagc caacaccatc atggtcgcga atcaaccgta tctcagctgc cttgagagca    60
ggtgtgacgg at                                                       72

<210> SEQ ID NO 496
<211> LENGTH: 72
<212> TYPE: DNA
<213> ORGANISM: Artificial Sequence
<220> FEATURE:
<223> OTHER INFORMATION: chemically synthesized

<400> SEQUENCE: 496
atccgtcaca cctgctctca aggcagctga gatacggttg attcgcgacc atgatggtgt    60
tggctcccgt at                                                       72

<210> SEQ ID NO 497
<211> LENGTH: 72
<212> TYPE: DNA
<213> ORGANISM: Artificial Sequence
<220> FEATURE:
<223> OTHER INFORMATION: chemically synthesized

<400> SEQUENCE: 497
atacgggagc caacaccacc cgtttttgat ctaatgagga tacaatattc gtctagagca    60
ggtgtgacgg at                                                       72

<210> SEQ ID NO 498
<211> LENGTH: 72
<212> TYPE: DNA
<213> ORGANISM: Artificial Sequence
<220> FEATURE:
```

<223> OTHER INFORMATION: chemically synthesized

<400> SEQUENCE: 498
atccgtcaca cctgctctag acgaatattg tatcctcatt agatcaaaaa cggtggtgt   60 tggctcccgt at                                                       72

<210> SEQ ID NO 499
<211> LENGTH: 72
<212> TYPE: DNA
<213> ORGANISM: Artificial Sequence
<220> FEATURE:
<223> OTHER INFORMATION: chemically synthesized

<400> SEQUENCE: 499
atacgggagc caacaccata taaaaggcga acggtcactt tggtcggagt acgtagagca   60
ggtgtgacgg at                                                       72

<210> SEQ ID NO 500
<211> LENGTH: 72
<212> TYPE: DNA
<213> ORGANISM: Artificial Sequence
<220> FEATURE:
<223> OTHER INFORMATION: chemically synthesized

<400> SEQUENCE: 500
atccgtcaca cctgctctac gtactccgac caaagtgacc gttcgccttt tatatggtgt   60
tggctcccgt at                                                       72

<210> SEQ ID NO 501
<211> LENGTH: 57
<212> TYPE: DNA
<213> ORGANISM: Artificial Sequence
<220> FEATURE:
<223> OTHER INFORMATION: chemically synthesized

<400> SEQUENCE: 501
atacgggagc caacaccagt gttggcgtct tccctgatca gagcaggtgt gacggat      57

<210> SEQ ID NO 502
<211> LENGTH: 57
<212> TYPE: DNA
<213> ORGANISM: Artificial Sequence
<220> FEATURE:
<223> OTHER INFORMATION: chemically synthesized

<400> SEQUENCE: 502
atccgtcaca cctgctctga tcagggaaga cgccaacact ggtgttggct cccgtat      57

<210> SEQ ID NO 503
<211> LENGTH: 72
<212> TYPE: DNA
<213> ORGANISM: Artificial Sequence
<220> FEATURE:
<223> OTHER INFORMATION: chemically synthesized

<400> SEQUENCE: 503
atacgggagc caacaccaga ggtgagaagc ccattacacc gagcggacct gcagagagca   60
ggtgtgacgg at                                                       72

<210> SEQ ID NO 504
<211> LENGTH: 72
<212> TYPE: DNA
<213> ORGANISM: Artificial Sequence
<220> FEATURE:

<223> OTHER INFORMATION: chemically synthesized

<400> SEQUENCE: 504
atccgtcaca cctgctctct gcaggtccgc tcggtgtaat gggcttctca cctctggtgt    60
tggctcccgt at    72

<210> SEQ ID NO 505
<211> LENGTH: 72
<212> TYPE: DNA
<213> ORGANISM: Artificial Sequence
<220> FEATURE:
<223> OTHER INFORMATION: chemically synthesized

<400> SEQUENCE: 505
atacgggagc caacaccaga cgaaatcaaa tctaaaagtg ataagccaga agtcagagca    60
ggtgtgacgg at    72

<210> SEQ ID NO 506
<211> LENGTH: 72
<212> TYPE: DNA
<213> ORGANISM: Artificial Sequence
<220> FEATURE:
<223> OTHER INFORMATION: chemically synthesized

<400> SEQUENCE: 506
atccgtcaca cctgctctga cttctggctt atcacttta gatttgattt cgtctggtgt    60
tggctcccgt at    72

<210> SEQ ID NO 507
<211> LENGTH: 72
<212> TYPE: DNA
<213> ORGANISM: Artificial Sequence
<220> FEATURE:
<223> OTHER INFORMATION: chemically synthesized

<400> SEQUENCE: 507
atacgggagc caacaccacc cgttttgat ctaatgagga tacaatattc gtctagagca    60
ggtgtgacgg at    72

<210> SEQ ID NO 508
<211> LENGTH: 72
<212> TYPE: DNA
<213> ORGANISM: Artificial Sequence
<220> FEATURE:
<223> OTHER INFORMATION: chemically synthesized

<400> SEQUENCE: 508
atccgtcaca cctgctctag acgaatattg tatcctcatt agatcaaaaa cgggtggtgt    60
tggctcccgt at    72

<210> SEQ ID NO 509
<211> LENGTH: 72
<212> TYPE: DNA
<213> ORGANISM: Artificial Sequence
<220> FEATURE:
<223> OTHER INFORMATION: chemically synthesized

<400> SEQUENCE: 509
atacgggagc caacaccaac acgcagaaga gatgcattgt atgatcggtg tacgagagca    60
ggtgtgacgg at    72

<210> SEQ ID NO 510

```
<211> LENGTH: 72
<212> TYPE: DNA
<213> ORGANISM: Artificial Sequence
<220> FEATURE:
<223> OTHER INFORMATION: chemically synthesized

<400> SEQUENCE: 510
atccgtcaca cctgctctcg tacaccgatc atacaatgca tctcttctgc gtgttggtgt    60
tggctcccgt at                                                       72

<210> SEQ ID NO 511
<211> LENGTH: 72
<212> TYPE: DNA
<213> ORGANISM: Artificial Sequence
<220> FEATURE:
<223> OTHER INFORMATION: chemically synthesized

<400> SEQUENCE: 511
atacgggagc caacaccacg ccaacagtgt tttagagtca tgcacaaaag tatcagagca    60
ggtgtgacgg at                                                       72

<210> SEQ ID NO 512
<211> LENGTH: 72
<212> TYPE: DNA
<213> ORGANISM: Artificial Sequence
<220> FEATURE:
<223> OTHER INFORMATION: chemically synthesized

<400> SEQUENCE: 512
atccgtcaca cctgctctga tacttttgtg catgactcta aaacactgtt ggcgtggtgt    60
tggctcccgt at                                                       72

<210> SEQ ID NO 513
<211> LENGTH: 72
<212> TYPE: DNA
<213> ORGANISM: Artificial Sequence
<220> FEATURE:
<223> OTHER INFORMATION: chemically synthesized

<400> SEQUENCE: 513
atacgggagc caacaccagg gtggtttacg atcggcaggt cgtgcgtgcg acacagagca    60
ggtgtgacgg at                                                       72

<210> SEQ ID NO 514
<211> LENGTH: 72
<212> TYPE: DNA
<213> ORGANISM: Artificial Sequence
<220> FEATURE:
<223> OTHER INFORMATION: chemically synthesized

<400> SEQUENCE: 514
atccgtcaca cctgctctgt gtcgcacgca cgacctgccg atcgtaaacc accctggtgt    60
tggctcccgt at                                                       72

<210> SEQ ID NO 515
<211> LENGTH: 72
<212> TYPE: DNA
<213> ORGANISM: Artificial Sequence
<220> FEATURE:
<223> OTHER INFORMATION: chemically synthesized

<400> SEQUENCE: 515
atacgggagc caacaccaac ggcgacgggc gagtacacag gtgtaagtcg gggtagagca    60
```

-continued

```
ggtgtgacgg at                                                         72

<210> SEQ ID NO 516
<211> LENGTH: 72
<212> TYPE: DNA
<213> ORGANISM: Artificial Sequence
<220> FEATURE:
<223> OTHER INFORMATION: chemically synthesized

<400> SEQUENCE: 516
atccgtcaca cctgctctac cccgacttac acctgtgtac tcgcccgtcg ccgttggtgt      60
tggctcccgt at                                                         72

<210> SEQ ID NO 517
<211> LENGTH: 72
<212> TYPE: DNA
<213> ORGANISM: Artificial Sequence
<220> FEATURE:
<223> OTHER INFORMATION: chemically synthesized

<400> SEQUENCE: 517
atacgggagc caacaccaag caatagaaca cccctttgtcg cactggatgc gatgagagca    60
ggtgtgacgg at                                                         72

<210> SEQ ID NO 518
<211> LENGTH: 72
<212> TYPE: DNA
<213> ORGANISM: Artificial Sequence
<220> FEATURE:
<223> OTHER INFORMATION: chemically synthesized

<400> SEQUENCE: 518
atccgtcaca cctgctctca tcgcatccag tgcgacaaag ggtgttctat tgcttggtgt     60
tggctcccgt at                                                         72

<210> SEQ ID NO 519
<211> LENGTH: 72
<212> TYPE: DNA
<213> ORGANISM: Artificial Sequence
<220> FEATURE:
<223> OTHER INFORMATION: chemically synthesized

<400> SEQUENCE: 519
atacgggagc caacaccaca aagtgttgta agggcaaaac aaatatgtac ctcgagagca     60
ggtgtgacgg at                                                         72

<210> SEQ ID NO 520
<211> LENGTH: 72
<212> TYPE: DNA
<213> ORGANISM: Artificial Sequence
<220> FEATURE:
<223> OTHER INFORMATION: chemically synthesized

<400> SEQUENCE: 520
atccgtcaca cctgctctcg aggtacatat ttgttttgcc cttacaacac tttgtggtgt     60
tggctcccgt at                                                         72

<210> SEQ ID NO 521
<211> LENGTH: 72
<212> TYPE: DNA
<213> ORGANISM: Artificial Sequence
<220> FEATURE:
<223> OTHER INFORMATION: chemically synthesized
```

```
<400> SEQUENCE: 521
atacgggagc caacaccaag ccaaagaccc ttatcaaacg gccatgcccg gggcagagca      60
ggtgtgacgg at                                                         72

<210> SEQ ID NO 522
<211> LENGTH: 72
<212> TYPE: DNA
<213> ORGANISM: Artificial Sequence
<220> FEATURE:
<223> OTHER INFORMATION: chemically synthesized

<400> SEQUENCE: 522
atccgtcaca cctgctctgc cccgggcatg gccgtttgat aagggtcttt ggcttggtgt      60
tggctcccgt at                                                         72

<210> SEQ ID NO 523
<211> LENGTH: 72
<212> TYPE: DNA
<213> ORGANISM: Artificial Sequence
<220> FEATURE:
<223> OTHER INFORMATION: chemically synthesized

<400> SEQUENCE: 523
atacgggagc caacaccaca ttaaccccaa aggatacatg tttgtcccat cgcaagagca      60
ggtgtgacgg at                                                         72

<210> SEQ ID NO 524
<211> LENGTH: 72
<212> TYPE: DNA
<213> ORGANISM: Artificial Sequence
<220> FEATURE:
<223> OTHER INFORMATION: chemically synthesized

<400> SEQUENCE: 524
atccgtcaca cctgctcttg cgatgggaca aacatgtatc ctttggggtt aatgtggtgt      60
tggctcccgt at                                                         72

<210> SEQ ID NO 525
<211> LENGTH: 72
<212> TYPE: DNA
<213> ORGANISM: Artificial Sequence
<220> FEATURE:
<223> OTHER INFORMATION: chemically synthesized

<400> SEQUENCE: 525
atacgggagc caacaccata tcacggaccc cccaggttgc cgaattactc ttacagagca      60
ggtgtgacgg at                                                         72

<210> SEQ ID NO 526
<211> LENGTH: 72
<212> TYPE: DNA
<213> ORGANISM: Artificial Sequence
<220> FEATURE:
<223> OTHER INFORMATION: chemically synthesized

<400> SEQUENCE: 526
atccgtcaca cctgctctgt aagagtaatt cggcaacctg gggggtccgt gatatggtgt      60
tggctcccgt at                                                         72

<210> SEQ ID NO 527
<211> LENGTH: 70
<212> TYPE: DNA
```

<213> ORGANISM: Artificial Sequence
<220> FEATURE:
<223> OTHER INFORMATION: chemically synthesized

<400> SEQUENCE: 527
atacgggagc caacaccatt cccgcatcgc gcgttttcag cctttgaccg ttagagcagg    60
tgtgacggat    70

<210> SEQ ID NO 528
<211> LENGTH: 70
<212> TYPE: DNA
<213> ORGANISM: Artificial Sequence
<220> FEATURE:
<223> OTHER INFORMATION: chemically synthesized

<400> SEQUENCE: 528
atccgtcaca cctgctctaa cggtcaaagg ctgaaaacgc gcgatgcggg aatggtgttg    60
gctcccgtat    70

<210> SEQ ID NO 529
<211> LENGTH: 72
<212> TYPE: DNA
<213> ORGANISM: Artificial Sequence
<220> FEATURE:
<223> OTHER INFORMATION: chemically synthesized

<400> SEQUENCE: 529
atacgggagc caacaccaac gtgtgctgtg ttactgccct tctctgtagc cgtgagagca    60
ggtgtgacgg at    72

<210> SEQ ID NO 530
<211> LENGTH: 72
<212> TYPE: DNA
<213> ORGANISM: Artificial Sequence
<220> FEATURE:
<223> OTHER INFORMATION: chemically synthesized

<400> SEQUENCE: 530
atccgtcaca cctgctctca cggctacaga gaagggcagt aacacagcac acgttggtgt    60
tggctcccgt at    72

<210> SEQ ID NO 531
<211> LENGTH: 72
<212> TYPE: DNA
<213> ORGANISM: Artificial Sequence
<220> FEATURE:
<223> OTHER INFORMATION: chemically synthesized

<400> SEQUENCE: 531
atacgggagc caacaccacc ttttaaaacg ctagccagct tagtccattc caccagagca    60
ggtgtgacgg at    72

<210> SEQ ID NO 532
<211> LENGTH: 72
<212> TYPE: DNA
<213> ORGANISM: Artificial Sequence
<220> FEATURE:
<223> OTHER INFORMATION: chemically synthesized

<400> SEQUENCE: 532
atccgtcaca cctgctctgg tggaatggac taagctggct agcgttttaa aaggtggtgt    60
tggctcccgt at    72

<210> SEQ ID NO 533
<211> LENGTH: 72
<212> TYPE: DNA
<213> ORGANISM: Artificial Sequence
<220> FEATURE:
<223> OTHER INFORMATION: chemically synthesized

<400> SEQUENCE: 533
atacgggagc caacaccaat ctaacagatt gcagctcgcc tgtcccggcg tactagagca    60
ggtgtgacgg at    72

<210> SEQ ID NO 534
<211> LENGTH: 72
<212> TYPE: DNA
<213> ORGANISM: Artificial Sequence
<220> FEATURE:
<223> OTHER INFORMATION: chemically synthesized

<400> SEQUENCE: 534
atccgtcaca cctgctctag tacgccggga caggcgagct gcaatctgtt agattggtgt    60
tggctcccgt at    72

<210> SEQ ID NO 535
<211> LENGTH: 72
<212> TYPE: DNA
<213> ORGANISM: Artificial Sequence
<220> FEATURE:
<223> OTHER INFORMATION: chemically synthesized

<400> SEQUENCE: 535
atacgggagc caacaccacc tattacagac ccaatttcca cctggcattt ctatagagca    60
ggtgtgacgg at    72

<210> SEQ ID NO 536
<211> LENGTH: 72
<212> TYPE: DNA
<213> ORGANISM: Artificial Sequence
<220> FEATURE:
<223> OTHER INFORMATION: chemically synthesized

<400> SEQUENCE: 536
atccgtcaca cctgctctat agaaatgcca ggtggaaatt gggtctgtaa taggtggtgt    60
tggctcccgt at    72

<210> SEQ ID NO 537
<211> LENGTH: 72
<212> TYPE: DNA
<213> ORGANISM: Artificial Sequence
<220> FEATURE:
<223> OTHER INFORMATION: chemically synthesized

<400> SEQUENCE: 537
atacgggagc caacaccaca tatcctacac tcccataccc cactgtagac acgcagagca    60
ggtgtgacgg at    72

<210> SEQ ID NO 538
<211> LENGTH: 72
<212> TYPE: DNA
<213> ORGANISM: Artificial Sequence
<220> FEATURE:
<223> OTHER INFORMATION: chemically synthesized

<400> SEQUENCE: 538

```
atccgtcaca cctgctctgc gtgtctacag tggggtatgg gagtgtagga tatgtggtgt    60
tggctcccgt at                                                       72

<210> SEQ ID NO 539
<211> LENGTH: 72
<212> TYPE: DNA
<213> ORGANISM: Artificial Sequence
<220> FEATURE:
<223> OTHER INFORMATION: chemically synthesized

<400> SEQUENCE: 539
atacgggagc caacaccaaa ccgagtgctg gtggccctct ctgccatata agtgagagca    60
ggtgtgacgg at                                                       72

<210> SEQ ID NO 540
<211> LENGTH: 72
<212> TYPE: DNA
<213> ORGANISM: Artificial Sequence
<220> FEATURE:
<223> OTHER INFORMATION: chemically synthesized

<400> SEQUENCE: 540
atccgtcaca cctgctctca cttatatggc agagagggcc accagcactc ggtttggtgt    60
tggctcccgt at                                                       72

<210> SEQ ID NO 541
<211> LENGTH: 73
<212> TYPE: DNA
<213> ORGANISM: Artificial Sequence
<220> FEATURE:
<223> OTHER INFORMATION: chemically synthesized

<400> SEQUENCE: 541
atacgggagc caacaccacc ttttaaaacg ctagctagct tagtccaatt ccaccagagc    60
aggtgtgacg gat                                                      73

<210> SEQ ID NO 542
<211> LENGTH: 73
<212> TYPE: DNA
<213> ORGANISM: Artificial Sequence
<220> FEATURE:
<223> OTHER INFORMATION: chemically synthesized

<400> SEQUENCE: 542
atccgtcaca cctgctctgg tggaattgga ctaagctagc tagcgtttta aaaggtggtg    60
ttggctcccg tat                                                      73

<210> SEQ ID NO 543
<211> LENGTH: 72
<212> TYPE: DNA
<213> ORGANISM: Artificial Sequence
<220> FEATURE:
<223> OTHER INFORMATION: chemically synthesized

<400> SEQUENCE: 543
atacgggagc caacaccatg acattgcaac tatacgctta cccacgtcag ctccagagca    60
ggtgtgacgg at                                                       72

<210> SEQ ID NO 544
<211> LENGTH: 72
<212> TYPE: DNA
<213> ORGANISM: Artificial Sequence
<220> FEATURE:
```

<223> OTHER INFORMATION: chemically synthesized

<400> SEQUENCE: 544
atccgtcaca cctgctctgg agctgacgtg ggtaagcgta tagttgcaat gtcatggtgt    60
tggctcccgt at    72

<210> SEQ ID NO 545
<211> LENGTH: 72
<212> TYPE: DNA
<213> ORGANISM: Artificial Sequence
<220> FEATURE:
<223> OTHER INFORMATION: chemically synthesized

<400> SEQUENCE: 545
atacgggagc caacaccatt aacctgaaag taccagtgtc agtttaccct acctagagca    60
ggtgtgacgg at    72

<210> SEQ ID NO 546
<211> LENGTH: 72
<212> TYPE: DNA
<213> ORGANISM: Artificial Sequence
<220> FEATURE:
<223> OTHER INFORMATION: chemically synthesized

<400> SEQUENCE: 546
atccgtcaca cctgctctag gtagggtaaa ctgacactgg tactttcagg ttaatggtgt    60
tggctcccgt at    72

<210> SEQ ID NO 547
<211> LENGTH: 72
<212> TYPE: DNA
<213> ORGANISM: Artificial Sequence
<220> FEATURE:
<223> OTHER INFORMATION: chemically synthesized

<400> SEQUENCE: 547
atacgggagc caacaccagg cattagtgta aagcactaag agtcaggctg tagcagagca    60
ggtgtgacgg at    72

<210> SEQ ID NO 548
<211> LENGTH: 72
<212> TYPE: DNA
<213> ORGANISM: Artificial Sequence
<220> FEATURE:
<223> OTHER INFORMATION: chemically synthesized

<400> SEQUENCE: 548
atccgtcaca cctgctctgc tacagcctga ctcttagtgc tttacactaa tgcctggtgt    60
tggctcccgt at    72

<210> SEQ ID NO 549
<211> LENGTH: 72
<212> TYPE: DNA
<213> ORGANISM: Artificial Sequence
<220> FEATURE:
<223> OTHER INFORMATION: chemically synthesized

<400> SEQUENCE: 549
atacgggagc caacaccatg acacgccgat tatggacgtt gcgaactagt tggtagagca    60
ggtgtgacgg at    72

<210> SEQ ID NO 550

```
<211> LENGTH: 72
<212> TYPE: DNA
<213> ORGANISM: Artificial Sequence
<220> FEATURE:
<223> OTHER INFORMATION: chemically synthesized

<400> SEQUENCE: 550
atccgtcaca cctgctctac caactagttc gcaacgtcca taatcggcgt gtcatggtgt    60
tggctcccgt at                                                         72

<210> SEQ ID NO 551
<211> LENGTH: 72
<212> TYPE: DNA
<213> ORGANISM: Artificial Sequence
<220> FEATURE:
<223> OTHER INFORMATION: chemically synthesized

<400> SEQUENCE: 551
atacgggagc caacaccact caatcccacc cttatttaga gcggttacat cacaagagca    60
ggtgtgacgg at                                                         72

<210> SEQ ID NO 552
<211> LENGTH: 72
<212> TYPE: DNA
<213> ORGANISM: Artificial Sequence
<220> FEATURE:
<223> OTHER INFORMATION: chemically synthesized

<400> SEQUENCE: 552
atccgtcaca cctgctcttg tgatgtaacc gctctaaata agggtgggat tgagtggtgt    60
tggctcccgt at                                                         72

<210> SEQ ID NO 553
<211> LENGTH: 72
<212> TYPE: DNA
<213> ORGANISM: Artificial Sequence
<220> FEATURE:
<223> OTHER INFORMATION: chemically synthesized

<400> SEQUENCE: 553
atacgggagc caacaccaat ttgtgaaaat attcccgtgt tttccttgag cagcagagca    60
ggtgtgacgg at                                                         72

<210> SEQ ID NO 554
<211> LENGTH: 72
<212> TYPE: DNA
<213> ORGANISM: Artificial Sequence
<220> FEATURE:
<223> OTHER INFORMATION: chemically synthesized

<400> SEQUENCE: 554
atccgtcaca cctgctctgc tgctcaagga aaacacggga atattttcac aaattggtgt    60
tggctcccgt at                                                         72

<210> SEQ ID NO 555
<211> LENGTH: 72
<212> TYPE: DNA
<213> ORGANISM: Artificial Sequence
<220> FEATURE:
<223> OTHER INFORMATION: chemically synthesized

<400> SEQUENCE: 555
atacgggagc caacaccagc gtaaaacctt gtaccaattg atgacactag cggtagagca    60
```

```
ggtgtgacgg at                                                         72

<210> SEQ ID NO 556
<211> LENGTH: 72
<212> TYPE: DNA
<213> ORGANISM: Artificial Sequence
<220> FEATURE:
<223> OTHER INFORMATION: chemically synthesized

<400> SEQUENCE: 556
atccgtcaca cctgctctac cgctagtgtc atcaattggt acaaggtttt acgctggtgt     60
tggctcccgt at                                                         72

<210> SEQ ID NO 557
<211> LENGTH: 72
<212> TYPE: DNA
<213> ORGANISM: Artificial Sequence
<220> FEATURE:
<223> OTHER INFORMATION: chemically synthesized

<400> SEQUENCE: 557
atacgggagc caacaccaca gctcaccgcg cttgccgtgc cttacgtctg tccaagagca     60
ggtgtgacgg at                                                         72

<210> SEQ ID NO 558
<211> LENGTH: 72
<212> TYPE: DNA
<213> ORGANISM: Artificial Sequence
<220> FEATURE:
<223> OTHER INFORMATION: chemically synthesized

<400> SEQUENCE: 558
atccgtcaca cctgctcttg gacagacgta aggcacggca agcgcggtga gctgtggtgt     60
tggctcccgt at                                                         72

<210> SEQ ID NO 559
<211> LENGTH: 71
<212> TYPE: DNA
<213> ORGANISM: Artificial Sequence
<220> FEATURE:
<223> OTHER INFORMATION: chemically synthesized

<400> SEQUENCE: 559
atacgggagc caacaccatc accgtactgg agccatcgtt catccagcaa tctagagcag     60
gtgtgacgga t                                                          71

<210> SEQ ID NO 560
<211> LENGTH: 71
<212> TYPE: DNA
<213> ORGANISM: Artificial Sequence
<220> FEATURE:
<223> OTHER INFORMATION: chemically synthesized

<400> SEQUENCE: 560
atccgtcaca cctgctctag attgctggat gaacgatggc tccagtacgg tgatggtgtt     60
ggctcccgta t                                                          71

<210> SEQ ID NO 561
<211> LENGTH: 72
<212> TYPE: DNA
<213> ORGANISM: Artificial Sequence
<220> FEATURE:
<223> OTHER INFORMATION: chemically synthesized
```

```
<400> SEQUENCE: 561
atacgggagc caacaccacc tctcacatta tattgtgaat acttcgtgct gtttagagca    60
ggtgtgacgg at                                                       72

<210> SEQ ID NO 562
<211> LENGTH: 72
<212> TYPE: DNA
<213> ORGANISM: Artificial Sequence
<220> FEATURE:
<223> OTHER INFORMATION: chemically synthesized

<400> SEQUENCE: 562
atccgtcaca cctgctctaa acagcacgaa gtattcacaa tataatgtga gaggtggtgt    60
tggctcccgt at                                                       72

<210> SEQ ID NO 563
<211> LENGTH: 72
<212> TYPE: DNA
<213> ORGANISM: Artificial Sequence
<220> FEATURE:
<223> OTHER INFORMATION: chemically synthesized

<400> SEQUENCE: 563
atacgggagc caacaccagt gcttctgcct tccttatgtt ctatctgatt atctagagca    60
ggtgtgacgg at                                                       72

<210> SEQ ID NO 564
<211> LENGTH: 72
<212> TYPE: DNA
<213> ORGANISM: Artificial Sequence
<220> FEATURE:
<223> OTHER INFORMATION: chemically synthesized

<400> SEQUENCE: 564
atccgtcaca cctgctctag ataatcagat agaacataag gaaggcagaa gcactggtgt    60
tggctcccgt at                                                       72

<210> SEQ ID NO 565
<211> LENGTH: 72
<212> TYPE: DNA
<213> ORGANISM: Artificial Sequence
<220> FEATURE:
<223> OTHER INFORMATION: chemically synthesized

<400> SEQUENCE: 565
atacgggagc caacaccaaa attaacgtgt tgagatatgt ggaacctcta ctaaagagca    60
ggtgtgacgg at                                                       72

<210> SEQ ID NO 566
<211> LENGTH: 72
<212> TYPE: DNA
<213> ORGANISM: Artificial Sequence
<220> FEATURE:
<223> OTHER INFORMATION: chemically synthesized

<400> SEQUENCE: 566
atccgtcaca cctgctcttt agtagaggtt ccacatatct caacacgtta attttggtgt    60
tggctcccgt at                                                       72

<210> SEQ ID NO 567
<211> LENGTH: 72
<212> TYPE: DNA
```

<213> ORGANISM: Artificial Sequence
<220> FEATURE:
<223> OTHER INFORMATION: chemically synthesized

<400> SEQUENCE: 567
atacgggagc caacaccagt ccccattccc gtctgaatga ctgtccataa caggagagca    60
ggtgtgacgg at    72

<210> SEQ ID NO 568
<211> LENGTH: 72
<212> TYPE: DNA
<213> ORGANISM: Artificial Sequence
<220> FEATURE:
<223> OTHER INFORMATION: chemically synthesized

<400> SEQUENCE: 568
atccgtcaca cctgctctcc tgttatggac agtcattcag acgggaatgg ggactggtgt    60
tggctcccgt at    72

<210> SEQ ID NO 569
<211> LENGTH: 72
<212> TYPE: DNA
<213> ORGANISM: Artificial Sequence
<220> FEATURE:
<223> OTHER INFORMATION: chemically synthesized

<400> SEQUENCE: 569
atacgggagc caacaccacc tgaatactaa cactaagacc cgacttgtgt tcacagagca    60
ggtgtgacgg at    72

<210> SEQ ID NO 570
<211> LENGTH: 72
<212> TYPE: DNA
<213> ORGANISM: Artificial Sequence
<220> FEATURE:
<223> OTHER INFORMATION: chemically synthesized

<400> SEQUENCE: 570
atccgtcaca cctgctctgt gaacacaagt cgggtcttag tgttagtatt caggtggtgt    60
tggctcccgt at    72

<210> SEQ ID NO 571
<211> LENGTH: 72
<212> TYPE: DNA
<213> ORGANISM: Artificial Sequence
<220> FEATURE:
<223> OTHER INFORMATION: chemically synthesized

<400> SEQUENCE: 571
atacgggagc caacaccagc taggatgtca ccaccggtca cttcatgtcg agacagagca    60
ggtgtgacgg at    72

<210> SEQ ID NO 572
<211> LENGTH: 72
<212> TYPE: DNA
<213> ORGANISM: Artificial Sequence
<220> FEATURE:
<223> OTHER INFORMATION: chemically synthesized

<400> SEQUENCE: 572
atccgtcaca cctgctctgt ctcgacatga agtgaccggt ggtgacatcc tagctggtgt    60
tggctcccgt at    72

<210> SEQ ID NO 573
<211> LENGTH: 72
<212> TYPE: DNA
<213> ORGANISM: Artificial Sequence
<220> FEATURE:
<223> OTHER INFORMATION: chemically synthesized

<400> SEQUENCE: 573
atacgggagc caacaccata actattggcc tcgagccgct ccagtcatca tcctagagca    60
ggtgtgacgg at    72

<210> SEQ ID NO 574
<211> LENGTH: 72
<212> TYPE: DNA
<213> ORGANISM: Artificial Sequence
<220> FEATURE:
<223> OTHER INFORMATION: chemically synthesized

<400> SEQUENCE: 574
atccgtcaca cctgctctag gatgatgact ggagcggctc gaggccaata gttatggtgt    60
tggctcccgt at    72

<210> SEQ ID NO 575
<211> LENGTH: 72
<212> TYPE: DNA
<213> ORGANISM: Artificial Sequence
<220> FEATURE:
<223> OTHER INFORMATION: chemically synthesized

<400> SEQUENCE: 575
atacgggagc caacaccaga gcttgctttt cttacgtcgt tgccgggagc cggaagagca    60
ggtgtgacgg at    72

<210> SEQ ID NO 576
<211> LENGTH: 72
<212> TYPE: DNA
<213> ORGANISM: Artificial Sequence
<220> FEATURE:
<223> OTHER INFORMATION: chemically synthesized

<400> SEQUENCE: 576
atccgtcaca cctgctcttc cggctcccgg caacgacgta agaaaagcaa gctctggtgt    60
tggctcccgt at    72

<210> SEQ ID NO 577
<211> LENGTH: 72
<212> TYPE: DNA
<213> ORGANISM: Artificial Sequence
<220> FEATURE:
<223> OTHER INFORMATION: chemically synthesized

<400> SEQUENCE: 577
atacgggagc caacaccacc ggggacacta tacattctct agacaatata gtttagagca    60
ggtgtgacgg at    72

<210> SEQ ID NO 578
<211> LENGTH: 72
<212> TYPE: DNA
<213> ORGANISM: Artificial Sequence
<220> FEATURE:
<223> OTHER INFORMATION: chemically synthesized

<400> SEQUENCE: 578

```
atccgtcaca cctgctctaa actatattgt ctagagaatg tatagtgtcc ccgtggtgt    60 tggctcccgt at                                                       72
```

<210> SEQ ID NO 579
<211> LENGTH: 72
<212> TYPE: DNA
<213> ORGANISM: Artificial Sequence
<220> FEATURE:
<223> OTHER INFORMATION: chemically synthesized

<400> SEQUENCE: 579

```
atacgggagc caacaccaga tagttgtcct gcatatgttg tcgtgtgcta atgtagagca    60
ggtgtgacgg at                                                        72
```

<210> SEQ ID NO 580
<211> LENGTH: 72
<212> TYPE: DNA
<213> ORGANISM: Artificial Sequence
<220> FEATURE:
<223> OTHER INFORMATION: chemically synthesized

<400> SEQUENCE: 580

```
atccgtcaca cctgctctac attagcacac gacaacatat gcaggacaac tatctggtgt    60
tggctcccgt at                                                        72
```

<210> SEQ ID NO 581
<211> LENGTH: 72
<212> TYPE: DNA
<213> ORGANISM: Artificial Sequence
<220> FEATURE:
<223> OTHER INFORMATION: chemically synthesized

<400> SEQUENCE: 581

```
atacgggagc caacaccaac tctacagcct aatctgcact ttacaggata cgtcagagca    60
ggtgtgacgg at                                                        72
```

<210> SEQ ID NO 582
<211> LENGTH: 72
<212> TYPE: DNA
<213> ORGANISM: Artificial Sequence
<220> FEATURE:
<223> OTHER INFORMATION: chemically synthesized

<400> SEQUENCE: 582

```
atccgtcaca cctgctctga cgtatcctgt aaagtgcaga ttaggctgta gagttggtgt    60
tggctcccgt at                                                        72
```

<210> SEQ ID NO 583
<211> LENGTH: 72
<212> TYPE: DNA
<213> ORGANISM: Artificial Sequence
<220> FEATURE:
<223> OTHER INFORMATION: chemically synthesized

<400> SEQUENCE: 583

```
atacgggagc caacaccacg cacgtggtct acacggccac ctattctcat ttgtagagca    60
ggtgtgacgg at                                                        72
```

<210> SEQ ID NO 584
<211> LENGTH: 72
<212> TYPE: DNA
<213> ORGANISM: Artificial Sequence
<220> FEATURE:

-continued

<223> OTHER INFORMATION: chemically synthesized

<400> SEQUENCE: 584
atccgtcaca cctgctctac aaatgagaat aggtggccgt gtagaccacg tgcgtggtgt    60
tggctcccgt at                                                        72

<210> SEQ ID NO 585
<211> LENGTH: 72
<212> TYPE: DNA
<213> ORGANISM: Artificial Sequence
<220> FEATURE:
<223> OTHER INFORMATION: chemically synthesized

<400> SEQUENCE: 585
atacgggagc caacaccatc ctctgttctt cacgcgggag cactttctat ctttagagca    60
ggtgtgacgg at                                                        72

<210> SEQ ID NO 586
<211> LENGTH: 72
<212> TYPE: DNA
<213> ORGANISM: Artificial Sequence
<220> FEATURE:
<223> OTHER INFORMATION: chemically synthesized

<400> SEQUENCE: 586
atccgtcaca cctgctctaa agatagaaag tgctcccgcg tgaagaacag aggatggtgt    60
tggctcccgt at                                                        72

<210> SEQ ID NO 587
<211> LENGTH: 72
<212> TYPE: DNA
<213> ORGANISM: Artificial Sequence
<220> FEATURE:
<223> OTHER INFORMATION: chemically synthesized

<400> SEQUENCE: 587
atacgggagc caacaccatc aatggcaagt tgttccatat tgaccatggt tcacagagca    60
ggtgtgacgg at                                                        72

<210> SEQ ID NO 588
<211> LENGTH: 72
<212> TYPE: DNA
<213> ORGANISM: Artificial Sequence
<220> FEATURE:
<223> OTHER INFORMATION: chemically synthesized

<400> SEQUENCE: 588
atccgtcaca cctgctctgt gaaccatggt caatatggaa caacttgcca ttgatggtgt    60
tggctcccgt at                                                        72

<210> SEQ ID NO 589
<211> LENGTH: 72
<212> TYPE: DNA
<213> ORGANISM: Artificial Sequence
<220> FEATURE:
<223> OTHER INFORMATION: chemically synthesized

<400> SEQUENCE: 589
atacgggagc caacaccaca ctaccgtccc accccctccc agctcctccg gccgagagca    60
ggtgtgacgg at                                                        72

<210> SEQ ID NO 590

```
<211> LENGTH: 72
<212> TYPE: DNA
<213> ORGANISM: Artificial Sequence
<220> FEATURE:
<223> OTHER INFORMATION: chemically synthesized

<400> SEQUENCE: 590
atccgtcaca cctgctctcg gccggaggag ctgggagggg gtgggacggt agtgtggtgt     60
tggctcccgt at                                                        72

<210> SEQ ID NO 591
<211> LENGTH: 72
<212> TYPE: DNA
<213> ORGANISM: Artificial Sequence
<220> FEATURE:
<223> OTHER INFORMATION: chemically synthesized

<400> SEQUENCE: 591
atacgggagc caacaccact caagtagtcc catacaccac gcaagcctct ctctagagca     60
ggtgtgacgg at                                                        72

<210> SEQ ID NO 592
<211> LENGTH: 72
<212> TYPE: DNA
<213> ORGANISM: Artificial Sequence
<220> FEATURE:
<223> OTHER INFORMATION: chemically synthesized

<400> SEQUENCE: 592
atccgtcaca cctgctctag agagaggctt gcgtggtgta tgggactact tgagtggtgt     60
tggctcccgt at                                                        72

<210> SEQ ID NO 593
<211> LENGTH: 72
<212> TYPE: DNA
<213> ORGANISM: Artificial Sequence
<220> FEATURE:
<223> OTHER INFORMATION: chemically synthesized

<400> SEQUENCE: 593
atacgggagc caacaccaat cttactagtt tgggaaaaaa attaaatata agcaagagca     60
ggtgtgacgg at                                                        72

<210> SEQ ID NO 594
<211> LENGTH: 72
<212> TYPE: DNA
<213> ORGANISM: Artificial Sequence
<220> FEATURE:
<223> OTHER INFORMATION: chemically synthesized

<400> SEQUENCE: 594
atccgtcaca cctgctcttg cttatattta attttttttcc caaactagta agattggtgt     60
tggctcccgt at                                                        72

<210> SEQ ID NO 595
<211> LENGTH: 72
<212> TYPE: DNA
<213> ORGANISM: Artificial Sequence
<220> FEATURE:
<223> OTHER INFORMATION: chemically synthesized

<400> SEQUENCE: 595
atacgggagc caacaccaca ctaccgtccc accccctccc agctcctccg gccgagagca     60
```

-continued ggtgtgacgg at                                                            72

<210> SEQ ID NO 596
<211> LENGTH: 72
<212> TYPE: DNA
<213> ORGANISM: Artificial Sequence
<220> FEATURE:
<223> OTHER INFORMATION: chemically synthesized

<400> SEQUENCE: 596
atccgtcaca cctgctctcg gccggaggag ctgggagggg gtgggacggt agtgtggtgt      60
tggctcccgt at                                                            72

<210> SEQ ID NO 597
<211> LENGTH: 72
<212> TYPE: DNA
<213> ORGANISM: Artificial Sequence
<220> FEATURE:
<223> OTHER INFORMATION: chemically synthesized

<400> SEQUENCE: 597
atacgggagc caacaccagc ctagctcgct cccaaaagag tccacgcccc ggatagagca      60
ggtgtgacgg at                                                            72

<210> SEQ ID NO 598
<211> LENGTH: 72
<212> TYPE: DNA
<213> ORGANISM: Artificial Sequence
<220> FEATURE:
<223> OTHER INFORMATION: chemically synthesized

<400> SEQUENCE: 598
atccgtcaca cctgctctat ccggggcgtg gactcttttg ggagcgagct aggctggtgt      60
tggctcccgt at                                                            72

<210> SEQ ID NO 599
<211> LENGTH: 72
<212> TYPE: DNA
<213> ORGANISM: Artificial Sequence
<220> FEATURE:
<223> OTHER INFORMATION: chemically synthesized

<400> SEQUENCE: 599
atacgggagc caacaccaac aaatttccag cgctatgggc cctaattacc actaagagca      60
ggtgtgacgg at                                                            72

<210> SEQ ID NO 600
<211> LENGTH: 72
<212> TYPE: DNA
<213> ORGANISM: Artificial Sequence
<220> FEATURE:
<223> OTHER INFORMATION: chemically synthesized

<400> SEQUENCE: 600
atccgtcaca cctgctctta gtggtaatta gggcccatag cgctggaaat ttgttggtgt      60
tggctcccgt at                                                            72

<210> SEQ ID NO 601
<211> LENGTH: 72
<212> TYPE: DNA
<213> ORGANISM: Artificial Sequence
<220> FEATURE:
<223> OTHER INFORMATION: chemically synthesized

```
<400> SEQUENCE: 601
atacgggagc caacaccacc tgccttacac ctttacactt ccgataaatt gccgagagca    60
ggtgtgacgg at                                                        72

<210> SEQ ID NO 602
<211> LENGTH: 72
<212> TYPE: DNA
<213> ORGANISM: Artificial Sequence
<220> FEATURE:
<223> OTHER INFORMATION: chemically synthesized

<400> SEQUENCE: 602
atccgtcaca cctgctctcg gcaatttatc ggaagtgtaa aggtgtaagg caggtggtgt    60
tggctcccgt at                                                        72

<210> SEQ ID NO 603
<211> LENGTH: 72
<212> TYPE: DNA
<213> ORGANISM: Artificial Sequence
<220> FEATURE:
<223> OTHER INFORMATION: chemically synthesized

<400> SEQUENCE: 603
atacgggagc caacaccata aagtcaattc caacgcagac catcctcacc cccaagagca    60
ggtgtgacgg at                                                        72

<210> SEQ ID NO 604
<211> LENGTH: 72
<212> TYPE: DNA
<213> ORGANISM: Artificial Sequence
<220> FEATURE:
<223> OTHER INFORMATION: chemically synthesized

<400> SEQUENCE: 604
atccgtcaca cctgctcttg ggggtgagga tggtctgcgt tggaattgac tttatggtgt    60
tggctcccgt at                                                        72

<210> SEQ ID NO 605
<211> LENGTH: 71
<212> TYPE: DNA
<213> ORGANISM: Artificial Sequence
<220> FEATURE:
<223> OTHER INFORMATION: chemically synthesized

<400> SEQUENCE: 605
atacgggagc caacaccaaa ggacgccccc cttcgtcccg cgctcggtag caaagagcag    60
gtgtgacgga t                                                         71

<210> SEQ ID NO 606
<211> LENGTH: 71
<212> TYPE: DNA
<213> ORGANISM: Artificial Sequence
<220> FEATURE:
<223> OTHER INFORMATION: chemically synthesized

<400> SEQUENCE: 606
atccgtcaca cctgctcttt gctaccgagc gcgggacgaa gggggggcgtc ctttggtgtt    60 ggctcccgta t                                                         71

<210> SEQ ID NO 607
<211> LENGTH: 72
<212> TYPE: DNA
```

<213> ORGANISM: Artificial Sequence
<220> FEATURE:
<223> OTHER INFORMATION: chemically synthesized

<400> SEQUENCE: 607

```
atacgggagc caacaccatg tcccttgggc acacacaacc aatccccact ctccagagca    60
ggtgtgacgg at                                                        72
```

<210> SEQ ID NO 608
<211> LENGTH: 72
<212> TYPE: DNA
<213> ORGANISM: Artificial Sequence
<220> FEATURE:
<223> OTHER INFORMATION: chemically synthesized

<400> SEQUENCE: 608

```
atccgtcaca cctgctctgg agagtgggga ttggttgtgt gtgcccaagg gacatggtgt    60
tggctcccgt at                                                        72
```

<210> SEQ ID NO 609
<211> LENGTH: 72
<212> TYPE: DNA
<213> ORGANISM: Artificial Sequence
<220> FEATURE:
<223> OTHER INFORMATION: chemically synthesized

<400> SEQUENCE: 609

```
atacgggagc caacaccacc ctgctggctt cggtccgttt catggtctgc aagcagagca    60
ggtgtgacgg at                                                        72
```

<210> SEQ ID NO 610
<211> LENGTH: 72
<212> TYPE: DNA
<213> ORGANISM: Artificial Sequence
<220> FEATURE:
<223> OTHER INFORMATION: chemically synthesized

<400> SEQUENCE: 610

```
atccgtcaca cctgctctgc ttgcagacca tgaaacggac cgaagccagc agggtggtgt    60
tggctcccgt at                                                        72
```

<210> SEQ ID NO 611
<211> LENGTH: 72
<212> TYPE: DNA
<213> ORGANISM: Artificial Sequence
<220> FEATURE:
<223> OTHER INFORMATION: chemically synthesized

<400> SEQUENCE: 611

```
atacgggagc caacaccaca ctaccgtccc acccctccc agctcctccg gccgagagca     60
ggtgtgacgg ag                                                        72
```

<210> SEQ ID NO 612
<211> LENGTH: 72
<212> TYPE: DNA
<213> ORGANISM: Artificial Sequence
<220> FEATURE:
<223> OTHER INFORMATION: chemically synthesized

<400> SEQUENCE: 612

```
atccgtcaca cctgctctcg gccggaggag ctgggagggg gtgggacggt agtgtggtgt    60
tggctcccgt at                                                        72
```

<210> SEQ ID NO 613
<211> LENGTH: 72
<212> TYPE: DNA
<213> ORGANISM: Artificial Sequence
<220> FEATURE:
<223> OTHER INFORMATION: chemically synthesized

<400> SEQUENCE: 613
atacgggagc caacaccatg ctgcgggacc gccatctacc tgttcatgtg tctgagagca    60
ggtgtgacgg at    72

<210> SEQ ID NO 614
<211> LENGTH: 72
<212> TYPE: DNA
<213> ORGANISM: Artificial Sequence
<220> FEATURE:
<223> OTHER INFORMATION: chemically synthesized

<400> SEQUENCE: 614
atccgtcaca cctgctctca gacacatgaa caggtagatg gcggtcccgc agcatggtgt    60
tggctcccgt at    72

<210> SEQ ID NO 615
<211> LENGTH: 71
<212> TYPE: DNA
<213> ORGANISM: Artificial Sequence
<220> FEATURE:
<223> OTHER INFORMATION: chemically synthesized

<400> SEQUENCE: 615
atacgggagc caacaccagg atgcggctta cattacgcct gtttgtcatc tggagagcag    60
gtgtgacgga t    71

<210> SEQ ID NO 616
<211> LENGTH: 71
<212> TYPE: DNA
<213> ORGANISM: Artificial Sequence
<220> FEATURE:
<223> OTHER INFORMATION: chemically synthesized

<400> SEQUENCE: 616
atccgtcaca cctgctctcc agatgacaaa caggcgtaat gtaagccgca tcctggtgtt    60
ggctcccgta t    71

<210> SEQ ID NO 617
<211> LENGTH: 72
<212> TYPE: DNA
<213> ORGANISM: Artificial Sequence
<220> FEATURE:
<223> OTHER INFORMATION: chemically synthesized

<400> SEQUENCE: 617
atacgggagc caacaccagt gccctggaga cggactgtcg gggatcgttc actcagagca    60
ggtgtgacgg at    72

<210> SEQ ID NO 618
<211> LENGTH: 72
<212> TYPE: DNA
<213> ORGANISM: Artificial Sequence
<220> FEATURE:
<223> OTHER INFORMATION: chemically synthesized

<400> SEQUENCE: 618

```
atccgtcaca cctgctctga gtgaacgatc cccgacagtc cgtctccagg gcactggtgt    60
tggctcccgt at                                                        72
```

<210> SEQ ID NO 619
<211> LENGTH: 72
<212> TYPE: DNA
<213> ORGANISM: Artificial Sequence
<220> FEATURE:
<223> OTHER INFORMATION: chemically synthesized

<400> SEQUENCE: 619

```
atacgggagc caacaccata ttctgcctgg agatctagtc ccctgctctc ccacagagca    60
ggtgtgacgg at                                                        72
```

<210> SEQ ID NO 620
<211> LENGTH: 72
<212> TYPE: DNA
<213> ORGANISM: Artificial Sequence
<220> FEATURE:
<223> OTHER INFORMATION: chemically synthesized

<400> SEQUENCE: 620

```
atccgtcaca cctgctctgt gggagagcag gggactagat ctccaggcag aatatggtgt    60
tggctcccgt at                                                        72
```

<210> SEQ ID NO 621
<211> LENGTH: 72
<212> TYPE: DNA
<213> ORGANISM: Artificial Sequence
<220> FEATURE:
<223> OTHER INFORMATION: chemically synthesized

<400> SEQUENCE: 621

```
atacgggagc caacaccatc aagggcttca ctcataaatt attaatgtgt ccccagagca    60
ggtgtgacgg at                                                        72
```

<210> SEQ ID NO 622
<211> LENGTH: 72
<212> TYPE: DNA
<213> ORGANISM: Artificial Sequence
<220> FEATURE:
<223> OTHER INFORMATION: chemically synthesized

<400> SEQUENCE: 622

```
atccgtcaca cctgctctgg ggacacatta ataatttatg agtgaagccc ttgatggtgt    60
tggctcccgt at                                                        72
```

<210> SEQ ID NO 623
<211> LENGTH: 72
<212> TYPE: DNA
<213> ORGANISM: Artificial Sequence
<220> FEATURE:
<223> OTHER INFORMATION: chemically synthesized

<400> SEQUENCE: 623

```
atacgggagc caacaccacc cactctcccc ccgctcccgc tcctccgctc cgcgagagca    60
ggtgtgacgg at                                                        72
```

<210> SEQ ID NO 624
<211> LENGTH: 72
<212> TYPE: DNA
<213> ORGANISM: Artificial Sequence
<220> FEATURE:

<223> OTHER INFORMATION: chemically synthesized

<400> SEQUENCE: 624
atccgtcaca cctgctctcg cggagcggag gagcgggagc ggggggagag tgggtggtgt    60
tggctcccgt at    72

<210> SEQ ID NO 625
<211> LENGTH: 72
<212> TYPE: DNA
<213> ORGANISM: Artificial Sequence
<220> FEATURE:
<223> OTHER INFORMATION: chemically synthesized

<400> SEQUENCE: 625
atacgggagc caacaccata tctatgtact accacaatca agttcttcct cactagagca    60
ggtgtgacgg at    72

<210> SEQ ID NO 626
<211> LENGTH: 72
<212> TYPE: DNA
<213> ORGANISM: Artificial Sequence
<220> FEATURE:
<223> OTHER INFORMATION: chemically synthesized

<400> SEQUENCE: 626
atccgtcaca cctgctctag tgaggaagaa cttgattgtg gtagtacata gatatggtgt    60
tggctcccgt at    72

<210> SEQ ID NO 627
<211> LENGTH: 72
<212> TYPE: DNA
<213> ORGANISM: Artificial Sequence
<220> FEATURE:
<223> OTHER INFORMATION: chemically synthesized

<400> SEQUENCE: 627
atacgggagc caacaccacc ttttaaaacg ctagctagct tagtccattc caccagagca    60
ggtgtgacgg at    72

<210> SEQ ID NO 628
<211> LENGTH: 72
<212> TYPE: DNA
<213> ORGANISM: Artificial Sequence
<220> FEATURE:
<223> OTHER INFORMATION: chemically synthesized

<400> SEQUENCE: 628
atccgtcaca cctgctctgg tggaatggac taagctagct agcgttttaa aaggtggtgt    60
tggctcccgt at    72

<210> SEQ ID NO 629
<211> LENGTH: 72
<212> TYPE: DNA
<213> ORGANISM: Artificial Sequence
<220> FEATURE:
<223> OTHER INFORMATION: chemically synthesized

<400> SEQUENCE: 629
atacgggagc caacaccatt agtgatcggt ggctcaaact tacgctcgct ccgaagagca    60
ggtgtgacgg at    72

<210> SEQ ID NO 630

```
<211> LENGTH: 72
<212> TYPE: DNA
<213> ORGANISM: Artificial Sequence
<220> FEATURE:
<223> OTHER INFORMATION: chemically synthesized

<400> SEQUENCE: 630
atccgtcaca cctgctcttc ggagcgagcg taagtttgag ccaccgatca ctaatggtgt    60
tggctcccgt at                                                       72

<210> SEQ ID NO 631
<211> LENGTH: 72
<212> TYPE: DNA
<213> ORGANISM: Artificial Sequence
<220> FEATURE:
<223> OTHER INFORMATION: chemically synthesized

<400> SEQUENCE: 631
atacgggagc caacaccagt cgtggttcgc cgtttactga cgttccagtt gccaagagca    60
ggtgtgacgg at                                                       72

<210> SEQ ID NO 632
<211> LENGTH: 72
<212> TYPE: DNA
<213> ORGANISM: Artificial Sequence
<220> FEATURE:
<223> OTHER INFORMATION: chemically synthesized

<400> SEQUENCE: 632
atccgtcaca cctgctcttg gcaactggaa cgtcagtaaa cggcgaacca cgactggtgt    60
tggctcccgt at                                                       72

<210> SEQ ID NO 633
<211> LENGTH: 72
<212> TYPE: DNA
<213> ORGANISM: Artificial Sequence
<220> FEATURE:
<223> OTHER INFORMATION: chemically synthesized

<400> SEQUENCE: 633
atacgggagc caacaccaat ggttttccta cgacaagaat agaaaaattg ccgaagagca    60
ggtgtgacgg at                                                       72

<210> SEQ ID NO 634
<211> LENGTH: 72
<212> TYPE: DNA
<213> ORGANISM: Artificial Sequence
<220> FEATURE:
<223> OTHER INFORMATION: chemically synthesized

<400> SEQUENCE: 634
atccgtcaca cctgctcttc ggcaattttt ctattcttgt cgtaggaaaa ccattggtgt    60
tggctcccgt at                                                       72

<210> SEQ ID NO 635
<211> LENGTH: 72
<212> TYPE: DNA
<213> ORGANISM: Artificial Sequence
<220> FEATURE:
<223> OTHER INFORMATION: chemically synthesized

<400> SEQUENCE: 635
atacgggagc caacaccact tcatcttctg tactttattt ggcagacccc tcccagagca    60
```

```
ggtgtgacgg at                                                            72

<210> SEQ ID NO 636
<211> LENGTH: 72
<212> TYPE: DNA
<213> ORGANISM: Artificial Sequence
<220> FEATURE:
<223> OTHER INFORMATION: chemically synthesized

<400> SEQUENCE: 636
atccgtcaca cctgctctgg gagggtctg ccaaataaag tacagaagat gaagtggtgt         60
tggctcccgt at                                                            72

<210> SEQ ID NO 637
<211> LENGTH: 71
<212> TYPE: DNA
<213> ORGANISM: Artificial Sequence
<220> FEATURE:
<223> OTHER INFORMATION: chemically synthesized

<400> SEQUENCE: 637
atacgggagc caacaccacc ttttaaaacg ctagctagct tatccattcc accagagcag        60
gtgtgacgga t                                                             71

<210> SEQ ID NO 638
<211> LENGTH: 71
<212> TYPE: DNA
<213> ORGANISM: Artificial Sequence
<220> FEATURE:
<223> OTHER INFORMATION: chemically synthesized

<400> SEQUENCE: 638
atccgtcaca cctgctctgg tggaatggat aagctagcta gcgttttaaa aggtggtgtt        60
ggctcccgta t                                                             71

<210> SEQ ID NO 639
<211> LENGTH: 72
<212> TYPE: DNA
<213> ORGANISM: Artificial Sequence
<220> FEATURE:
<223> OTHER INFORMATION: chemically synthesized

<400> SEQUENCE: 639
atacgggagc caacaccaga tagtgttcca ccttatacgg agccccctca ctgaagagca        60
ggtgtgacgg at                                                            72

<210> SEQ ID NO 640
<211> LENGTH: 72
<212> TYPE: DNA
<213> ORGANISM: Artificial Sequence
<220> FEATURE:
<223> OTHER INFORMATION: chemically synthesized

<400> SEQUENCE: 640
atccgtcaca cctgctcttc agtgaggggg ctccgtataa ggtggaacac tatctggtgt        60
tggctcccgt at                                                            72

<210> SEQ ID NO 641
<211> LENGTH: 72
<212> TYPE: DNA
<213> ORGANISM: Artificial Sequence
<220> FEATURE:
<223> OTHER INFORMATION: chemically synthesized
```

```
<400> SEQUENCE: 641
atacgggagc caacaccaac gcacatcagg agaatgaaga actcaccccc ccccagagca    60
ggtgtgacgg at                                                       72

<210> SEQ ID NO 642
<211> LENGTH: 72
<212> TYPE: DNA
<213> ORGANISM: Artificial Sequence
<220> FEATURE:
<223> OTHER INFORMATION: chemically synthesized

<400> SEQUENCE: 642
atccgtcaca cctgctctgg ggggggtga gttcttcatt ctcctgatgt gcgttggtgt     60
tggctcccgt at                                                       72

<210> SEQ ID NO 643
<211> LENGTH: 72
<212> TYPE: DNA
<213> ORGANISM: Artificial Sequence
<220> FEATURE:
<223> OTHER INFORMATION: chemically synthesized

<400> SEQUENCE: 643
atacgggagc caacaccact aacatgcgcg agggctctgt ccccgtccga catcagagca    60
ggtgtgacgg at                                                       72

<210> SEQ ID NO 644
<211> LENGTH: 72
<212> TYPE: DNA
<213> ORGANISM: Artificial Sequence
<220> FEATURE:
<223> OTHER INFORMATION: chemically synthesized

<400> SEQUENCE: 644
atccgtcaca cctgctctga tgtcggacgg ggacagagcc ctcgcgcatg ttagtggtgt    60
tggctcccgt at                                                       72

<210> SEQ ID NO 645
<211> LENGTH: 72
<212> TYPE: DNA
<213> ORGANISM: Artificial Sequence
<220> FEATURE:
<223> OTHER INFORMATION: chemically synthesized

<400> SEQUENCE: 645
atacgggagc caacaccaac ctggctatct gcatgcggtc ggtcgccttg ttggagagca    60
ggtgtgacgg at                                                       72

<210> SEQ ID NO 646
<211> LENGTH: 72
<212> TYPE: DNA
<213> ORGANISM: Artificial Sequence
<220> FEATURE:
<223> OTHER INFORMATION: chemically synthesized

<400> SEQUENCE: 646
atccgtcaca cctgctctcc aacaaggcga ccgaccgcat gcagatagcc aggttggtgt    60
tggctcccgt at                                                       72

<210> SEQ ID NO 647
<211> LENGTH: 72
<212> TYPE: DNA
```

```
<213> ORGANISM: Artificial Sequence
<220> FEATURE:
<223> OTHER INFORMATION: chemically synthesized

<400> SEQUENCE: 647
atacgggagc caacaccacg taccctcaac ctttaacttc tcataaccgg ctgtagagca      60
ggtgtgacgg at                                                          72

<210> SEQ ID NO 648
<211> LENGTH: 72
<212> TYPE: DNA
<213> ORGANISM: Artificial Sequence
<220> FEATURE:
<223> OTHER INFORMATION: chemically synthesized

<400> SEQUENCE: 648
atccgtcaca cctgctctac agccggttat gagaagttaa aggttgaggg tacgtggtgt      60
tggctcccgt at                                                          72

<210> SEQ ID NO 649
<211> LENGTH: 72
<212> TYPE: DNA
<213> ORGANISM: Artificial Sequence
<220> FEATURE:
<223> OTHER INFORMATION: chemically synthesized

<400> SEQUENCE: 649
atacgggagc caacaccatg cgtgcctaat gccggccatt ctactgcttg gcctagagca      60
ggtgtgacgg at                                                          72

<210> SEQ ID NO 650
<211> LENGTH: 72
<212> TYPE: DNA
<213> ORGANISM: Artificial Sequence
<220> FEATURE:
<223> OTHER INFORMATION: chemically synthesized

<400> SEQUENCE: 650
atccgtcaca cctgctctag gccaagcagt agaatggccg gcattaggca cgcatggtgt      60
tggctcccgt at                                                          72

<210> SEQ ID NO 651
<211> LENGTH: 72
<212> TYPE: DNA
<213> ORGANISM: Artificial Sequence
<220> FEATURE:
<223> OTHER INFORMATION: chemically synthesized

<400> SEQUENCE: 651
atacgggagc caacaccatg tgtactaatg tagctgttgc aacgttccta acttagagca      60
ggtgtgacgg at                                                          72

<210> SEQ ID NO 652
<211> LENGTH: 72
<212> TYPE: DNA
<213> ORGANISM: Artificial Sequence
<220> FEATURE:
<223> OTHER INFORMATION: chemically synthesized

<400> SEQUENCE: 652
atccgtcaca cctgctctaa gttaggaacg ttgcaacagc tacattagta cacatggtgt      60
tggctcccgt at                                                          72
```

<210> SEQ ID NO 653
<211> LENGTH: 72
<212> TYPE: DNA
<213> ORGANISM: Artificial Sequence
<220> FEATURE:
<223> OTHER INFORMATION: chemically synthesized

<400> SEQUENCE: 653
atacgggagc caacaccact ggtgaggcgc ctgcgccgac tggccgtccc cccgagagca    60
ggtgtgacgg at    72

<210> SEQ ID NO 654
<211> LENGTH: 72
<212> TYPE: DNA
<213> ORGANISM: Artificial Sequence
<220> FEATURE:
<223> OTHER INFORMATION: chemically synthesized

<400> SEQUENCE: 654
atccgtcaca cctgctctcg gggggacggc cagtcggcgc aggcgcctca ccagtggtgt    60
tggctcccgt at    72

<210> SEQ ID NO 655
<211> LENGTH: 72
<212> TYPE: DNA
<213> ORGANISM: Artificial Sequence
<220> FEATURE:
<223> OTHER INFORMATION: chemically synthesized

<400> SEQUENCE: 655
atacgggagc caacaccagg gggcctcgtt ctacgagcct gggtgtgtcc ctccagagca    60
ggtgtgacgg at    72

<210> SEQ ID NO 656
<211> LENGTH: 72
<212> TYPE: DNA
<213> ORGANISM: Artificial Sequence
<220> FEATURE:
<223> OTHER INFORMATION: chemically synthesized

<400> SEQUENCE: 656
atccgtcaca cctgctctgg agggacacac ccaggctcgt agaacgaggc ccctggtgt    60 tggctcccgt at    72

<210> SEQ ID NO 657
<211> LENGTH: 72
<212> TYPE: DNA
<213> ORGANISM: Artificial Sequence
<220> FEATURE:
<223> OTHER INFORMATION: chemically synthesized

<400> SEQUENCE: 657
atacgggagc caacaccatt gctgggccca cctatcggcg taccgaaccc ccgcagagca    60
ggtgtgacgg at    72

<210> SEQ ID NO 658
<211> LENGTH: 72
<212> TYPE: DNA
<213> ORGANISM: Artificial Sequence
<220> FEATURE:
<223> OTHER INFORMATION: chemically synthesized

<400> SEQUENCE: 658

```
atccgtcaca cctgctctgc gggggttcgg tacgccgata ggtgggccca gcaatggtgt    60
tggctcccgt at                                                         72
```

<210> SEQ ID NO 659
<211> LENGTH: 72
<212> TYPE: DNA
<213> ORGANISM: Artificial Sequence
<220> FEATURE:
<223> OTHER INFORMATION: chemically synthesized

<400> SEQUENCE: 659

```
atacgggagc caacaccacg ccgggacccc cccacgatgg ctgcctatat gtccagagca    60
ggtgtgacgg at                                                         72
```

<210> SEQ ID NO 660
<211> LENGTH: 72
<212> TYPE: DNA
<213> ORGANISM: Artificial Sequence
<220> FEATURE:
<223> OTHER INFORMATION: chemically synthesized

<400> SEQUENCE: 660

```
atccgtcaca cctgctctgg acatataggc agccatcgtg gggggtccc ggcgtggtgt     60 tggctcccgt at                                                         72
```

<210> SEQ ID NO 661
<211> LENGTH: 72
<212> TYPE: DNA
<213> ORGANISM: Artificial Sequence
<220> FEATURE:
<223> OTHER INFORMATION: chemically synthesized

<400> SEQUENCE: 661

```
atacgggagc caacaccacc ctacttatca tgtccttatc ccgccttact ggccagagca    60
ggtgtgacgg at                                                         72
```

<210> SEQ ID NO 662
<211> LENGTH: 72
<212> TYPE: DNA
<213> ORGANISM: Artificial Sequence
<220> FEATURE:
<223> OTHER INFORMATION: chemically synthesized

<400> SEQUENCE: 662

```
atccgtcaca cctgctctgg ccagtaaggc gggataagga catgataagt agggtggtgt    60
tggctcccgt at                                                         72
```

<210> SEQ ID NO 663
<211> LENGTH: 72
<212> TYPE: DNA
<213> ORGANISM: Artificial Sequence
<220> FEATURE:
<223> OTHER INFORMATION: chemically synthesized

<400> SEQUENCE: 663

```
atacgggagc caacaccatt accactcctt acttgtacgt gaccttgtac caccagagca    60
ggtgtgacgg at                                                         72
```

<210> SEQ ID NO 664
<211> LENGTH: 72
<212> TYPE: DNA
<213> ORGANISM: Artificial Sequence
<220> FEATURE:

<223> OTHER INFORMATION: chemically synthesized

<400> SEQUENCE: 664
atccgtcaca cctgctctgg tggtacaagg tcacgtacaa gtaaggagtg gtaatggtgt    60
tggctcccgt at    72

<210> SEQ ID NO 665
<211> LENGTH: 72
<212> TYPE: DNA
<213> ORGANISM: Artificial Sequence
<220> FEATURE:
<223> OTHER INFORMATION: chemically synthesized

<400> SEQUENCE: 665
atacgggagc caacaccatt cctgctaact tgctgcctgc cctccacggg gctcagagca    60
ggtgtgacgg at    72

<210> SEQ ID NO 666
<211> LENGTH: 72
<212> TYPE: DNA
<213> ORGANISM: Artificial Sequence
<220> FEATURE:
<223> OTHER INFORMATION: chemically synthesized

<400> SEQUENCE: 666
atccgtcaca cctgctctga gccccgtgga gggcaggcag caagttagca ggaatggtgt    60
tggctcccgt at    72

<210> SEQ ID NO 667
<211> LENGTH: 72
<212> TYPE: DNA
<213> ORGANISM: Artificial Sequence
<220> FEATURE:
<223> OTHER INFORMATION: chemically synthesized

<400> SEQUENCE: 667
atacgggagc caacaccatc tcatggtagc tgcgctggtt ttgtgcgtga tattagagca    60
ggtgtgacgg at    72

<210> SEQ ID NO 668
<211> LENGTH: 72
<212> TYPE: DNA
<213> ORGANISM: Artificial Sequence
<220> FEATURE:
<223> OTHER INFORMATION: chemically synthesized

<400> SEQUENCE: 668
atccgtcaca cctgctctaa tatcacgcac aaaaccagcg cagctaccat gagatggtgt    60
tggctcccgt at    72

<210> SEQ ID NO 669
<211> LENGTH: 72
<212> TYPE: DNA
<213> ORGANISM: Artificial Sequence
<220> FEATURE:
<223> OTHER INFORMATION: chemically synthesized

<400> SEQUENCE: 669
atacgggagc caacaccatg taaactttca ggttggatag tacgggctca cacaagagca    60
ggtgtgacgg at    72

<210> SEQ ID NO 670

```
<211> LENGTH: 72
<212> TYPE: DNA
<213> ORGANISM: Artificial Sequence
<220> FEATURE:
<223> OTHER INFORMATION: chemically synthesized

<400> SEQUENCE: 670
atccgtcaca cctgctcttg tgtgagcccg tactatccaa cctgaaagtt tacatggtgt    60
tggctcccgt at                                                        72

<210> SEQ ID NO 671
<211> LENGTH: 72
<212> TYPE: DNA
<213> ORGANISM: Artificial Sequence
<220> FEATURE:
<223> OTHER INFORMATION: chemically synthesized

<400> SEQUENCE: 671
atacgggagc caacaccatg tgtccgccct tgttttttgtg tcgtccggca atcgagagca    60
ggtgtgacgg at                                                        72

<210> SEQ ID NO 672
<211> LENGTH: 72
<212> TYPE: DNA
<213> ORGANISM: Artificial Sequence
<220> FEATURE:
<223> OTHER INFORMATION: chemically synthesized

<400> SEQUENCE: 672
atccgtcaca cctgctctcg attgccggac gacacaaaaa caagggcgga cacatggtgt    60
tggctcccgt at                                                        72

<210> SEQ ID NO 673
<211> LENGTH: 71
<212> TYPE: DNA
<213> ORGANISM: Artificial Sequence
<220> FEATURE:
<223> OTHER INFORMATION: chemically synthesized

<400> SEQUENCE: 673
atacgggagc caacaccagc agcataacgt ccgtatccca atccatgacg atcagagcag    60
gtgtgacgga t                                                         71

<210> SEQ ID NO 674
<211> LENGTH: 71
<212> TYPE: DNA
<213> ORGANISM: Artificial Sequence
<220> FEATURE:
<223> OTHER INFORMATION: chemically synthesized

<400> SEQUENCE: 674
atccgtcaca cctgctctga tcgtcatgga ttgggatacg gacgttatgc tgctggtgtt    60
ggctcccgta t                                                         71

<210> SEQ ID NO 675
<211> LENGTH: 72
<212> TYPE: DNA
<213> ORGANISM: Artificial Sequence
<220> FEATURE:
<223> OTHER INFORMATION: chemically synthesized

<400> SEQUENCE: 675
atacgggagc caacaccatt taggataagt ggtcacgccg tctcgattta actgagagca    60
```
ggtgtgacgg at 72

<210> SEQ ID NO 676
<211> LENGTH: 72
<212> TYPE: DNA
<213> ORGANISM: Artificial Sequence
<220> FEATURE:
<223> OTHER INFORMATION: chemically synthesized

<400> SEQUENCE: 676
atccgtcaca cctgctctca gttaaatcga gacggcgtga ccacttatcc taaatggtgt 60
tggctcccgt at 72

<210> SEQ ID NO 677
<211> LENGTH: 72
<212> TYPE: DNA
<213> ORGANISM: Artificial Sequence
<220> FEATURE:
<223> OTHER INFORMATION: chemically synthesized

<400> SEQUENCE: 677
atacgggagc caacaccaat tccgtatcca tgctctggct gcgtatcccc tttgagagca 60
ggtgtgacgg at 72

<210> SEQ ID NO 678
<211> LENGTH: 72
<212> TYPE: DNA
<213> ORGANISM: Artificial Sequence
<220> FEATURE:
<223> OTHER INFORMATION: chemically synthesized

<400> SEQUENCE: 678
atccgtcaca cctgctctca aagggatac gcagccagag catggatacg gaattggtgt 60
tggctcccgt at 72

<210> SEQ ID NO 679
<211> LENGTH: 72
<212> TYPE: DNA
<213> ORGANISM: Artificial Sequence
<220> FEATURE:
<223> OTHER INFORMATION: chemically synthesized

<400> SEQUENCE: 679
atacgggagc caacaccagg aaccggaata gggaatcccc cttaccaacc ccccagagca 60
ggtgtgacgg at 72

<210> SEQ ID NO 680
<211> LENGTH: 72
<212> TYPE: DNA
<213> ORGANISM: Artificial Sequence
<220> FEATURE:
<223> OTHER INFORMATION: chemically synthesized

<400> SEQUENCE: 680
atccgtcaca cctgctctgg ggggttggta aggggattc cctattccgg ttcctggtgt 60
tggctcccgt at 72

<210> SEQ ID NO 681
<211> LENGTH: 72
<212> TYPE: DNA
<213> ORGANISM: Artificial Sequence
<220> FEATURE:
<223> OTHER INFORMATION: chemically synthesized -continued

```
<400> SEQUENCE: 681
atacgggagc caacaccaga acaccgcccc ctgtctgttc caattgctgt tatcagagca        60
ggtgtgacgg at                                                           72

<210> SEQ ID NO 682
<211> LENGTH: 72
<212> TYPE: DNA
<213> ORGANISM: Artificial Sequence
<220> FEATURE:
<223> OTHER INFORMATION: chemically synthesized

<400> SEQUENCE: 682
atccgtcaca cctgctctga taacagcaat tggaacagac aggggcggt gttctggtgt         60 tggctcccgt at                                                           72

<210> SEQ ID NO 683
<211> LENGTH: 72
<212> TYPE: DNA
<213> ORGANISM: Artificial Sequence
<220> FEATURE:
<223> OTHER INFORMATION: chemically synthesized

<400> SEQUENCE: 683
atacgggagc caacaccacc cggttttaac ttttgttggt atgtctcgaa tcccagagca        60
ggtgtgacgg at                                                           72

<210> SEQ ID NO 684
<211> LENGTH: 72
<212> TYPE: DNA
<213> ORGANISM: Artificial Sequence
<220> FEATURE:
<223> OTHER INFORMATION: chemically synthesized

<400> SEQUENCE: 684
atccgtcaca cctgctctgg gattcgagac ataccaacaa aagttaaaac cgggtggtgt        60
tggctcccgt at                                                           72

<210> SEQ ID NO 685
<211> LENGTH: 71
<212> TYPE: DNA
<213> ORGANISM: Artificial Sequence
<220> FEATURE:
<223> OTHER INFORMATION: chemically synthesized

<400> SEQUENCE: 685
atacgggagc caacaccaaa tagagtattc gaaagtagcg tacttcaggt cctagagcag        60
gtgtgacgga t                                                            71

<210> SEQ ID NO 686
<211> LENGTH: 71
<212> TYPE: DNA
<213> ORGANISM: Artificial Sequence
<220> FEATURE:
<223> OTHER INFORMATION: chemically synthesized

<400> SEQUENCE: 686
atccgtcaca cctgctctag gacctgaagt acgctacttt cgaatactct atttggtgtt       60
ggctcccgta t                                                            71

<210> SEQ ID NO 687
<211> LENGTH: 70
<212> TYPE: DNA
```

```
<213> ORGANISM: Artificial Sequence
<220> FEATURE:
<223> OTHER INFORMATION: chemically synthesized

<400> SEQUENCE: 687
atacgggagc caacaccacc gaattgattg ataaaaaggg ttagatcgct ccagagcagg    60
tgtgacggat                                                          70

<210> SEQ ID NO 688
<211> LENGTH: 70
<212> TYPE: DNA
<213> ORGANISM: Artificial Sequence
<220> FEATURE:
<223> OTHER INFORMATION: chemically synthesized

<400> SEQUENCE: 688
atccgtcaca cctgctctgg agcgatctaa ccctttttat caatcaattc ggtggtgttg    60
gctcccgtat                                                          70

<210> SEQ ID NO 689
<211> LENGTH: 71
<212> TYPE: DNA
<213> ORGANISM: Artificial Sequence
<220> FEATURE:
<223> OTHER INFORMATION: chemically synthesized

<400> SEQUENCE: 689
atacgggagc caacaccatt ggcgacagag ttcgacgtcc cctagtggca gagagagcag    60
gtgtgacgga t                                                        71

<210> SEQ ID NO 690
<211> LENGTH: 71
<212> TYPE: DNA
<213> ORGANISM: Artificial Sequence
<220> FEATURE:
<223> OTHER INFORMATION: chemically synthesized

<400> SEQUENCE: 690
atccgtcaca cctgctctct ctgccactag gggacgtcga actctgtcgc caatggtgtt    60
ggctcccgta t                                                        71

<210> SEQ ID NO 691
<211> LENGTH: 72
<212> TYPE: DNA
<213> ORGANISM: Artificial Sequence
<220> FEATURE:
<223> OTHER INFORMATION: chemically synthesized

<400> SEQUENCE: 691
atacgggagc caacaccaat cgctctcaca aatttgccct agactcatac catcagagca    60
ggtgtgacgg at                                                       72

<210> SEQ ID NO 692
<211> LENGTH: 72
<212> TYPE: DNA
<213> ORGANISM: Artificial Sequence
<220> FEATURE:
<223> OTHER INFORMATION: chemically synthesized

<400> SEQUENCE: 692
atccgtcaca cctgctctga tggtatgagt ctagggcaaa tttgtgagag cgattggtgt    60
tggctcccgt at                                                       72
```

```
<210> SEQ ID NO 693
<211> LENGTH: 71
<212> TYPE: DNA
<213> ORGANISM: Artificial Sequence
<220> FEATURE:
<223> OTHER INFORMATION: chemically synthesized

<400> SEQUENCE: 693
atacgggagc ccacaccaca actttgaaga tccttgagcc gcgctcacca cctagagcag      60
gtgtgacgga t                                                          71

<210> SEQ ID NO 694
<211> LENGTH: 71
<212> TYPE: DNA
<213> ORGANISM: Artificial Sequence
<220> FEATURE:
<223> OTHER INFORMATION: chemically synthesized

<400> SEQUENCE: 694
atccgtcaca cctgctctag gtggtgagcg cggctcaagg atcttcaaag ttgtggtgtg      60
ggctcccgta t                                                          71

<210> SEQ ID NO 695
<211> LENGTH: 72
<212> TYPE: DNA
<213> ORGANISM: Artificial Sequence
<220> FEATURE:
<223> OTHER INFORMATION: chemically synthesized

<400> SEQUENCE: 695
atacgggagc caacaccaca aagtttagcg ttatgcaact cccccttata ctcgagagca      60
ggtgtgacgg at                                                         72

<210> SEQ ID NO 696
<211> LENGTH: 72
<212> TYPE: DNA
<213> ORGANISM: Artificial Sequence
<220> FEATURE:
<223> OTHER INFORMATION: chemically synthesized

<400> SEQUENCE: 696
atccgtcaca cctgctctcg agtataaggg ggagttgcat aacgctaaac tttgtggtgt      60
tggctcccgt at                                                         72

<210> SEQ ID NO 697
<211> LENGTH: 72
<212> TYPE: DNA
<213> ORGANISM: Artificial Sequence
<220> FEATURE:
<223> OTHER INFORMATION: chemically synthesized

<400> SEQUENCE: 697
atacgggagc caacaccaca aagtttagcg ttatgcaact cccccttata ctcgagagca      60
ggtgtgacgg at                                                         72

<210> SEQ ID NO 698
<211> LENGTH: 72
<212> TYPE: DNA
<213> ORGANISM: Artificial Sequence
<220> FEATURE:
<223> OTHER INFORMATION: chemically synthesized

<400> SEQUENCE: 698
```

```
atccgtcaca cctgctctcg agtataaggg ggagttgcat aacgctaaac tttgtggtgt    60
tggctcccgt at                                                       72

<210> SEQ ID NO 699
<211> LENGTH: 71
<212> TYPE: DNA
<213> ORGANISM: Artificial Sequence
<220> FEATURE:
<223> OTHER INFORMATION: chemically synthesized

<400> SEQUENCE: 699
atacgggagc caacaccata cggctatacc cgcccgacgt acaccacatc cccagagcag    60
gtgtgacgga t                                                        71

<210> SEQ ID NO 700
<211> LENGTH: 71
<212> TYPE: DNA
<213> ORGANISM: Artificial Sequence
<220> FEATURE:
<223> OTHER INFORMATION: chemically synthesized

<400> SEQUENCE: 700
atccgtcaca cctgctctgg ggatgtggtg tacgtcgggc gggtatagcc gtatggtgtt    60
ggctcccgta t                                                        71

<210> SEQ ID NO 701
<211> LENGTH: 72
<212> TYPE: DNA
<213> ORGANISM: Artificial Sequence
<220> FEATURE:
<223> OTHER INFORMATION: chemically synthesized

<400> SEQUENCE: 701
atacgggagc caacaccagt gtaacttgga gccctgacga gctcttcccg tagcagagca    60
ggtgtgacgg at                                                       72

<210> SEQ ID NO 702
<211> LENGTH: 72
<212> TYPE: DNA
<213> ORGANISM: Artificial Sequence
<220> FEATURE:
<223> OTHER INFORMATION: chemically synthesized

<400> SEQUENCE: 702
atccgtcaca cctgctctgc tacgggaaga gctcgtcagg gctccaagtt acactggtgt    60
tggctcccgt at                                                       72

<210> SEQ ID NO 703
<211> LENGTH: 72
<212> TYPE: DNA
<213> ORGANISM: Artificial Sequence
<220> FEATURE:
<223> OTHER INFORMATION: chemically synthesized

<400> SEQUENCE: 703
atacgggagc caacaccata gtttagcatg ctcaatagta caccagatca gtggagagca    60
ggtgtgacgg at                                                       72

<210> SEQ ID NO 704
<211> LENGTH: 72
<212> TYPE: DNA
<213> ORGANISM: Artificial Sequence
<220> FEATURE:
```

<223> OTHER INFORMATION: chemically synthesized

<400> SEQUENCE: 704
atccgtcaca cctgctctcc actgatctgg tgtactattg agcatgctaa actatggtgt    60
tggctcccgt at    72

<210> SEQ ID NO 705
<211> LENGTH: 72
<212> TYPE: DNA
<213> ORGANISM: Artificial Sequence
<220> FEATURE:
<223> OTHER INFORMATION: chemically synthesized

<400> SEQUENCE: 705
atacgggagc caacaccatt cgtgtgtctg tctaagtgga actgcctgta attaagagca    60
ggtgtgacgg at    72

<210> SEQ ID NO 706
<211> LENGTH: 72
<212> TYPE: DNA
<213> ORGANISM: Artificial Sequence
<220> FEATURE:
<223> OTHER INFORMATION: chemically synthesized

<400> SEQUENCE: 706
atccgtcaca cctgctctta attacaggca gttccactta gacagacaca cgaatggtgt    60
tggctcccgt at    72

<210> SEQ ID NO 707
<211> LENGTH: 72
<212> TYPE: DNA
<213> ORGANISM: Artificial Sequence
<220> FEATURE:
<223> OTHER INFORMATION: chemically synthesized

<400> SEQUENCE: 707
atacgggagc caacaccaca tgagtggcgg gcttagcggg ctgcaaggcg cgttagagca    60
ggtgtgacgg at    72

<210> SEQ ID NO 708
<211> LENGTH: 72
<212> TYPE: DNA
<213> ORGANISM: Artificial Sequence
<220> FEATURE:
<223> OTHER INFORMATION: chemically synthesized

<400> SEQUENCE: 708
atccgtcaca cctgctctaa cgcgccttgc agcccgctaa gcccgccact catgtggtgt    60
tggctcccgt at    72

<210> SEQ ID NO 709
<211> LENGTH: 72
<212> TYPE: DNA
<213> ORGANISM: Artificial Sequence
<220> FEATURE:
<223> OTHER INFORMATION: chemically synthesized

<400> SEQUENCE: 709
atacgggagc caacaccatg tggcataaac agacgaattt gtcctataac gagtagagca    60
ggtgtgacgg at    72

<210> SEQ ID NO 710

-continued

```
<211> LENGTH: 72
<212> TYPE: DNA
<213> ORGANISM: Artificial Sequence
<220> FEATURE:
<223> OTHER INFORMATION: chemically synthesized

<400> SEQUENCE: 710
atccgtcaca cctgctctac tcgttatagg acaaattcgt ctgtttatgc cacatggtgt      60
tggctcccgt at                                                         72

<210> SEQ ID NO 711
<211> LENGTH: 72
<212> TYPE: DNA
<213> ORGANISM: Artificial Sequence
<220> FEATURE:
<223> OTHER INFORMATION: chemically synthesized

<400> SEQUENCE: 711
atacgggagc caacaccact tattaccgat ttagcttgag actcctcccc tacaagagca      60
ggtgtgacgg at                                                         72

<210> SEQ ID NO 712
<211> LENGTH: 72
<212> TYPE: DNA
<213> ORGANISM: Artificial Sequence
<220> FEATURE:
<223> OTHER INFORMATION: chemically synthesized

<400> SEQUENCE: 712
atccgtcaca cctgctcttg taggggagga gtctcaagct aaatcggtaa taagtggtgt      60
tggctcccgt at                                                         72

<210> SEQ ID NO 713
<211> LENGTH: 72
<212> TYPE: DNA
<213> ORGANISM: Artificial Sequence
<220> FEATURE:
<223> OTHER INFORMATION: chemically synthesized

<400> SEQUENCE: 713
atacgggagc caacaccatc gttttgtact ttatgagccg cacggagccc ccccagagca      60
ggtgtgacgg at                                                         72

<210> SEQ ID NO 714
<211> LENGTH: 72
<212> TYPE: DNA
<213> ORGANISM: Artificial Sequence
<220> FEATURE:
<223> OTHER INFORMATION: chemically synthesized

<400> SEQUENCE: 714
atccgtcaca cctgctctgg gggggctccg tgcggctcat aaagtacaaa acgatggtgt      60
tggctcccgt at                                                         72

<210> SEQ ID NO 715
<211> LENGTH: 72
<212> TYPE: DNA
<213> ORGANISM: Artificial Sequence
<220> FEATURE:
<223> OTHER INFORMATION: chemically synthesized

<400> SEQUENCE: 715
atacgggagc caacaccatc tcgctaagct ctgttgggac taacttccgc tattagagca      60
```

```
ggtgtgacgg at                                                           72
```

<210> SEQ ID NO 716
<211> LENGTH: 72
<212> TYPE: DNA
<213> ORGANISM: Artificial Sequence
<220> FEATURE:
<223> OTHER INFORMATION: chemically synthesized

<400> SEQUENCE: 716

```
atccgtcaca cctgctctaa tagcggaagt tagtcccaac agagcttagc gagatggtgt       60
tggctcccgt at                                                           72
```

<210> SEQ ID NO 717
<211> LENGTH: 72
<212> TYPE: DNA
<213> ORGANISM: Artificial Sequence
<220> FEATURE:
<223> OTHER INFORMATION: chemically synthesized

<400> SEQUENCE: 717

```
atacgggagc caacaccatc caccctacgt cataatatga aatgaaacat atatagagca       60
ggtgtgacgg at                                                           72
```

<210> SEQ ID NO 718
<211> LENGTH: 72
<212> TYPE: DNA
<213> ORGANISM: Artificial Sequence
<220> FEATURE:
<223> OTHER INFORMATION: chemically synthesized

<400> SEQUENCE: 718

```
atccgtcaca cctgctctat atatgtttca tttcatatta tgacgtaggg tggatggtgt       60
tggctcccgt at                                                           72
```

<210> SEQ ID NO 719
<211> LENGTH: 72
<212> TYPE: DNA
<213> ORGANISM: Artificial Sequence
<220> FEATURE:
<223> OTHER INFORMATION: chemically synthesized

<400> SEQUENCE: 719

```
atacgggagc caacaccacc cactctcccc ccgctcccgc tcccccgctc cgcgagagca       60
ggtgtgacgg at                                                           72
```

<210> SEQ ID NO 720
<211> LENGTH: 72
<212> TYPE: DNA
<213> ORGANISM: Artificial Sequence
<220> FEATURE:
<223> OTHER INFORMATION: chemically synthesized

<400> SEQUENCE: 720

```
atccgtcaca cctgctctcg cggagcgggg gagcgggagc gggggagag tgggtggtgt        60 tggctcccgt at                                                           72
```

<210> SEQ ID NO 721
<211> LENGTH: 72
<212> TYPE: DNA
<213> ORGANISM: Artificial Sequence
<220> FEATURE:
<223> OTHER INFORMATION: chemically synthesized

```
<400> SEQUENCE: 721
atacgggagc caacaccaat agttgcgtct tgtcatgtac gcctccttgc cagcagagca    60
ggtgtgacgg at                                                       72

<210> SEQ ID NO 722
<211> LENGTH: 72
<212> TYPE: DNA
<213> ORGANISM: Artificial Sequence
<220> FEATURE:
<223> OTHER INFORMATION: chemically synthesized

<400> SEQUENCE: 722
atccgtcaca cctgctctgc tggcaaggag gcgtacatga caagacgcaa ctattggtgt    60
tggctcccgt at                                                       72

<210> SEQ ID NO 723
<211> LENGTH: 72
<212> TYPE: DNA
<213> ORGANISM: Artificial Sequence
<220> FEATURE:
<223> OTHER INFORMATION: chemically synthesized

<400> SEQUENCE: 723
atacgggagc caacaccagc gggtttctta gttctgattg gacgctctgt ttgcagagca    60
ggtgtgacgg at                                                       72

<210> SEQ ID NO 724
<211> LENGTH: 72
<212> TYPE: DNA
<213> ORGANISM: Artificial Sequence
<220> FEATURE:
<223> OTHER INFORMATION: chemically synthesized

<400> SEQUENCE: 724
atccgtcaca cctgctctgc aaacagagcg tccaatcaga actaagaaac ccgctggtgt    60
tggctcccgt at                                                       72

<210> SEQ ID NO 725
<211> LENGTH: 72
<212> TYPE: DNA
<213> ORGANISM: Artificial Sequence
<220> FEATURE:
<223> OTHER INFORMATION: chemically synthesized

<400> SEQUENCE: 725
atacgggagc caacaccaag agcacctgca ccctcccgcc ctctattgca ttctagagca    60
ggtgtgacgg at                                                       72

<210> SEQ ID NO 726
<211> LENGTH: 72
<212> TYPE: DNA
<213> ORGANISM: Artificial Sequence
<220> FEATURE:
<223> OTHER INFORMATION: chemically synthesized

<400> SEQUENCE: 726
atccgtcaca cctgctctag aatgcaatag agggcgggag ggtgcaggtg ctcttggtgt    60
tggctcccgt at                                                       72

<210> SEQ ID NO 727
<211> LENGTH: 72
<212> TYPE: DNA
```

<213> ORGANISM: Artificial Sequence
<220> FEATURE:
<223> OTHER INFORMATION: chemically synthesized

<400> SEQUENCE: 727
atacgggagc caacaccaca tcataccttg ttctaccggc agcctctcta aataagagca    60
ggtgtgacgg at    72

<210> SEQ ID NO 728
<211> LENGTH: 72
<212> TYPE: DNA
<213> ORGANISM: Artificial Sequence
<220> FEATURE:
<223> OTHER INFORMATION: chemically synthesized

<400> SEQUENCE: 728
atccgtcaca cctgctctta tttagagagg ctgccggtag aacaaggtat gatgtggtgt    60
tggctcccgt at    72

<210> SEQ ID NO 729
<211> LENGTH: 72
<212> TYPE: DNA
<213> ORGANISM: Artificial Sequence
<220> FEATURE:
<223> OTHER INFORMATION: chemically synthesized

<400> SEQUENCE: 729
atacgggagc caacaccatt ccaaatgaac agttctcgat cccacttctc atctagagca    60
ggtgtgacgg at    72

<210> SEQ ID NO 730
<211> LENGTH: 72
<212> TYPE: DNA
<213> ORGANISM: Artificial Sequence
<220> FEATURE:
<223> OTHER INFORMATION: chemically synthesized

<400> SEQUENCE: 730
atccgtcaca cctgctctag atgagaagtg ggatcgagaa ctgttcattt ggaatggtgt    60
tggctcccgt at    72

<210> SEQ ID NO 731
<211> LENGTH: 72
<212> TYPE: DNA
<213> ORGANISM: Artificial Sequence
<220> FEATURE:
<223> OTHER INFORMATION: chemically synthesized

<400> SEQUENCE: 731
atacgggagc caacaccaga cctactgccc cctgtctcc ctttgtctgc ccttagagca    60
ggtgtgacgg at    72

<210> SEQ ID NO 732
<211> LENGTH: 72
<212> TYPE: DNA
<213> ORGANISM: Artificial Sequence
<220> FEATURE:
<223> OTHER INFORMATION: chemically synthesized

<400> SEQUENCE: 732
atccgtcaca cctgctctaa gggcagacaa agggagacag gggggcagta ggtctggtgt    60
tggctcccgt at    72

<210> SEQ ID NO 733
<211> LENGTH: 72
<212> TYPE: DNA
<213> ORGANISM: Artificial Sequence
<220> FEATURE:
<223> OTHER INFORMATION: chemically synthesized

<400> SEQUENCE: 733
atacgggagc caacaccaac catcccggaa tgtgggtttt atgtaaatat aagcagagca      60
ggtgtgacgg at                                                         72

<210> SEQ ID NO 734
<211> LENGTH: 72
<212> TYPE: DNA
<213> ORGANISM: Artificial Sequence
<220> FEATURE:
<223> OTHER INFORMATION: chemically synthesized

<400> SEQUENCE: 734
atccgtcaca cctgctctgc ttatatttac ataaaaccca cattccggga tggttggtgt      60
tggctcccgt at                                                         72

<210> SEQ ID NO 735
<211> LENGTH: 72
<212> TYPE: DNA
<213> ORGANISM: Artificial Sequence
<220> FEATURE:
<223> OTHER INFORMATION: chemically synthesized

<400> SEQUENCE: 735
atacgggagc caacaccacc cctaactcct atatttaatc cttatcaaat ttctagagca      60
ggtgtgacgg at                                                         72

<210> SEQ ID NO 736
<211> LENGTH: 72
<212> TYPE: DNA
<213> ORGANISM: Artificial Sequence
<220> FEATURE:
<223> OTHER INFORMATION: chemically synthesized

<400> SEQUENCE: 736
atccgtcaca cctgctctag aaatttgata aggattaaat ataggagtta ggggtggtgt      60
tggctcccgt at                                                         72

<210> SEQ ID NO 737
<211> LENGTH: 72
<212> TYPE: DNA
<213> ORGANISM: Artificial Sequence
<220> FEATURE:
<223> OTHER INFORMATION: chemically synthesized

<400> SEQUENCE: 737
atacgggagc caacaccacc agcagtaaag ttccagcatt gcgcttaata gactagagca      60
ggtgtgacgg at                                                         72

<210> SEQ ID NO 738
<211> LENGTH: 72
<212> TYPE: DNA
<213> ORGANISM: Artificial Sequence
<220> FEATURE:
<223> OTHER INFORMATION: chemically synthesized

<400> SEQUENCE: 738

```
atccgtcaca cctgctctag tctattaagc gcaatgctgg aactttactg ctggtggtgt    60
tggctcccgt at                                                        72

<210> SEQ ID NO 739
<211> LENGTH: 72
<212> TYPE: DNA
<213> ORGANISM: Artificial Sequence
<220> FEATURE:
<223> OTHER INFORMATION: chemically synthesized

<400> SEQUENCE: 739
atacgggagc caacaccaag tccaagccaa acaagagcat aacaccaaat ctggagagca    60
ggtgtgacgg at                                                        72

<210> SEQ ID NO 740
<211> LENGTH: 72
<212> TYPE: DNA
<213> ORGANISM: Artificial Sequence
<220> FEATURE:
<223> OTHER INFORMATION: chemically synthesized

<400> SEQUENCE: 740
atccgtcaca cctgctctcc agatttggtg ttatgctctt gtttggcttg gacttggtgt    60
tggctcccgt at                                                        72

<210> SEQ ID NO 741
<211> LENGTH: 72
<212> TYPE: DNA
<213> ORGANISM: Artificial Sequence
<220> FEATURE:
<223> OTHER INFORMATION: chemically synthesized

<400> SEQUENCE: 741
atacgggagc caacaccact caatacgtct tatcgtctct gagtacatct ggccagagca    60
ggtgtgacgg at                                                        72

<210> SEQ ID NO 742
<211> LENGTH: 72
<212> TYPE: DNA
<213> ORGANISM: Artificial Sequence
<220> FEATURE:
<223> OTHER INFORMATION: chemically synthesized

<400> SEQUENCE: 742
atccgtcaca cctgctctgg ccagatgtac tcagagacga taagacgtat tgagtggtgt    60
tggctcccgt at                                                        72

<210> SEQ ID NO 743
<211> LENGTH: 72
<212> TYPE: DNA
<213> ORGANISM: Artificial Sequence
<220> FEATURE:
<223> OTHER INFORMATION: chemically synthesized

<400> SEQUENCE: 743
atacgggagc caacaccagg gccgctgcga tttctacgct acctgccgtt ggtaagagca    60
ggtgtgacgg at                                                        72

<210> SEQ ID NO 744
<211> LENGTH: 72
<212> TYPE: DNA
<213> ORGANISM: Artificial Sequence
<220> FEATURE:
```

<223> OTHER INFORMATION: chemically synthesized

<400> SEQUENCE: 744
atccgtcaca cctgctctta ccaacggcag gtagcgtaga aatcgcagcg gccctggtgt    60
tggctcccgt at    72

<210> SEQ ID NO 745
<211> LENGTH: 72
<212> TYPE: DNA
<213> ORGANISM: Artificial Sequence
<220> FEATURE:
<223> OTHER INFORMATION: chemically synthesized

<400> SEQUENCE: 745
atacgggagc caacaccaca accggctaat gacaaatcaa agatttttc ggcgagagca    60 ggtgtgacgg at    72

<210> SEQ ID NO 746
<211> LENGTH: 72
<212> TYPE: DNA
<213> ORGANISM: Artificial Sequence
<220> FEATURE:
<223> OTHER INFORMATION: chemically synthesized

<400> SEQUENCE: 746
atccgtcaca cctgctctcg ccgaaaaaat ctttgatttg tcattagccg gttgtggtgt    60
tggctcccgt at    72

<210> SEQ ID NO 747
<211> LENGTH: 72
<212> TYPE: DNA
<213> ORGANISM: Artificial Sequence
<220> FEATURE:
<223> OTHER INFORMATION: chemically synthesized

<400> SEQUENCE: 747
atacgggagc caacaccagc acaacttaag tgcaagcaaa ttcggattaa ccaaagagca    60
ggtgtgacgg at    72

<210> SEQ ID NO 748
<211> LENGTH: 72
<212> TYPE: DNA
<213> ORGANISM: Artificial Sequence
<220> FEATURE:
<223> OTHER INFORMATION: chemically synthesized

<400> SEQUENCE: 748
atccgtcaca cctgctcttt ggttaatccg aatttgcttg cacttaagtt gtgctggtgt    60
tggctcccgt at    72

<210> SEQ ID NO 749
<211> LENGTH: 72
<212> TYPE: DNA
<213> ORGANISM: Artificial Sequence
<220> FEATURE:
<223> OTHER INFORMATION: chemically synthesized

<400> SEQUENCE: 749
atacgggagc caacaccatc cgaacagtta gtttaagacc gtcctccttt cttaagagca    60
ggtgtgacgg at    72

<210> SEQ ID NO 750

```
<211> LENGTH: 72
<212> TYPE: DNA
<213> ORGANISM: Artificial Sequence
<220> FEATURE:
<223> OTHER INFORMATION: chemically synthesized

<400> SEQUENCE: 750
atccgtcaca cctgctctta agaaaggagg acggtcttaa actaactgtt cggatggtgt     60
tggctcccgt at                                                        72

<210> SEQ ID NO 751
<211> LENGTH: 72
<212> TYPE: DNA
<213> ORGANISM: Artificial Sequence
<220> FEATURE:
<223> OTHER INFORMATION: chemically synthesized

<400> SEQUENCE: 751
atacgggagc caacaccact tcaaaagtca gatacaaaga cagagattgg acttagagca     60
ggtgtgacgg at                                                        72

<210> SEQ ID NO 752
<211> LENGTH: 72
<212> TYPE: DNA
<213> ORGANISM: Artificial Sequence
<220> FEATURE:
<223> OTHER INFORMATION: chemically synthesized

<400> SEQUENCE: 752
atccgtcaca cctgctctaa gtccaatctc tgtctttgta tctgactttt gaagtggtgt     60
tggctcccgt at                                                        72

<210> SEQ ID NO 753
<211> LENGTH: 71
<212> TYPE: DNA
<213> ORGANISM: Artificial Sequence
<220> FEATURE:
<223> OTHER INFORMATION: chemically synthesized

<400> SEQUENCE: 753
atacgggagc caacaccact tccgttataa cgtttctgga atttactacg attagagcag     60
gtgtgacgga t                                                         71

<210> SEQ ID NO 754
<211> LENGTH: 71
<212> TYPE: DNA
<213> ORGANISM: Artificial Sequence
<220> FEATURE:
<223> OTHER INFORMATION: chemically synthesized

<400> SEQUENCE: 754
atccgtcaca cctgctctaa tcgtagtaaa ttccagaaac gttataacgg aagtggtgtt     60
ggctcccgta t                                                         71

<210> SEQ ID NO 755
<211> LENGTH: 71
<212> TYPE: DNA
<213> ORGANISM: Artificial Sequence
<220> FEATURE:
<223> OTHER INFORMATION: chemically synthesized

<400> SEQUENCE: 755
atacgggagc caacaccaac cacggatgtt gaatatccga cgatcacgta attagagcag     60
```
gtgtgacgga t                                                                  71

<210> SEQ ID NO 756
<211> LENGTH: 71
<212> TYPE: DNA
<213> ORGANISM: Artificial Sequence
<220> FEATURE:
<223> OTHER INFORMATION: chemically synthesized

<400> SEQUENCE: 756
atccgtcaca cctgctctaa ttacgtgatc gtcggatatt caacatccgt ggttggtgtt    60
ggctcccgta t                                                                  71

<210> SEQ ID NO 757
<211> LENGTH: 71
<212> TYPE: DNA
<213> ORGANISM: Artificial Sequence
<220> FEATURE:
<223> OTHER INFORMATION: chemically synthesized

<400> SEQUENCE: 757
atacgggagc caacaccata gacttaagct ctctccagga gcttgtcgct tgcagagcag    60
gtgtgacgga t                                                                  71

<210> SEQ ID NO 758
<211> LENGTH: 71
<212> TYPE: DNA
<213> ORGANISM: Artificial Sequence
<220> FEATURE:
<223> OTHER INFORMATION: chemically synthesized

<400> SEQUENCE: 758
atccgtcaca cctgctctgc aagcgacaag ctcctggaga gagcttaagt ctatggtgtt    60
ggctcccgta t                                                                  71

<210> SEQ ID NO 759
<211> LENGTH: 72
<212> TYPE: DNA
<213> ORGANISM: Artificial Sequence
<220> FEATURE:
<223> OTHER INFORMATION: chemically synthesized

<400> SEQUENCE: 759
atacgggagc caacaccacg ggggcatctt ccattaaccc attacctcac cccaagagca    60
ggtgtgacgg at                                                                 72

<210> SEQ ID NO 760
<211> LENGTH: 72
<212> TYPE: DNA
<213> ORGANISM: Artificial Sequence
<220> FEATURE:
<223> OTHER INFORMATION: chemically synthesized

<400> SEQUENCE: 760
atccgtcaca cctgctcttg gggtgaggta atgggttaat ggaagatgcc cccgtggtgt    60
tggctcccgt at                                                                 72

<210> SEQ ID NO 761
<211> LENGTH: 71
<212> TYPE: DNA
<213> ORGANISM: Artificial Sequence
<220> FEATURE:
<223> OTHER INFORMATION: chemically synthesized

<400> SEQUENCE: 761
atacgggagc caacaccaca cagacaacca ttgattacgg ggacaattcg ggcagagcag    60
gtgtgacgga t                                                         71

<210> SEQ ID NO 762
<211> LENGTH: 71
<212> TYPE: DNA
<213> ORGANISM: Artificial Sequence
<220> FEATURE:
<223> OTHER INFORMATION: chemically synthesized

<400> SEQUENCE: 762
atccgtcaca cctgctctgc ccgaattgtc cccgtaatca atggttgtct gtgtggtgtt    60
ggctcccgta t                                                         71

<210> SEQ ID NO 763
<211> LENGTH: 71
<212> TYPE: DNA
<213> ORGANISM: Artificial Sequence
<220> FEATURE:
<223> OTHER INFORMATION: chemically synthesized

<400> SEQUENCE: 763
atacgggagc caacaccact ggtaggtgag tgtgtgtctg tactcgcatc gttagagcag    60
gtgtgacgga t                                                         71

<210> SEQ ID NO 764
<211> LENGTH: 71
<212> TYPE: DNA
<213> ORGANISM: Artificial Sequence
<220> FEATURE:
<223> OTHER INFORMATION: chemically synthesized

<400> SEQUENCE: 764
atccgtcaca cctgctctaa cgatgcgagt acagacacac actcacctac cagtggtgtt    60
ggctcccgta t                                                         71

<210> SEQ ID NO 765
<211> LENGTH: 70
<212> TYPE: DNA
<213> ORGANISM: Artificial Sequence
<220> FEATURE:
<223> OTHER INFORMATION: chemically synthesized

<400> SEQUENCE: 765
atacgggagc caacaccacc gaattgattg ataaaaaggg ttagatcgct ccagagcagg    60
tgtgacggat                                                           70

<210> SEQ ID NO 766
<211> LENGTH: 70
<212> TYPE: DNA
<213> ORGANISM: Artificial Sequence
<220> FEATURE:
<223> OTHER INFORMATION: chemically synthesized

<400> SEQUENCE: 766
atccgtcaca cctgctctgg agcgatctaa ccctttttat caatcaattc ggtggtgttg    60
gctcccgtat                                                           70

<210> SEQ ID NO 767
<211> LENGTH: 71
<212> TYPE: DNA

```
<213> ORGANISM: Artificial Sequence
<220> FEATURE:
<223> OTHER INFORMATION: chemically synthesized

<400> SEQUENCE: 767
atacgggagc caacaccacc taggccccca acatgtgtgg tataagtttc cgtagagcag    60
gtgtgacgga t                                                        71

<210> SEQ ID NO 768
<211> LENGTH: 71
<212> TYPE: DNA
<213> ORGANISM: Artificial Sequence
<220> FEATURE:
<223> OTHER INFORMATION: chemically synthesized

<400> SEQUENCE: 768
atccgtcaca cctgctctac ggaaacttat accacacatg ttgggggcct aggtggtgtt    60
ggctcccgta t                                                        71

<210> SEQ ID NO 769
<211> LENGTH: 71
<212> TYPE: DNA
<213> ORGANISM: Artificial Sequence
<220> FEATURE:
<223> OTHER INFORMATION: chemically synthesized

<400> SEQUENCE: 769
atacgggagc caacaccatc agaaactata gtgccatagt tttatctttg tacagagcag    60
gtgtgacgga t                                                        71

<210> SEQ ID NO 770
<211> LENGTH: 71
<212> TYPE: DNA
<213> ORGANISM: Artificial Sequence
<220> FEATURE:
<223> OTHER INFORMATION: chemically synthesized

<400> SEQUENCE: 770
atccgtcaca cctgctctgt acaaagataa aactatggca ctatagtttc tgatggtgtt    60
ggctcccgta t                                                        71

<210> SEQ ID NO 771
<211> LENGTH: 72
<212> TYPE: DNA
<213> ORGANISM: Artificial Sequence
<220> FEATURE:
<223> OTHER INFORMATION: chemically synthesized

<400> SEQUENCE: 771
atacgggagc caacaccaat agatggataa ggggaaact gccattcggt tagtagagca     60
ggtgtgacgg at                                                       72

<210> SEQ ID NO 772
<211> LENGTH: 72
<212> TYPE: DNA
<213> ORGANISM: Artificial Sequence
<220> FEATURE:
<223> OTHER INFORMATION: chemically synthesized

<400> SEQUENCE: 772
atccgtcaca cctgctctac taaccgaatg gcagtttccc ccttatccat ctattggtgt    60
tggctcccgt at                                                       72
```

```
<210> SEQ ID NO 773
<211> LENGTH: 72
<212> TYPE: DNA
<213> ORGANISM: Artificial Sequence
<220> FEATURE:
<223> OTHER INFORMATION: chemically synthesized

<400> SEQUENCE: 773
atacgggagc caacaccacc aacgaatact accaggccta gcacaataca caacagagca      60
ggtgtgacgg at                                                         72

<210> SEQ ID NO 774
<211> LENGTH: 72
<212> TYPE: DNA
<213> ORGANISM: Artificial Sequence
<220> FEATURE:
<223> OTHER INFORMATION: chemically synthesized

<400> SEQUENCE: 774
atccgtcaca cctgctctgt tgtgtattgt gctaggcctg gtagtattcg ttggtggtgt      60
tggctcccgt at                                                         72

<210> SEQ ID NO 775
<211> LENGTH: 71
<212> TYPE: DNA
<213> ORGANISM: Artificial Sequence
<220> FEATURE:
<223> OTHER INFORMATION: chemically synthesized

<400> SEQUENCE: 775
atacgggagc caacaccaaa cttgagatat gggcgctatg ttccttttca tccagagcag      60
gtgtgacgga t                                                          71

<210> SEQ ID NO 776
<211> LENGTH: 71
<212> TYPE: DNA
<213> ORGANISM: Artificial Sequence
<220> FEATURE:
<223> OTHER INFORMATION: chemically synthesized

<400> SEQUENCE: 776
atccgtcaca cctgctctgg atgaaaagga acatagcgcc catatctcaa gtttggtgtt      60
ggctcccgta t                                                          71

<210> SEQ ID NO 777
<211> LENGTH: 71
<212> TYPE: DNA
<213> ORGANISM: Artificial Sequence
<220> FEATURE:
<223> OTHER INFORMATION: chemically synthesized

<400> SEQUENCE: 777
atacgggagc caacaccagc cgaccggtaa gtttatataa acttccgccg cctagagcag      60
gtgtgacgga t                                                          71

<210> SEQ ID NO 778
<211> LENGTH: 71
<212> TYPE: DNA
<213> ORGANISM: Artificial Sequence
<220> FEATURE:
<223> OTHER INFORMATION: chemically synthesized

<400> SEQUENCE: 778
```

```
atccgtcaca cctgctctag gcggcggaag tttatataaa cttaccggtc ggctggtgtt    60
ggctcccgta t                                                         71
```

<210> SEQ ID NO 779
<211> LENGTH: 71
<212> TYPE: DNA
<213> ORGANISM: Artificial Sequence
<220> FEATURE:
<223> OTHER INFORMATION: chemically synthesized

<400> SEQUENCE: 779

```
atacgggagc caacaccatg actcacgctt ctcgcccgca cgaagagtct ccaagagcag    60
gtgtgacgga t                                                         71
```

<210> SEQ ID NO 780
<211> LENGTH: 71
<212> TYPE: DNA
<213> ORGANISM: Artificial Sequence
<220> FEATURE:
<223> OTHER INFORMATION: chemically synthesized

<400> SEQUENCE: 780

```
atccgtcaca cctgctcttg gagactcttc gtgcgggcga aagcgtgag tcatggtgtt     60 ggctcccgta t                                                         71
```

<210> SEQ ID NO 781
<211> LENGTH: 71
<212> TYPE: DNA
<213> ORGANISM: Artificial Sequence
<220> FEATURE:
<223> OTHER INFORMATION: chemically synthesized

<400> SEQUENCE: 781

```
atacgggagc caacaccatg acgaccatgc aagaaatccg acaattcctc acgagagcag    60
gtgtgacgga t                                                         71
```

<210> SEQ ID NO 782
<211> LENGTH: 71
<212> TYPE: DNA
<213> ORGANISM: Artificial Sequence
<220> FEATURE:
<223> OTHER INFORMATION: chemically synthesized

<400> SEQUENCE: 782

```
atccgtcaca cctgctctcg tgaggaattg tcggatttct tgcatggtcg tcatggtgtt    60
ggctcccgta t                                                         71
```

<210> SEQ ID NO 783
<211> LENGTH: 71
<212> TYPE: DNA
<213> ORGANISM: Artificial Sequence
<220> FEATURE:
<223> OTHER INFORMATION: chemically synthesized

<400> SEQUENCE: 783

```
atacgggagc caacaccaag catttagatt cgctccttga acccacttcc ttcagagcag    60
gtgtgacgga t                                                         71
```

<210> SEQ ID NO 784
<211> LENGTH: 71
<212> TYPE: DNA
<213> ORGANISM: Artificial Sequence
<220> FEATURE:

<223> OTHER INFORMATION: chemically synthesized

<400> SEQUENCE: 784

```
atccgtcaca cctgctctga aggaagtggg ttcaaggagc gaatctaaat gcttggtgtt    60
ggctcccgta t                                                        71
```

<210> SEQ ID NO 785
<211> LENGTH: 71
<212> TYPE: DNA
<213> ORGANISM: Artificial Sequence
<220> FEATURE:
<223> OTHER INFORMATION: chemically synthesized

<400> SEQUENCE: 785

```
atacgggagc caacaccagg tgcttctctt acgtggccgc tattccaaag tgaagagcag    60
gtgtgacgga t                                                        71
```

<210> SEQ ID NO 786
<211> LENGTH: 71
<212> TYPE: DNA
<213> ORGANISM: Artificial Sequence
<220> FEATURE:
<223> OTHER INFORMATION: chemically synthesized

<400> SEQUENCE: 786

```
atccgtcaca cctgctcttc actttggaat agcggccacg taagagaagc acctggtgtt    60
ggctcccgta t                                                        71
```

<210> SEQ ID NO 787
<211> LENGTH: 71
<212> TYPE: DNA
<213> ORGANISM: Artificial Sequence
<220> FEATURE:
<223> OTHER INFORMATION: chemically synthesized

<400> SEQUENCE: 787

```
atacgggagc caacaccagc ccgggcatgt cgtttgtatg aagctagcta actagagcag    60
gtgtgacgga t                                                        71
```

<210> SEQ ID NO 788
<211> LENGTH: 71
<212> TYPE: DNA
<213> ORGANISM: Artificial Sequence
<220> FEATURE:
<223> OTHER INFORMATION: chemically synthesized

<400> SEQUENCE: 788

```
atccgtcaca cctgctctag ttagctagct tcatacaaac gacatgcccg ggctggtgtt    60
ggctcccgta t                                                        71
```

<210> SEQ ID NO 789
<211> LENGTH: 71
<212> TYPE: DNA
<213> ORGANISM: Artificial Sequence
<220> FEATURE:
<223> OTHER INFORMATION: chemically synthesized

<400> SEQUENCE: 789

```
atacgggagc caacaccatg accatcaata cagacaaata gaatcgcgtt atgagagcag    60
gtgtgacgga t                                                        71
```

<210> SEQ ID NO 790

```
<211> LENGTH: 71
<212> TYPE: DNA
<213> ORGANISM: Artificial Sequence
<220> FEATURE:
<223> OTHER INFORMATION: chemically synthesized

<400> SEQUENCE: 790
atccgtcaca cctgctctca taacgcgatt ctatttgtct gtattgatgg tcatggtgtt      60
ggctcccgta t                                                          71

<210> SEQ ID NO 791
<211> LENGTH: 72
<212> TYPE: DNA
<213> ORGANISM: Artificial Sequence
<220> FEATURE:
<223> OTHER INFORMATION: chemically synthesized

<400> SEQUENCE: 791
atacgggagc caacaccatg agggtttcct cacatgggga ggtcctccat gtggagagca      60
ggtgtgacgg at                                                         72

<210> SEQ ID NO 792
<211> LENGTH: 72
<212> TYPE: DNA
<213> ORGANISM: Artificial Sequence
<220> FEATURE:
<223> OTHER INFORMATION: chemically synthesized

<400> SEQUENCE: 792
atccgtcaca cctgctctcc acatggagga cctccccatg tgaggaaacc ctcatggtgt      60
tggctcccgt at                                                         72

<210> SEQ ID NO 793
<211> LENGTH: 71
<212> TYPE: DNA
<213> ORGANISM: Artificial Sequence
<220> FEATURE:
<223> OTHER INFORMATION: chemically synthesized

<400> SEQUENCE: 793
atacgggagc caacaccagg actaacatta taagaattgc gaataatcat tggagagcag      60
gtgtgacgga t                                                          71

<210> SEQ ID NO 794
<211> LENGTH: 71
<212> TYPE: DNA
<213> ORGANISM: Artificial Sequence
<220> FEATURE:
<223> OTHER INFORMATION: chemically synthesized

<400> SEQUENCE: 794
atccgtcaca cctgctctcc aatgattatt cgcaattctt ataatgttag tcctggtgtt      60
ggctcccgta t                                                          71

<210> SEQ ID NO 795
<211> LENGTH: 71
<212> TYPE: DNA
<213> ORGANISM: Artificial Sequence
<220> FEATURE:
<223> OTHER INFORMATION: chemically synthesized

<400> SEQUENCE: 795
atacgggagc caacaccatt gtaccttaac tatactcagc tacattatgc caaagagcag      60
```
gtgtgacgga t                                                           71

<210> SEQ ID NO 796
<211> LENGTH: 71
<212> TYPE: DNA
<213> ORGANISM: Artificial Sequence
<220> FEATURE:
<223> OTHER INFORMATION: chemically synthesized

<400> SEQUENCE: 796
atccgtcaca cctgctcttt ggcataatgt agctgagtat agttaaggta caatggtgtt    60
ggctcccgta t                                                          71

<210> SEQ ID NO 797
<211> LENGTH: 71
<212> TYPE: DNA
<213> ORGANISM: Artificial Sequence
<220> FEATURE:
<223> OTHER INFORMATION: chemically synthesized

<400> SEQUENCE: 797
atacgggagc caacaccact catgttggat attacgaaca gtgcgttagg ctgagagcag    60
gtgtgacgga t                                                          71

<210> SEQ ID NO 798
<211> LENGTH: 71
<212> TYPE: DNA
<213> ORGANISM: Artificial Sequence
<220> FEATURE:
<223> OTHER INFORMATION: chemically synthesized

<400> SEQUENCE: 798
atccgtcaca cctgctctca gcctaacgca ctgttcgtaa tatccaacat gagtggtgtt    60
ggctcccgta t                                                          71

<210> SEQ ID NO 799
<211> LENGTH: 71
<212> TYPE: DNA
<213> ORGANISM: Artificial Sequence
<220> FEATURE:
<223> OTHER INFORMATION: chemically synthesized

<400> SEQUENCE: 799
atacgggagc caacaccatg aacgcatcac agttgcttca cactcgacta gctagagcag    60
gtgtgacgga t                                                          71

<210> SEQ ID NO 800
<211> LENGTH: 71
<212> TYPE: DNA
<213> ORGANISM: Artificial Sequence
<220> FEATURE:
<223> OTHER INFORMATION: chemically synthesized

<400> SEQUENCE: 800
atccgtcaca cctgctctag ctagtcgagt gtgaagcaac tgtgatgcgt tcatggtgtt    60
ggctcccgta t                                                          71

<210> SEQ ID NO 801
<211> LENGTH: 71
<212> TYPE: DNA
<213> ORGANISM: Artificial Sequence
<220> FEATURE:
<223> OTHER INFORMATION: chemically synthesized -continued

```
<400> SEQUENCE: 801
atacgggagc caacaccaaa aactactctc tacggatcgt acatcatggg cgtagagcag    60
gtgtgacgga t                                                        71

<210> SEQ ID NO 802
<211> LENGTH: 71
<212> TYPE: DNA
<213> ORGANISM: Artificial Sequence
<220> FEATURE:
<223> OTHER INFORMATION: chemically synthesized

<400> SEQUENCE: 802
atccgtcaca cctgctctac gcccatgatg tacgatccgt agagagtagt ttttggtgtt    60
ggctcccgta t                                                        71

<210> SEQ ID NO 803
<211> LENGTH: 72
<212> TYPE: DNA
<213> ORGANISM: Artificial Sequence
<220> FEATURE:
<223> OTHER INFORMATION: chemically synthesized

<400> SEQUENCE: 803
atacgggagc caacaccacc cactctcccc ccgctcccgc tcccccgctc cgcgagagca    60
ggtgtgacgg at                                                       72

<210> SEQ ID NO 804
<211> LENGTH: 72
<212> TYPE: DNA
<213> ORGANISM: Artificial Sequence
<220> FEATURE:
<223> OTHER INFORMATION: chemically synthesized

<400> SEQUENCE: 804
atccgtcaca cctgctctcg cggagcgggg gagcgggagc gggggagag tgggtggtgt    60 tggctcccgt at                                                       72

<210> SEQ ID NO 805
<211> LENGTH: 71
<212> TYPE: DNA
<213> ORGANISM: Artificial Sequence
<220> FEATURE:
<223> OTHER INFORMATION: chemically synthesized

<400> SEQUENCE: 805
atacgggagc caacaccata gggcaattaa ggccaagagt gttggccgtc gctagagcag    60
gtgtgacgga t                                                        71

<210> SEQ ID NO 806
<211> LENGTH: 71
<212> TYPE: DNA
<213> ORGANISM: Artificial Sequence
<220> FEATURE:
<223> OTHER INFORMATION: chemically synthesized

<400> SEQUENCE: 806
atccgtcaca cctgctctag cgacggccaa cactcttggc cttaattgcc ctatggtgtt    60
ggctcccgta t                                                        71

<210> SEQ ID NO 807
<211> LENGTH: 71
<212> TYPE: DNA
```

<213> ORGANISM: Artificial Sequence
<220> FEATURE:
<223> OTHER INFORMATION: chemically synthesized

<400> SEQUENCE: 807
atacgggagc caacaccaaa acgggaaact gcatttccca cgcctcgtac cccagagcag   60
gtgtgacgga t                                                       71

<210> SEQ ID NO 808
<211> LENGTH: 71
<212> TYPE: DNA
<213> ORGANISM: Artificial Sequence
<220> FEATURE:
<223> OTHER INFORMATION: chemically synthesized

<400> SEQUENCE: 808
atccgtcaca cctgctctgg ggtacgaggc gtgggaaatg cagtttcccg ttttggtgtt   60
ggctcccgta t                                                       71

<210> SEQ ID NO 809
<211> LENGTH: 71
<212> TYPE: DNA
<213> ORGANISM: Artificial Sequence
<220> FEATURE:
<223> OTHER INFORMATION: chemically synthesized

<400> SEQUENCE: 809
atacgggagc caacaccaaa ccgaaggatc gccgggtcag acctatctca agcagagcag   60
gtgtgacgga t                                                       71

<210> SEQ ID NO 810
<211> LENGTH: 71
<212> TYPE: DNA
<213> ORGANISM: Artificial Sequence
<220> FEATURE:
<223> OTHER INFORMATION: chemically synthesized

<400> SEQUENCE: 810
atccgtcaca cctgctctgc ttgagatagg tctgacccgg cgatccttcg gtttggtgtt   60
ggctcccgta t                                                       71

<210> SEQ ID NO 811
<211> LENGTH: 71
<212> TYPE: DNA
<213> ORGANISM: Artificial Sequence
<220> FEATURE:
<223> OTHER INFORMATION: chemically synthesized

<400> SEQUENCE: 811
atacgggagc caacaccatt tgctgacgaa ccattggcta gcttgattgt cacagagcag   60
gtgtgacgga t                                                       71

<210> SEQ ID NO 812
<211> LENGTH: 71
<212> TYPE: DNA
<213> ORGANISM: Artificial Sequence
<220> FEATURE:
<223> OTHER INFORMATION: chemically synthesized

<400> SEQUENCE: 812
atccgtcaca cctgctctgt gacaatcaag ctagccaatg gttcgtcagc aaatggtgtt   60
ggctcccgta t                                                       71

```
<210> SEQ ID NO 813
<211> LENGTH: 71
<212> TYPE: DNA
<213> ORGANISM: Artificial Sequence
<220> FEATURE:
<223> OTHER INFORMATION: chemically synthesized

<400> SEQUENCE: 813
atacgggagc caacaccaga cttttttgctg ccatcccggg tgtcgttgca agtagagcag    60
gtgtgacgga t                                                          71

<210> SEQ ID NO 814
<211> LENGTH: 71
<212> TYPE: DNA
<213> ORGANISM: Artificial Sequence
<220> FEATURE:
<223> OTHER INFORMATION: chemically synthesized

<400> SEQUENCE: 814
atccgtcaca cctgctctac ttgcaacgac acccgggatg gcagcaaaaa gtctggtgtt    60
ggctcccgta t                                                          71

<210> SEQ ID NO 815
<211> LENGTH: 72
<212> TYPE: DNA
<213> ORGANISM: Artificial Sequence
<220> FEATURE:
<223> OTHER INFORMATION: chemically synthesized

<400> SEQUENCE: 815
atacgggagc caacaccacg catccccgc cgggcccgcg ccccgctcgc agacagagca    60
ggtgtgacgg at                                                         72

<210> SEQ ID NO 816
<211> LENGTH: 72
<212> TYPE: DNA
<213> ORGANISM: Artificial Sequence
<220> FEATURE:
<223> OTHER INFORMATION: chemically synthesized

<400> SEQUENCE: 816
atccgtcaca cctgctctgt ctgcgagcgg ggcgcgggcc cggcggggga tgcgtggtgt    60
tggctcccgt at                                                         72

<210> SEQ ID NO 817
<211> LENGTH: 71
<212> TYPE: DNA
<213> ORGANISM: Artificial Sequence
<220> FEATURE:
<223> OTHER INFORMATION: chemically synthesized

<400> SEQUENCE: 817
atacgggagc caacaccaca atcattaaac cttttttactc ttcctgaatc accagagcag    60
gtgtgacgga t                                                          71

<210> SEQ ID NO 818
<211> LENGTH: 71
<212> TYPE: DNA
<213> ORGANISM: Artificial Sequence
<220> FEATURE:
<223> OTHER INFORMATION: chemically synthesized

<400> SEQUENCE: 818
```

```
atccgtcaca cctgctctgg tgattcagga agagtaaaaa ggtttaatga ttgtggtgtt    60
ggctcccgta t                                                         71
```

<210> SEQ ID NO 819
<211> LENGTH: 71
<212> TYPE: DNA
<213> ORGANISM: Artificial Sequence
<220> FEATURE:
<223> OTHER INFORMATION: chemically synthesized

<400> SEQUENCE: 819

```
atacgggagc caacaccaac ttatgcgacc cttccggtag ctggaggtta ttaagagcag    60
gtgtgacgga t                                                         71
```

<210> SEQ ID NO 820
<211> LENGTH: 71
<212> TYPE: DNA
<213> ORGANISM: Artificial Sequence
<220> FEATURE:
<223> OTHER INFORMATION: chemically synthesized

<400> SEQUENCE: 820

```
atccgtcaca cctgctctta ataacctcca gctaccggaa gggtcgcata agttggtgtt    60
ggctcccgta t                                                         71
```

<210> SEQ ID NO 821
<211> LENGTH: 72
<212> TYPE: DNA
<213> ORGANISM: Artificial Sequence
<220> FEATURE:
<223> OTHER INFORMATION: chemically synthesized

<400> SEQUENCE: 821

```
atacgggagc caacaccagg gccgcctctt tccgattcgt gggagccttc ttgaagagca    60
ggtgtgacgg at                                                        72
```

<210> SEQ ID NO 822
<211> LENGTH: 72
<212> TYPE: DNA
<213> ORGANISM: Artificial Sequence
<220> FEATURE:
<223> OTHER INFORMATION: chemically synthesized

<400> SEQUENCE: 822

```
atccgtcaca cctgctcttc aagaaggctc ccacgaatcg gaaagaggcg gccctggtgt    60
tggctcccgt at                                                        72
```

<210> SEQ ID NO 823
<211> LENGTH: 72
<212> TYPE: DNA
<213> ORGANISM: Artificial Sequence
<220> FEATURE:
<223> OTHER INFORMATION: chemically synthesized

<400> SEQUENCE: 823

```
atacgggagc caacaccatg ttccgtcaca ggtctcctgt tcttaatttg ttttagagca    60
ggtgtgacgg at                                                        72
```

<210> SEQ ID NO 824
<211> LENGTH: 72
<212> TYPE: DNA
<213> ORGANISM: Artificial Sequence
<220> FEATURE:

<223> OTHER INFORMATION: chemically synthesized

<400> SEQUENCE: 824
atccgtcaca cctgctctaa aacaaattaa gaacaggaga cctgtgacgg aacatggtgt 60
tggctcccgt at 72

<210> SEQ ID NO 825
<211> LENGTH: 71
<212> TYPE: DNA
<213> ORGANISM: Artificial Sequence
<220> FEATURE:
<223> OTHER INFORMATION: chemically synthesized

<400> SEQUENCE: 825
atacgggagc caacaccata cgacctggaa actgctcgtc agagtctgaa atgagagcag 60
gtgtgacgga t 71

<210> SEQ ID NO 826
<211> LENGTH: 71
<212> TYPE: DNA
<213> ORGANISM: Artificial Sequence
<220> FEATURE:
<223> OTHER INFORMATION: chemically synthesized

<400> SEQUENCE: 826
atccgtcaca cctgctctca tttcagactc tgacgagcag tttccaggtc gtatggtgtt 60
ggctcccgta t 71

<210> SEQ ID NO 827
<211> LENGTH: 71
<212> TYPE: DNA
<213> ORGANISM: Artificial Sequence
<220> FEATURE:
<223> OTHER INFORMATION: chemically synthesized

<400> SEQUENCE: 827
atacgggagc caacaccaag ttgtcactgg atgacattcg ggttcgcttg cacagagcag 60
gtgtgacgga t 71

<210> SEQ ID NO 828
<211> LENGTH: 71
<212> TYPE: DNA
<213> ORGANISM: Artificial Sequence
<220> FEATURE:
<223> OTHER INFORMATION: chemically synthesized

<400> SEQUENCE: 828
atccgtcaca cctgctctgt gcaagcgaac ccgaatgtca tccagtgaca acttggtgtt 60
ggctcccgta t 71

<210> SEQ ID NO 829
<211> LENGTH: 71
<212> TYPE: DNA
<213> ORGANISM: Artificial Sequence
<220> FEATURE:
<223> OTHER INFORMATION: chemically synthesized

<400> SEQUENCE: 829
atacgggagc caacaccaaa gtggattgcg acgtgcttct accagatacc cggagagcag 60
gtgtgacgga t 71

<210> SEQ ID NO 830

```
<211> LENGTH: 71
<212> TYPE: DNA
<213> ORGANISM: Artificial Sequence
<220> FEATURE:
<223> OTHER INFORMATION: chemically synthesized

<400> SEQUENCE: 830
atccgtcaca cctgctctcc gggtatctgg tagaagcacg tcgcaatcca ctttggtgtt    60
ggctcccgta t                                                        71

<210> SEQ ID NO 831
<211> LENGTH: 71
<212> TYPE: DNA
<213> ORGANISM: Artificial Sequence
<220> FEATURE:
<223> OTHER INFORMATION: chemically synthesized

<400> SEQUENCE: 831
atacgggagc caacaccagc acacggcacg cccctccgaa ccacgccccc gaaagagcag    60
gtgtgacgga t                                                        71

<210> SEQ ID NO 832
<211> LENGTH: 71
<212> TYPE: DNA
<213> ORGANISM: Artificial Sequence
<220> FEATURE:
<223> OTHER INFORMATION: chemically synthesized

<400> SEQUENCE: 832
atccgtcaca cctgctcttt cggggggcgtg gttcggaggg gcgtgccgtg tgctggtgtt    60
ggctcccgta t                                                        71

<210> SEQ ID NO 833
<211> LENGTH: 71
<212> TYPE: DNA
<213> ORGANISM: Artificial Sequence
<220> FEATURE:
<223> OTHER INFORMATION: chemically synthesized

<400> SEQUENCE: 833
atacgggagc caacaccagc gacgacagtt atataatccg agaatagtac atgagagcag    60
gtgtgacgga t                                                        71

<210> SEQ ID NO 834
<211> LENGTH: 71
<212> TYPE: DNA
<213> ORGANISM: Artificial Sequence
<220> FEATURE:
<223> OTHER INFORMATION: chemically synthesized

<400> SEQUENCE: 834
atccgtcaca cctgctctca tgtactattc tcggattata taactgtcgt cgctggtgtt    60
ggctcccgta t                                                        71

<210> SEQ ID NO 835
<211> LENGTH: 70
<212> TYPE: DNA
<213> ORGANISM: Artificial Sequence
<220> FEATURE:
<223> OTHER INFORMATION: chemically synthesized

<400> SEQUENCE: 835
atacgggagc caacaccagc acacggcacg ccccccgaac cacgccccg aaagagcagg    60
```

```
tgtgacggat                                                              70

<210> SEQ ID NO 836
<211> LENGTH: 70
<212> TYPE: DNA
<213> ORGANISM: Artificial Sequence
<220> FEATURE:
<223> OTHER INFORMATION: chemically synthesized

<400> SEQUENCE: 836
atccgtcaca cctgctcttt cgggggcgtg gttcgggggg cgtgccgtgt gctggtgttg      60
gctcccgtat                                                              70

<210> SEQ ID NO 837
<211> LENGTH: 71
<212> TYPE: DNA
<213> ORGANISM: Artificial Sequence
<220> FEATURE:
<223> OTHER INFORMATION: chemically synthesized

<400> SEQUENCE: 837
atacgggagc caacaccata tttcaatctg ttgaaataat tcatacatgc ttaagagcag      60
gtgtgacgga t                                                            71

<210> SEQ ID NO 838
<211> LENGTH: 71
<212> TYPE: DNA
<213> ORGANISM: Artificial Sequence
<220> FEATURE:
<223> OTHER INFORMATION: chemically synthesized

<400> SEQUENCE: 838
atccgtcaca cctgctctta agcatgtatg aattatttca acagattgaa atatggtgtt      60
ggctcccgta t                                                            71

<210> SEQ ID NO 839
<211> LENGTH: 72
<212> TYPE: DNA
<213> ORGANISM: Artificial Sequence
<220> FEATURE:
<223> OTHER INFORMATION: chemically synthesized

<400> SEQUENCE: 839
atacgggagc caacaccatc ctcctgcgac gtctggagaa cagcctctac tttaagagca      60
ggtgtgacgg at                                                           72

<210> SEQ ID NO 840
<211> LENGTH: 72
<212> TYPE: DNA
<213> ORGANISM: Artificial Sequence
<220> FEATURE:
<223> OTHER INFORMATION: chemically synthesized

<400> SEQUENCE: 840
atccgtcaca cctgctctta aagtagaggc tgttctccag acgtcgcagg aggatggtgt      60
tggctcccgt at                                                           72

<210> SEQ ID NO 841
<211> LENGTH: 71
<212> TYPE: DNA
<213> ORGANISM: Artificial Sequence
<220> FEATURE:
<223> OTHER INFORMATION: chemically synthesized
```

<400> SEQUENCE: 841
atacgggagc caacaccagg ctgcgtacat gaacaggcac tacaaatgtc ccaagagcag    60
gtgtgacgga t                                                         71

<210> SEQ ID NO 842
<211> LENGTH: 71
<212> TYPE: DNA
<213> ORGANISM: Artificial Sequence
<220> FEATURE:
<223> OTHER INFORMATION: chemically synthesized

<400> SEQUENCE: 842
atccgtcaca cctgctcttg ggacatttgt agtgcctgtt catgtacgca gcctggtgtt    60
ggctcccgta t                                                         71

<210> SEQ ID NO 843
<211> LENGTH: 72
<212> TYPE: DNA
<213> ORGANISM: Artificial Sequence
<220> FEATURE:
<223> OTHER INFORMATION: chemically synthesized

<400> SEQUENCE: 843
atacgggagc caacaccaca gagagaagta cgtaacatca aaaacgcggt cagaagagca    60
ggtgtgacgg at                                                        72

<210> SEQ ID NO 844
<211> LENGTH: 72
<212> TYPE: DNA
<213> ORGANISM: Artificial Sequence
<220> FEATURE:
<223> OTHER INFORMATION: chemically synthesized

<400> SEQUENCE: 844
atccgtcaca cctgctcttc tgaccgcgtt tttgatgtta cgtacttctc tctgtggtgt    60
tggctcccgt at                                                        72

<210> SEQ ID NO 845
<211> LENGTH: 70
<212> TYPE: DNA
<213> ORGANISM: Artificial Sequence
<220> FEATURE:
<223> OTHER INFORMATION: chemically synthesized

<400> SEQUENCE: 845
atacgggagc caacaccaac acaaccgagc caatagacaa tcagtgtttc acagagcagg    60
tgtgacggat                                                           70

<210> SEQ ID NO 846
<211> LENGTH: 70
<212> TYPE: DNA
<213> ORGANISM: Artificial Sequence
<220> FEATURE:
<223> OTHER INFORMATION: chemically synthesized

<400> SEQUENCE: 846
atccgtcaca cctgctctgt gaaacactga ttgtctattg gctcggttgt gttggtgttg    60
gctcccgtat                                                           70

<210> SEQ ID NO 847
<211> LENGTH: 72
<212> TYPE: DNA

```
<213> ORGANISM: Artificial Sequence
<220> FEATURE:
<223> OTHER INFORMATION: chemically synthesized

<400> SEQUENCE: 847
atacgggagc caacaccacc ctaaattcca gagtgtacaa gagaacgaac taccagagca      60
ggtgtgacgg at                                                         72

<210> SEQ ID NO 848
<211> LENGTH: 72
<212> TYPE: DNA
<213> ORGANISM: Artificial Sequence
<220> FEATURE:
<223> OTHER INFORMATION: chemically synthesized

<400> SEQUENCE: 848
atccgtcaca cctgctctgg tagttcgttc tcttgtacac tctggaattt agggtggtgt      60
tggctcccgt at                                                         72

<210> SEQ ID NO 849
<211> LENGTH: 72
<212> TYPE: DNA
<213> ORGANISM: Artificial Sequence
<220> FEATURE:
<223> OTHER INFORMATION: chemically synthesized

<400> SEQUENCE: 849
atacgggagc caacaccaat agatggataa gggggaaact gccattcggt tagtagagca      60
ggtgtgacgg at                                                         72

<210> SEQ ID NO 850
<211> LENGTH: 72
<212> TYPE: DNA
<213> ORGANISM: Artificial Sequence
<220> FEATURE:
<223> OTHER INFORMATION: chemically synthesized

<400> SEQUENCE: 850
atccgtcaca cctgctctac taaccgaatg gcagtttccc ccttatccat ctattggtgt      60
tggctcccgt at                                                         72

<210> SEQ ID NO 851
<211> LENGTH: 72
<212> TYPE: DNA
<213> ORGANISM: Artificial Sequence
<220> FEATURE:
<223> OTHER INFORMATION: chemically synthesized

<400> SEQUENCE: 851
atacgggagc caacaccaaa acccgcacta catctcctct gcccccttct gataagagca      60
ggtgtgacgg at                                                         72

<210> SEQ ID NO 852
<211> LENGTH: 72
<212> TYPE: DNA
<213> ORGANISM: Artificial Sequence
<220> FEATURE:
<223> OTHER INFORMATION: chemically synthesized

<400> SEQUENCE: 852
atccgtcaca cctgctctta tcagaagggg gcagaggaga tgtagtgcgg gttttggtgt      60
tggctcccgt at                                                         72
```

-continued

<210> SEQ ID NO 853
<211> LENGTH: 69
<212> TYPE: DNA
<213> ORGANISM: Artificial Sequence
<220> FEATURE:
<223> OTHER INFORMATION: chemically synthesized

<400> SEQUENCE: 853
atacgggagc caacaccatc gaatggtctc ccaactaaag aaactctcca tccagagcag    60
gtgtgacgg                                                            69

<210> SEQ ID NO 854
<211> LENGTH: 69
<212> TYPE: DNA
<213> ORGANISM: Artificial Sequence
<220> FEATURE:
<223> OTHER INFORMATION: chemically synthesized

<400> SEQUENCE: 854
ccgtcacacc tgctctggat ggagagtttc tttagttggg agaccattcg atggtgttgg    60
ctcccgtat                                                            69

<210> SEQ ID NO 855
<211> LENGTH: 72
<212> TYPE: DNA
<213> ORGANISM: Artificial Sequence
<220> FEATURE:
<223> OTHER INFORMATION: chemically synthesized

<400> SEQUENCE: 855
atacgggagc caacaccacg ggggcatctt ccattaaccc attacctcac cccaagagca    60
ggtgtgacgg at                                                        72

<210> SEQ ID NO 856
<211> LENGTH: 72
<212> TYPE: DNA
<213> ORGANISM: Artificial Sequence
<220> FEATURE:
<223> OTHER INFORMATION: chemically synthesized

<400> SEQUENCE: 856
atccgtcaca cctgctcttg gggtgaggta atgggttaat ggaagatgcc cccgtggtgt    60
tggctcccgt at                                                        72

<210> SEQ ID NO 857
<211> LENGTH: 71
<212> TYPE: DNA
<213> ORGANISM: Artificial Sequence
<220> FEATURE:
<223> OTHER INFORMATION: chemically synthesized

<400> SEQUENCE: 857
atacgggagc caacaccatg gacgtactga ctgccccgta ctcttttcag ttgagagcag    60
gtgtgacgga t                                                         71

<210> SEQ ID NO 858
<211> LENGTH: 71
<212> TYPE: DNA
<213> ORGANISM: Artificial Sequence
<220> FEATURE:
<223> OTHER INFORMATION: chemically synthesized

<400> SEQUENCE: 858

```
atccgtcaca cctgctctca actgaaaaga gtacggggca gtcagtacgt ccatggtgtt      60
ggctcccgta t                                                          71
```

<210> SEQ ID NO 859
<211> LENGTH: 71
<212> TYPE: DNA
<213> ORGANISM: Artificial Sequence
<220> FEATURE:
<223> OTHER INFORMATION: chemically synthesized

<400> SEQUENCE: 859

```
atacgggagc caacaccaac taactactca agatgaacac tgtcggcgtt tacagagcag      60
gtgtgacgga t                                                          71
```

<210> SEQ ID NO 860
<211> LENGTH: 71
<212> TYPE: DNA
<213> ORGANISM: Artificial Sequence
<220> FEATURE:
<223> OTHER INFORMATION: chemically synthesized

<400> SEQUENCE: 860

```
atccgtcaca cctgctctgt aaacgccgac agtgttcatc ttgagtagtt agttggtgtt      60
ggctcccgta t                                                          71
```

<210> SEQ ID NO 861
<211> LENGTH: 71
<212> TYPE: DNA
<213> ORGANISM: Artificial Sequence
<220> FEATURE:
<223> OTHER INFORMATION: chemically synthesized

<400> SEQUENCE: 861

```
atacgggagc caacaccagc ccttaagcgt tgcctaacgg actctgaggc aatagagcag      60
gtgtgacgga t                                                          71
```

<210> SEQ ID NO 862
<211> LENGTH: 71
<212> TYPE: DNA
<213> ORGANISM: Artificial Sequence
<220> FEATURE:
<223> OTHER INFORMATION: chemically synthesized

<400> SEQUENCE: 862

```
atccgtcaca cctgctctat tgcctcagag tccgttaggc aacgcttaag ggctggtgtt      60
ggctcccgta t                                                          71
```

<210> SEQ ID NO 863
<211> LENGTH: 71
<212> TYPE: DNA
<213> ORGANISM: Artificial Sequence
<220> FEATURE:
<223> OTHER INFORMATION: chemically synthesized

<400> SEQUENCE: 863

```
atacgggagc caacaccaac ctcacttaca actcgatttt ttatggacag ccgagagcag      60
gtgtgacgga t                                                          71
```

<210> SEQ ID NO 864
<211> LENGTH: 71
<212> TYPE: DNA
<213> ORGANISM: Artificial Sequence
<220> FEATURE:

-continued

<223> OTHER INFORMATION: chemically synthesized

<400> SEQUENCE: 864
atccgtcaca cctgctctcg gctgtccata aaaaatcgag ttgtaagtga ggttggtgtt    60
ggctcccgta t    71

<210> SEQ ID NO 865
<211> LENGTH: 72
<212> TYPE: DNA
<213> ORGANISM: Artificial Sequence
<220> FEATURE:
<223> OTHER INFORMATION: chemically synthesized

<400> SEQUENCE: 865
atacgggagc caacaccatt tgagcggcag ctaaccggcc gaccaattcg ctacagagca    60
ggtgtgacgg at    72

<210> SEQ ID NO 866
<211> LENGTH: 72
<212> TYPE: DNA
<213> ORGANISM: Artificial Sequence
<220> FEATURE:
<223> OTHER INFORMATION: chemically synthesized

<400> SEQUENCE: 866
atccgtcaca cctgctctgt agcgaattgg tcggccggtt agctgccgct caaatggtgt    60
tggctcccgt at    72

<210> SEQ ID NO 867
<211> LENGTH: 72
<212> TYPE: DNA
<213> ORGANISM: Artificial Sequence
<220> FEATURE:
<223> OTHER INFORMATION: chemically synthesized

<400> SEQUENCE: 867
atacgggagc caacaccacc ttttaaaacg ctagctagct tagtccattc caccagagca    60
ggtgtgacgg at    72

<210> SEQ ID NO 868
<211> LENGTH: 72
<212> TYPE: DNA
<213> ORGANISM: Artificial Sequence
<220> FEATURE:
<223> OTHER INFORMATION: chemically synthesized

<400> SEQUENCE: 868
atccgtcaca cctgctctgg tggaatggac taagctagct agcgttttaa aaggtggtgt    60
tggctcccgt at    72

<210> SEQ ID NO 869
<211> LENGTH: 72
<212> TYPE: DNA
<213> ORGANISM: Artificial Sequence
<220> FEATURE:
<223> OTHER INFORMATION: chemically synthesized

<400> SEQUENCE: 869
atacgggagc caacaccagc cctgggccag cccgtgactt tccccggcg tccaagagca     60 ggtgtgacgg at    72

<210> SEQ ID NO 870

```
<211> LENGTH: 72
<212> TYPE: DNA
<213> ORGANISM: Artificial Sequence
<220> FEATURE:
<223> OTHER INFORMATION: chemically synthesized

<400> SEQUENCE: 870
atccgtcaca cctgctcttg dacgccgggg gaaagtcacg ggctggccca gggctggtgt    60
tggctcccgt at                                                        72

<210> SEQ ID NO 871
<211> LENGTH: 72
<212> TYPE: DNA
<213> ORGANISM: Artificial Sequence
<220> FEATURE:
<223> OTHER INFORMATION: chemically synthesized

<400> SEQUENCE: 871
atacgggagc caacaccatc ctcctgcggc gtctggagaa cagcctctac tttaagagca    60
ggtgtgacgg at                                                        72

<210> SEQ ID NO 872
<211> LENGTH: 72
<212> TYPE: DNA
<213> ORGANISM: Artificial Sequence
<220> FEATURE:
<223> OTHER INFORMATION: chemically synthesized

<400> SEQUENCE: 872
atccgtcaca cctgctctta agtagaggc tgttctccag acgccgcagg aggatggtgt     60
tggctcccgt at                                                        72

<210> SEQ ID NO 873
<211> LENGTH: 72
<212> TYPE: DNA
<213> ORGANISM: Artificial Sequence
<220> FEATURE:
<223> OTHER INFORMATION: chemically synthesized

<400> SEQUENCE: 873
atacgggagc caacaccacc aacgaatact accaggccta gcacaataca caacagagca    60
ggtgtgacgg at                                                        72

<210> SEQ ID NO 874
<211> LENGTH: 72
<212> TYPE: DNA
<213> ORGANISM: Artificial Sequence
<220> FEATURE:
<223> OTHER INFORMATION: chemically synthesized

<400> SEQUENCE: 874
atccgtcaca cctgctctgt tgtgtattgt gctaggcctg gtagtattcg ttggtggtgt    60
tggctcccgt at                                                        72

<210> SEQ ID NO 875
<211> LENGTH: 72
<212> TYPE: DNA
<213> ORGANISM: Artificial Sequence
<220> FEATURE:
<223> OTHER INFORMATION: chemically synthesized

<400> SEQUENCE: 875
atacgggagc caacaccacc gaatgtgctg caagactaat ctggatggcc atgcagagca    60
```

-continued ggtgtgacgg at					72

<210> SEQ ID NO 876
<211> LENGTH: 72
<212> TYPE: DNA
<213> ORGANISM: Artificial Sequence
<220> FEATURE:
<223> OTHER INFORMATION: chemically synthesized

<400> SEQUENCE: 876
atccgtcaca cctgctctgc atggccatcc agattagtct tgcagcacat tcggtggtgt		60 tggctcccgt at					72

<210> SEQ ID NO 877
<211> LENGTH: 71
<212> TYPE: DNA
<213> ORGANISM: Artificial Sequence
<220> FEATURE:
<223> OTHER INFORMATION: chemically synthesized

<400> SEQUENCE: 877
atacgggagc caacaccatt gaggggctgg gatactgcaa cttaaagtcc aggagagcag		60 gtgtgacgga t					71

<210> SEQ ID NO 878
<211> LENGTH: 71
<212> TYPE: DNA
<213> ORGANISM: Artificial Sequence
<220> FEATURE:
<223> OTHER INFORMATION: chemically synthesized

<400> SEQUENCE: 878
atccgtcaca cctgctctcc tggactttaa gttgcagtat cccagcccct caatggtgtt		60 ggctcccgta t					71

<210> SEQ ID NO 879
<211> LENGTH: 71
<212> TYPE: DNA
<213> ORGANISM: Artificial Sequence
<220> FEATURE:
<223> OTHER INFORMATION: chemically synthesized

<400> SEQUENCE: 879
atacgggagc caacaccaat aagcgactag tgtattggta ctggcctttt ccgagagcag		60 gtgtgacgga t					71

<210> SEQ ID NO 880
<211> LENGTH: 71
<212> TYPE: DNA
<213> ORGANISM: Artificial Sequence
<220> FEATURE:
<223> OTHER INFORMATION: chemically synthesized

<400> SEQUENCE: 880
atccgtcaca cctgctctcg gaaaaggcca gtaccaatac actagtcgct tattggtgtt		60 ggctcccgta t					71

<210> SEQ ID NO 881
<211> LENGTH: 72
<212> TYPE: DNA
<213> ORGANISM: Artificial Sequence
<220> FEATURE:
<223> OTHER INFORMATION: chemically synthesized

```
<400> SEQUENCE: 881
atacgggagc caacaccaat cttactagtt tgggaaaaaa attaaatata agcaagagca    60
ggtgtgacgg at                                                       72

<210> SEQ ID NO 882
<211> LENGTH: 72
<212> TYPE: DNA
<213> ORGANISM: Artificial Sequence
<220> FEATURE:
<223> OTHER INFORMATION: chemically synthesized

<400> SEQUENCE: 882
atccgtcaca cctgctcttg cttatattta atttttttcc caaactagta agattggtgt    60
tggctcccgt at                                                       72

<210> SEQ ID NO 883
<211> LENGTH: 72
<212> TYPE: DNA
<213> ORGANISM: Artificial Sequence
<220> FEATURE:
<223> OTHER INFORMATION: chemically synthesized

<400> SEQUENCE: 883
atacgggagc caacaccagt ccgttatgac atgtccggac ccgtacgcgt gtcaagagca    60
ggtgtgacgg at                                                       72

<210> SEQ ID NO 884
<211> LENGTH: 72
<212> TYPE: DNA
<213> ORGANISM: Artificial Sequence
<220> FEATURE:
<223> OTHER INFORMATION: chemically synthesized

<400> SEQUENCE: 884
atccgtcaca cctgctcttg acacgcgtac gggtccggac atgtcataac ggactggtgt    60
tggctcccgt at                                                       72

<210> SEQ ID NO 885
<211> LENGTH: 71
<212> TYPE: DNA
<213> ORGANISM: Artificial Sequence
<220> FEATURE:
<223> OTHER INFORMATION: chemically synthesized

<400> SEQUENCE: 885
atacgggagc caacaccagg gattgcatta cccatgacta agagtaggtc gcaagagcag    60
gtgtgacgga t                                                        71

<210> SEQ ID NO 886
<211> LENGTH: 71
<212> TYPE: DNA
<213> ORGANISM: Artificial Sequence
<220> FEATURE:
<223> OTHER INFORMATION: chemically synthesized

<400> SEQUENCE: 886
atccgtcaca cctgctcttg cgacctactc ttagtcatgg gtaatgcaat ccctggtgtt    60
ggctcccgta t                                                        71

<210> SEQ ID NO 887
<211> LENGTH: 72
<212> TYPE: DNA
```

```
<213> ORGANISM: Artificial Sequence
<220> FEATURE:
<223> OTHER INFORMATION: chemically synthesized

<400> SEQUENCE: 887
atacgggagc caacaccata gaagtatgtt gttattctat ggaaataaaa cgacagagca    60
ggtgtgacgg at                                                        72

<210> SEQ ID NO 888
<211> LENGTH: 72
<212> TYPE: DNA
<213> ORGANISM: Artificial Sequence
<220> FEATURE:
<223> OTHER INFORMATION: chemically synthesized

<400> SEQUENCE: 888
atccgtcaca cctgctctgt cgttttattt ccatagaata caacatact tctatggtgt    60 tggctcccgt at                                                        72

<210> SEQ ID NO 889
<211> LENGTH: 72
<212> TYPE: DNA
<213> ORGANISM: Artificial Sequence
<220> FEATURE:
<223> OTHER INFORMATION: chemically synthesized

<400> SEQUENCE: 889
atacgggagc caacaccatc ccgttgtgat cagagagcat gaaatgatgt tttgagagca    60
ggtgtgacgg at                                                        72

<210> SEQ ID NO 890
<211> LENGTH: 72
<212> TYPE: DNA
<213> ORGANISM: Artificial Sequence
<220> FEATURE:
<223> OTHER INFORMATION: chemically synthesized

<400> SEQUENCE: 890
atccgtcaca cctgctctca aaacatcatt tcatgctctc tgatcacaac gggatggtgt    60
tggctcccgt at                                                        72

<210> SEQ ID NO 891
<211> LENGTH: 72
<212> TYPE: DNA
<213> ORGANISM: Artificial Sequence
<220> FEATURE:
<223> OTHER INFORMATION: chemically synthesized

<400> SEQUENCE: 891
atacgggagc caacaccatg catgggacct gttatcctaa caagctgtca aggcagagca    60
ggtgtgacgg at                                                        72

<210> SEQ ID NO 892
<211> LENGTH: 72
<212> TYPE: DNA
<213> ORGANISM: Artificial Sequence
<220> FEATURE:
<223> OTHER INFORMATION: chemically synthesized

<400> SEQUENCE: 892
atccgtcaca cctgctctgc cttgacagct tgttaggata acaggtccca tgcatggtgt    60
tggctcccgt at                                                        72
```

<210> SEQ ID NO 893
<211> LENGTH: 71
<212> TYPE: DNA
<213> ORGANISM: Artificial Sequence
<220> FEATURE:
<223> OTHER INFORMATION: chemically synthesized

<400> SEQUENCE: 893
atacgggagc caacaccaca aaacgttccg agggagtaag cacttaataa tgtagagcag    60
gtgtgacgga t                                                         71

<210> SEQ ID NO 894
<211> LENGTH: 71
<212> TYPE: DNA
<213> ORGANISM: Artificial Sequence
<220> FEATURE:
<223> OTHER INFORMATION: chemically synthesized

<400> SEQUENCE: 894
atccgtcaca cctgctctac attattaagt gcttactccc tcggaacgtt ttgtggtgtt    60
ggctcccgta t                                                         71

<210> SEQ ID NO 895
<211> LENGTH: 72
<212> TYPE: DNA
<213> ORGANISM: Artificial Sequence
<220> FEATURE:
<223> OTHER INFORMATION: chemically synthesized

<400> SEQUENCE: 895
atacgggagc caacaccacg tcttatagat gtctgtattg tttatcgctc gcccagagca    60
ggtgtgacgg at                                                        72

<210> SEQ ID NO 896
<211> LENGTH: 72
<212> TYPE: DNA
<213> ORGANISM: Artificial Sequence
<220> FEATURE:
<223> OTHER INFORMATION: chemically synthesized

<400> SEQUENCE: 896
atccgtcaca cctgctctgg gcgagcgata acaatacag acatctataa gacgtggtgt     60
tggctcccgt at                                                        72

<210> SEQ ID NO 897
<211> LENGTH: 72
<212> TYPE: DNA
<213> ORGANISM: Artificial Sequence
<220> FEATURE:
<223> OTHER INFORMATION: chemically synthesized

<400> SEQUENCE: 897
atacgggagc caacaccacc atctctggtg ataaccagtg atcttaacta tagcagagca    60
ggtgtgacgg at                                                        72

<210> SEQ ID NO 898
<211> LENGTH: 72
<212> TYPE: DNA
<213> ORGANISM: Artificial Sequence
<220> FEATURE:
<223> OTHER INFORMATION: chemically synthesized

<400> SEQUENCE: 898

-continued atccgtcaca cctgctctgc tatagttaag atcactggtt atcaccagag atggtggtgt    60
tggctcccgt at    72

<210> SEQ ID NO 899
<211> LENGTH: 72
<212> TYPE: DNA
<213> ORGANISM: Artificial Sequence
<220> FEATURE:
<223> OTHER INFORMATION: chemically synthesized

<400> SEQUENCE: 899
atacgggagc caacaccacc acctcactac agtgatcttt tgctctgaat agccagagca    60
ggtgtgacgg at    72

<210> SEQ ID NO 900
<211> LENGTH: 72
<212> TYPE: DNA
<213> ORGANISM: Artificial Sequence
<220> FEATURE:
<223> OTHER INFORMATION: chemically synthesized

<400> SEQUENCE: 900
atccgtcaca cctgctctgg ctattcagag caaaagatca ctgtagtgag gtggtggtgt    60
tggctcccgt at    72

<210> SEQ ID NO 901
<211> LENGTH: 72
<212> TYPE: DNA
<213> ORGANISM: Artificial Sequence
<220> FEATURE:
<223> OTHER INFORMATION: chemically synthesized

<400> SEQUENCE: 901
atacgggagc caacaccatg tctcttagga tacaaagcca aactgagccc gtgcagagca    60
ggtgtgacgg at    72

<210> SEQ ID NO 902
<211> LENGTH: 72
<212> TYPE: DNA
<213> ORGANISM: Artificial Sequence
<220> FEATURE:
<223> OTHER INFORMATION: chemically synthesized

<400> SEQUENCE: 902
atccgtcaca cctgctctgc acgggctcag tttggctttg tatcctaaga gacatggtgt    60
tggctcccgt at    72

<210> SEQ ID NO 903
<211> LENGTH: 72
<212> TYPE: DNA
<213> ORGANISM: Artificial Sequence
<220> FEATURE:
<223> OTHER INFORMATION: chemically synthesized

<400> SEQUENCE: 903
atacgggagc caacaccacc tccaatagcc aaaagaaatc gccaactaac ggcaagagca    60
ggtgtgacgg at    72

<210> SEQ ID NO 904
<211> LENGTH: 72
<212> TYPE: DNA
<213> ORGANISM: Artificial Sequence
<220> FEATURE:

<223> OTHER INFORMATION: chemically synthesized

<400> SEQUENCE: 904
atccgtcaca cctgctcttg ccgttagttg gcgatttctt ttggctattg gaggtggtgt    60
tggctcccgt at    72

<210> SEQ ID NO 905
<211> LENGTH: 72
<212> TYPE: DNA
<213> ORGANISM: Artificial Sequence
<220> FEATURE:
<223> OTHER INFORMATION: chemically synthesized

<400> SEQUENCE: 905
atacgggagc caacaccatc actactttta taatttcatt cttctggcgt ccctagagca    60
ggtgtgacgg at    72

<210> SEQ ID NO 906
<211> LENGTH: 72
<212> TYPE: DNA
<213> ORGANISM: Artificial Sequence
<220> FEATURE:
<223> OTHER INFORMATION: chemically synthesized

<400> SEQUENCE: 906
atccgtcaca cctgctctag ggacgccaga agaatgaaat tataaaagta gtgatggtgt    60
tggctcccgt at    72

US 8,658,613 B2

METHODS AND COMPOSITIONS OF NUCLEIC ACID LIGANDS FOR DETECTION OF CLINICAL ANALYTES RELATED TO HUMAN HEALTH

PRIORITY INFORMATION

This application is based upon and claims priority from U.S. Provisional application Ser. No. 61/402,491 filed on Aug. 31, 2010, and Ser. No. 61/463,020 filed on Feb. 10, 2011, which are incorporated herein by reference.

BACKGROUND OF THE INVENTION

1. Field of the Invention

The present invention pertains to the field of aptamer- and nucleic acid ligand (DNA and RNA ligand)-based diagnostics. More specifically, the application relates to single-stranded deoxyribonucleic acid ("DNA") and ribonucleic acid ("RNA") ligand sequences, whether individual or linked together to form longer multiple binding site "receptors," that specifically target and bind to clinically relevant analytes on one or more binding sites or "epitopes" from humans such a cardiovascular biomarkers, bone metabolism markers, glucose, natural or recombinant human growth hormone ("hGH" or somatotropin) and vitamins. The invention includes general DNA ligand or aptamer-based detection and quantitation of these analytes in body fluids such as blood plasma, serum, sputum or saliva, interstitial, synovial, or cerebrospinal fluid aspirates, mucus, and urine or solid biopsy samples.

2. Background Information

These individual or linked DNA ligand (aptamer) sequences represent valuable target analyte-responsive components of diagnostic devices or biosensors. A "biosensor" is defined as any device that employs a biologically-derived molecule as the sensing component and transduces a target analyte binding event into a detectable physical signal (including, but not limited to, changes in light intensity, absorbance, transmittance, refraction (Surface Plasmon Resonance or "SPR"), wavelength, color, agglutination of cells or particles, fluorescence intensity, fluorescence lifetime, fluorescence polarization or anisotropy, fluorescence correlation spectroscopy ("FCS"), fluorescence or Förster resonance energy transfer ("FRET"; nonradiative dipole-dipole coupling of fluorophores or fluorophores and quenchers), upconverting phosphor, two-photon interaction phenomena, Raman spectroscopy or surface-enhanced Raman spectroscopy ("SERS"), electrical conduction, electrical resistance or other electrical properties, mass, photon or radioactive particle emissions, etc).

Once bonded with the target, these DNA ligand sequences can be used to qualitatively determine the presence of analyte, as well as to quantify or semi-quantify the target analyte amount in a sample using a broad variety of assay types and diagnostic or sensor platforms including, but not limited to, affinity-based lateral flow test strips, membrane blotting, SPR, surface acoustic waveguides ("SAW" devices), magnetic bead ("MB")-based capture, plastic-adherent sandwich assays ("PASA"), chemiluminescence ("CL"), electrochemiluminescence ("ECL"), radioisotopic, fluorescence intensity, including quantum dot ("QD") or other fluorescent nanoparticle ("FNP") of dye-based, fluorescence lifetime, and fluorescence polarization ("FP") assays or enzyme-linked ("ELISA-like") microplate assays. ELISA-like assays refer to microwell or microplate assays similar to traditional Enzyme-Linked Immunosorbent Assays ("ELISA") in which an aptamer or nucleic acid ligand is substituted for the antibody or receptor component or components, but the other components such as peroxidase or alkaline phosphatase enzymes and color-producing substrates remain the same.

In addition, these DNA ligand sequences are valuable in competitive displacement assays which are not solely dependent on high affinity (strong attractive forces between a receptor and its ligand) or high avidity (high tensile or physical strength of receptor-ligand bonds) to produce sensitive detection (sub-nanoMolar or sub-nanogram levels), because the equilibrium constant (generally $K_a=10^6$ to $10^8$ to enable competition) must allow reasonable displacement of previously bound target materials to detect a change at or below nanogram or nanoMolar levels.

In a competitive displacement assay, labeled DNA ligand plus labeled analyte complexes compete with unlabeled analyte to bind with the labeled DNA. After allowing the labeled and unlabeled analytes to come to equilibrium with the labeled DNA, the unlabeled target analyte may be quantitatively assayed by fluorescence intensity or other methods. Such assays would include competitive displacement FRET assays or DNA ligand "beacon" FRET assays. In a competitive displacement FRET assay the fluorophore ("F") and quencher ("Q") are placed in a putative binding loop or pocket so as to reside within the Förster distance of 60-85 Angstroms to enable quenching.

In an aptamer beacon assay, the F and Q labels are placed on the 5' and 3' ends and binding of the target analyte to the beacon opens the beacon beyond the Förster quenching distance so that F is no longer quenched and emits light generally in proportion to the amount of target analyte introduced into the liquid system. Each of these types of aptamer assays and detection platforms has different applications in either central medical laboratories or in point-of-care ("POC") sensor devices for use in emergency rooms, intensive care units, cardiac care units, or physician's offices and clinics.

SUMMARY OF THE INVENTION

The DNA ligand sequences listed herein (Table 9) were derived by iterative cycles of affinity-based selection, washing, heated elution, and polymerase chain reaction ("PCR") amplification of bound DNA ligands from a randomized library using immobilized target analytes for affinity selection and PCR amplification followed by cloning and Sanger dideoxynucleotide DNA sequencing.

Sanger dideoxynucleotide sequencing refers to DNA chain termination due to a lack of a 3' hydroxyl (—OH) group to link incoming bases to during DNA synthesis followed by automated fluorescence reading of the DNA sequence from an electrophoresis gel containing all of the terminated DNA fragments. DNA sequencing may be accomplished by PCR doped with dideoxynucleotides lacking hydroxyl groups at the 2' and 3' sugar ring positions and thereby disallowing chain formation. PCR refers to the enzymatic amplification or copying of DNA molecules with a thermo-stable DNA polymerase such as *Thermus aquaticus* polymerase (Taq) with known "primer" regions or short oligonucleotides of known sequence that can hybridize to a longer target DNA sequence to enable priming of the chain reaction (exponential doubling of the DNA target copy number with each round of amplification).

A randomized library can be chemically synthesized by linking together the four deoxynucleotide triphosphate bases (adenine; A, cytosine; C, guanine; G, and thymine; T) in equal amounts (25% each), so that a combinatorial oligonucleotide arises with sequence diversity equal to 4 raised to the nth power ($4^n$) where n is the desired length of the randomized region in bases. In other words, if position 1 in an oligonucleotide is allowed to consist of A, C, G, or T (diversity=4) by equal availability of all 4 bases and these 4 possibilities are multiplied by each base linking to 4 more possible bases at position 2, then this process yields 16 possible 2-base oligonucleotides (i.e., AA, AC, AG, AT, CA, CC, CG, CT, GA, GC, GG, GT, TA, TC, TG, TT) and so on for the entire chosen length (n) of the randomized region. This combinatorial progression displays immense diversity as a function of oligonucleotide chain length. For 1,048,576 unique DNA sequences from which to chose or select one or more DNA sequences that bind a given immobilized target analyte with the strongest affinities.

The randomized oligonucleotide or DNA is designed to be flanked on either side by short primer regions of known and fixed sequences to enable PCR amplification (exponential copying) of the rare sequences that are selected from the random library by binding to the target after the non-binding members of the random library are washed away (not selected).

Additional assays, such as ELISA-like plate assays or fluorescence (e.g., intensity and FRET) assays, may be used to screen or verify the value of particular DNA and RNA ligands or aptamer sequences for detection of a given target analyte in a given assay format or type of biosensor. Some of the sequences operate (bind and transduce the binding signal) more effectively in affinity-based (ELISA-like or fluorescence intensity) assays, while other DNA ligand sequences against the same targets function better in lower affinity competitive or other assays, thereby leading to more sensitive detection with lower limits of detection (sub-nanoMolar or sub-nanogram) and less cross-reactivity or more specificity for the target analyte. "Specificity" or "selectivity" means the ability to selectively exclude molecules similar in structure to the true target analyte that may interfere with the assay and give false indications of detection. All of the listed DNA ligand nucleotide sequences have potential applications in some type of assay format, because they have survived at least 5 rounds of affinity-based selection and enrichment (by PCR amplification), although some of the sequences will undoubtedly perform better in certain assay formats or configurations (in tubes, square cuvettes, membranes, or on biochips) than others.

Combinations of the DNA ligands, whether in whole or in part (i.e., their binding sites of approximately 5-10 or more nucleotides or bases), could be linked together in a linear or 2-dimensional ("2-D") or 3-dimensional ("3-D") fashion similar to dendrimers as shown in FIG. 1B to bind multiple epitopes or binding sites on a complex target analyte (Ag or antigen) such as a virus or whole prokaryotic (bacterial) or eukaryotic (animal, fungal or plant) cell surface having numerous spatially separated epitopes of different types. The advantage of linking aptamers or their shorter binding pockets, loops or binding sites is that the nascent linear, 2-D, or 3-D aptamer construct will likely have improved affinity or "avidity" (tensile binding strength) making it more difficult to remove or dissociate from the target antigen. Higher affinity and avidity generally lead to greater assay sensitivity and specificity which are typically desirable traits in many assays.

The linked aptamer complex will be likely to gain specificity as well since the probability of binding to multiple epitopes with any degree of success is multiplicative. Thus, the ability to bind to epitopes A, B and C equals the product of the probability of binding to A with high affinity times the probability of binding to B with high affinity times the probability of binding to C with high affinity. The product of those three fractional probabilities is clearly much less than the probability of binding to only A, B, or C independently in the absence of binding the other two or any combination of the two epitopes therein in the absence or binding the third. Hence by linking two or more aptamers or their binding regions with or without DNA or other "spacer" regions, the selectivity or specificity of aptamers or DNA ligands can be increased.

This approach to binding site linkage emulates the nature of antibodies which demonstrate linkage of their "hypervariable" ("HV") regions on the antigen combining sites of the immunoglobulin ("Ig") light and heavy chains. In the HV regions, the variability of the 20 amino acid types is quite high and essentially represents a selection of one combination from a large combinatorial library in the protein realm (similar to down selection of a few candidate aptamers from a large diverse starting library). The trait of HV region linkage contributes to Ig affinity, avidity and specificity. Similarly, linking aptamers or aptamer binding sites for various epitopes in one, two or three dimensions will enhance larger aptamer or DNA ligand construct affinity, avidity, and selectivity or specificity as illustrated in FIG. 1.

The present invention provides specific DNA sequence information for nucleic acid ligands (aptamers) or their linked constructs selected from randomized pools to bind clinically important proteins, peptides, hormones, sugars, vitamins, post-translational N-acetylglucosamine (NAG or O-GlcNAc) modifications of key proteins, etc. in a variety of assay formats and sensor or diagnostic platforms for assessment of human health status. While all of the candidate sequences have been shown to bind their cognate targets, some are shown to function more effectively in affinity-based assays versus fluorescence resonance energy transfer (FRET) or other assay formats that rely more on physical parameters other than affinity such as fluorophore-quencher proximity (i.e., the Förster distance). Therefore, all of the sequences are potentially valuable for simple qualitative detection or quantitative assays, but some may function better in terms of sensitive and specific detection than others in particular assay formats.

BRIEF DESCRIPTION OF THE DRAWINGS

FIG. 2 represents secondary stem-loop structures of DNA ligands or aptamers (SEQ ID NOs 3 and 4).

DETAILED DESCRIPTION OF THE PREFERRED EMBODIMENTS

Figure 1:
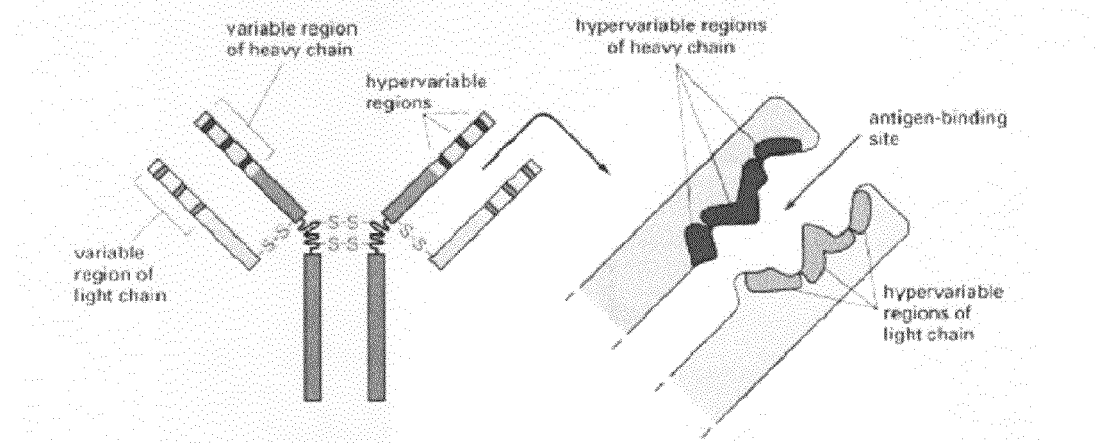
FIG. 1A illustrates an antibody, revealing the multiple hypervariable antigen combining of binding sites on both the heavy and light chains.
FIG. 1B illustrates the concept of linking aptamers or their binding sites in a linear fashion (although 2-D and 3-D linkages are also possible) to mimic the linkage of multiple hypervariable (HV) regions in antigen combining sites of antibody chains to enhance affinity, avidity, and specificity against complex target antigens (Ag) containing two or more distinct epitopes.
Figure 1:
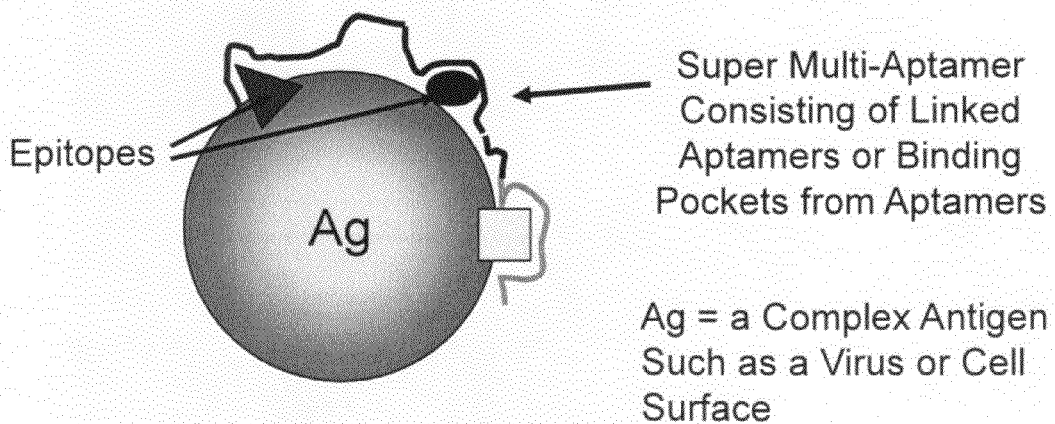

There is no single preferred embodiment for use of the DNA aptamer ligand sequences or linked aptamer constructs identified herein. Rather, the sequences are useful to varying extents in a variety of assay formats and sensors or diagnostic devices chosen from at least the following list: lateral flow test strips, Surface Enhanced Raman (SERS), Surface Plasmon Resonance (SPR), Surface Acoustic or Transverse Wave (SAW or STW) detection, electrical, electrochemical, colorimetric absorbance, agglutination, ELISA-like or enzyme-linked microplate assays, magnetic bead-based capture assays, ECL or other chemiluminescence assays, radioisotopic assays and a variety of fluorescence assays including, but not limited to, fluorescence intensity, fluorescence lifetime, fluorescence polarization (FP) and Fluorescence or Förster Resonance Energy Transfer (FRET) assays (both beacon and competitive FRET (Bruno et al., 2010, 2011) in round tubes, square or flat cuvettes, or immobilized on magnetic beads, other types of microbeads, or flat surfaces such as nitrocellulose, nylon, or other membranes or on glass or plastic DNA microarrays or "biochips."

While there may appear to be considerable variability among sequences that bind the same clinical analyte targets, "epitopes" and their cognate aptamer binding sites are usually quite small (e.g., 5-10 bases) and a single target may contain numerous individual binding sites or epitopes for multiple aptamer binding. In addition, however, there is often a common or consensus sequence (designated herein by slashes between clone numbers in Table 9, e.g. —aptamer clones CTx 2, 13, 19, 20, 25, 32F or R series are identical and only listed once as SEQ ID NO 3 and 4) or common segments of 5-10 or more nucleotides in a row within otherwise different aptamer sequences that can bind a specific target epitope that may dominate the other binding sites by being more physically accessible or having stronger electrostatic, hydrogen bonding, or other attractive forces (summation of van der Waals or other weak forces). Variations in nucleotide sequences around these consensus segments or common binding sequence segments may serve to modulate the binding segment's affinity or specificity or may have no effect at all. These properties must be determined by empirical comparisons.

DNA Ligand (Aptamer) Selection and Generation

General methods for developing DNA ligands or aptamers to the immobilized proteins, peptides, or small molecules (defined as less than 1,000 daltons) are as follows. The protein, peptide or an amino-derivative of the small molecule (such as glucosamine in the case of D-glucose or dextrose) is then added to $2 \times 10^9$ tosyl-coated magnetic beads (MBs; e.g., Dynal brand from Invitrogen Corp. Carlsbad, Calif., 2. 8 micron size) for 2 hours at 37° C. The tosyl group is a "leaving" group that allows the formation of a very stable covalent bond between primary amine groups in the target protein, peptide or amino-derivatized small molecule and therefore immobilizes the target on the surfaces of the MBs so that they can be used to probe the randomized DNA library for DNA ligands. Target molecule-conjugated MBs (or target-MBs) are collected for 2 minutes in a magnetic collection device using an external magnet and the supernate is carefully withdrawn with a pipette tip. Target-MBs are then resuspended by vortexing briefly in 1×Binding Buffer (1×BB; 0.5M NaCl, 10 mM Tris-HCl, and 1 mM $MgCl_2$, pH 7.5-7.6,) and washed by agitation for 5 minutes. MBs are collected and washed three times in this manner and then resuspended in 1 ml of 1×BB.

MB-based DNA ligand or aptamer development is then performed using a template library sequence such as: 5'-ATC-CGTCACACCTGCTCT-$N_{36}$-TGGTGTTGGCTCCCG-TAT-3', where $N_{36}$ represents the randomized 36-base region of the DNA library (maximal sequence diversity=$4^{36}$ in theory). Primer sequences are: 5'-ATACGGGAGCCAA-CACCA-3' (designated forward) and 5'-ATCCGTCACAC-CTGCTCT-3' (designated reverse) to prime the template and nascent strands for PCR, respectively. The random library is reconstituted in 500 µl of sterile nuclease-free water and heated to 95° C. for 5 minutes to ensure that the DNA library is completely single-stranded and linear. The hot DNA library solution is added to 100 µl of target-MBs ($2\times10^8$ beads) with 600 µl of sterile 2× Binding Buffer (2×BB). The DNA library and target-MB suspension (1.2 ml) is mixed at room temperature (RT, approximately 25° C.) for 1 hour. Target-MBs with any bound DNA (round 1 aptamers) are magnetically collected. The DNA-target-MB complexes are washed three times in 400 µl of sterile 1×BB. Following the third wash, the DNA-target-MB pellet (about 75 µl) is used in a PCR reaction to amplify the bound DNA as follows. The MB pellet is split into 15 µl aliquots and added to five pre-made PCR tubes which contain most of the nonperishable ingredients of a PCR reaction beneath a wax seal. A total of 3 µl of 1:10 primer mix (10% forward primer plus 10% reverse primer) in nuclease-free deionized water or ~20 nanomoles of each primer per ml plus 1 µl (5 U) of Taq DNA polymerase and 5 µl of 2 mM $MgCl_2$ are added to each of the five tubes. PCR reactions are supplemented with 0.5 µl of E. coli single-strand binding protein (SSBP, Stratagene Inc., La Jolla, Calif.) to inhibit high molecular weight concatamer (end to end aggregates of the DNA ligands) formation. PCR is carried out as follows: an initial 95° C. phase for 5 minutes, followed by 20 cycles of 1 minute at 95° C., 1 minute at 53° C., and 1 minute at 72° C. followed by a 72° C. completion stage for 7 minute, and refrigeration at 4° C. This constitutes the first of multiple rounds of MB-aptamer development. Iterations of the MB-aptamer development process are repeated until the desired affinity or assay sensitivity and specificity are achieved. Typically, 5-10 rounds of the MB-aptamer development process are required to achieve low ng/ml detection of target analytes. To begin the second round and all subsequent rounds, 4 complete tubes of the original PCR tubes are heated to 95° C. for 5 minutes to release bound DNA from the target-MBs. The fifth tube is always retained and refrigerated as a back-up for that round of the aptamer generation process. All available DNA (25 µl per tube) is siphoned out of the hot tubes without removing the target-MBs before the tubes cool significantly and the DNA is pooled. The 100 µl of hot DNA is added to 100 µl of fresh target-MBs in 200 µl of 2×BB and allowed to mix for 1 hr at RT. Thereafter, the selection and amplification process are repeated for 3-8 more rounds with checking for 72 bp aptamer PCR products by ethidium bromide-stained 2% agarose electrophoresis after each round. Following the last round of aptamer development, aptamers are cloned into chemically competent E. coli using a cloning kit from Lucigen Corp. (Middleton, Wis.) and clones are sent to Sequetech, Inc. (Mountain View, Calif.) for DNA sequencing.

Screening of Aptamers for Highest Affinity, Lowest Cross-Reactivity and to Determine Lower Limit of Detection by Target Titration in ELISA-Like Plate Assay ("ELASA")

To evaluate, screen, and rank aptamers based on affinity against clinically relevant targets, an enzyme-linked plate assay is conducted by first immobilizing 100 µl of 1:10 diluted target (about 0.1 mg of total protein, peptide or small molecule) in $0.1M NaHCO_3$ (pH 8.5) overnight at 4° C. in a covered polystyrene 96-well plate. The plate is decanted and washed three times in 250 µl of 1×BB. Each of the different 5'-biotinylated aptamers raised against the target is dissolved in 1×BB at 1.00 nmoles to 4.50 nmoles per 100 microliters and applied to their corresponding plate wells for 1 hour at room temperature (RT; ~25° C.) with gentle mixing on an orbital shaker. The plate is decanted and washed three times in 250 µl of 1×BB for at least 5 minutes per wash with gentle mixing. One hundred µl of a 1:2,000 dilution of streptavidin-peroxidase from a 5 mg/ml stock solution in 1×BB is added per well for 30 minutes at RT with gentle mixing. The plate is decanted and washed three times with 250 µl of 1×BB per well as before. One hundred µl of ABTS (2,2'-azino-bis(3-ethylbenzthiazoline-6-sulphonic acid) substrate with stabilized hydrogen peroxide (Kirkegaard Perry Laboratories, Inc., Gaithersburg, Md.) is added per well for 10 minute at RT. Finally absorbance is quantified using a microplate reader with 405 nm optical filter.

As Tables 1-8 illustrate for several cardiovascular biomarker targets (Brain Natriuretic Peptide; BNP, D-Dimer; DD, Creatine Kinase-MB types I and II; MB1 and MB2, Interleukin-18; IL 18, and Troponin-T; Tpn all at (1 µg/ml) the initial ELASA screening is useful for ranking the relative affinity of aptamers for their respective targets by simple ranking of absorbance values at 405 nm from highest to lowest. Each of the Tables (1-8) illustrates general consistency between ELASA trials as well (i.e., the highest affinity aptamers consistently rank among the highest absorbance values between ELASA trials or plates 1-4 maximally).

TABLE 1

DNA Ligand ELASA Rankings for Brain Natriuretic Peptide (BNP)

| Plate 1 | | | Plate 2 | | | Plate 3 | | |
| --- | --- | --- | --- | --- | --- | --- | --- | --- |
| Well | Aptamer | A 405 nm | Well | Aptamer | A 405 nm | Well | Aptamer | A 405 nm |
| A12 | BNP - 6R | 2.766 | A12 | BNP - 6R | 2.171 | A12 | BNP - 6R | 2.285 |
| C1 | BNP - 14bF | 2.283 | A3 | BNP - 2F | 2.110 | D5 | BNP - 22F | 2.272 |
| A3 | BNP - 2F | 2.276 | C1 | BNP - 14bF | 2.089 | E3 | BNP - 25cF | 2.240 |
| B1 | BNP - 7F | 2.227 | A8 | BNP - 4/9R | 1.989 | D4 | BNP - 21bR | 2.212 |
| E3 | BNP - 25cF | 2.215 | A1 | BNP - 1F | 1.987 | C1 | BNP - 14bF | 2.206 |
| A1 | BNP - 1F | 2.184 | B9 | BNP - 13F | 1.986 | B4 | BNP - 8R | 2.197 |
| B4 | BNP - 8R | 2.176 | A9 | BNP - 5/11/15b/19/25bF | 1.977 | A9 | BNP - 5/11/15b/19/25bF | 2.196 |
| A8 | BNP - 4/9R | 2.163 | C2 | BNP - 14bR | 1.971 | A3 | BNP - 2F | 2.176 |
| C3 | BNP - 15aF | 2.162 | D9 | BNP - 23bF | 1.961 | C3 | BNP - 15aF | 2.165 |
| D4 | BNP - 21bR | 2.149 | B4 | BNP - 8R | 1.953 | B5 | BNP - 10F (70) | 2.157 |

TABLE 2

DNA Ligand ELASA Rankings for D-Dimer (DD)

| Plate 1 | | | Plate 2 | | | Plate 3 | | | Plate 4 | | |
|---|---|---|---|---|---|---|---|---|---|---|---|
| Well | Aptamer | A 405 nm | Well | Aptamer | A 405 nm | Well | Aptamer | A 405 nm | Well | Aptamer | A 405 nm |
| A10 | DD - 5R | 1.888 | A10 | DD - 5R | 1.809 | B1 | DD - 7F (71) | 0.803 | C1 | DD - 14F (71) | 0.816 |
| B10 | DD - 12R | 1.427 | A4 | DD - 2R (71) | 1.620 | C1 | DD - 14F (71) | 0.652 | B1 | DD - 7F (71) | 0.806 |
| C7 | DD - 17F (71) | 1.261 | C7 | DD - 17F (71) | 1.237 | A10 | DD - 5R | 0.576 | A10 | DD - 5R | 0.749 |
| B8 | DD - 11R (71) | 1.122 | B10 | DD - 12R | 1.213 | B4 | DD - 9R (71) | 0.545 | B10 | DD - 12R | 0.732 |
| B12 | DD - 13R (71) | 1.088 | A12 | DD - 6R (71) | 1.005 | B2 | DD - 7R (71) | 0.510 | B4 | DD - 9R (71) | 0.645 |
| B1 | DD - 7F (71) | 1.027 | B7 | DD - 11F (71) | 1.003 | C4 | DD - 15R | 0.508 | C3 | DD - 15F | 0.635 |
| B7 | DD - 11F (71) | 1.021 | B8 | DD - 11R (71) | 0.986 | B5 | DD - 10F (71) | 0.418 | B5 | DD - 10F (71) | 0.563 |
| B2 | DD - 7R (71) | 1.017 | B1 | DD - 7F (71) | 0.964 | C12 | DD - 20R (71) | 0.404 | B2 | DD - 7R (71) | 0.535 |
| A12 | DD - 6R (71) | 0.989 | C11 | DD - 20F (71) | 0.932 | B10 | DD - 12R | 0.386 | A5 | DD - 3F (71) | 0.526 |
| C12 | DD - 20R (71) | 0.952 | B6 | DD - 10R (71) | 0.930 | A5 | DD - 3F (71) | 0.370 | C4 | DD - 15R | 0.512 |

TABLE 3

DNA Ligand ELASA Rankings for Creatine Kinase-MB Type I (MBI)

| Plate 1 | | | Plate 2 | | | Plate 3 | | | Plate 4 | | |
|---|---|---|---|---|---|---|---|---|---|---|---|
| Well | Aptamer | A 405 nm | Well | Aptamer | A 405 nm | Well | Aptamer | A 405 nm | Well | Aptamer | A 405 nm |
| F1 | MBI - 20F | 2.917 | F1 | MBI - 20F | 2.692 | F1 | MBI - 20F | 1.863 | F1 | MBI - 20F | 1.948 |
| D2 | MBI - 1/4/5/8/9/17R (71) | 2.725 | D2 | MBI - 1/4/5/8/9/17R (71) | 2.680 | D2 | MBI - 1/4/5/8/9/17R (71) | 1.858 | D3 | MBI - 2F (71) | 1.823 |
| D6 | MBI - 3R (70) | 2.668 | D6 | MBI - 3R (70) | 2.647 | D3 | MBI - 2F (71) | 1.808 | D6 | MBI - 3R (70) | 1.746 |
| E10 | MBI - 16R | 2.665 | E1 | MBI - 11F | 2.612 | E3 | MBI - 12F (70) | 1.753 | D2 | MBI - 1/4/5/8/9/17R (71) | 1.744 |
| E1 | MBI - 11F | 2.658 | E10 | MBI - 16R | 2.612 | E2 | MBI - 11R | 1.716 | F2 | MBI - 20R | 1.742 |
| E2 | MBI - 11R | 2.651 | D3 | MBI - 2F (71) | 2.511 | E5 | MBI - 14/18F | 1.692 | D1 | MBI - 1/4/5/8/9/17F (71) | 1.733 |
| E11 | MBI - 19F (69) | 2.589 | E2 | MBI - 11R | 2.499 | D4 | MBI - 2R (71) | 1.663 | E2 | MBI - 11R | 1.659 |
| E7 | MBI - 15F | 2.578 | D1 | MBI - 1/4/5/8/9/17F (71) | 2.497 | E4 | MBI - 12R (70) | 1.642 | E3 | MBI - 12F (70) | 1.647 |
| D1 | MBI - 1/4/5/8/9/17F (71) | 2.556 | F2 | MBI - 20R | 2.424 | E1 | MBI - 11F | 1.640 | D5 | MBI - 3F (70) | 1.629 |
| D4 | MBI - 2R (71) | 2.522 | D4 | MBI - 2R (71) | 2.419 | F2 | MBI - 20R | 1.619 | D4 | MBI - 2R (71) | 1.607 |

TABLE 4

DNA Ligand ELASA Rankings for Creatine Kinase-MB Type II (MBII)

| Plate 1 | | | Plate 2 | | |
|---|---|---|---|---|---|
| Well | Aptamer | A 405 nm | Well | Aptamer | A 405 nm |
| G1 | MBII 6/8F | 2.206 | G1 | MBII 6/8F | 2.120 |
| G12 | MBII - 12R (71) | 2.191 | G4 | MBII - 7R | 1.931 |
| F12 | MBII - 5R | 2.173 | G12 | MBII - 12R (71) | 1.850 |
| H6 | MBII - 14R | 1.989 | H5 | MBII - 14F | 1.688 |
| G4 | MBII - 7R | 1.910 | F7 | MBII - 3F (71) | 1.682 |
| H7 | MBII - 15F (71) | 1.838 | G5 | MBII - 9F | 1.675 |
| G11 | MBII - 12F (71) | 1.827 | G11 | MBII - 12F (71) | 1.640 |
| H5 | MBII - 14F | 1.794 | H7 | MBII - 15F (71) | 1.611 |
| F10 | MBII - 4R (71) | 1.751 | F12 | MBII - 5R | 1.588 |
| G9 | MBII - 11F | 1.732 | F9 | MBII - 4F (71) | 1.586 |

TABLE 5

DNA Ligand ELASA Rankings for Interleukin-18 (IL18)

| Plate 1 | | | Plate 2 | | | Plate 3 | | | Plate 4 | | |
|---|---|---|---|---|---|---|---|---|---|---|---|
| Aptamer | Well | A 405 nm | Aptamer | Well | A 405 nm | Aptamer | Well | A 405 nm | Aptamer | Well | A 405 nm |
| IL18 - 29F | D1 | 1.433 | IL18 - 22R | C4 | 1.738 | IL18 - 29F | D1 | 1.288 | IL18 - 21R | C2 | 1.060 |
| IL18 - 10F | B1 | 1.428 | IL18 - 21R | C2 | 1.697 | IL18 - 21R | C2 | 1.202 | IL18 - 26F (71) | C7 | 0.841 |
| IL18 - 5F | A7 | 1.393 | IL18 - 10F | B1 | 1.673 | IL18 - 22R | C4 | 0.993 | IL18 - 4R | A6 | 0.835 |
| IL18 - 22R | C4 | 1.373 | IL18 - 29F | D1 | 1.655 | IL18 - 10F | B1 | 0.917 | IL18 - 22F | C3 | 0.677 |
| IL18 - 21R | C2 | 1.367 | IL18 - 5F | A7 | 1.596 | IL18 - 26F (71) | C7 | 0.886 | IL18 - 22R | C4 | 0.662 |

TABLE 5-continued

DNA Ligand ELASA Rankings for Interleukin-18 (IL18)

| Plate 1 | | | Plate 2 | | | Plate 3 | | | Plate 4 | | |
|---|---|---|---|---|---|---|---|---|---|---|---|
| Aptamer | Well | A 405 nm | Aptamer | Well | A 405 nm | Aptamer | Well | A 405 nm | Aptamer | Well | A 405 nm |
| IL18 - 21F | C1 | 1.270 | IL18 - 22F | C3 | 1.594 | IL18 - 22F | C3 | 0.855 | IL18 - 27/31F (70) | C9 | 0.613 |
| IL18 - 29R | D2 | 1.219 | IL18 - 26F (71) | C7 | 1.553 | IL18 - 2F | A1 | 0.844 | IL18 - 33R | D8 | 0.608 |
| IL18 - 3F | A3 | 1.217 | IL18 - 21F | C1 | 1.534 | IL18 - 29R | D2 | 0.795 | IL18 - 27/31R (70) | C10 | 0.601 |
| IL18 - 15R | B6 | 1.209 | IL18 - 29R | D2 | 1.528 | IL18 - 5F | A7 | 0.791 | IL18 - 5F | A7 | 0.589 |
| IL18 - 22F | C3 | 1.204 | IL18 - 30F (71) | D3 | 1.525 | IL18 - 4R | A6 | 0.785 | IL18 - 29F | D1 | 0.550 |

TABLE 6

DNA Ligand ELASA Rankings for Troponin-T (Tpn)

| Plate 1 | | | Plate 2 | | | Plate 3 | | | Plate 4 | | |
|---|---|---|---|---|---|---|---|---|---|---|---|
| Aptamer | Well | A 405 nm | Aptamer | Well | A 405 nm | Aptamer | Well | A 405 nm | Aptamer | Well | A 405 nm |
| Tpn - 20F (71) | H3 | 2.325 | Tpn - 20F (71) | H3 | 2.642 | Tpn - 20F (71) | H3 | 2.482 | Tpn - 20F (71) | H3 | 2.507 |
| Tpn - 12R (71) | G2 | 2.070 | Tpn - 20R (71) | H4 | 2.479 | Tpn - 20R (71) | H4 | 2.249 | Tpn - 20R (71) | H4 | 2.259 |
| Tpn - 20R (71) | H4 | 2.053 | Tpn - 1F (71) | E1 | 2.374 | Tpn - 16R (71) | G10 | 1.854 | Tpn - 16F (71) | G9 | 1.525 |
| Tpn - 7F (71) | F3 | 2.030 | Tpn - 12R (71) | G2 | 2.357 | Tpn - 16F (71) | G9 | 1.811 | Tpn - 6R (71) | F2 | 1.514 |
| Tpn - 18F | H1 | 1.986 | Tpn - 6R (71) | F2 | 2.342 | Tpn - 6R (71) | F2 | 1.656 | Tpn - 16R (71) | G10 | 1.507 |
| Tpn - 18R | H2 | 1.971 | Tpn - 18R | H2 | 2.304 | Tpn - 7F (71) | F3 | 1.599 | Tpn - 18F | H1 | 1.396 |
| Tpn - 6R (71) | F2 | 1.962 | Tpn - 7F (71) | F3 | 2.298 | Tpn - 15R (71) | G8 | 1.535 | Tpn - 11F (71) | F11 | 1.386 |
| Tpn - 1R (71) | E2 | 1.949 | Tpn - 12F (71) | G1 | 2.252 | Tpn - 9R | F8 | 1.517 | Tpn - 4bR (71) | E10 | 1.350 |
| Tpn - 15F (71) | G7 | 1.898 | Tpn - 1R (71) | E2 | 2.249 | TPn - 1F (71) | E1 | 1.487 | Tpn - 1F (71) | E1 | 1.318 |
| Tpn - 1F (71) | E1 | 1.871 | Tpn - 6F (71) | F1 | 2.195 | Tpn - 4bR (71) | E10 | 1.477 | Tpn - 7F (71) | F3 | 1.264 |

TABLE 7

DNA Ligand ELASA Rankings for C-Reactive Protein (CRP)

| Rank | Aptamer | Abs 405 nm |
|---|---|---|
| 1 | CRP-5R | 2.332 |
| 2 | CRP-10R | 2.27 |
| 3 | CRP-2R | 2.210 |
| 4 | CRP-11R | 2.173 |
| 5 | CRP-17R | 2.165 |
| 6 | CRP-23F | 2.139 |
| 7 | CRP-10F | 2.100 |
| 8 | CRP-2F | 2.072 |
| 9 | CRP-9R | 2.066 |
| 10 | CRP-9F | 2.055 |

TABLE 8

DNA Ligand ELASA Rankings for Myoglobin (Myo)

| Rank | Aptamer | Abs 405 nm |
|---|---|---|
| 1 | Myo-3R/4R | 2.395 |
| 2 | Myo-22F | 2.367 |
| 3 | Myo-15F | 2.344 |
| 4 | Myo-3F/6F | 2.337 |
| 5 | Myo-5R | 2.327 |
| 6 | Myo-24F | 2.294 |
| 7 | Myo-18R/27F | 2.272 |
| 8 | Myo-15R | 2.269 |
| 9 | Myo-28F | 2.264 |
| 10 | Myo-8F | 2.250 |

Aptamer Beacons and Competitive FRET-Aptamer Assays

Figure 8:
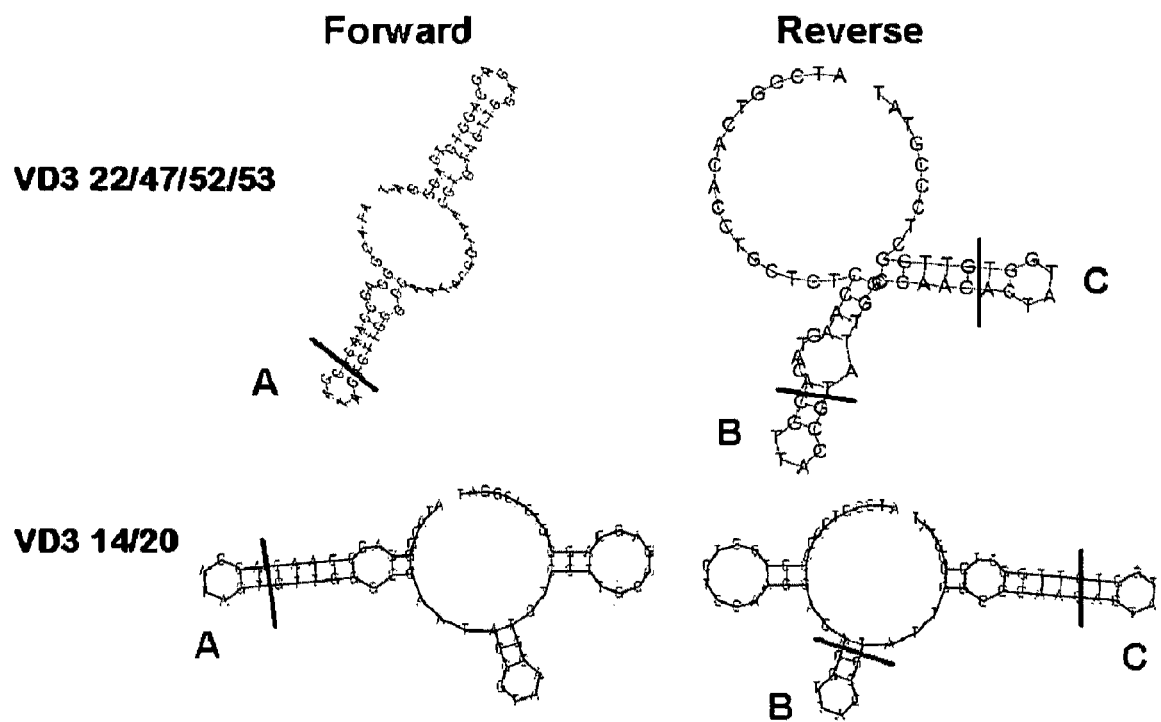
FIG. 8 illustrates the secondary stem-loop structures of several aptamers which dominated a sequenced pool of vitamin D3 aptamers (abbreviated VD3 and from the SEQ ID NOs 429-526).
Figure 9:
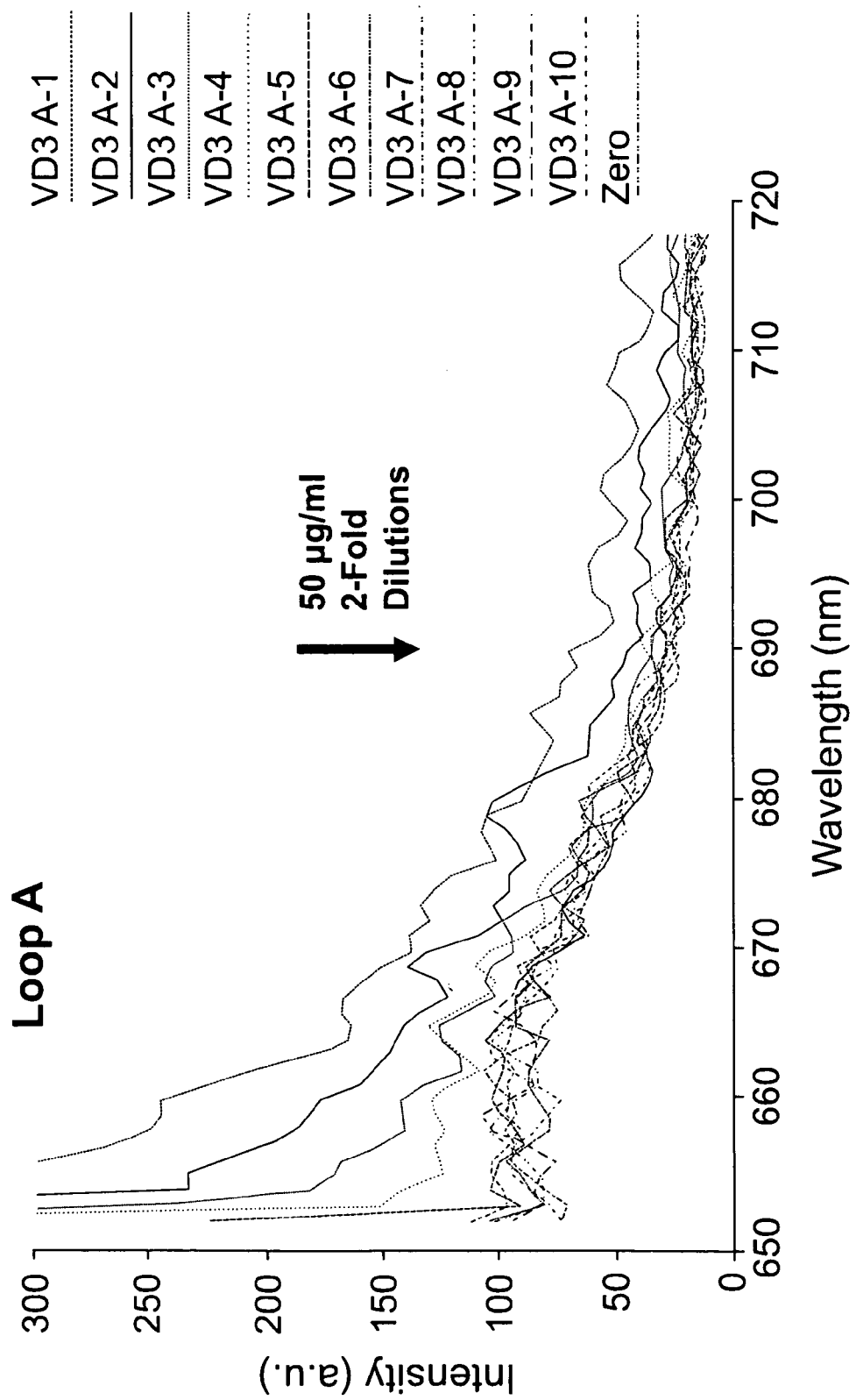
FIG. 9 illustrates the FRET responses of loops A, B, and C for the aptamers shown in FIG. 8.
Figure 9:
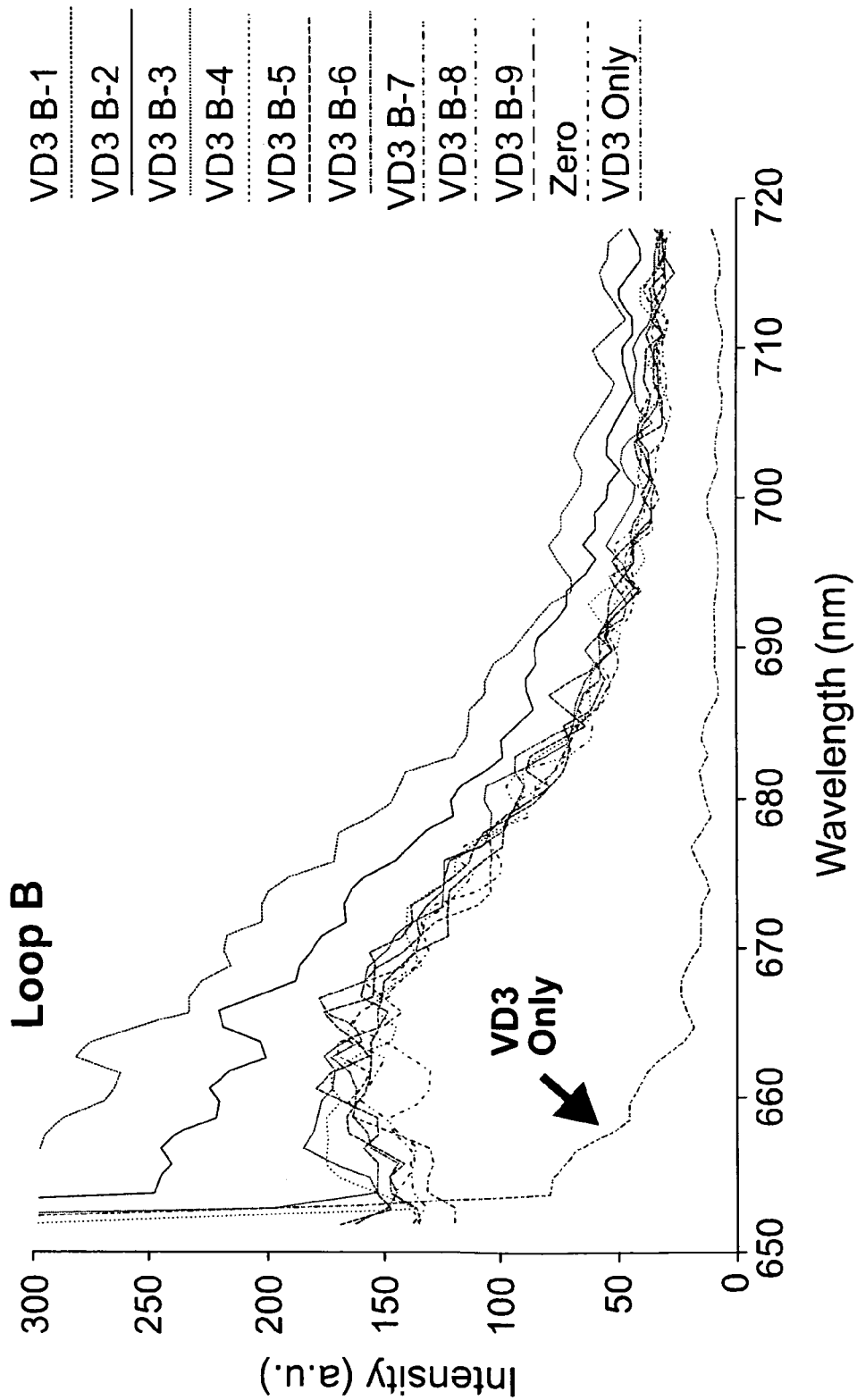
Figure 9:
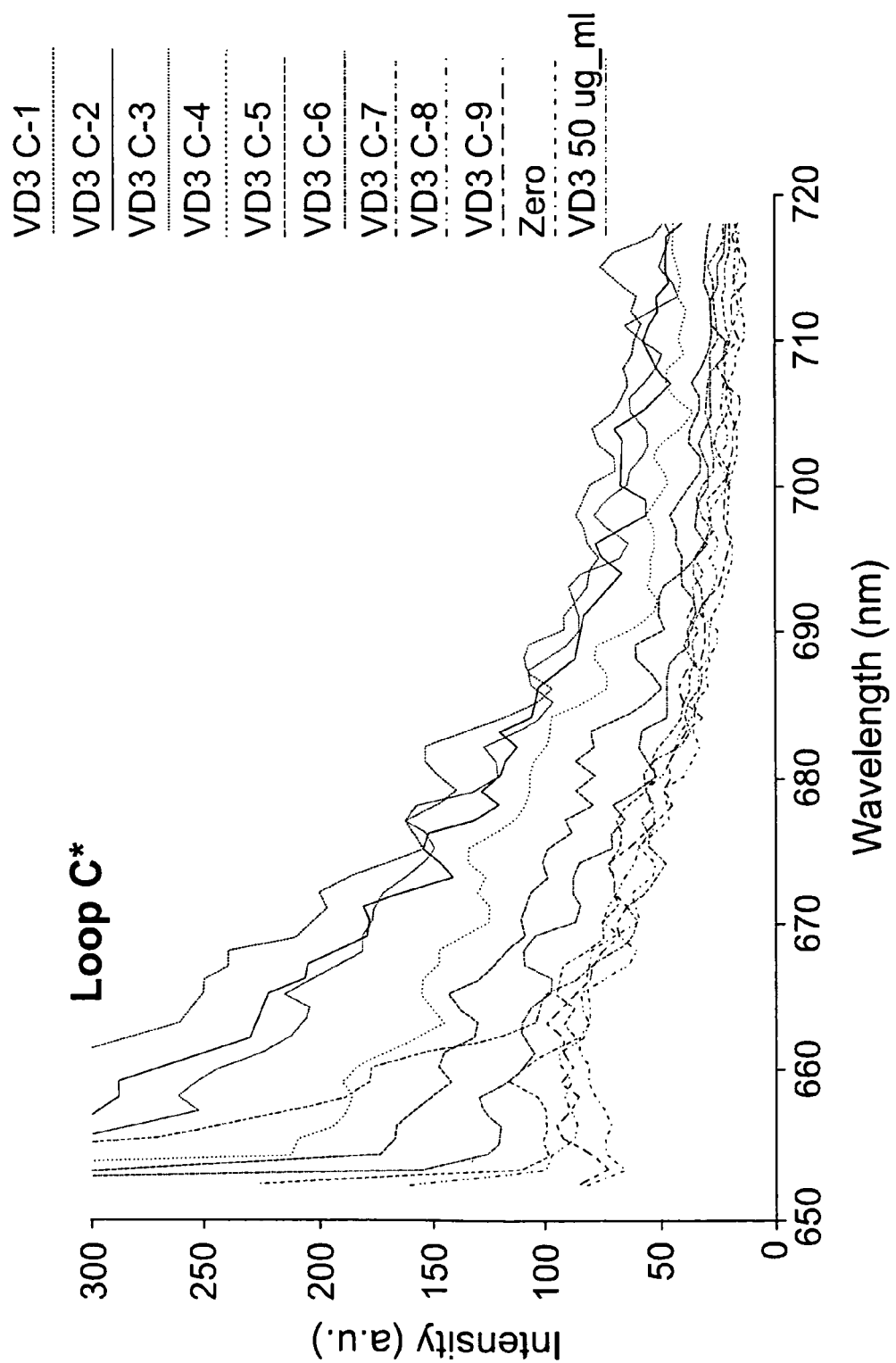
Figure 9:
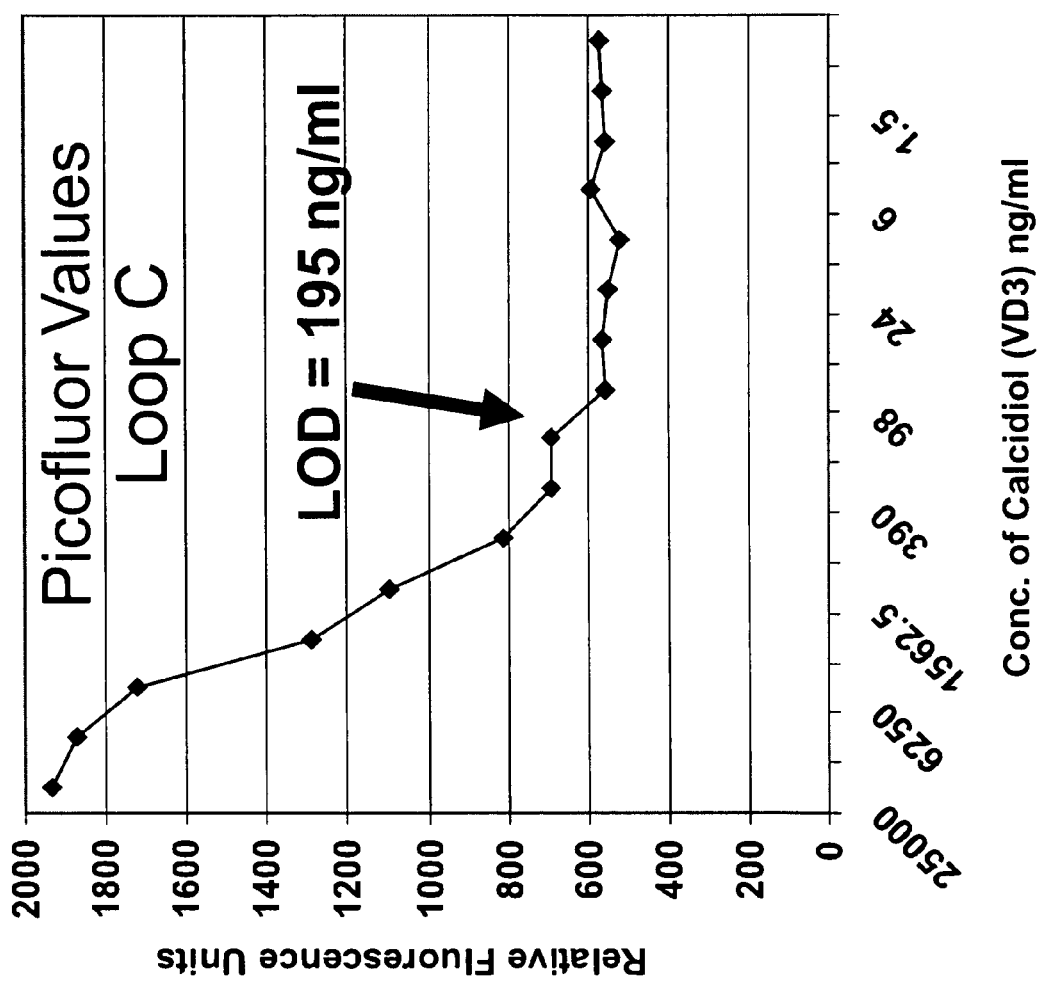

Once key aptamers have been identified by the commonality of their sequences or their secondary stem-loop structures, the assay developer decides upon secondary structure loops (potential binding pockets) to label with a fluorophore (F) or quencher (Q) as illustrated by dotted lines that define the borders or limits of potential binding loops in FIGS. 2 and 8. Secondary stem-loop structures are easily generated by Gibbs free energy minimization with common software such as M-fold and Vienna RNA (using DNA parameters) that is freely available for public use. The researcher or inventor simply enters the DNA sequence and selects a temperature and secondary stem-loop structures like those shown in FIG. 2 are generated. At this point, one can empirically assess candidate aptamer "beacon" potential in FRET analyte titration experiments such as those shown in FIG. 3. The suspected short aptamer beacon loop is re-synthesized independent of the original larger parent aptamer sequence with a fluorophore (F) such as TYE 665 attached to the 5' end and a matched quencher (Q) such as Iowa Black attached to the 3' end (or vice versa), purified by HPLC or other form of chromatography and assessed for fluorescence output or intensity as a function of different levels of the target analyte (e.g., FIGS. 3 and 9). The greatest separation of fluorescence peak values or spectral emissions (e.g., FIGS. 3 and 9) is used to define the optimal beacon since separation of fluorescence values as a function of analyte concentration is essentially the definition of a good quality fluorescence assay.

Alternatively, one may label the suspected binding loops internally and place an F or Q somewhere in the mid-section of the suspected loop other than the 3' or 5' end (i.e., intrachain FRET). Attachment of F or Q is usually accomplished via succinimide linkage of F- or Q-succinimides added to amino-modified aptamers at specifically chosen locations in the binding pockets. Primary amine linker moieties such as the "UniLink™" can be added internally at the time of chemical synthesis of aptamers. Typically 1 mg or more of an aptamer sequence is synthesized with a primary amine linker moiety (UniLink™) located at the approximate center of each loop structure (suspected binding pockets). Each of these internally amine-labeled aptamers is then labeled with 100 µl (0.1 mg) of F-succinimide (or alternatively Q-succinimide) for 2 hours in a 37° C. incubator, followed by purification through a 1×BB-equilibrated PD-10 (Sephadex G-25; GE Healthcare) column. In the meantime, an equal molar amount of primary amine-modified target molecule is labeled with 0.1 mg of spectrally matched Q-succinimide (to accept photons from F) at 37° C. for 2 hours and then washed three times by centrifugation at 14,000 rpm for 10 minutes per wash and resuspension in 1 ml of 1×BB. "Spectrally matched" means that most of the wavelengths of light emitted by F can be effectively absorbed by Q because its absorbance spectrum largely overlaps the emission spectrum of F. Naturally, if the aptamer is labeled with a Q-succinimide in the alternate form of the assay, the amine-modified target must be labeled with an appropriately matched F-succinimide to be quenched when bound to the Q-labeled aptamer. Pooled one ml fractions of purified F-labeled DNA aptamers are mixed with an equimolar amount of Q-labeled-amino-target analyte (or vice versa in the alternate embodiment) for 30 minutes at RT with mixing in 1×BB or phosphate buffered saline (PBS, 0.1M phosphates in 8.5 g/L sodium chloride at pH 7.2 to 7.4) and then purified through an appropriate size-exclusion chromatography column (according to molecular weight of the combined F-aptamer plus Q-target complex) to produce a purified "competitive FRET complex" consisting of F-aptamer conjugate bound to Q-labeled target. This competitive FRET complex can later be competed against unlabeled cognate analyte concentrations to increase the fluorescent light output of the liquid assay system and quantify the unlabeled analyte concentration.

Generally, the aptamer beacons or competitive FRET-aptamer complexes are then diluted to a final concentration of 1-5 µg/ml in 1×BB and equally dispensed to polystyrene or methacrylate cuvettes in which 1 ml of unlabeled target at various concentrations in 1×BB, PBS or diluted blood, plasma, serum, saliva, aspirate or urine has been added already. Cuvettes are gently mixed for 15 to 20 minutes at RT prior to reading their fluorescence in the homogeneous beacon or competitive-displacement FRET assay formats using a spectrofluorometer having gratings to vary the excitation wavelength and emission scanning ability or a stationary, handheld or otherwise portable fluorometer having a more restricted or fixed excitation and emission optical filter set with a range of wavelengths for excitation and emission.

Aptamer or Aptamer Binding Site Linkage in One or More Dimensions

The linkage of binding sites is beneficial in terms of enhancing receptor affinity, avidity (tensile binding strength), and selectivity versus complex targets with two or more distinct epitopes. This linkage can be sequential and linear (one-dimensional as in antibody heavy and light chain linkage of HV regions, FIG. 1A) or could be expanded into two or three dimensions much like DNA dendrimers or other more complex structures known to those skilled in the art. Linear linkage by chemical synthesis is quite facile, if one knows that aptamer DNA sequences or shorter (approximately 5-10 base) binding site sequences to be linked. One can simply design one long sequence to incorporate the desired aptamers or binding sites with repetitive poly-adenine (A), poly-cytosine (C), poly-guanine (G), poly-thymine (T), poly-uridine (U), or other intervening sequences that are unlikely to bind the target epitopes. The length of the composite aptamer construct will be limited by current chemical synthesis technology to about 200 bases. However, cellular biosynthesis or enzymatic synthesis by polymerase chain reaction (PCR) or asymmetric PCR (producing predominately single-stranded ss-DNA from a template) would not be so limited and should produce aptamer constructs up to 2,000 bases before the Taq polymerase falls off the template. The 2 kilobase Taq polymerase limit is the basis for the well-known RAPD (Random Amplification of Polymorphic DNA) method of DNA or genetic "fingerprint" analyses in which primers greater than 2 kilobases apart fail to produce a PCR product or amplicon, because Taq becomes disengaged from the template DNA before traveling 2,000 bases. In this way, lengthy aptamer constructs of less than 2 kilobases could be made from complementary DNA templates that would enable binding of different epitopes that are distal on the surface of relatively large objects such as viruses and whole bacterial or eukaryotic cells. Again, poly-A, C, G, T, or U or other linker nucleotide segments could be designed into the cDNA template to produce the resultant nascent strand to ligate aptamers or aptamer binding sites together into one contiguous linear chain with intervening linkers.

For 2-D or 3-D linked aptamer structures a variety of linker chemistries are available, but the preferred embodiment is probably addition of a UniLink™ primary amine group somewhere in the mid-section of a larger multi-aptamer construct followed by covalent linkage of two or more such multi-aptamer constructs by means of bifunctional linkers such as low levels (≤1%) of glutaraldehyde, carbodiimides, sulfo-EGS, sulfo-SMCC or other such bifunctional linkers familiar to those skilled in conjugate chemistry. This strategy would result in a larger flower-like 2-D or 3-D structure consisting of two or more lengthy multi-aptamer structures.

Referring to the figures, FIG. 1A is illustrates the general structure of an IgG antibody showing the linkage of hypervariable (HV) amino acid regions used for actual binding to target epitopes on complex antigens. Linear linkage of HV binding sites adds affinity, avidity and specificity the antibody binding to complex targets. Likewise in FIG. 1B, aptamers or their shorter (5-10 base) binding sites can be linked during chemical or biochemical (enzymatic) synthesis to enhance aptamer binding affinity, avidity or specificity for improved assay sensitivity and selectivity.

FIG. 2 is a diagram of secondary structures for two "finalists" (SEQ ID NOs 3 and 4) from the pool of 24 unique candidate aptamers (SEQ ID NOs. 1-24) that bind human Type I bone collagen C-telopeptide (CTx) indicative of bone loss when found in the urine. These 2 aptamer sequences (forward and reverse or F and R-primed) dominated the aptamer pool (12 of 38 total clones=31.6%) and were therefore considered prime candidates to investigate for possible binding pockets (secondary loop structures). These potential binding pockets are shown as loops cut off from the rest of the aptamer by dotted lines and designated according to the 12 hour clock as 2 O'clock (or second hour or 2 h), 6 O'clock (6 h) and 10 O'clock (10 h). The overall 5' and 3' ends as well as a numbering system from bases 1 (at the 5' end) to base 72 (at the 3' end) are also indicated. A variation on the CTx 2R-2h loop or beacon consisting of 13 and 15 bases (13b or 15b) is also indicated. The 2 O'clock or second hour (2 h) aptamer was subsequently synthesized to produce an aptamer beacon (3' end labeled with a quencher molecule and the 5' end labeled with a fluorophore) as demarcated by the dotted lines which is capable of detecting CTx peptide to low nanogram per ml levels.

Figure 3:
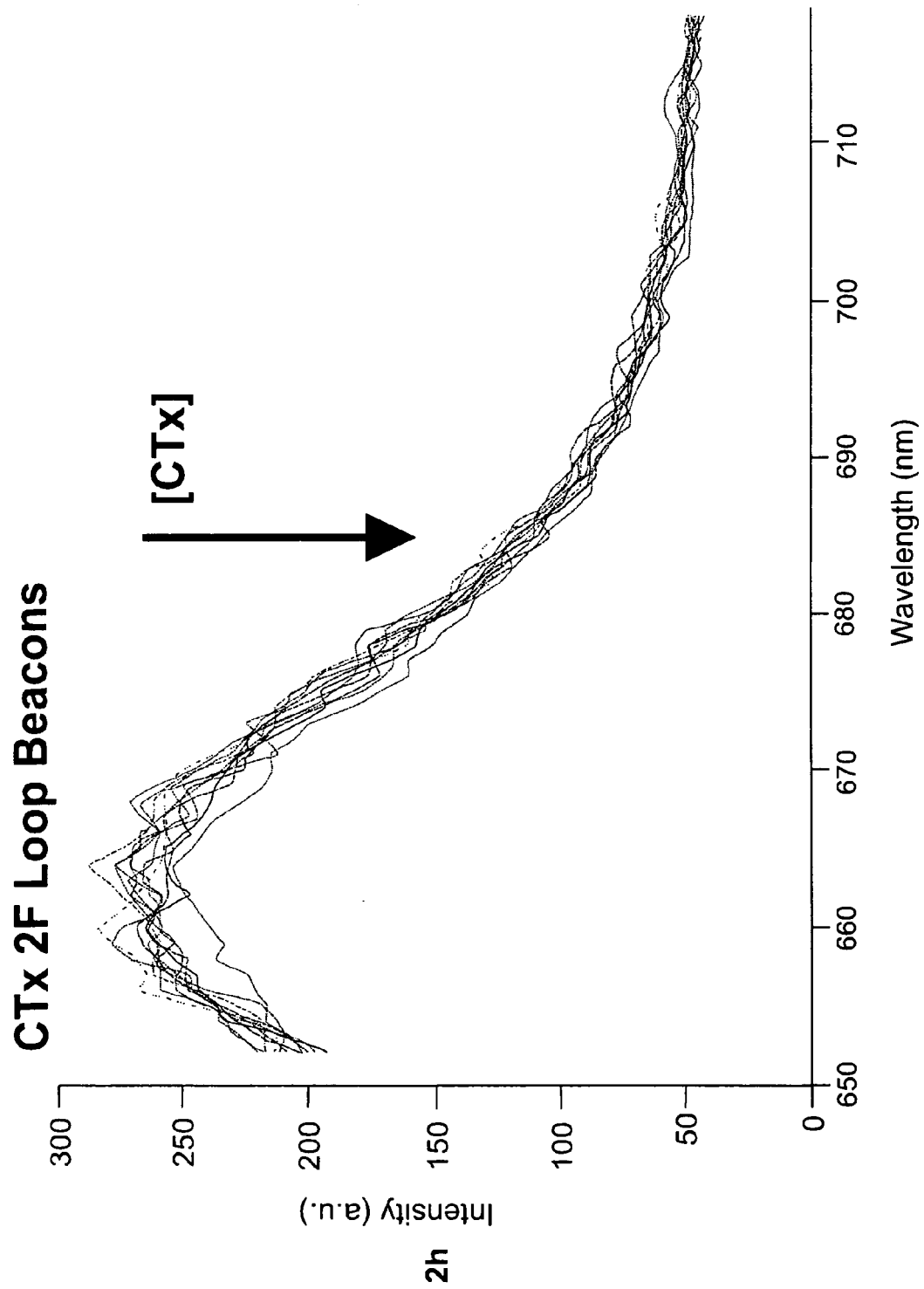
FIG. 3 shows how the aptamer beacons from FIG. 2 behaved as a function of decreasing CTx peptide concentration.
Figure 3:
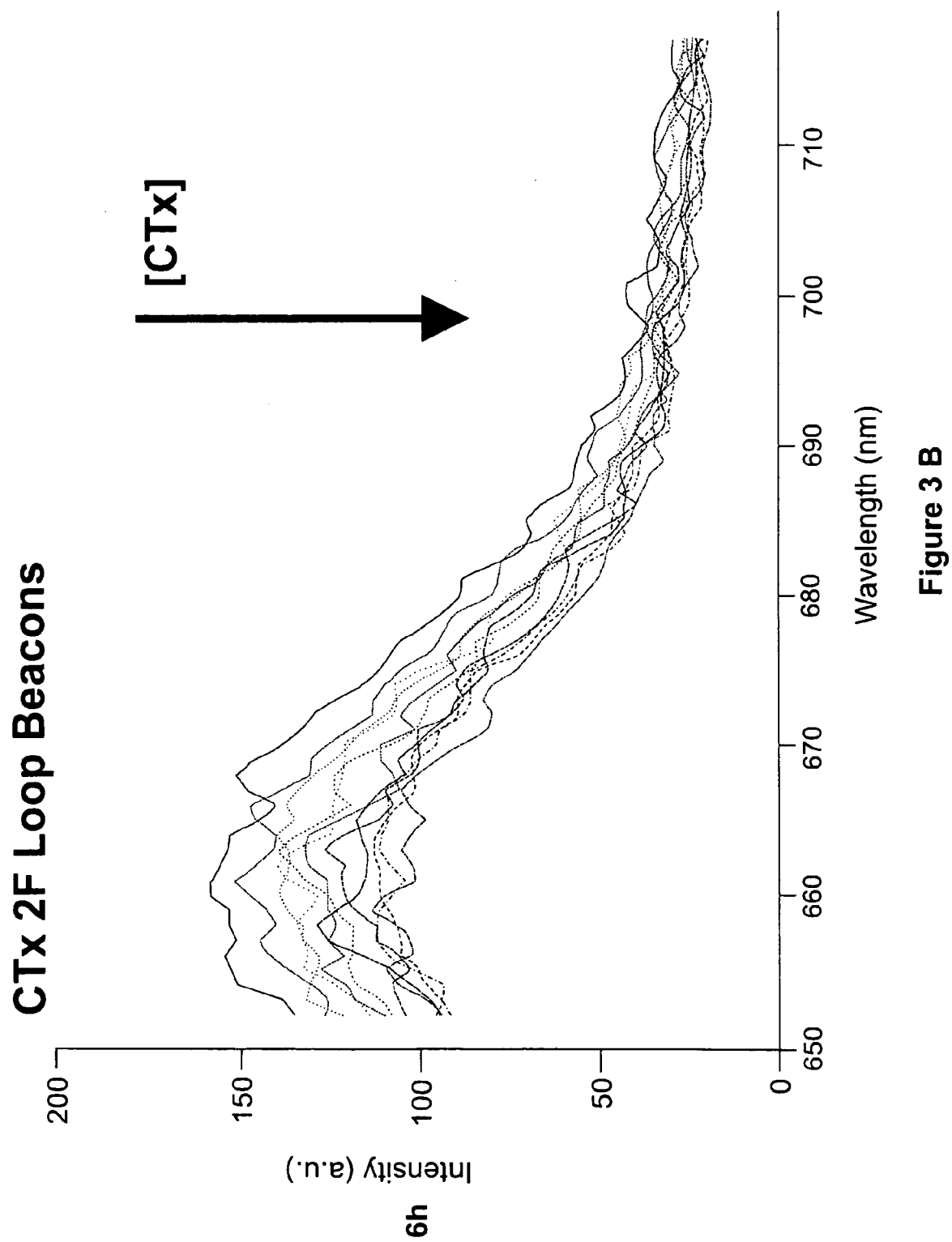
Figure 3:
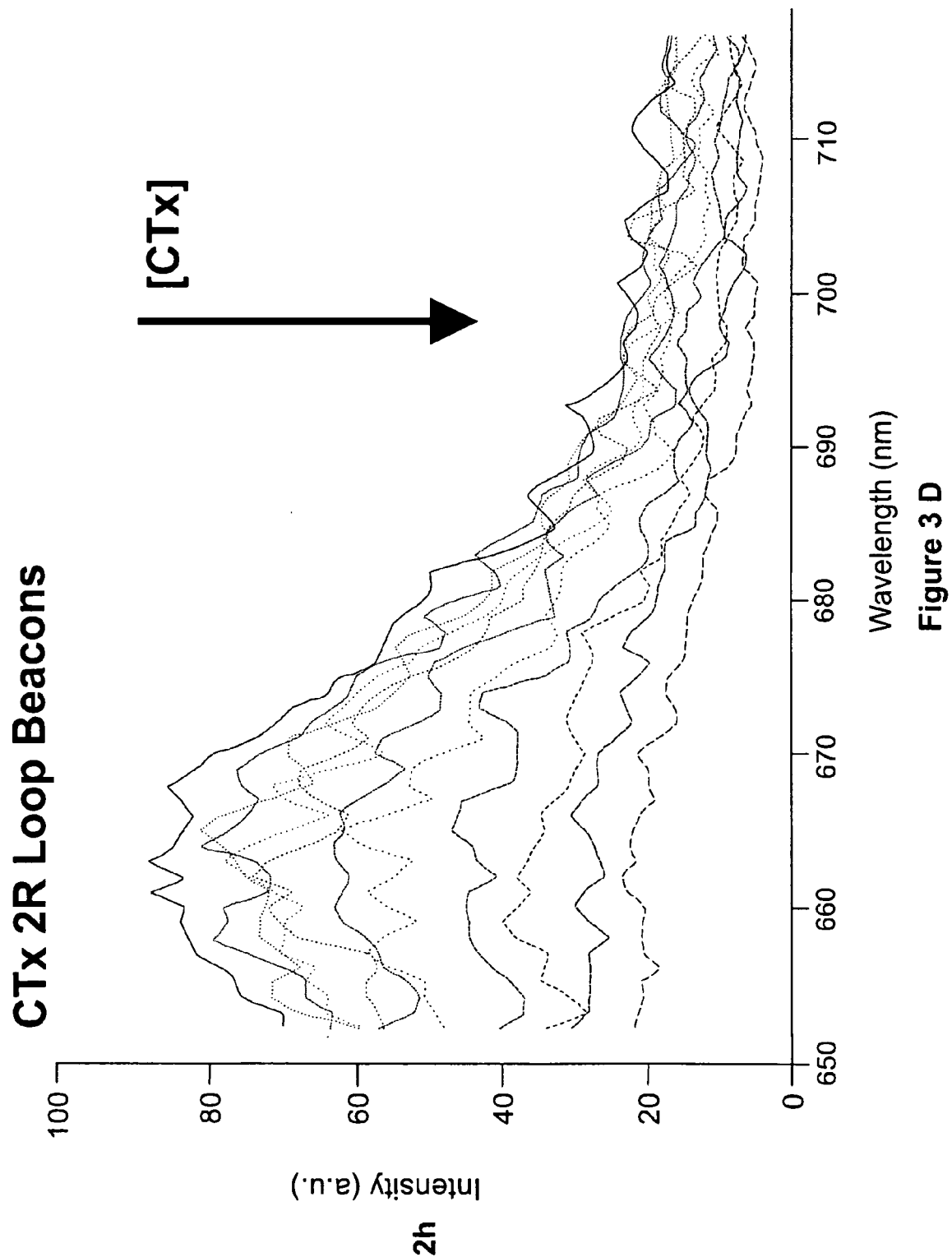
Figure 3:
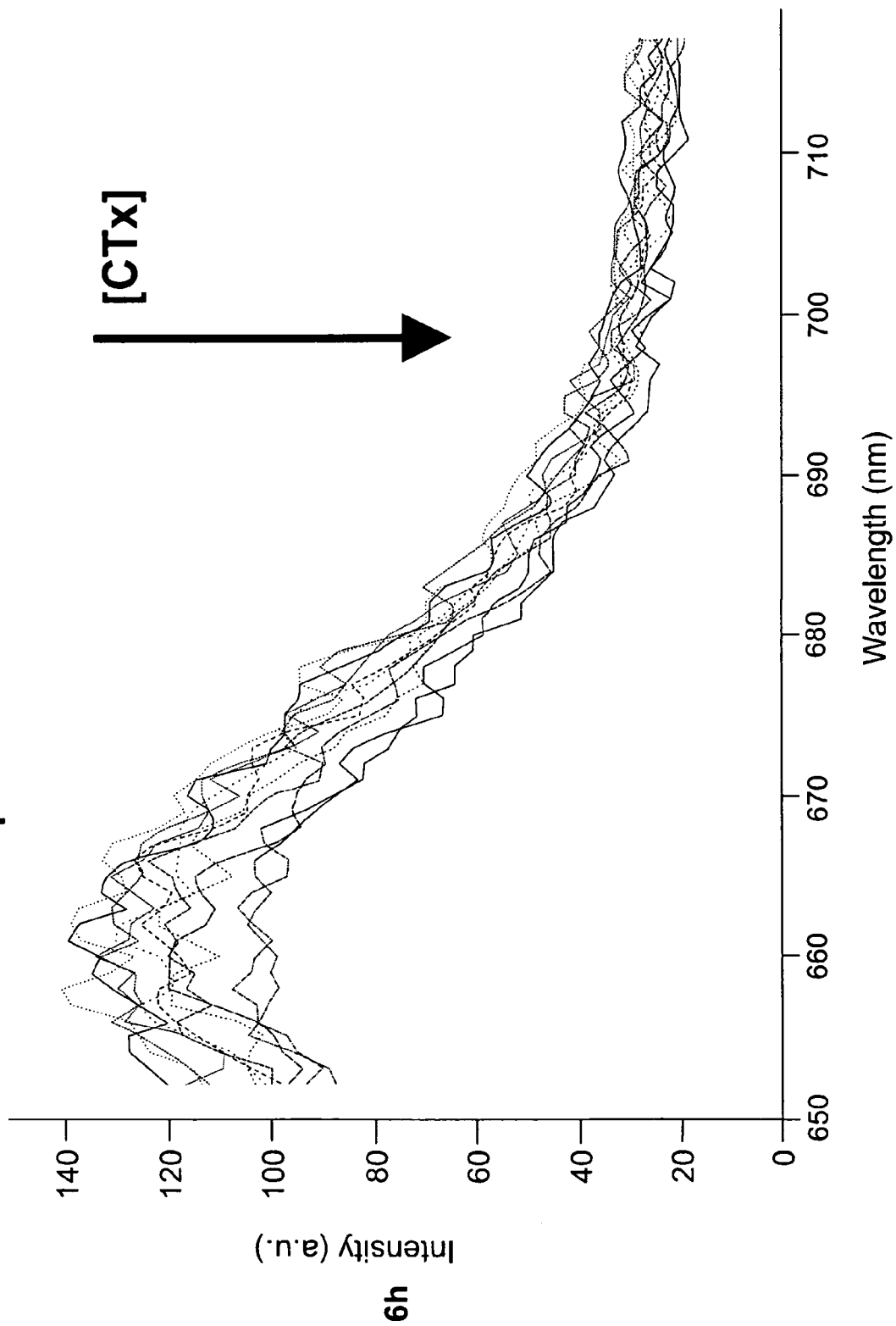
Figure 3:
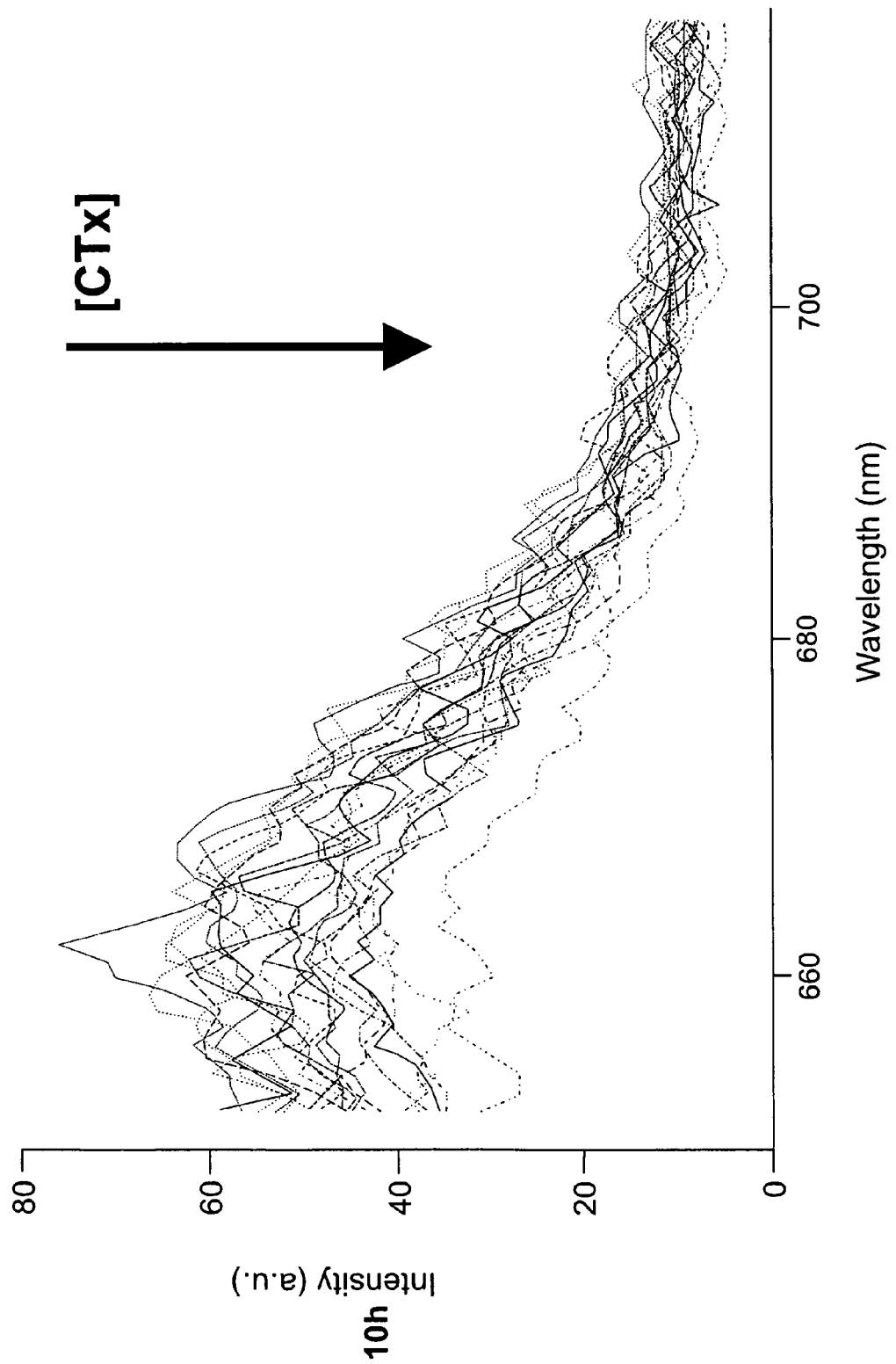
Figure 4:
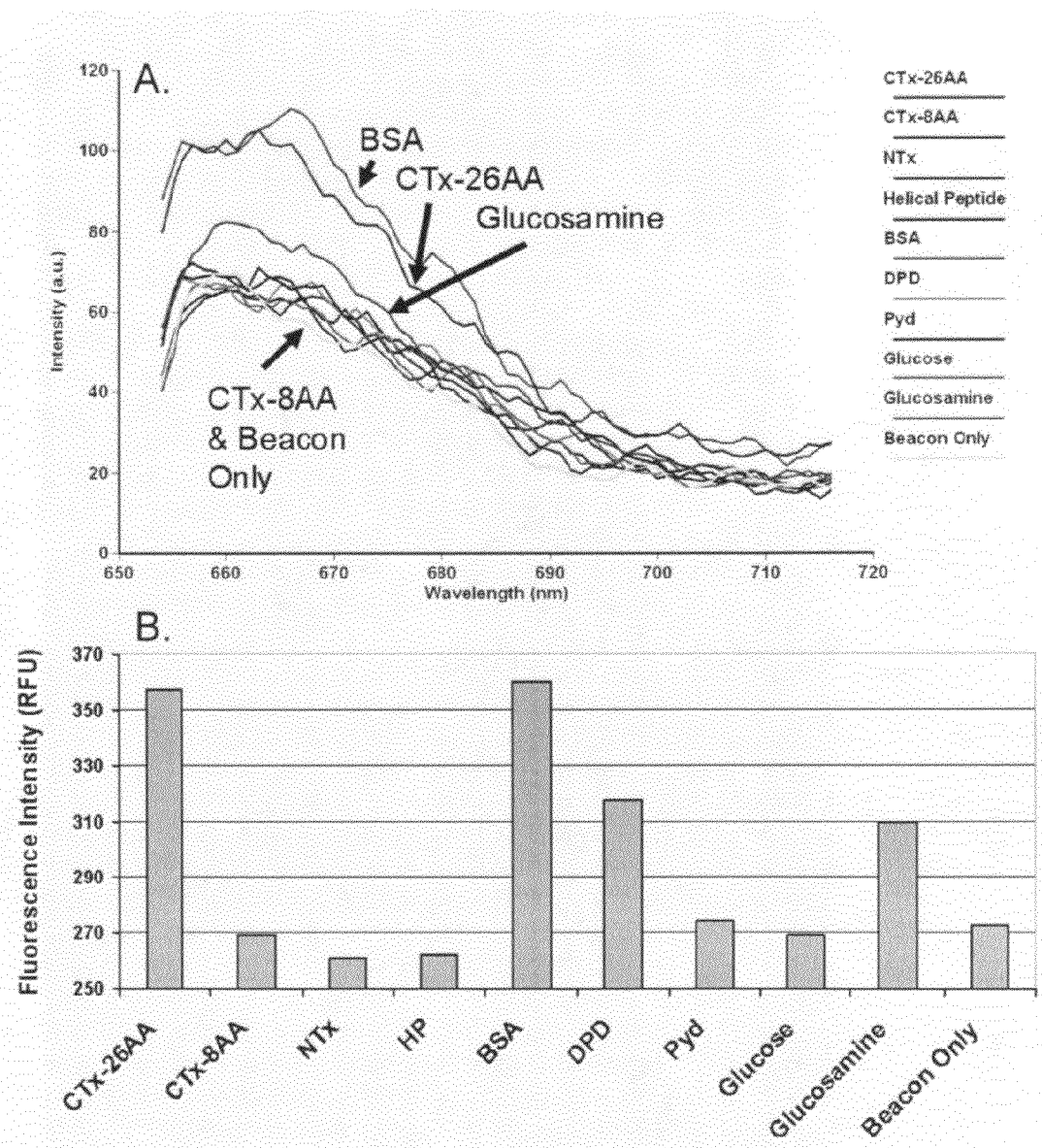
FIG. 4A illustrates specificity of the 15-base CTx 2R-2h aptamer beacon for the full-length 26-amino acid (AA) version of the CTx peptide.
FIG. 4B shows the same samples evaluated by a handheld fluorometer that only reports fluorescence peak height, but confirms the level of specificity.
Figure 5:
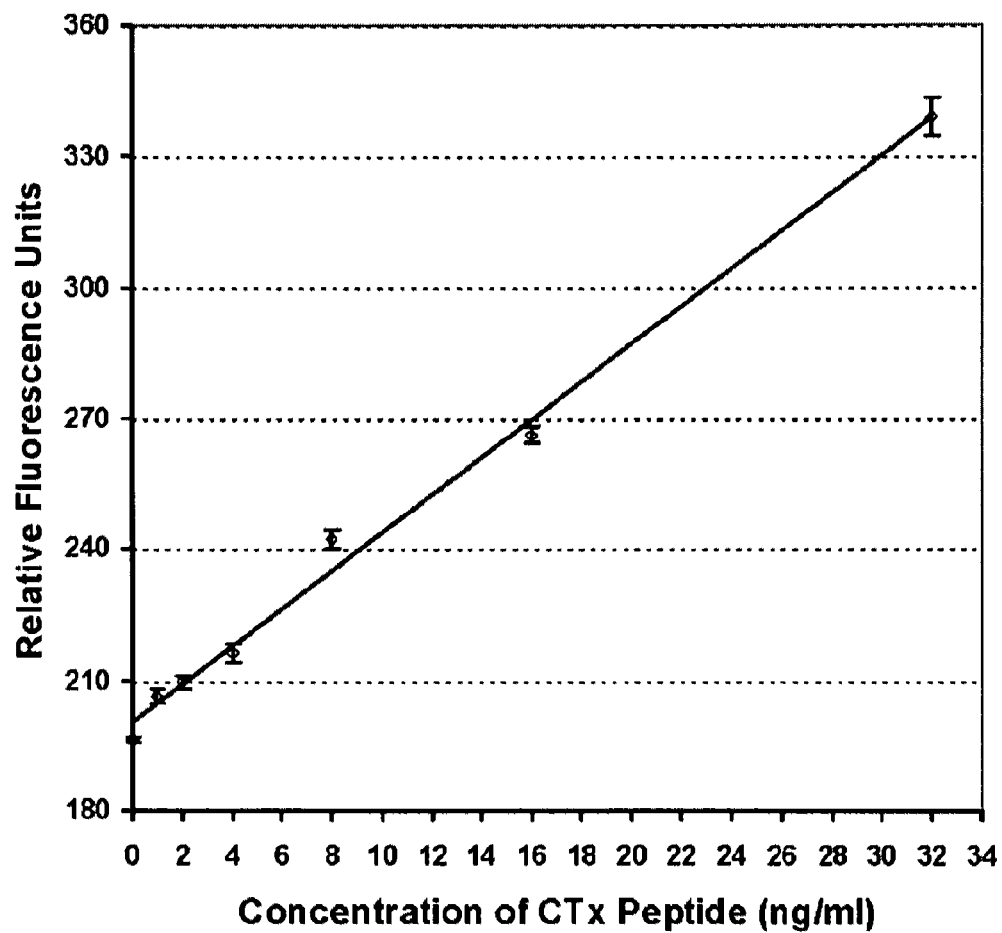
FIG. 5 shows the relative linearity and sensitivity of the 15-base CTx 2R-2h aptamer beacon assay.
Figure 6:
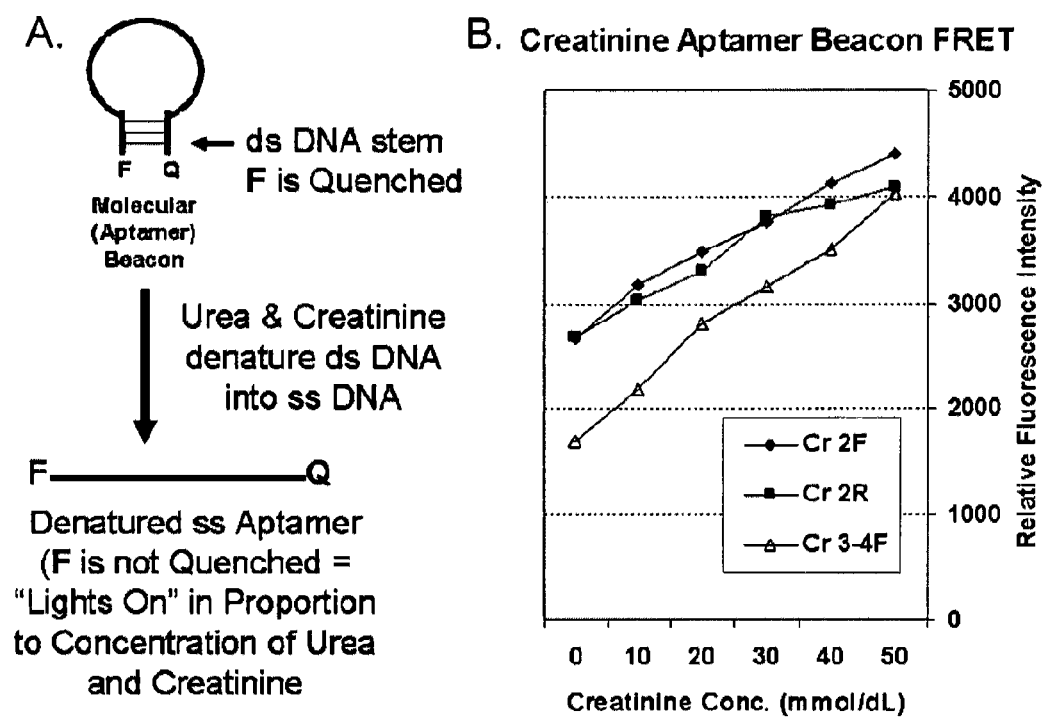
FIG. 6A illustrates the ability to normalize urine concentration readings with simple aptamer beacon fluorescence readings.
FIG. 6B shows a quantitative estimation of creatinine and urea levels in urine or serum using the aptamer beacon denaturation approach.
Figure 7:
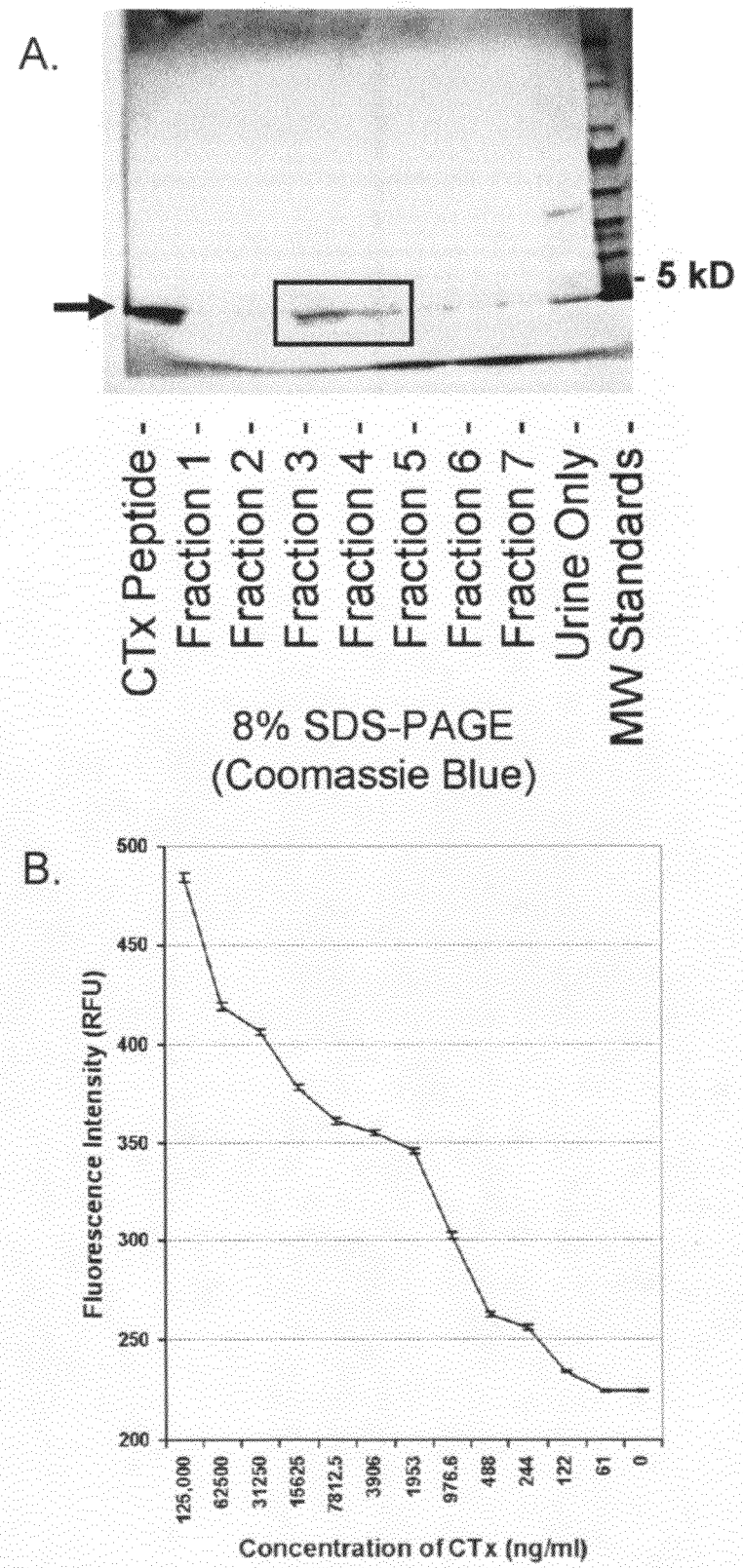
FIG. 7A illustrates that the 2,942 dalton (26-amino acid) CTx bone peptide can be extracted from urine to avoid the denaturing effects of creatinine and urea on the CTx 2R-2h aptamer beacon assay by use of a desalting size-exclusion polyacrylamide bead column.
FIG. 7B shows that CTx peptide extracted from human urine by means of a desalting column can still be detected to a level of at least 122 ng/ml by the CTx 2R-2h aptamer beacon.

FIG. 3 shows how each of the aptamer beacons derived and defined from FIG. 2 behaved as a function of decreasing CTx peptide concentration (serial two-fold dilutions beginning with 100 micrograms per ml and ending with zero CTx peptide) in 1× binding buffer (1×BB; 0.5 M NaCl, 10 mM Tris-HCl, pH 7.5-7.6, 1 mM $MgCl_2$). In the figure "h" means hour or O'clock so that 2 h refers to the 2 O'clock loop from FIG.

2, while F means forward-primed and R means reverse-primed by reference to FIG. 2 as well. FIG. 3 demonstrates that there is in fact a significant difference in the ability of each candidate loop or candidate beacon from FIG. 2 to bind and detect a 26-amino acid (AA; full-length) CTx peptide in 1×BB. The figure shows that the 15-base CTx 2R-2h loop (5'-GGTGGTGTTGGCTCC-3') acts as a superior aptamer beacon for detection of CTx peptide, because it gives the greatest fluorescence spread as a function of CTx peptide concentration. The CTx 2R-2h loop was optimal for FRET-based detection because it gives the greatest spread or separation for various two-fold serial dilutions of the 26-AA CTx peptide beginning at 100 μg/ml. The CTx 2F-10h loop was also noteworthy, but could not discriminate many of the different CTx concentrations. The candidate loops or beacons from this experiment were 5' labeled with TYE665 fluorophore and 3' labeled with Iowa Black RQ quencher and HPLC-purified prior to use at Integrated DNA Technologies, Inc. (Coralville, Iowa). Excitation on a spectrofluorometer was at 645 nm with 5 nm slits and a PMT (photomultiplier tube) setting of 900 V. A slightly shorter 13-base version of the CTx-2R-2h beacon ((5'-GTGGTGTTGGCTC-3') has also been shown to work almost as well as the 15-base version, but has slightly higher background fluorescence. Excitation in all cases was at 645±5 nm to maximally excite TYE 665 dye (fluorophore) on the 5' end of each potential aptamer beacon with a photomultiplier tube (PMT) detector setting of 1,000 Volts.

FIGS. 4A and B demonstrate relative specificity of the CTx 2R-2h aptamer beacon. FIG. 4A illustrates specificity or preference of the beacon for binding to the full-length 26-AA version of the CTx peptide based on its more intense fluorescence with the full-length CTx peptide, but not with a shorter 8-amino acid segment of the same peptide using a spectrofluorometer. Since the 8-AA version of the CTx peptide (one letter amino acid sequence: EKAHDGGR) represents a subset of the larger 26-AA peptide (amino acid sequence: SAGFDFSFLPQPPQEKAHDGGRYYRA), this observation indicates where the aptamer does not bind on the larger CTx peptide and narrows down the possible binding sites to SAGFDFSFLPQPPQ or YYRA). The aptamer beacon does unexpectedly cross-react with and bind an epitope on bovine serum albumin (BSA) and since the 607 amino acid BSA protein shares its longest region of commonality with the CTx peptide at the amino acid sequence SFL or serine-phenylalanine-leucine, this may be the actual binding site of the CTx 2R-2h aptamer beacon to CTx bone peptide, although other sites cannot be ruled out completely. Again, intact bovine proteins and epitopes are not expected in human clinical samples, making the CTx 2R-2h aptamer beacon specific for its target bone peptide.

FIG. 4B shows the same samples FIG. 4A evaluated by a handheld fluorometer that only reports fluorescence peak height, but confirms the level of specificity seen in the spectra above. The beacon was again 5' labeled with TYE665 fluorophore and 3' labeled with Iowa Black quencher and HPLC-purified prior to use in assays. Excitation on the spectrofluorometer was at 645 nm with 5 nm slits and a PMT (photomultiplier tube) setting of 900 V. Handheld fluorometer values were obtained with an optically modified (red light emitting diode with peak excitation at 650 nm with a 660-720 nm emission filter) Quantifluor™ device from Promega Corp. Other abbreviations used in FIG. 3 are: NTx; N-terminal telopeptide of human Type I bone collagen, HP; helical peptide of human bone, BSA; bovine serum albumin, DPD; deoxypyridinoline, and Pyd; pyridinoline.

FIG. 5 compares the 15-base CTx 2R-2h aptamer beacon assay's titration versus different levels of the full-length CTx peptide (26 amino acids) in 1× binding buffer for 30 minutes at room temperature as assessed by the handheld Quantifluor™ from 0 to 32 ng/ml of CTx peptide with a limit of detection (LOD) of 1 ng/ml with a photodiode standard value setting of 999.0. It shows the relative linearity and sensitivity of the 15-base CTx 2R-2h aptamer beacon assay.

FIG. 6 illustrates the linear normalization response of three different aptamer beacons raised against creatinine from the SEQ ID NOs 239-294 family to the denaturing effects of creatinine across the physiologic range found in human urine. The non-specific linear response of aptamer beacons in general to the denaturing (linearizing) effects of creatinine and urea across the physiologic range of these substances found in human urine suggest that addition of almost any aptamer beacon to urine could be used to estimate creatinine and urea levels in urine and normalize the values for other analytes in urine. It is a common practice in clinical diagnostics in which the creatinine or urea level of urine is used as a divisor for the amount of other analytes detected in urine to normalize readings between different patients. In essence, the creatinine or urea levels indicate how concentrated the urine is and that information can be used to adjust or normalize (divide by) the creatinine level to place the levels of other analytes in proper perspective (i.e., high analyte levels in a dehydrated individual may be misleading). Quantitative estimation of creatinine and urea levels in urine or serum using the aptamer beacon denaturation approach is simple (one step bind and detect), rapid (within 10-15 minutes) and facile as compared to the more complicated multi-component alkaline picrate colorimetric and time-consuming Jaffe method (i.e., results obtained greater than 35 minutes after reagent and sample preparation).

FIG. 7 illustrates that the 2,942 dalton (26 amino acid) CTx peptide can be extracted from urine to avoid the denaturing effects of creatinine and urea on the CTx 2R-2h aptamer beacon assay (demonstrated in FIG. 5) by use of a desalting size-exclusion polyacrylamide column. FIG. 7A shows fractions collected from a desalting column (with a 1,800 dalton molecular weight cut off) and run in an 8% polyacrylamide-sodium dodecyl sulfate (SDS) electrophoresis gel which was run against molecular weight protein standards (last lane) and Coomassie blue stained to reveal the location of the 2.9 kilodalton CTx peptide which emerged in the void volume fractions 4 and 5 (boxed). The far right lane of this gel shows molecular weight protein standards beginning at 5 kD. FIG. 7B shows that CTx peptide extracted from human urine by means of a desalting column can still be sensitively detected to a level of at least 122 ng/ml by the CTx 2R-2h aptamer beacon.

FIG. 8 illustrates the secondary stem-loop structures of several candidate aptamers (SEQ ID NOs 433 and 434) which dominated: the sequenced pool of vitamin D3 aptamers (abbreviated VD3 and from the SEQ ID NOs 429-526). Again, the lines and capital letters demarcate the loops which were considered further as binding pockets or for aptamer beacons to detect vitamin D and its isoforms or congeners.

FIG. 9 illustrates the FRET responses of loops A, B, and C for the VD3 aptamers shown in FIG. 8 as well as handheld (Quantifluor™-P) fluorometer peak fluorescence values as a function of 25-hydroxy-vitamin D3 (calcidiol) level in 1×BB. Loop C (5'-ACTATGGT-3') proved to be the optimal aptamer beacon based on its maximal spread or separation of fluorescence spectra as a function of vitamin D concentration as shown in the upper right quadrant after Loop C was separately synthesized with 5'-TYE 665 dye and 3'-Iowa Black quencher to convert it into a beacon for the titration experiment. The spectra were obtained by serial two-fold dilutions of calcidiol beginning at 100 μg/ml in 1×BB. The candidate VD3 loop beacons were 5' labeled with TYE665 fluorophore and 3' labeled with Iowa Black quencher and HPLC-purified prior to use in assays. Excitation on a spectrofluorometer was at 645 nm with 5 nm slits and a PMT setting of 900 V. Handheld fluorometer values (lower right quadrant) were obtained with an optically modified (red light emitting diode with peak excitation at 650 nm with a 660-720 nm emission filter) Quantifluor™-P device from Promega Corp. and show a lower limit of detection of about 195 ng/ml in 1×BB.

Figure 10:
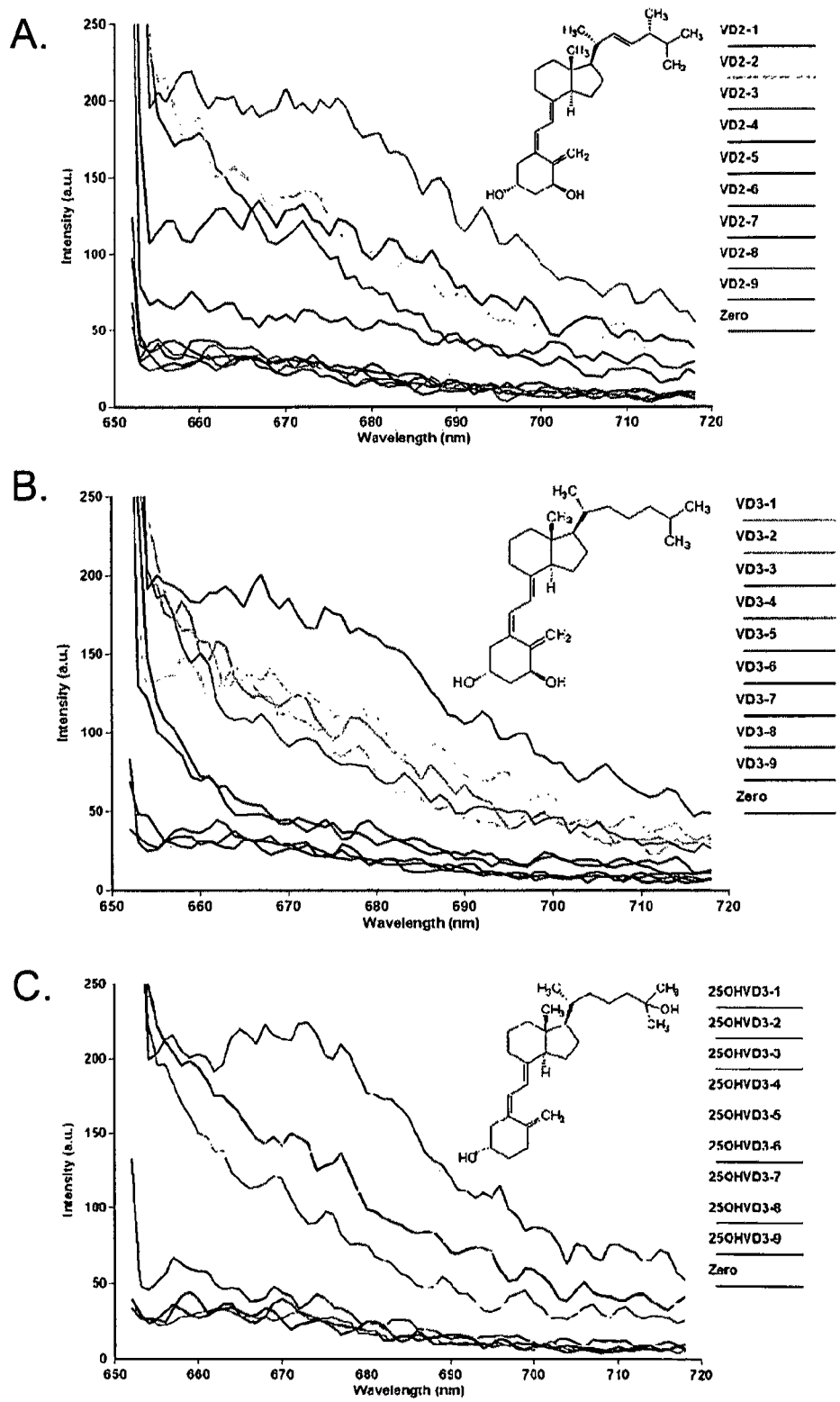
FIG. 10 reveal that the VD3 Loop C beacon appears to react equally well with (A) 1-hydroxy-vitamin D2, (B) 1-hydroxy-vitamin D3 and (C) 25-hydroxy-vitamin D3.

FIG. 10 shows that the VD3 Loop C beacon appears to react equally well with 1-hydroxy vitamin D2, 1-hydroxy-vitamin D3 and 25-hydroxy-vitamin D3 as assessed by spectrofluorometry in 1×BB (binding buffer). Hence the Loop C beacon is only specific for the vitamin D family and cannot discriminate individual congeners. Cross-reactivity is not problematic since a number of immunoassays for vitamin D detect the total of the major forms of vitamin D2 and D3 together. Hence, the inability of the Loop C VD3 aptamer to discriminate the minor variants of vitamin D is not viewed as a limiting factor. The figure again shows serial two-fold dilutions for each of the types of vitamin D beginning at 100 μg/ml in 1×BB with 1-hydroxy-vitamin D2 spectra in the top panel, 1-hydroxy-vitamin D3 spectra in the middle panel, and 25-hydroxy-vitamin D3 spectra in the bottom panel.

Figure 11:
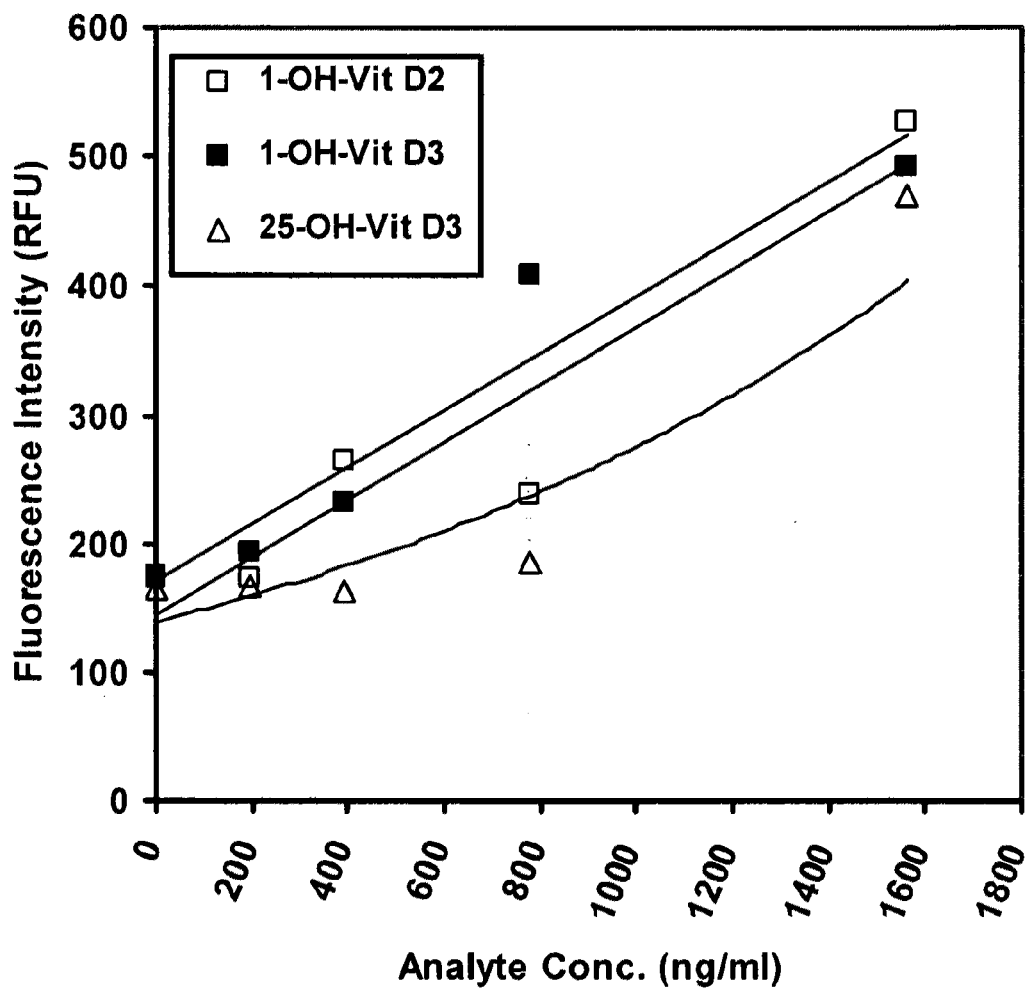
FIG. 11 shows an assessment of the VD3 Loop C beacon.

FIG. 11 shows a graphical assessment of the VD3 Loop C beacons by the handheld fluorometer (Quantifluor™-P) in 1×BB across a range of various vitamin D concentrations and for various forms of vitamin D. The handheld reader was modified with a red-emitting (650 nm) LED light source and 660-720 nm emission filter to better work in serum where the red region optics (>600 nm) can avoid much of the blue-green (<600 nm) autofluorescence background of blood, serum or urine. The range shown on the x-axis spans much higher levels than previously shown. Some of the higher levels are not physiological, but might be relevant to detection of vitamin D is some vitamin-rich foods or dairy products. Lines of best fit, whether linear or exponential, are shown for the three different types of vitamin D congeners as well. The highest standard value photodetector setting of 999.0 was used in all cases.

Figure 12:
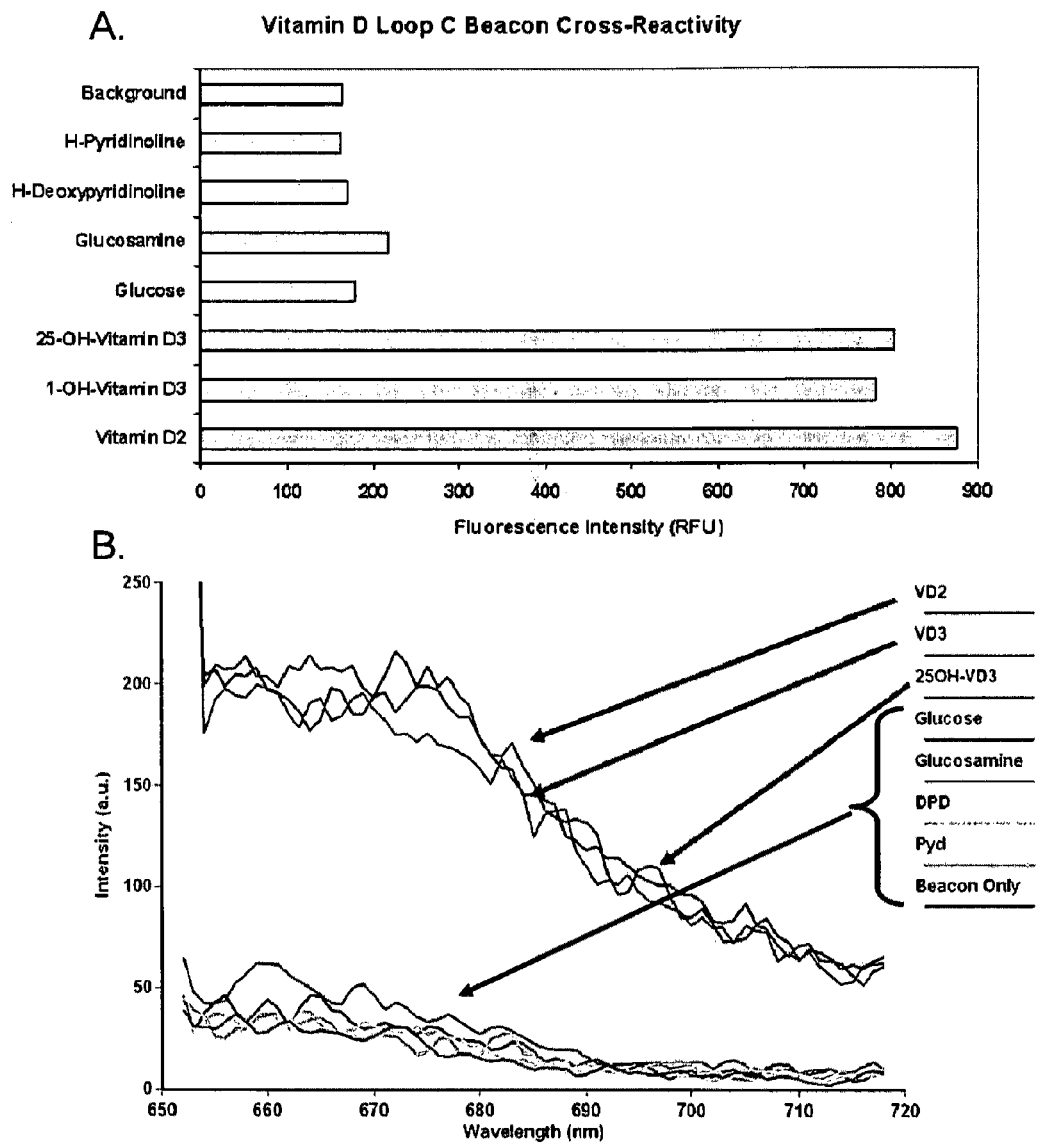
FIG. 12 summarizes assessment of the specificity or cross-reactivity of the VD3 Loop C aptamer beacon versus a variety of potential analytes or interfering species.

FIG. 12 further assesses the specificity or cross-reactivity of the VD3 Loop C aptamer beacon versus a variety of potential analytes or interfering species commonly found in blood and urine by the customized handheld fluorometer (FIG. 12A) and by spectrofluorometry (FIG. 12B) H-DPD; hydroxy-deoxypyridinoline and H-Pyd; hydroxyl-pyridinoline cross linkers from bone.

Figure 13:
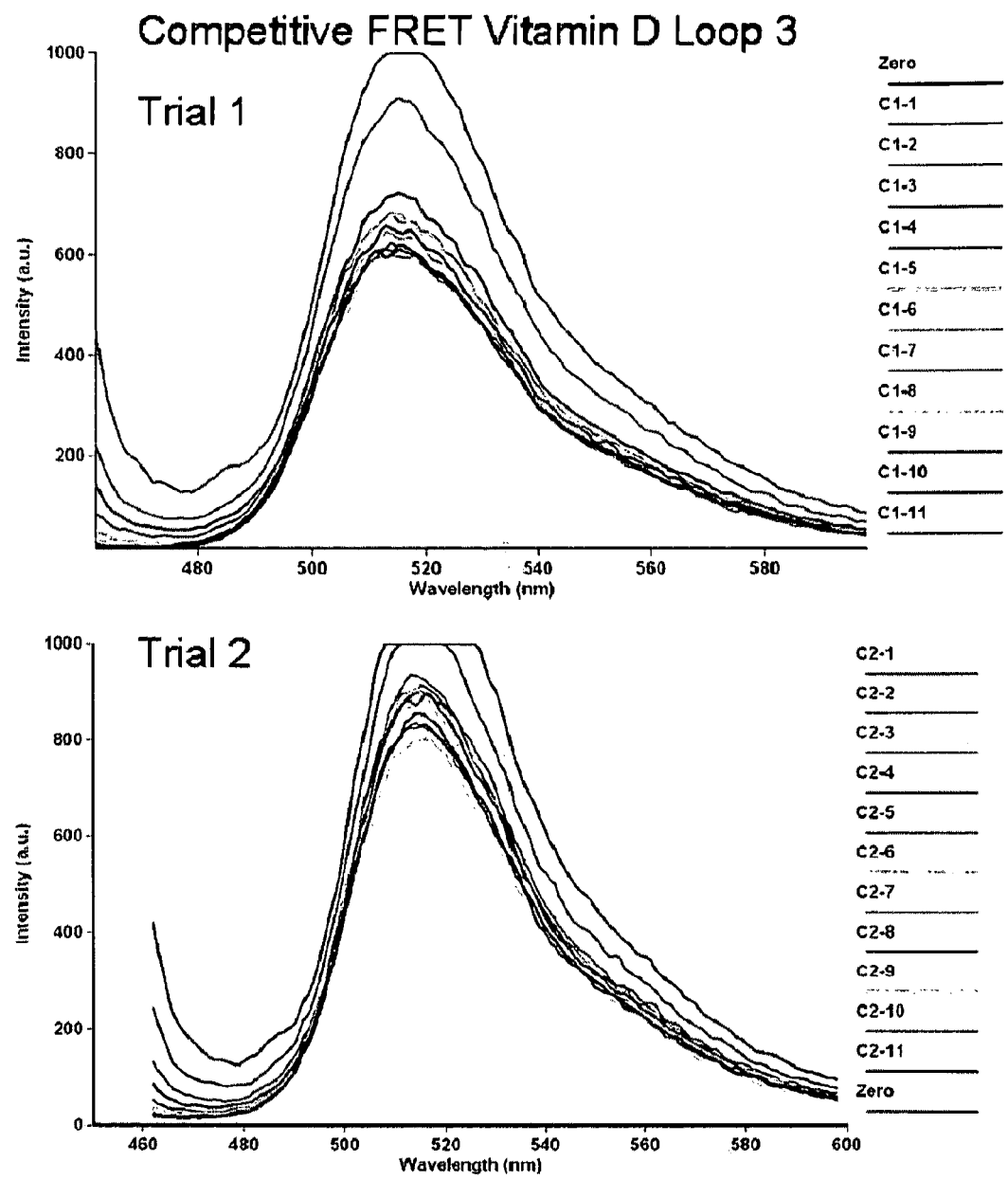
FIG. 13 shows fluorometric spectra from two separate trials of a competitive displacement FRET assay.

FIG. 13 shows fluorometric spectra from two separate trials of a competitive displacement FRET assay using the VD3 Loop C beacon versus various levels of 25-hydroxy-vitamin D3 (two-fold serial dilutions starting at 100 μg/ml) in 1×BB. In this case, 25-hydroxy-vitamin D3 was labeled with carboxyfluorescein by Fisher esterification (reaction of a hydroxyl group on the vitamin with a carboxyl group on the fluorescein to form a covalent ester bond at acidic pH of approximately 5) followed by binding to appropriately quencher-labeled VD3 aptamer Loop C and competition against levels of calcidiol≤100 micrograms per ml).

Figure 14:
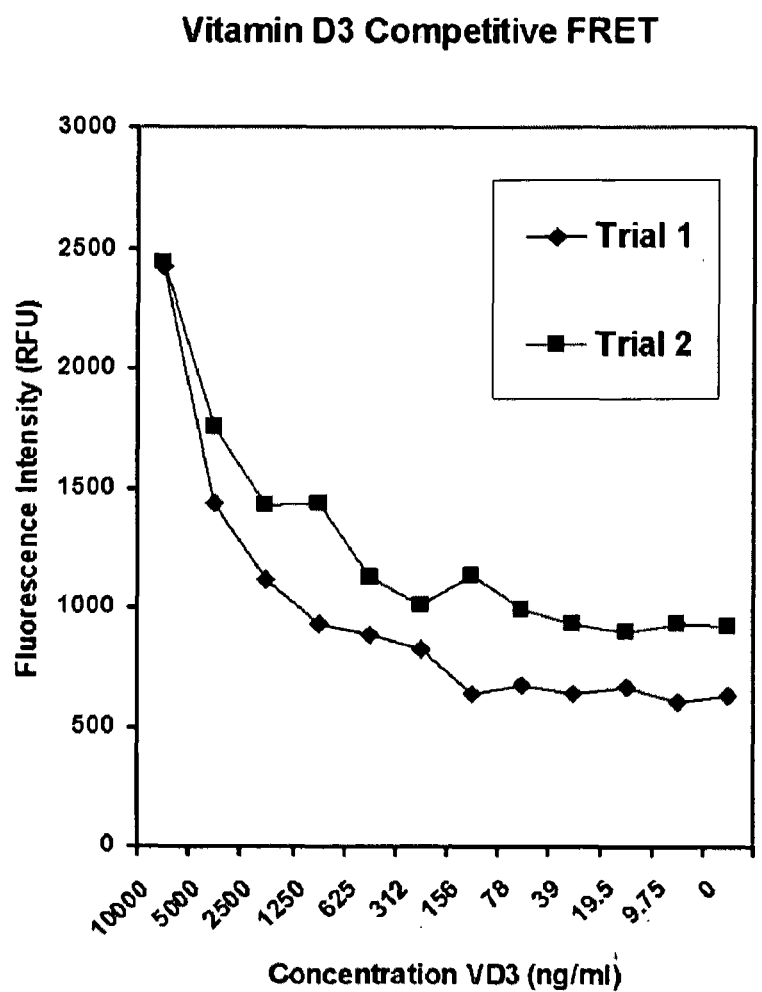
FIG. 14 shows the same samples from FIG. 13 assessed for fluorescence peak height.

FIG. 14 shows the same samples from FIG. 13 assessed for fluorescence peak height by the customized red-emitting handheld fluorometer assessed with the highest standard value photodetector setting of 999.0. The competitive FRET-aptamer assay appears to have a detection limit between 156 to 312 ng/ml in these experiments.

Figure 15:
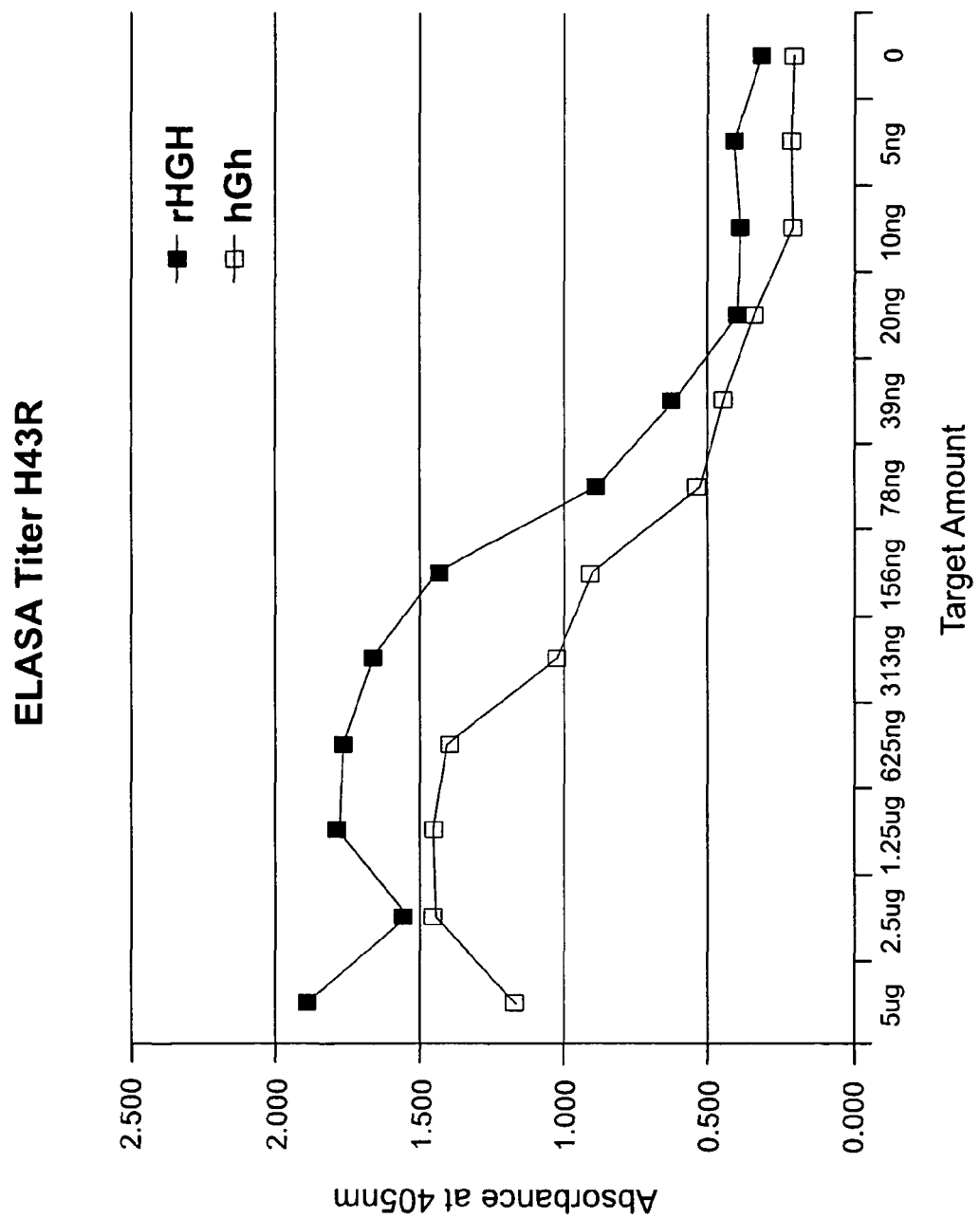
FIG. 15 shows four examples of aptamers from the pool of aptamers that bind recombinant human growth hormone.
Figure 15:
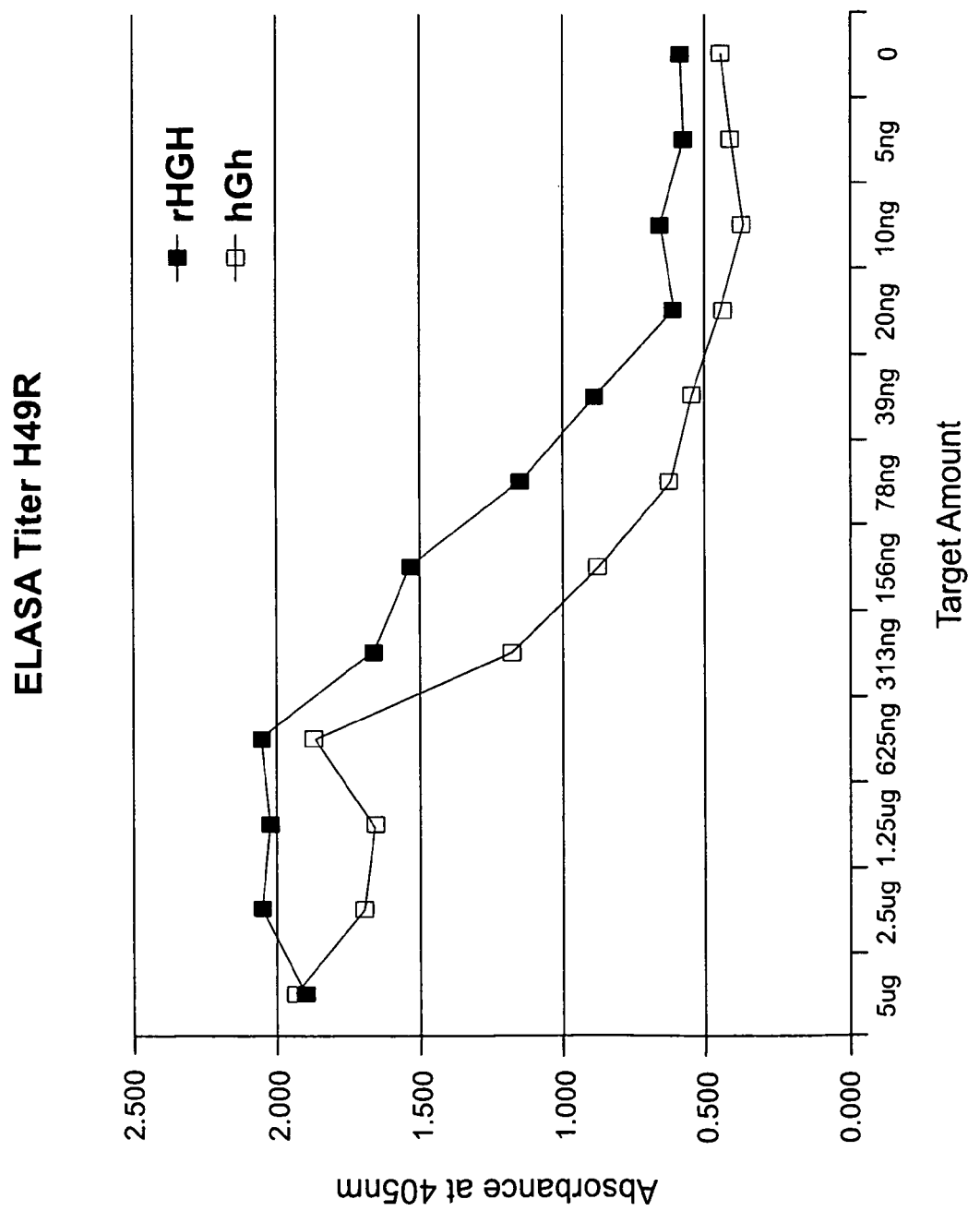
Figure 15:
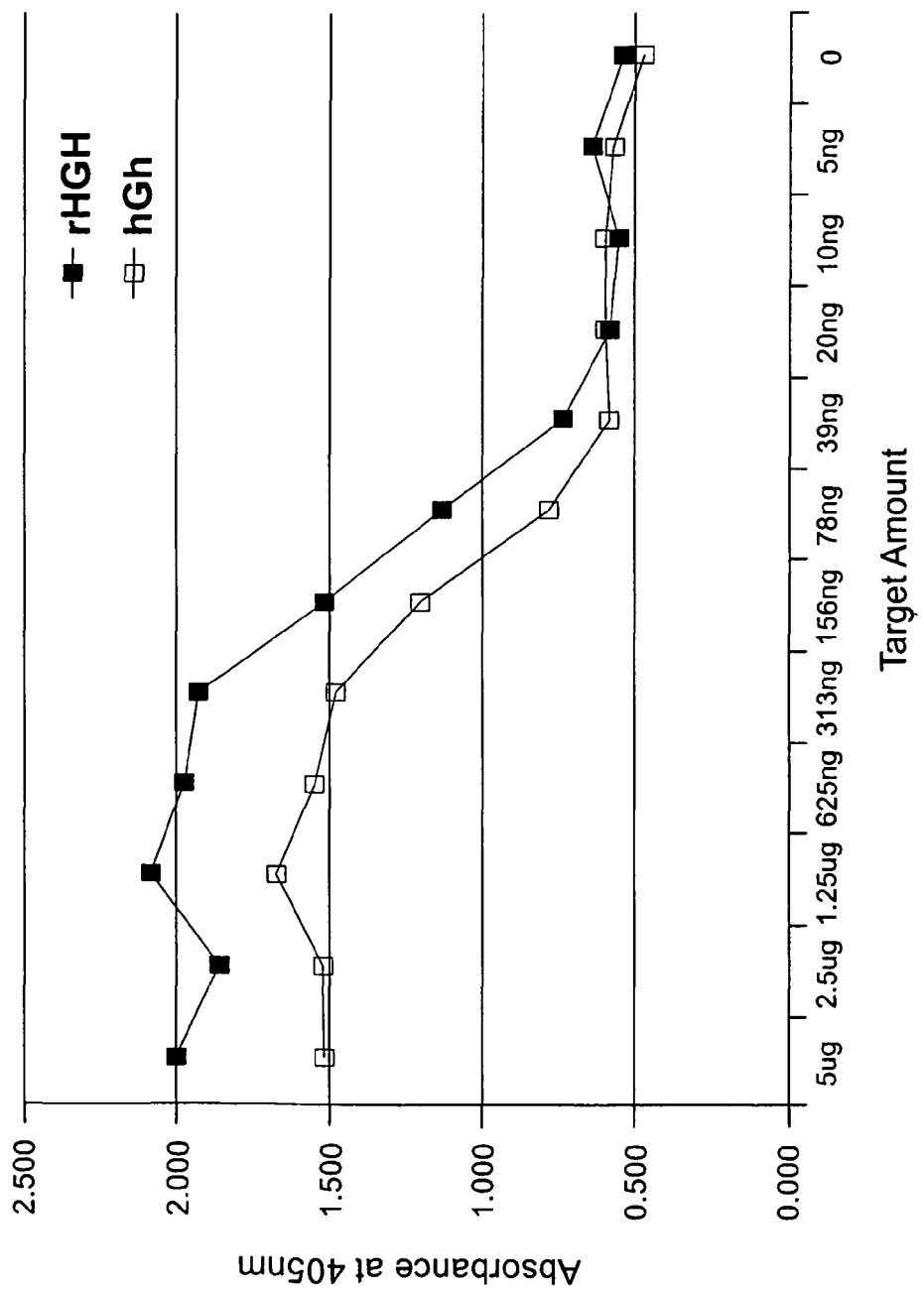
Figure 15:
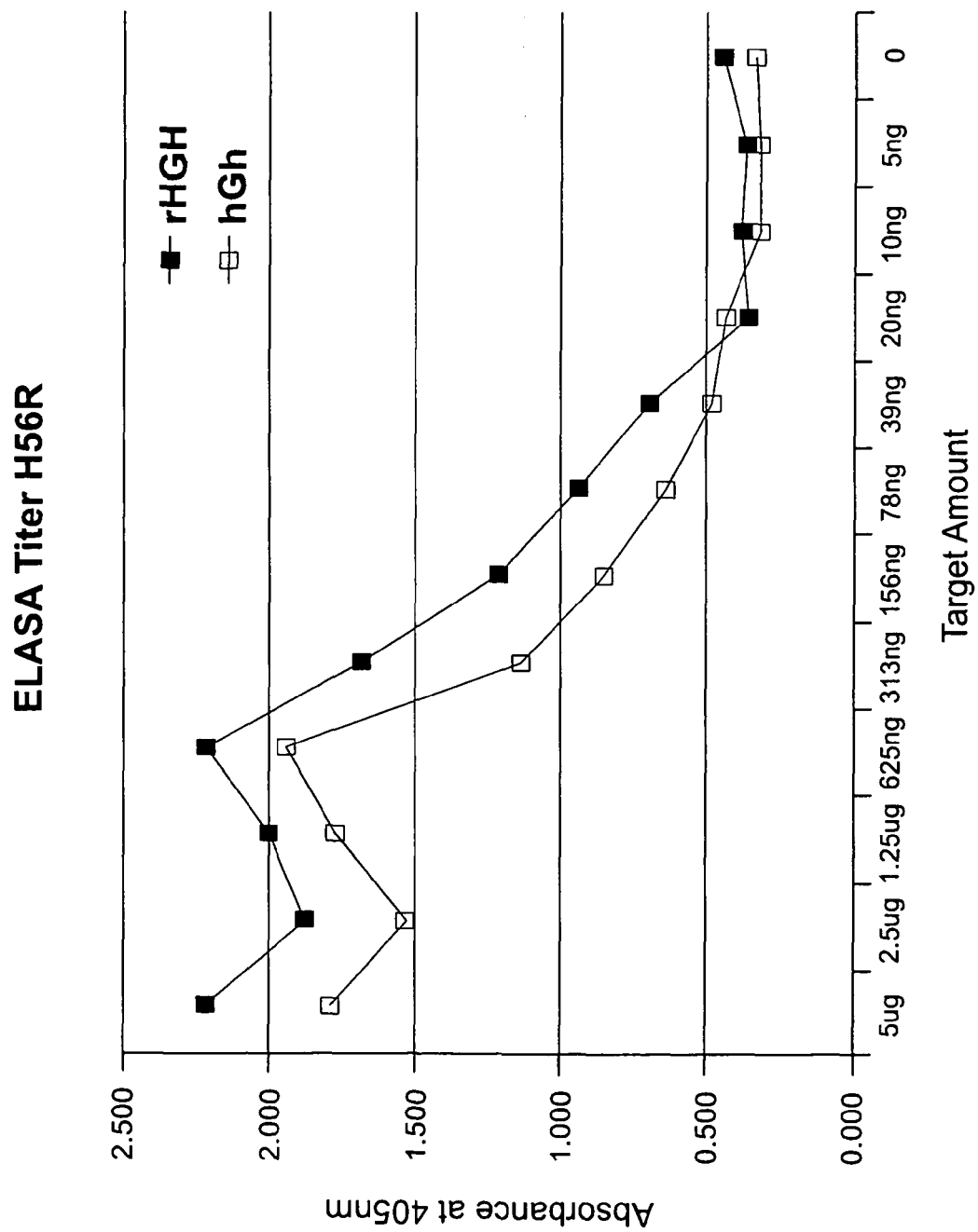

FIG. 15 shows four examples of aptamers from the SEQ ID NOs 325-526 that bind recombinant human growth hormone (r-hGH; >95% pure research grade) better than the natural form of hGH or somatotropin in ELISA-like assays to help discriminate the artificial form of hGH in potential drug or doping tests for athletes, or to monitor serum levels of exogenous doses of r-hGH administered to children with growth deficits. The ELISA-like assays were conducted with the named aptamers (SEQ ID NOs 336, 338, 343 and 345) instead of antibodies in each case and absorbances were red at 405 nm with an automated microplate reader after a 15 minute development time in the presence of ABTS substrate as is standard in the diagnostics industry.

Figure 16:
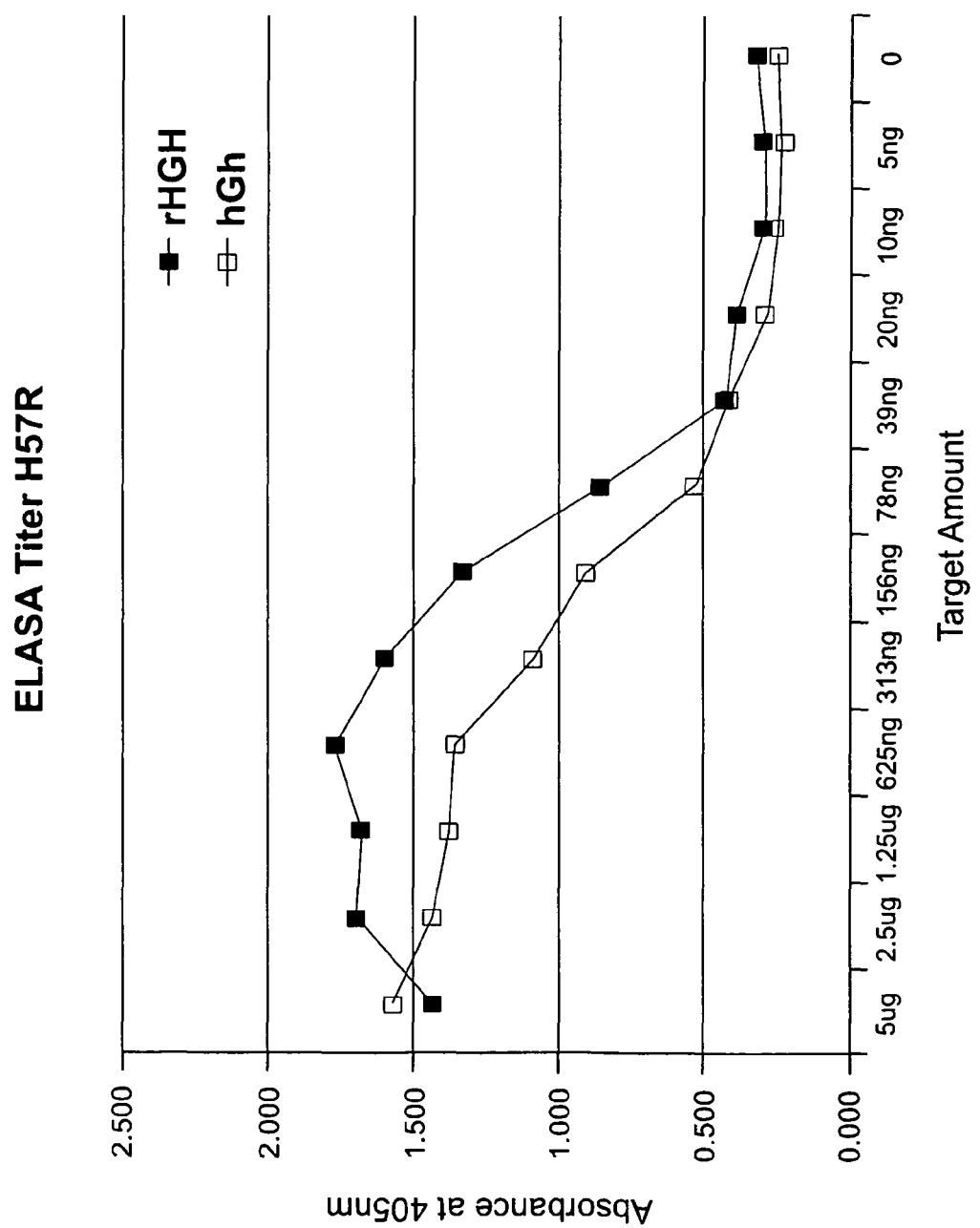
FIG. 16 shows four more examples of aptamers from the pool of aptamers that bind recombinant human growth hormone.
Figure 16:
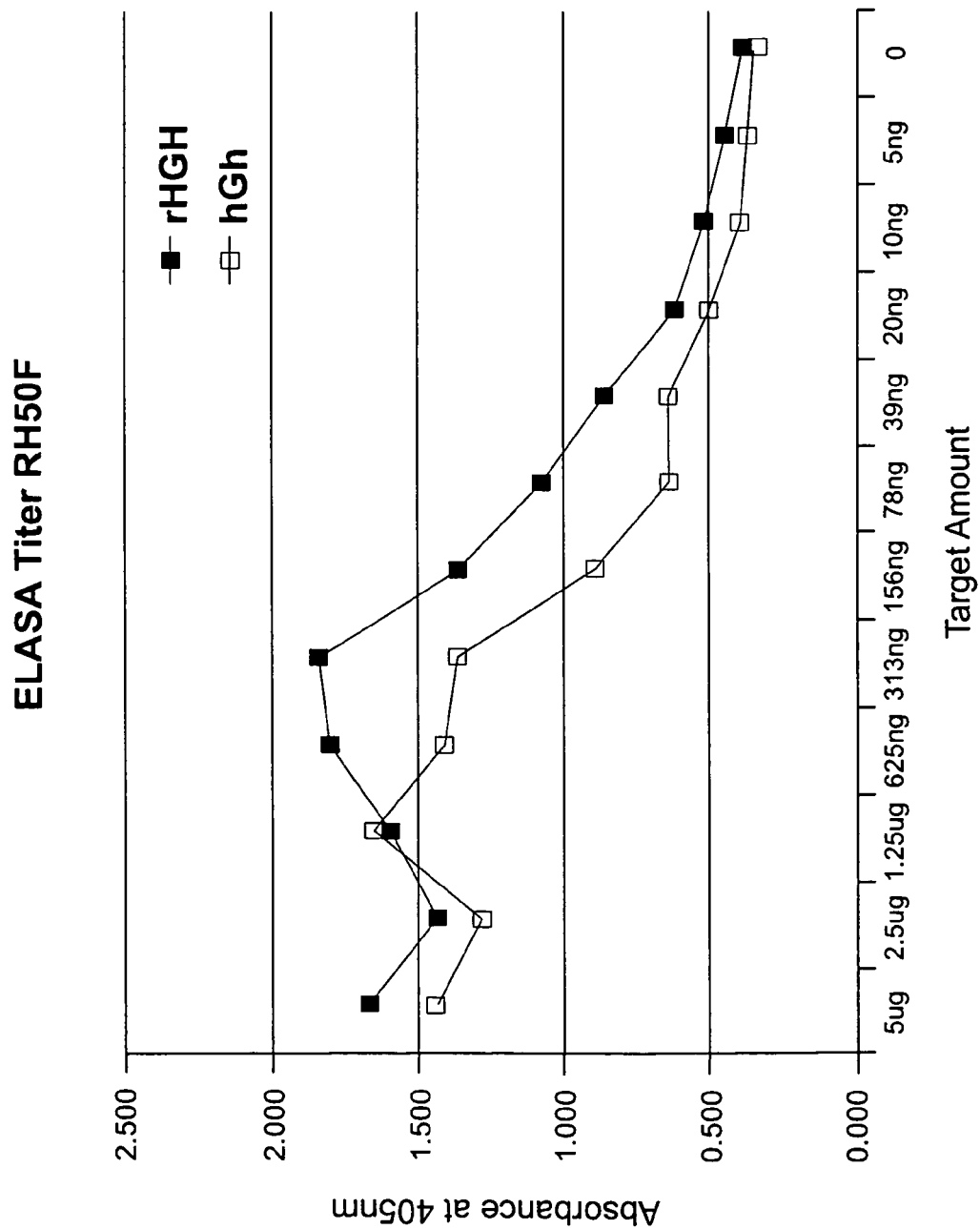
Figure 16:
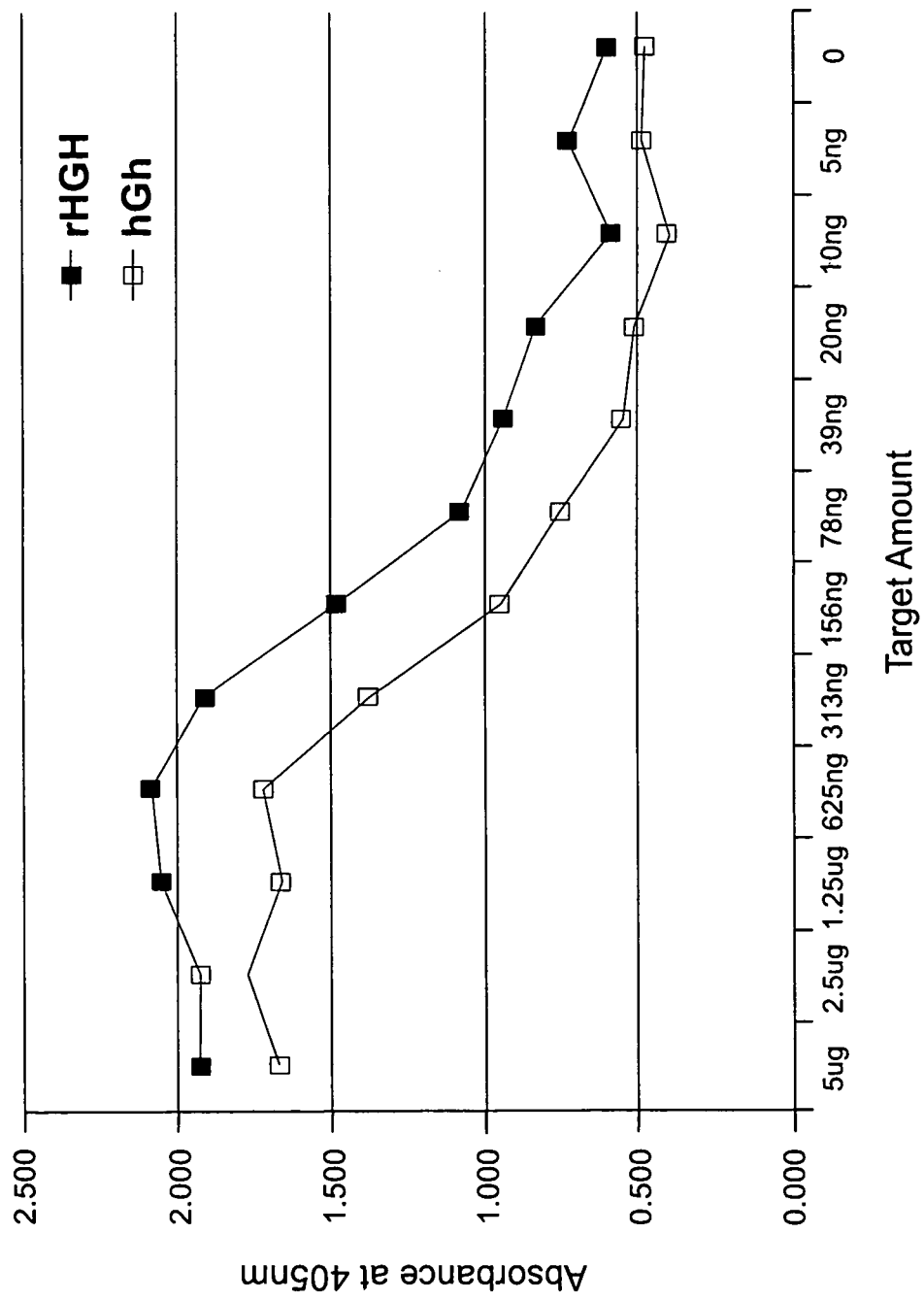
Figure 16:
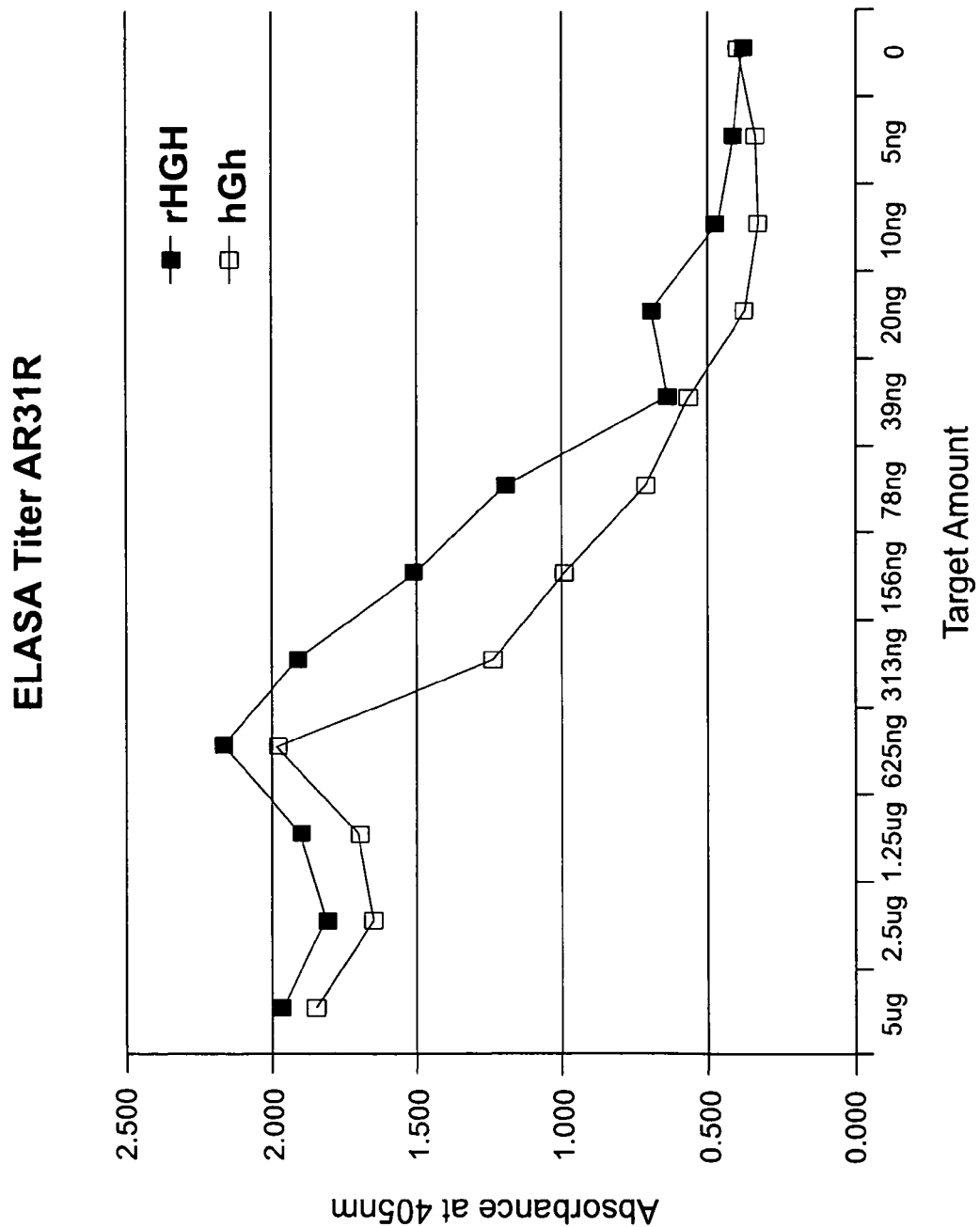

FIG. 16 shows four more examples of aptamers (from the SEQ ID NOs 325-526) that bind recombinant human growth hormone ("r-hGH") better than the natural form of hGH or somatotropin to help discriminate the artificial form in potential drug or doping tests for athletes and growth-challenged children. The ELISA-like assays were conducted with the named aptamers (SEQ ID NOs 348, 377, 379 and 388) instead of antibodies in each case and absorbances were red at 405 nm with an automated microplate reader after a 15 minute development time in the presence of ABTS substrate as is standard in the diagnostics industry.

Figure 17:
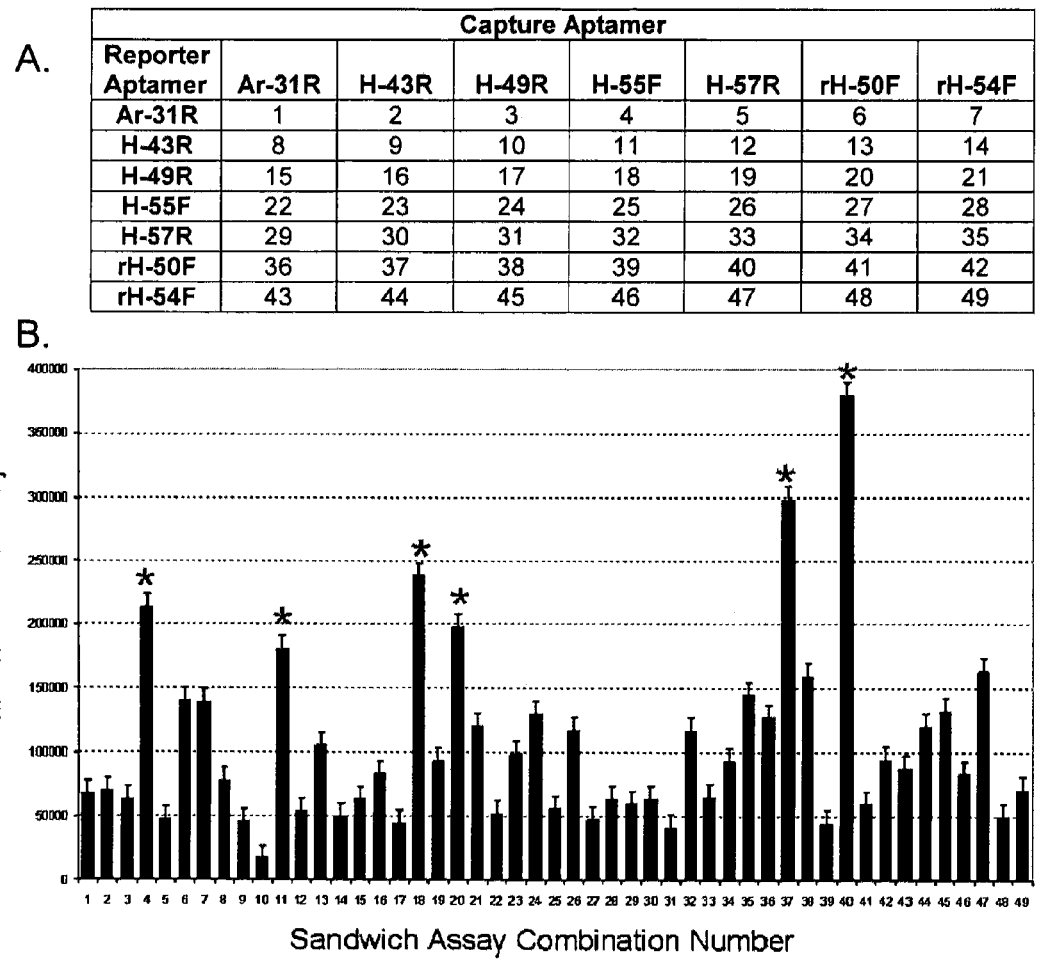
FIG. 17A shows an experimental matrix screening scheme for capture aptamer-conjugated magnetic microbeads.
FIG. 17B shows mean bar heights of three separate measurements.

FIG. 17A shows an experimental matrix screening scheme for capture aptamer-conjugated magnetic microbeads to be mixed with ruthenium trisbipyridine (Ru(bpy)$_3^{2+}$)-labeled reporter aptamers in a sandwich assay scheme to determine which of the 7×7 top hGH and r-hGH aptamer combinations (numbered 1-49 in the scheme table) gave the strongest electrochemiluminescence ("ECL") signal versus 10 pg/ml of r-hGH using an IGEN International Origen® ECL analyzer in phosphate buffered saline containing 0.2 M tripropylamine ("TPA"). ECL was induced by ramping the electrode voltage to 1.25 V.

FIG. 17B shows the results of this ECL matrix screening process. Mean bar heights of three separate measurements are plotted with standard deviation error bars and the best (most intense ECL) combinations are marked with asterisks.

Figure 18:
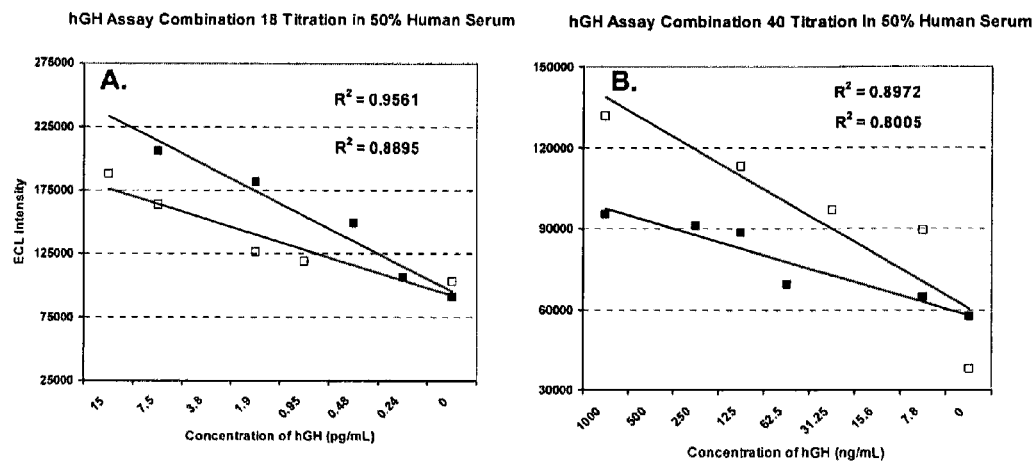
FIG. 18 gives ECL line plots for assay combinations 18 and 40 from the matrix in FIG. 17A.

FIG. 18 gives ECL line plots for assay combinations 18 and 40 from the matrix in FIG. 17A as a function of natural hGH concentrations showing sub-picogram and sub-nanogram per ml detection limits and relative linearity over the hGH ranges indicated in 50% human serum (serum diluted 1:1 in 1×BB buffer). The difference in assay regression line slope is due to doubling of the amount of aptamer-coated magnetic beads and reporter aptamer per tube in two different assay trials.

Figure 19:
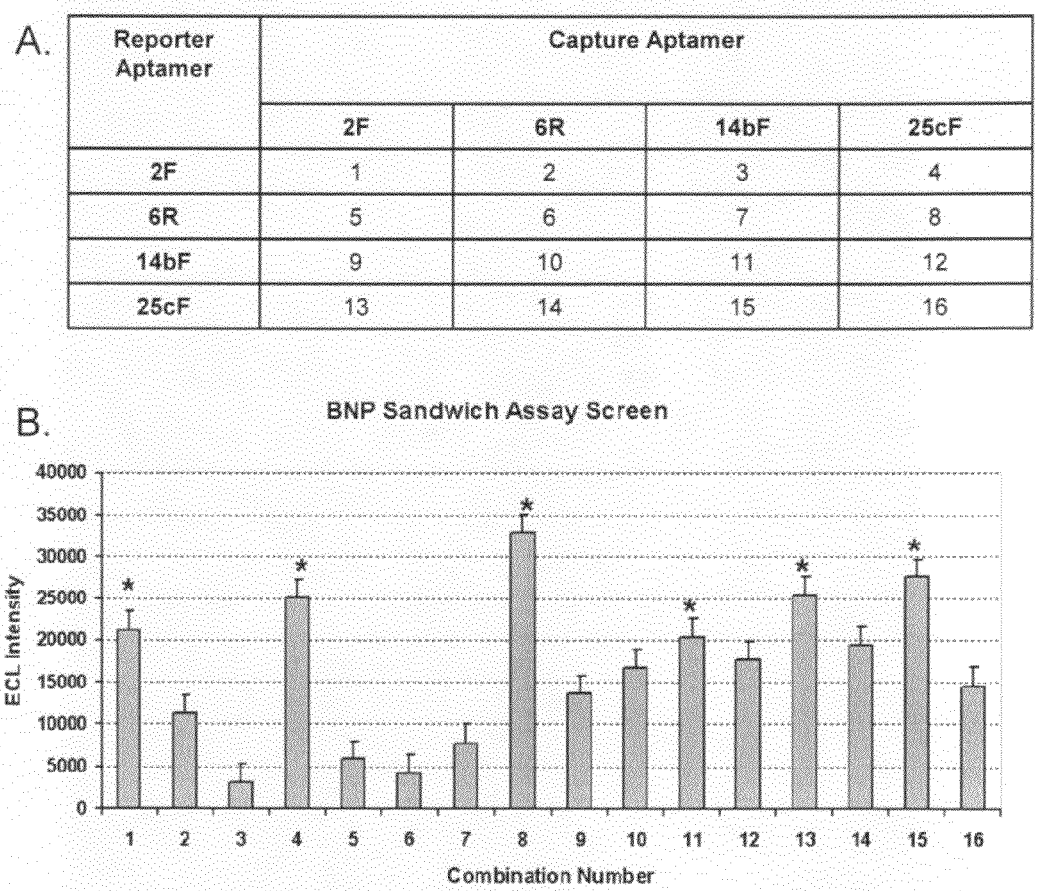
FIG. 19A shows an experimental matrix screening scheme for capture aptamer-conjugated magnetic microbeads.
FIG. 19B shows mean bar heights of three separate measurements.

FIG. 19A shows an experimental matrix screening scheme for capture aptamer-conjugated magnetic microbeads to be mixed with ruthenium trisbipyridine (Ru(bpy)$_3^{2+}$)-labeled reporter aptamers in a sandwich assay scheme to determine which of the 4×4 top Brain or B-type Natriuretic Peptide ("BNP") aptamer combinations numbered 1-16 (and selected from the SEQ ID Nos. 527-562) gave the strongest ECL signal versus 100 ng of BNP using an IGEN International Origen® ECL analyzer in phosphate buffered saline containing 0.2 M TPA.

FIG. 19B shows the results of this ECL matrix screening process. Bar heights represent the means of three separate measurements plotted with standard deviation error bars and the best (most intense ECL) combinations are marked with asterisks.

Figure 20:
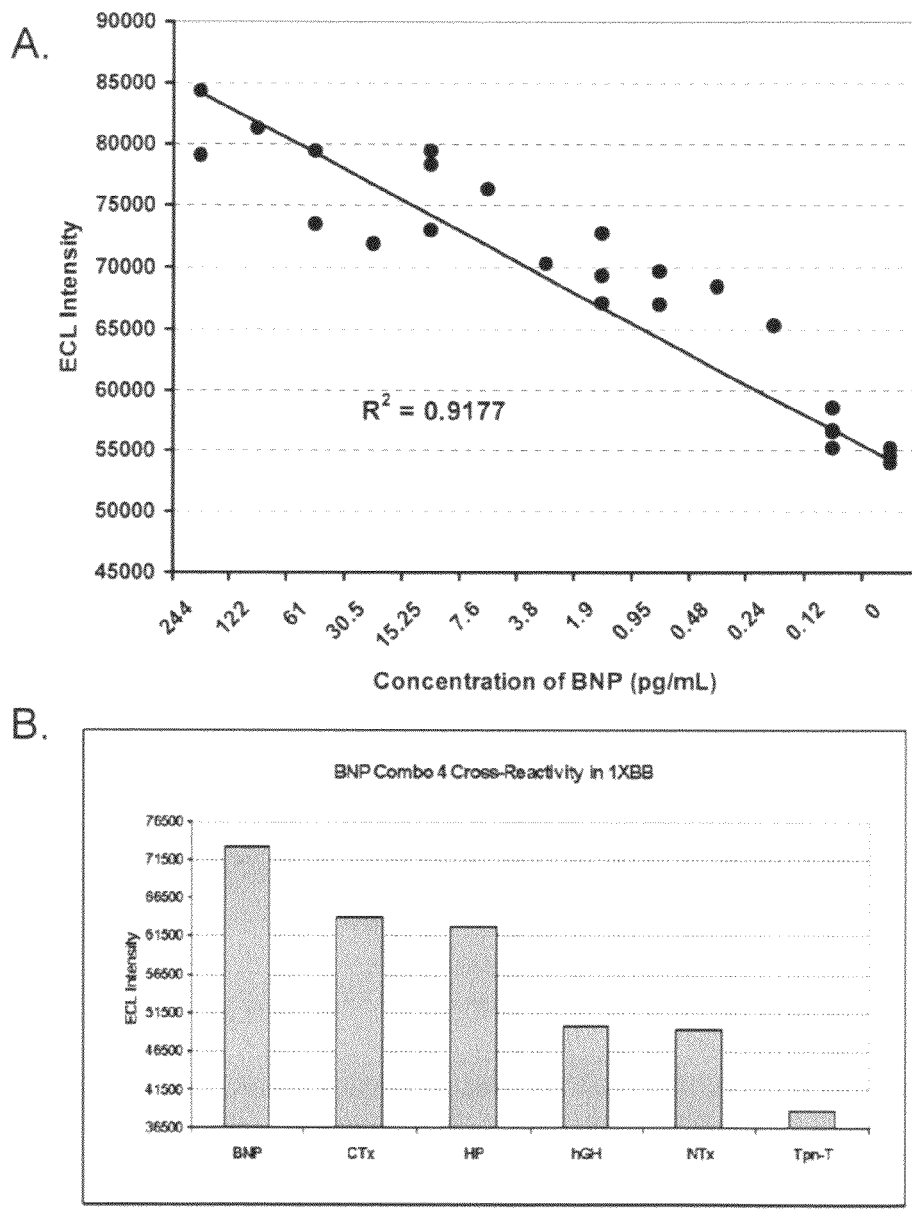
FIG. 20A shows the linear ECL response for the sandwich assay of FIG. 19.
FIG. 20B shows cross-reactivity of the combination number 4 BNP assay versus other peptide or protein analytes that might be found at the 100 ng/ml level in human blood.

FIG. 20A shows the linear ECL response for combination 4 (see FIG. 19A) sandwich assay versus picogram per ml levels of BNP in a 50% human serum and 1×BB diluent environment.

FIG. 20B shows cross-reactivity of the combination number 4 BNP assay versus other peptide or protein analytes that might be found at the 100 ng/ml level in human blood.

Although the invention and DNA ligand (aptamer) sequences have been described with reference to specific embodiments, these descriptions are not meant to be construed in a limited sense. Various modifications of the disclosed embodiments, as well as alternative embodiments of the inventions will become apparent to persons skilled in the art upon reference to the description of the invention. It is, therefore, contemplated that the appended claims will cover such modifications that fall within the scope of the invention.

I claim:
1. A DNA ligand sequence consisting of SEQ ID NO. 336.
2. A composition comprising the DNA ligand sequence of claim 1.

* * * * *